US012742160B2

(12) United States Patent
Henley et al.

(10) Patent No.: US 12,742,160 B2
(45) **Date of Patent: *Sep. 22, 2026**

(54) GENETIC ENGINEERING OF FUNGI TO MODULATE TRYPTAMINE EXPRESSION

(71) Applicant: EMPYREAN NEUROSCIENCE, INC., New York, NY (US)

(72) Inventors: Thomas Henley, New York, NY (US); Modassir Choudhry, New York, NY (US); Jose Fernandez-Gomez, New York, NY (US)

(73) Assignee: EMPYREAN NEUROSCIENCE, INC., New York, NY (US)

( * ) Notice: Subject to any disclaimer, the term of this patent is extended or adjusted under 35 U.S.C. 154(b) by 473 days.

This patent is subject to a terminal disclaimer.

(21) Appl. No.: 17/711,270

(22) Filed: Apr. 1, 2022

(65) Prior Publication Data

US 2022/0306997 A1 Sep. 29, 2022

Related U.S. Application Data

(63) Continuation of application No. PCT/US2020/053842, filed on Oct. 1, 2020.

(60) Provisional application No. 62/909,159, filed on Oct. 1, 2019.

(51) Int. Cl.

| | |
|---|---|
| ***C12N 9/02*** | (2006.01) |
| ***A61K 36/07*** | (2006.01) |
| ***C12N 9/10*** | (2006.01) |
| ***C12N 9/12*** | (2006.01) |
| ***C12N 9/88*** | (2006.01) |

(52) U.S. Cl.

CPC .......... *C12N 9/0083* (2013.01); *A61K 36/078* (2024.05); *C12N 9/1007* (2013.01); *C12N 9/1205* (2013.01); *C12N 9/88* (2013.01); *C12Y 114/99* (2013.01); *C12Y 201/01* (2013.01); *C12Y 207/01* (2013.01); *C12Y 401/01* (2013.01)

(58) Field of Classification Search

CPC ...................................................... A61K 36/07

See application file for complete search history.

(56) References Cited

U.S. PATENT DOCUMENTS

| | | | |
|---|---|---|---|
| 3,183,172 | A | 5/1965 | Heim et al. |
| 9,072,747 | B2 | 7/2015 | Lozinsky |
| 9,538,418 | B2 | 1/2017 | Sirotkin |
| 10,064,856 | B2 | 9/2018 | Bosse |
| 10,085,994 | B2 | 10/2018 | Lozinsky |
| 10,085,995 | B2 | 10/2018 | Lozinsky |
| 10,183,001 | B1 | 1/2019 | King |
| 10,457,667 | B2 | 10/2019 | Gaufreteau et al. |
| 10,519,175 | B2 | 12/2019 | Londesbrough et al. |
| 10,596,378 | B2 | 3/2020 | Rustick |
| 10,729,706 | B2 | 8/2020 | Küçüksen et al. |
| 10,881,606 | B2 | 1/2021 | Schmitz |
| 10,881,607 | B2 | 1/2021 | Schmitz |
| 10,933,073 | B2 | 3/2021 | Chadeayne |
| 10,947,257 | B2 | 3/2021 | Londesbrough |
| 10,954,259 | B1 | 3/2021 | Londesbrough |
| 11,000,534 | B1 | 5/2021 | Sippy |
| 11,149,044 | B2 | 10/2021 | Londesbrough |
| 11,180,517 | B2 | 11/2021 | Londesbrough |
| 11,242,318 | B2 | 2/2022 | Nivorozhkin |
| 11,292,765 | B2 | 4/2022 | Bryson |
| 11,298,388 | B2 | 4/2022 | Lightburn |
| 11,312,684 | B1 | 4/2022 | Nichols |
| 11,324,762 | B2 | 5/2022 | Sippy |
| 11,331,357 | B2 | 5/2022 | Lightburn |
| 11,344,564 | B1 | 5/2022 | Sippy |
| 11,358,934 | B2 | 6/2022 | Chadeayne |
| 11,364,221 | B2 | 6/2022 | Liechti |
| 2014/0255521 | A1 | 9/2014 | Lozinsky |
| 2014/0256688 | A1 | 9/2014 | Lozinsky |
| 2015/0272957 | A1 | 10/2015 | Lozinsky |
| 2016/0331725 | A1 | 11/2016 | Gillessen |
| 2017/0273975 | A1 | 9/2017 | Yada et al. |
| 2018/0221396 | A1 | 8/2018 | Chadeayne |
| 2019/0105313 | A1 | 4/2019 | Stamets |
| 2019/0161764 | A1 | 5/2019 | Winzer |
| 2019/0192498 | A1 | 6/2019 | Stamets |
| 2019/0350949 | A1 | 11/2019 | Küçüksen |
| 2020/0199161 | A1 | 6/2020 | Londesbrough |
| 2020/0331939 | A1 | 10/2020 | Londesbrough |
| 2020/0352206 | A1 | 11/2020 | Wagner-Salvini |
| 2020/0375967 | A1 | 12/2020 | Stamets |
| 2021/0010015 | A1 | 1/2021 | Mojzita et al. |
| 2021/0015738 | A1 | 1/2021 | Larosa |

(Continued)

FOREIGN PATENT DOCUMENTS

| | | | |
|---|---|---|---|
| AU | 2019208238 | A1 | 2/2021 |
| CA | 3046911 | A1 | 12/2020 |

(Continued)

OTHER PUBLICATIONS

Hoefgen, S., et al. "Facile assembly and fluorescence-based screening method for heterologous expression of biosynthetic pathways in fungi." Metabolic engineering 48 (2018): 44-51.

(Continued)

*Primary Examiner* — Suzanne M Noakes

(74) *Attorney, Agent, or Firm* — Greenberg Traurig, LLP

(57) ABSTRACT

Provided herein are methods for modulating the psilocybin biosynthesis pathway in fungi or other organisms. Also provided are genetically modified fungi and organisms with induced and/or increased expression of psilocybin and psilocin and psilocybin and/or psilocin compositions generated by the provided methods.

12 Claims, 11 Drawing Sheets

Specification includes a Sequence Listing.

(56) References Cited

U.S. PATENT DOCUMENTS

2021/0015833 A1 1/2021 Larosa
2021/0023052 A1 1/2021 Chadeayne
2021/0030014 A1 2/2021 Brown et al.
2021/0069170 A1 3/2021 Stamets
2021/0085671 A1 3/2021 Chadeayne
2021/0087212 A1 3/2021 Londesbrough
2021/0095301 A1 4/2021 Winzer
2021/0108238 A1 4/2021 Protzko
2021/0113644 A1 4/2021 Chadeayne
2021/0137854 A1 5/2021 Goren
2021/0145851 A1 5/2021 Stamets
2021/0147888 A1 5/2021 Vogan
2021/0155642 A1 5/2021 Londesbrough
2021/0161894 A1 6/2021 Le Couteur
2021/0236523 A1 8/2021 Schindler
2021/0246133 A1 8/2021 Hilpert et al.
2021/0246152 A1 8/2021 Londesbrough
2021/0251969 A1 8/2021 Abdallah
2021/0251976 A1 8/2021 Stamets
2021/0267966 A1 9/2021 Petcavich
2021/0267977 A1 9/2021 Liechti
2021/0275618 A1 9/2021 Davidson
2021/0315884 A1 10/2021 Liechti
2021/0322447 A1 10/2021 Plakogiannis
2021/0346341 A1 11/2021 Liechti
2021/0346346 A1 11/2021 Chadeayne
2021/0346347 A1 11/2021 Witowski
2021/0353615 A1 11/2021 Chadeayne
2021/0361679 A1 11/2021 Chadeayne
2021/0392933 A1 12/2021 Lilly
2021/0393716 A1 12/2021 Lightburn
2021/0403425 A1 12/2021 Bryson
2021/0407643 A1 12/2021 Liu
2022/0016104 A1 1/2022 Stamets
2022/0040246 A1 2/2022 Lightburn
2022/0054402 A1 2/2022 Kaufman
2022/0062310 A1 3/2022 Kelmendi
2022/0071946 A1 3/2022 Land
2022/0073548 A1 3/2022 Londesbrough
2022/0079881 A1 3/2022 Modi
2022/0088041 A1 3/2022 Londesbrough
2022/0096429 A1 3/2022 Liechti
2022/0096504 A1 3/2022 Blumstock
2022/0110955 A1 4/2022 Sippy
2022/0119346 A1 4/2022 Nivorozhkin
2022/0125091 A1 4/2022 Cave
2022/0125755 A1 4/2022 Hazen
2022/0125809 A1 4/2022 Stamets
2022/0125810 A1 4/2022 Cave
2022/0127058 A1 4/2022 Roth
2022/0143051 A1 5/2022 Manfredi
2022/0151993 A1 5/2022 Ross
2022/0160737 A1 5/2022 Stamets
2022/0169668 A1 6/2022 Londesbrough
2022/0202775 A1 6/2022 Rands
2022/0211660 A1 7/2022 Cave
2022/0211671 A1 7/2022 Moss
2022/0226405 A1 7/2022 Lightburn

FOREIGN PATENT DOCUMENTS

CA 2888449 C 1/2021
CA 3050553 A1 1/2021
EP 3371168 5/2020
EP 3371174 3/2021
IN 201647012284 7/2016
IN 201811011332 10/2019
IN 201821011763 10/2019
IN 201811018597 11/2019
IN 202014041837 10/2020
IN 201941029795 1/2021
IN 202121000935 1/2021
IN 202141031070 7/2021
IN 202041012021 9/2021
IN 202141043033 11/2021
IN 202121049931 12/2021
JP 201642862 W 4/2016
WO 2009073633 6/2009
WO 2010139703 12/2010
WO 2011020206 2/2011
WO 2013022881 2/2013
WO 2014008138 1/2014
WO 2014110540 7/2014
WO 2014195208 12/2014
WO 2015077292 5/2015
WO 2015136947 9/2015
WO 2015197567 12/2015
WO 2017076852 5/2017
WO 2018112459 6/2018
WO 2019090158 5/2019
WO 2019162949 8/2019
WO 2019173797 9/2019
WO 2019180309 9/2019
WO 2019224300 11/2019
WO 2020033955 2/2020
WO 2020172492 8/2020
WO 2020223728 11/2020
WO 2020255151 A1 12/2020
WO 2021052989 3/2021
WO 2021097452 5/2021
WO 2021138564 A1 7/2021
WO 2021158888 A1 8/2021
WO 2021173273 A1 9/2021
WO 2021173989 A1 9/2021
WO 2021178579 A1 9/2021
WO 2021188782 A1 9/2021
WO 2021188812 A1 9/2021
WO 2021188870 A1 9/2021
WO 2021202730 A1 10/2021
WO 2021205196 10/2021
WO 2021207137 A1 10/2021
WO 2021207824 A1 10/2021
WO 2021209815 A1 10/2021
WO 2021211358 A1 10/2021
WO 2021216489 A1 10/2021
WO 2021222885 A1 11/2021
WO 2021225796 A1 11/2021
WO 2021226041 A1 11/2021
WO 2021226416 A1 11/2021
WO 2021236759 A2 11/2021
WO 2021237162 11/2021
WO 2021243460 A1 12/2021
WO 2021248087 12/2021
WO 2021250434 A1 12/2021
WO 2021250435 A1 12/2021
WO 2021252692 A1 12/2021
WO 2021253116 A1 12/2021
WO 2021253123 A1 12/2021
WO 2021253124 A1 12/2021
WO 2021262871 A1 12/2021
WO 2022000091 A1 1/2022
WO 2022011350 A1 1/2022
WO 2022018709 A1 1/2022
WO 2022023812 A1 2/2022
WO 2022031551 A1 2/2022
WO 2022031552 A1 2/2022
WO 2022031907 A1 2/2022
WO 2022038299 A1 2/2022
WO 2022040802 A1 3/2022
WO 2022047579 A1 3/2022
WO 2022047580 A1 3/2022
WO 2022047583 A1 3/2022
WO 2022051578 A1 3/2022
WO 2022061196 A1 3/2022
WO 2022069690 A2 4/2022
WO 2022072808 A1 4/2022
WO 2022076642 A1 4/2022
WO 2022079574 A1 4/2022
WO 2022081549 A1 4/2022
WO 2022082058 A1 4/2022
WO 2022084480 A1 4/2022
WO 2022091051 A1 5/2022
WO 2022091061 A1 5/2022
WO 2022094054 A1 5/2022

(56) References Cited

FOREIGN PATENT DOCUMENTS

| | | |
|---|---|---|
| WO | 2022094719 A1 | 5/2022 |
| WO | 2022104475 A1 | 5/2022 |
| WO | 2022115798 A2 | 6/2022 |
| WO | 2022115944 A1 | 6/2022 |
| WO | 2022115960 A1 | 6/2022 |
| WO | 2022117359 A1 | 6/2022 |
| WO | 2022120181 A1 | 6/2022 |
| WO | 2022120289 A1 | 6/2022 |
| WO | 2022123232 A1 | 6/2022 |
| WO | 2022125616 A1 | 6/2022 |
| WO | 2022125949 A1 | 6/2022 |
| WO | 2022132691 A1 | 6/2022 |
| WO | 2022140841 A1 | 7/2022 |
| WO | 2022140842 A1 | 7/2022 |
| WO | 2022140846 A1 | 7/2022 |
| WO | 2022140851 A1 | 7/2022 |
| WO | 2022150530 A1 | 7/2022 |
| WO | 2022150563 A1 | 7/2022 |
| WO | 2022150675 A1 | 7/2022 |
| WO | 2022150840 A1 | 7/2022 |
| WO | 2022150854 A1 | 7/2022 |
| WO | 2022155352 A1 | 7/2022 |
| WO | 2022155591 A1 | 7/2022 |
| WO | 2022155751 A1 | 7/2022 |

OTHER PUBLICATIONS

Nichols, David E., Matthew W. Johnson, and Charles D. Nichols. "Psychedelics as medicines: an emerging new paradigm." Clinical Pharmacology & Therapeutics 101.2 (2017): 209-219.

Supplemental European Search Report issued Sep. 20, 2023 for EP Application No. 20871398.

Meyer, V., et al., "Growing a circular economy with fungal biotechnology: a white paper" Fungal Biol Biotechnol 7, 5(2020). https://doi.org/10.1186/s40694-020-00095-z.

Sorrentino, G., "Introduction to emerging industrial applications of cannabis (*Cannabis sativa* L.)" Rend Lincei Sci Fis Nat. 2021;32(2):233-243. doi: 10.1007/s12210-021-00979-1. Epub Mar. 19, 2021.

Befort, K., "Interactions of the opioid and cannabinoid systems in reward: Insights from knockout studies" Front Pharmacol. Feb. 5, 2015;6:6, pp. 1-15, doi: 10.3389/fphar.2015.00006.

COMPASS Pathways, "Responding to an urgent mental health crisis, Challenges and solutions for people suffering with treatment-resistant depression" A White Paper from COMPASS Pathways, Aug. 2021, 50 pages.

Eisenstein, M., "Base edit your way to better crops", Nature. Apr. 28, 2022;604(7907):790-792. doi: 10.1038/d41586-022-01117-z.

Fricke J, Blei F, Hoffmeister D., "Enzymatic Synthesis of Psilocybin" Angew Chem Int Ed Engl. Sep. 25, 2017;56(40):12352-12355. doi: 10.1002/anie.201705489.

Fricke, J., et al., "Production Options for Psilocybin: Making of the Magic", Chem. Eur. J., Jan. 18, 2019, 25(4):897-903, doi: 10.1002/chem.201802758.

GenBank entry KY984101 "Psilocybe cubensis strain FSU 12409 tryptophan decarboxylase (psiD) mRNA, complete cds" Aug. 26, 2017.

Gotvaldová, Klára , et al., "Stability of psilocybin and its four analogs in the biomass of the psychotropic mushroom *Psilocybe cubensis*" Drug Testing and Analysis, Feb. 2021, 13(2):439-446, doi:10.1002/dta.2950.

Halford, B., "Rediscovering Psychedelics", Chemical & Engineering News, Mar. 7, 2022, vol. 100; Issue 9; pp. 28-33.

ISR and written opinion for PCT/US2020/053842 mailed Mar. 26, 2021.

Lenz, C. et al., "Injury-Triggered Blueing Reactions of Psilocybe "Magic" Mushrooms." Angewandte Chemie (International Ed. in English) 59 (Nov. 14, 2019): 1450-1454.

Lenz, C., et al., Supporting Information for "Injury-Triggered Blueing Reactions of Psilocybe "Magic" Mushrooms." Angewandte Chemie (International Ed. in English) 59 (Nov. 14, 2019): 1450-1454, 36 pages.

Lin, H.-C., et al., "Biosynthesis of bioactive natural products from Basidiomycota" Organic & Biomolecular Chemistry, vol. 17, Issue 5, 2019, pp. 1027-1036, ISSN 1477-0520, doi: 10.1039/c8ob02774a.

Mahmood, Z., et al., "Bioactive alkaloids produced by fungi I. Updates on alkaloids from the species of the genera *Boletus, Fusarium* and *Psilocybe*", Jul. 2010, Pakistan Journal of Pharmaceutical Sciences 23(3):349-57.

Milne, N., et al., "Metabolic engineering of *Saccharomyces cerevisiae* for the de novo production of psilocybin and related tryptamine derivatives", Metabolic Engineering, vol. 60, Jul. 2020, pp. 25-36, ISSN 1096-7176, doi: 10.1016/j.ymben.2019.12.007: 10.1016/j.ymben.2019.12.007.

Reynolds, H. T., et al., "Horizontal gene cluster transfer increased hallucinogenic mushroom diversity" Evol Lett. Feb. 27, 2018;2(2):88-101. doi: 10.1002/evl3.42.

Ritter, S. K., "Magic mushroom enzyme mystery solved", Chemical & Engineering News, Aug. 14, 2017, 6 pages, https://cen.acs.org/articles/95/web/2017/08/Magic-mushroomenzyme-mystery-solved.html#.

Stamets, P. & Zwickey, H., "Medicinal Mushrooms: Ancient Remedies Meet Modern Science" Integrative Medicine: A Clinician's Journal, Feb. 2014;13(1):46-47.

Sugano, S.S., et al., "Genome editing in the mushroom-forming basidiomycete Coprinopsis cinerea, optimized by a high-throughput transformation system", Scientific Reports, Apr. 28, 2017, vol. 7, No. 1, article 1260, 9 pages.

GenBank entry MF000993.1 "Psilocybe cubensis strain FSU 12409 Putative Monooxygenase (psiH) gene, complete cds" Aug. 26, 2017.

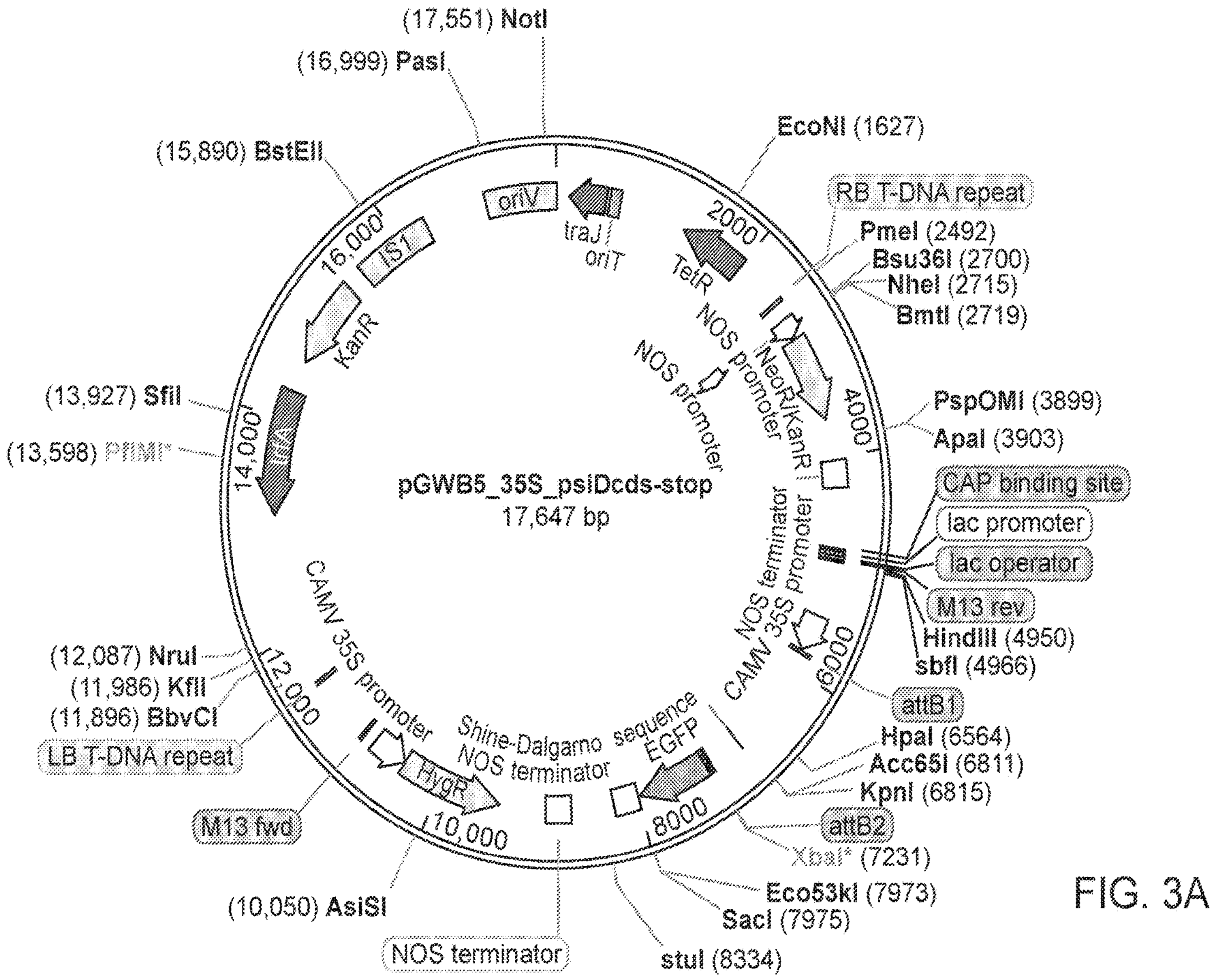
pGWB5_35S_psiDcds-stop
17,647 bp
(17,551) NotI
(16,999) PasI
(15,890) BstEII
(13,927) SfiI
(13,598) PflMI*
(12,087) NruI
(11,986) KflI
(11,896) BbvCI
LB T-DNA repeat
M13 fwd
(10,050) AsiSI
NOS terminator
stuI (8334)
SacI (7975)
Eco53kI (7973)
XbaI* (7231)
attB2
KpnI (6815)
Acc65I (6811)
HpaI (6564)
attB1
sbfI (4966)
HindIII (4950)
M13 rev
lac operator
lac promoter
CAP binding site
ApaI (3903)
PspOMI (3899)
BmtI (2719)
NheI (2715)
Bsu36I (2700)
PmeI (2492)
RB T-DNA repeat
EcoNI (1627)
2000
4000
6000
8000
10,000
12,000
14,000
16,000
oriV
traJ
oriT
TetR
NOS promoter
NeoR/KanR
NOS promoter
NOS terminator
CAMV 35S promoter
EGFP
Shine-Dalgarno sequence
NOS terminator
HygR
CAMV 35S promoter
KanR
IS1
FIG. 3A

SEQUENCE LISTING

<160> NUMBER OF SEQ ID NOS: 21

<210> SEQ ID NO 1
<211> LENGTH: 1320
<212> TYPE: DNA
<213> ORGANISM: Psilocybe cubensis

<400> SEQUENCE: 1
atgcaggtga tacccgcgtg caactcggca gcaataagat cactatgtcc tactcccgag 60
tcttttagaa acatgggatg gctctctgtc agcgatgcgg tctacagcga gttcatagga 120
gagttggcta cccgcgcttc caatcgaaat tactccaacg agttcggcct catgcaacct 180
atccaggaat tcaaggcttt cattgaaagc gacccggtgg tgcaccaaga atttattgac 240
atgttcgagg gcattcagga ctctccaagg aattatcagg aactatgtaa tatgttcaac 300
gatatctttc gcaaagctcc cgtctacgga gaccttggcc ctcccgttta tatgattatg 360
gccaaattaa tgaacacccg agcgggcttc tctgcattca cgagacaaag gttgaacctt 420
cacttcaaaa aacttttcga tacctgggga ttgttcctgt cttcgaaaga ttctcgaaat 480

-continued gttcttgtgg ccgaccagtt cgacgacaga cattgcggct ggttgaacga gcgggccttg 540
tctgctatgg ttaaacatta caatggacgc gcatttgatg aagtcttcct ctgcgataaa 600
aatgccccat actacggctt caactcttac gacgacttct ttaatcgcag atttcgaaac 660
cgagatatcg accgacctgt agtcggtgga gttaacaaca ccaccctcat ttctgctgct 720
tgcgaatcac tttcctacaa cgtctcttat gacgtccagt ctctcgacac tttagttttc 780
aaaggagaga cttattcgct taagcatttg ctgaataatg accctttcac cccacaattc 840
gagcatggga gtattctaca aggattcttg aacgtcaccg cttaccaccg atggcacgca 900
cccgtcaatg ggacaatcgt caaaatcatc aacgttccag gtacctactt tgcgcaagcc 960
ccgagcacga ttggcgaccc tatcccggat aacgattacg acccacctcc ttaccttaag 1020
tctcttgtct acttctctaa tattgccgca aggcaaatta tgtttattga agccgacaac 1080
aaggaaattg gcctcatttt ccttgtgttc atcggcatga ccgaaatctc gacatgtgaa 1140
gccacggtgt ccgaaggtca acacgtcaat cgtggcgatg acttgggaat gttccatttc 1200
ggtggttctt cgttcgcgct tggtctgagg aaggattgca gggcagagat cgttgaaaag 1260
ttcaccgaac ccggaacagt gatcagaatc aacgaagtcg tcgctgctct aaaggcttag 1320

<210> SEQ ID NO 2
<211> LENGTH: 2155
<212> TYPE: DNA
<213> ORGANISM: Psilocybe cubensis

<400> SEQUENCE: 2
atgatcgctg tactattctc cttcgtcatt gcaggatgca tatactacat cgtttctcgt 60
agagtgaggc ggtcgcgctt gccaccaggg ccgcctggca ttcctattcc cttcattggg 120
aacatgtttg atatgcctga agaatctcca tggttaacat ttctacaatg gggacgggat 180
tacagtctgt cttgccgcgt tgacttctaa tatatgaaca gctaatatat tgtcagacac 240
cgatattctc tacgtggatg ctggagggac agaaatggtt attcttaaca cgttggagac 300
cattaccgat ctattagaaa agcgagggtc catttattct ggccggtgag ctgatgttga 360 gtttttgca attgaatttg tggtcacacg tttccagact tgagagtaca atggtcaacg 420
aacttatggg gtgggagttt gacttagggt tcatcacata cggcgacagg tggcgcgaag 480
aaaggcgcat gttcgccaag gagttcagtg agaagggcat caagcaattt cgccatgctc 540
aagtgaaagc tgcccatcag cttgtccaac agcttaccaa aacgccagac cgctgggcac 600
aacatattcg ccagtaagta ctacttgagg aaaatagcgt acgcttcgct gaccggtccg 660
tacatcaaag tcagatagcg gcaatgtcac tggatattgg ttatggaatt gatcttgcag 720
aagacgaccc ttggctggaa gcgacccatt tggctaatga aggcctcgcc atagcatcag 780
tgccgggcaa attttgggtc gattcgttcc cttctcgtga gcatccttct tctatgtagg 840
aagggaagga gtctaacaag tgttagtaaa ataccttcct gcttggttcc caggtgctgt 900
cttcaagcgc aaagcgaagg tctggcgaga agccgccgac catatggttg acatgcctta 960
tgaaactatg aggaaattag cagttagtca aatgcgttct ccccgtattt tttcaatact 1020
ctaacttcag ctcacagcct caaggattga ctcgtccgtc gtatgcttca gctcgtctgc 1080
aagccatgga tctcaacggt gaccttgagc atcaagaaca cgtaatcaag aacacagccg 1140
cagaggttaa tgtcggtaag tcaaaagcgt ccgtcggcaa ttcaaaattc aggcgctaaa 1200
gtgggtcttc tcaccaaggt ggaggcgata ctgtaaggat ttctcaatcg ttagagtata 1260
agtgttctaa tgcagtacat actccaccaa ccagactgtc tctgctatgt ctgcgttcat 1320
cttggccatg gtgaagtacc ctgaggtcca gcgaaaggtt caagcggagc ttgatgctct 1380
gaccaataac ggccaaattc ctgactatga cgaagaagat gactccttgc catacctcac 1440
cgcatgtatc aaggagcttt tccggtggaa tcaaatcgca cccctcgcta taccgcacaa 1500
attaatgaag gacgacgtgt accgcgggta tctgattccc aagaacactc tagtcttcgc 1560
aaacacctgg tgaggctgtc cattcattcc tagtacatcc gttgccccac taatagcatc 1620
ttgataacag ggcagtatta aacgatccag aagtctatcc agatccctct gtgttccgcc 1680
cagaaagata tcttggtcct gacgggaagc ctgataacac tgtacgcgac ccacgtaaag 1740
cggcatttgg ctatggacga cgaaattggt aagtgcgctt tcagaacccc cccttccgtt 1800
gactagtgcc atgcgcgcat acaatatcgc tattgatctg atataacttc cctgcggcat 1860
ttattttggc attcctttag tcccggaatt catctagcgc agtcgacggt ttggattgca 1920
ggggcaaccc tcttatcagc gttcaatatc gagcgacctg tcgatcagaa tgggaagccc 1980
attgacatac cggctgattt tactacagga ttcttcaggt agctaatttc cgtctttgtg 2040
tgcataatac ccctaacgac gcacgtttac ctttttgtaa agacacccag tgcctttcca 2100
gtgcaggttt gttcctcgaa cagagcaagt ctcacagtcg gtatccggac cctga 2155

<210> SEQ ID NO 3
<211> LENGTH: 1089
<212> TYPE: DNA
<213> ORGANISM: Psilocybe cubensis

<400> SEQUENCE: 3
atggcgttcg atctcaagac tgaagacggc ctcatcacat atctcactaa acatctttct 60
ttggacgtcg acacgagcgg agtgaagcgc cttagcggag gctttgtcaa tgtaacctgg 120
cgcattaagc tcaatgctcc ttatcaaggt catacgagca tcatcctgaa gcatgctcag 180
ccgcacatgt ctacggatga ggattttaag ataggtgtag aacgttcggt ttacgaatac 240
caggctatca agctcatgat ggccaatcgg gaggttctgg gaggcgtgga tggcatagtt 300
tctgtgccag aaggcctgaa ctacgactta gagaataatg cattgatcat gcaagatgtc 360
gggaagatga agaccctttt agattatgtc accgccaaac cgccacttgc gacggatata 420
gcccgccttg ttgggacaga aattgggggg ttcgttgcca gactccataa catagccgc 480 gagaggcgag acgatcctga gttcaaattc ttctctggaa atattgtcgg aaggacgact 540
tcagaccagc tgtatcaaac catcataccc aacgcagcga aatatggcgt cgatgacccc 600
ttgctgccta ctgtggttaa ggaccttgtg gacgatgtca tgcacagcga agagacccct 660
gtcatggcgg acctgtggag tggaaatatt cttctccagt tggaggaggg aaacccatcg 720
aagctgcaga agatatatat cctggattgg gaactttgca agtacggccc agcgtcgttg 780
gacctgggct atttcttggg tgactgctat ttgatatccc gctttcaaga cgagcaggtc 840
ggtacgacga tgcggcaagc ctacttgcaa agctatgcgc gtacgagcaa gcattcgatc 900
aactacgcca aagtcactgc aggtattgct gctcatattg tgatgtggac cgactttatg 960
cagtggggga gcgaggaaga aaggataaat tttgtgaaaa agggggtagc tgcctttcac 1020
gacgccaggg gcaacaacga caatggggaa attacgtcta ccttactgaa ggaatcatcc 1080
actgcgtaa 1089

<210> SEQ ID NO 4
<211> LENGTH: 930
<212> TYPE: DNA

<213> ORGANISM: Psilocybe cubensis

<400> SEQUENCE: 4
atgcatatca gaaatcctta ccgtacacca attgactatc aagcactttc agaggccttc 60
cctcccctca agccatttgt gtctgtcaat gcagatggta ccagttctgt tgacctcact 120
atcccagaag cccagagggc gttcacggcc gctcttcttc atcgtgactt cgggctcacc 180
atgaccatac cagaagaccg tctgtgccca acagtcccca ataggttgaa ctacgttctg 240
tggattgaag atattttcaa ctacacgaac aaaaccctcg gcctgtcgga tgaccgtcct 300
attaaaggcg ttgatattgg tacaggagcc tccgcaattt atcctatgct tgcctgtgct 360
cggttcaagg catggtctat ggttggaaca gaggtcgaga ggaagtgcat tgacacggcc 420
cgcctcaatg tcgtcgcgaa caatctccaa gaccgtctct cgatattaga gacatccatt 480
gatggtccta ttctcgtccc cattttcgag gcgactgaag aatacgaata cgagtttact 540
atgtgtaacc ctccattcta cgacggtgct gccgatatgc agacttcgga tgctgccaaa 600
ggatttggat ttggcgtggg cgctccccat tctggaacag tcatcgaaat gtcgactgag 660
ggaggtgaat cggctttcgt cgctcagatg gtccgtgaga gcttgaagct tcgaacacga 720
tgcagatggt acacgagtaa cttgggaaag ctgaaatcct tgaaagaaat agtggggctg 780
ctgaaagaac ttgagataag caactatgcc attaacgaat acgttcaggg gtccacacgt 840
cgttatgccg ttgcgtggtc tttcactgat attcaactgc ctgaggagct ttctcgtccc 900
tctaaccccg agctcagctc tcttttctag 930

<210> SEQ ID NO 5
<211> LENGTH: 1572
<212> TYPE: DNA
<213> ORGANISM: Psilocybe cubensis

<400> SEQUENCE: 5
atgtctctgg agcgctcaac aagtccaaat cctaccgagc gtacatctct tctatctgac 60
actgcgtcta ccatttcatc cagagatgac gttgaacagt caagtctgaa gcaaaggcgc 120
acgcctatac caactggaca acttggcggt aaggtctcaa tgcattcaat tattataaac 180
gctgagggtc atttatggcc ttatattaac cagtttgtga atgatatcgg cgtctctgat 240
gggaatccac gtaatgttgg gttctacagt gggttgatcg aaagtgtatt tgcttgcgga 300
gaagtttgct ctatcttcat gctgtcgagg ctttcagata gaataggtcg tcgaccggtg 360
ctactcccat ctgcactggg tattgcagtg tttactgctc tgtttggttt atcaagctcg 420
tttaccatga tgttgactct tcgagtttgc gctggtctct tagccggagc gacgcctata 480
gtacactcca ttgtcagcga acttactgat gataccaata atgcactcgt tgtaccatta 540
tatggcctca taactcccat cggatttgcc attgggcccc tgatcggggg aacccttgaa 600
cacgctgcaa ctaagtatcc caacgtcttt ggatatgagc tttttcgaaa gtacccctac 660
ttcttaccat cgtttgttcc atgctgcatg gctatcgtgg gcgtcacatt cggctacttc 720
tttttaaaag aaacgcttcc tagtttagtc aagtctaaaa aaagacttga acgtcaacgg 780
tcctcctctt ctatatcatc agagaactct actctatacg gtgccacaga gcatatcagg 840
gactcaacag aagaaaccgc ggcggacgag gaacccgatt ccaagccgaa gggtattact 900
gagttaattc gggatccttc tatacgggct ataatggctt ctggtacatt tttgatgttt 960
ctatacacga gttccgatgt gatattctca ctctactgct ttactgctgt tgaggatgga 1020
ggcgttggat tgcctcccga gaagatcggt tatgcattct ccgttgcagg cctcatagct 1080

-continued

```
atgctcatgc agctttgcat aacgccatgg gtgctccgta cttttgacaa ggctaaagta   1140

taccacttct gcatgtgctc gttccctctc gtgtttgcac tcatgggatg cctgaatccc   1200

ctcgctcaaa ctgggtacag tgaaattaac aaaacacttc atccgaccac tacgggactg   1260

ctctatgctg caatagccat cttgctcctt ctagcccgtg tctgcgttat ggcattccct   1320

atcagcatga tgctggttaa acaaacggcc gataagcatt cgcttgccac tgcgaatggc   1380

ctcgtgcaag tggccatgac ccttgcaaga gcattctgcc ctacaatctc aagctcggtg   1440

tttgcttatt ctactagcca taatatcctg ggtggacatt tctgggtggt agtgatggta   1500

ttcatttccc tggttggggt atggcaatct acgaaaattg ccagggtcac aaaaacaaaa   1560

gagcaattgt ga                                                       1572
```

<210> SEQ ID NO 6
<211> LENGTH: 1416
<212> TYPE: DNA
<213> ORGANISM: Psilocybe cubensis

<400> SEQUENCE: 6

```
atgaatccta cgaccgccac cgatgctcat gaacgaacat cgctgttgtc tggaagaccg     60

caatctgctg caaattcgac ggctccatat gagcgacaag ttcaaccatc gcgaaaatcc    120

caatgcttta ctccagtgac cgtgatcacc ataattacgc tcatatatcg tctcgcgaca    180

acgatggtaa tcacgaccaa cattcgggtt ctccacacag ttgcatgcca gctttggtat    240

catgtcaacg atcccgacgt atttccaggg ggaaatatac cagaaaaata ttgtgcgcta    300

cctggtgtag acaagtatta tgctataatg gtgtctatga ccactgtcat agatggtctt    360

ggaggtatac ttgggaccgg catagccagc tacatgtcat ctcgttttgg cagaaagcct    420

gttctcatgt tcctgctttc ctgtaccatg atcgatcacc tcgccatcct gacagtccaa    480

aatgtatacg gatggaagca gttggtaaca tttgggttaa ttatgattgt tgaaaccatt    540

ggaaatgaga acaccacagt atttctggtg agcatgtacg tggttgatgt tactgaggct    600

gagagaagga ccgctgctct gagttcaatt actggctggc ttgttctcgg aggcgccctc    660

gcctattcaa taggcggatc tataacaact tttttacact ccaactctgc cgtatacatt    720

gtatcgttca gtgtcactgg catcgttcta acattcaccg cctttgttct ccctgaatca    780

ttccctgctg aaaaaagaga tctcttgcgg cttgaacgac tggcagaaac ccgtggacac    840

agccagtcct ggacccaaaa aatcaaagct gtggcaactg tcgcattgga acctatggaa    900

ttgctaaaac cgacatttaa ccccataacg gggaaggcaa attggcggct tgtatactgc    960

gccctccact cgtttattgt cactctagca gatgcgtatg ctcttcctgc catgttgata   1020

tttttcacta cccagtattc atatacaccc gctcagatgg gatatgttat gacgacgtac   1080

agtgtctcca gtgtgtttgt tttggcgata gccttacccc tgtttattcg atggttcaag   1140

cccctgtata ataatactca aacgaagtct gtcccagatg aaggggatgg actccgtgcg   1200

accgactctg gagaagcggg tgtgcacaca caagaggtcg ttgtttcgga aacctctgat   1260

cgcatggacg tccatatcac tgtcatatcc tggaccatag agtcattagc atacatagtt   1320

ctcggtactg tgggttcatt ttacgcacaa cttttaggtc ggccgttgcc tctattggct   1380

ttggatctgg acgcattcca ggaattcgaa gcctag                             1416
```

<210> SEQ ID NO 7
<211> LENGTH: 1077
<212> TYPE: DNA

<213> ORGANISM: Psilocybe cubensis

<400> SEQUENCE: 7

```
atggcacccg caacacccgc aactcacgat cctgccttgt cccacggagc ccctcctgct     60
ccaggtgctc cagctcctgc aaatgctcct ccaaacgcct caggagacat tgctggaatg    120
cagctcagcg gactcgatca gtcccagatc atgaaccttc ttcgttcatt gcctggcatg    180
ttctcgggcg gtaaaatacc cgaccaaggc caaggcaaca aagaggatgc tgctcaaacg    240
ctgtccaacc ttgcccaagc tcaaccgtat ggacaacaat taccccttca ctaccaagct    300
ggcggcccag gaggtctgcc aggaattaac gacccaggcc cgtccacaca tccccgcggc    360
cctcccaacc ttggccaact gagtgctgtg gcaatgcaag ccgcccccgc tccaattcag    420
catccagacc agcaaacgaa ccgcaacgat ggcgagcagg ctggcaatgc gagtgcaagt    480
acctccggaa aggatggtga caatgcagaa ttcgttcccc cacctgctcc tgctcctaca    540
actggtcgcc gtggtggacg cagcgccacc atgggaagtg acgaatggag cagacagagg    600
aaggataatc ataaagaggt tgagcgtcga cgccgcggca atatcaacga gggcatcaac    660
gagcttggcc gcattgtacc cagtgggtct ggcgagaagg ccaaaggcgc catcctttct    720
cgagctgtgc agtacatcca tcatttgaaa gagaacgaag ctcgcaatat cgagaagtgg    780
acccttgaga agcttctcat ggaccaggcc atgggtgacc tgcaggcgca actcgaagag    840
gtcaagcgtc tgtgggaaga agagcgtatg gcgcgcacaa gactcgaggc cgagctcgaa    900
gtgttgagaa atatgaacgg cgtgaatgct ggctcggccc cggcctcgaa agatgagagt    960
gctgcaggta ctaagaggag gagtaccgat ggagcagagg ccgccaccgc cgccactgaa   1020
agcagcaccg ccaatgccga gggcgaacgc gacggcaagc gacaaagaac cgagtga      1077
```

<210> SEQ ID NO 8
<211> LENGTH: 1320
<212> TYPE: DNA
<213> ORGANISM: Psilocybe cyanescens

<400> SEQUENCE: 8

```
atgcaggtac tgcccgcgtg ccaatcttcc gcgcttaaaa cattgtgccc atcccccgag     60
gcctttcgaa agctcggttg gctccctact agcgacgagg tttacaacga attcatcgat    120
gacttgaccg gtcgcacgtg caatgaaaag tactccagcc aggttacact tttgaagcct    180
atccaagatt tcaagacatt catcgagaat gatcccatag tgtatcaaga atttatctct    240
atgtttgaag gaatcgagca gtctcccacc aactaccacg agctatgtaa catgttcaac    300
gacatctttc gcaaagcccc actctacggc gatcttggtc ctccggttta catgatcatg    360
gccagaataa tgaatacgca ggcgggtttc tctgcgttca caaaagagag cttgaacttc    420
catttcaaaa agctcttcga cacctggggg ctattccttt cctcgaaaaa ctctcgaaac    480
gtgcttgttg cagaccagtt tgacgataag cattacgggt ggttcagcga gcgagccaag    540
actgccatga tgattaatta tccagggcgt acattcgaga aagtcttcat ctgcgacgag    600
cacgttccat accatggctt cacttcctat gacgatttct tcaatcgcag gttcagggac    660
aaggatacag atcggcccgt agtcggtggg gttactgaca ccactttaat cggggctgcc    720
tgtgaatcgt tgtcatataa cgtctctcac aacgtccagt ctcttgacac gctagtcatc    780
aagggagagg cctattcact taaacatcta cttcataacg accccttcac accgcaattc    840
gaacatggga gcatcattca aggattccta aatgtcaccg cttaccaccg ctggcactcc    900
cccgtcaatg gcacgattgt gaagatcgtc aacgttccag gtacctactt cgctcaagct    960
```

ccatatacaa ttggatctcc tatccccgat aacgaccgcg acccgcctcc ttacctcaag 1020
tcactcgtat acttctccaa catcgctgca cggcaaatta tgttcatcga ggccgacaac 1080
aaagacatcg gcctcatttt cttggtcttc attggaatga ctgagatctc gacttgcgag 1140
gcgacggtgt gcgaaggtca gcatgtcaac cgcggtgacg atttgggcat gttccatttc 1200
ggtggttcat cttttgccct tggcttgcgg aaggactcga aggcgaagat tttggaaaag 1260
ttcgcgaaac cggggaccgt tattaggatc aacgagctag ttgcatctgt aaggaagtag 1320

<210> SEQ ID NO 9
<211> LENGTH: 1521
<212> TYPE: DNA
<213> ORGANISM: Psilocybe cyanescens

<400> SEQUENCE: 9
atgattgttc tattggtctc gctcgtcctt gcaggatgca tatactacgc caacgctcgt 60
agagtaaggc gctcgcgctt accaccgggc ccgcctggca taccactgcc cttcattggg 120
aatatgtttg atatgccttc agagtcaccg tggttaagat ttcttcaatg gggacgggac 180
tatcacactg atatccttta cttgaatgct ggcggaacgg aaataattat tctgaacaca 240
ctggatgcta taaccgactt gttggaaaag cgagggtcga tgtattcggg tcgactcgag 300
agcaccatgg tgaacgaact catggggtgg gagttcgact tgggattcat aacctatggt 360
gaaagatggc gcgaagaaag acgcatgttc gccaaggagt tcagcgaaaa aaacatcagg 420
caattccgcc acgcccaaat taaagctgcc aatcagcttg ttcggcagct gatcaaaacg 480
ccagatcgtt ggtcgcagca catccggcat cagatagcag ccatgtctct agacattggt 540
tatggaattg atctcgcaga ggatgacccc tggattgcag caacccagct agctaacgaa 600
gggctcgccg aagcttcagt accgggcagt ttctgggtcg actcattccc cgccctcaaa 660
taccttcctt catggcttcc tggtgcagga ttcaagcgca aagcaaaggt atggaaggaa 720
ggtgctgacc atatggtgaa catgccgtat gaaacgatga aaaaattgac tgttcaaggc 780
ttggcccgac cttcatatgc ctcagctcgt ctgcaggcca tggaccccga tggcgatctc 840
gagcatcagg aacacgtgat cagaaacaca gcgactgagg tcaatgtcgg cggaggtgat 900
acgactgttt ctgctgtgtc agcctttatt ttggccatgg tcaaatatcc agaagttcaa 960
cgccaagtcc aagcagaact ggatgcactc accagcaaag gagttgtccc aaactatgac 1020
gaagaagacg actccttgcc ataccttacg gcttgcgtca aggaaatctt tcgatggaac 1080
caaatagcac cccttgctat ccctcatcgg ctgatcaaag acgatgttta tcgtgggtat 1140
ctcataccaa agaatgcttt ggtctacgcc aactcatggg ctgtgttgaa tgacccagag 1200
gagtacccaa atccctctga gttccgacca gaacgatatt tgagctctga cggaaagccc 1260
gacccaacgg tccgtgatcc ccgcaaagca gcatttggct atggtcgacg caactgtccc 1320
ggaatccacc tggcacaatc gacggtatgg attgctggag ccactcttct ctcggtattc 1380
aatatcgaac gtcctgttga tgggaatgga aaacccatcg acatccccgc gacgttcact 1440
accggattct tcagacatcc cgagcctttc cagtgcagat ttgtccctcg cactcaggag 1500
attctaaaat ccgtttccgg t 1521

<210> SEQ ID NO 10
<211> LENGTH: 1086
<212> TYPE: DNA
<213> ORGANISM: Psilocybe cyanescens

<400> SEQUENCE: 10
atgactttcg atctcaagac tgaagaaggc ctgctctcat acctcacaaa gcacctatcg 60
ctggacgttg ctcccaacgg ggtgaaacgt cttagtggag gcttcgtcaa cgttacctgg 120
cgggtcgggc tcaatgcccc ttatcatggt cacacgagca ttattctgaa gcatgctcaa 180
ccgcacctgt cttcagacat agatttcaag ataggtgttg aacgatcggc gtacgagtat 240
caagcgctca aaatcgtgtc agccaatagc tcccttctag gcagcagcga tattcgggtc 300
tctgtaccag aaggtcttca ctacgacgtc gttaataacg cattgatcat gcaagatgtc 360
gggacaatga agaccctgtt ggactatgtc actgccaaac caccaatttc tgcagagatc 420
gccagtctcg taggcagtca aattggtgca tttatcgcta ggctgcacaa cctcggccgc 480
gagaataaag acaaggacga cttcaagttc ttctctggaa acatcgtcgg gagaacaacc 540
gcagaccagt tgtatcaaac catcatacct aatgccgcta aatacggtat cgacgatcca 600
attctcccaa ttgtggtaaa ggagttggtg gaggaggtca tgaatagtga agaaacgctt 660
atcatggcgg atttatggag tggcaatatt cttctccagt ttgatgaaaa ctcgacggaa 720
ttgacgagga tatggctggt agactgggag ttgtgcaaat atggtccacc gtctttggac 780
atggggtact tcttaggcga ctgtttcctg gtcgctcgat ttcaagatca gctcgtaggg 840
acatcaatgc gacaggccta cttgaagagc tacgcaagga atgtcaagga gccaatcaat 900
tatgcaaaag ccaccgcagg catcggcgcg catctcgtca tgtggactga tttcatgaag 960
tgggggaacg atgaagagag ggaagagttt gttaagaaag gcgtggaagc cttccatgaa 1020
gcaaatgagg acaatagaaa cggggagatt acgtctatac ttgtgaagga agcatcgcgc 1080
acttag 1086

<210> SEQ ID NO 11
<211> LENGTH: 930
<212> TYPE: DNA
<213> ORGANISM: Psilocybe cyanescens

<400> SEQUENCE: 11
atgcatatca ggaacccata ccgcgatggt gttgactacc aagcactcgc tgaagcattt 60
ccggctctca aaccacatgt cacagtaaat tcagacaata cgacctccat cgactttgct 120
gtgccagaag cccaaagact gtatacagct gcccttctac accgggattt cggtcttacg 180
atcacactcc cggaagaccg tctttgtccg acagtgccta atcggctcaa ctatgtcctt 240
tgggttgaag atatccttaa agtcacttct gatgctctcg gtcttccgga taatcgtcaa 300
gttaagggga tcgatatcgg aactggcgca tcagcgatat atcccatgct cgcatgctct 360
cgttttaaga catggtccat ggttgcaaca gaggtagacc agaagtgtat tgacactgct 420
cgtctcaacg tcattgccaa caacctccaa gaacgtctcg caattatagc cacctccgtc 480
gatggtccta tacttgtccc cctcttgcag gcgaattctg attttgagta cgattttacg 540
atgtgtaatc cgcccttcta cgatggggca tccgacatgc agacatcgga tgctgcgaag 600
gggtttggat tcggtgtgaa cgctccgcat accggcacgg tgctcgagat ggccaccgag 660
ggaggtgaat cggccttcgt agcccaaatg gtccgcgaaa gtttgaatct tcaaacacga 720
tgcaggtggt tcacgagtaa tttggggaaa ttgaagtcct tgtacgaaat tgtggggctg 780
ctgcgagaac atcagataag taactacgca atcaacgaat acgtccaagg agccactcgt 840
cgatatgcga ttgcatggtc gttcatcgat gttcgactgc ctgatcattt gtcccgtcca 900
tctaaccccg acctaagctc tcttttctag 930

<210> SEQ ID NO 12
<211> LENGTH: 1587
<212> TYPE: DNA
<213> ORGANISM: Psilocybe cyanescens

<400> SEQUENCE: 12
atgtcgccag agcgctcagc aagtcttgaa ccagatgagc attcgtctct gctctccgat 60
acggcctcct acatctcgag agatgactta gaagactcaa aagcgaagca aatcccgacg 120
cctataccaa agaaacaact tggagtttta ttttccatca gattcacaga acctataatt 180
tacagtcatt tgtggcctta tatcaaccaa ttcgttaatg atatcggggt cgccgacggg 240
aaccctcgct atgttggatt ttacagtggt ttgatcgaaa gtgtatttgc ttgtggagaa 300
gtgtgttcta tcttcatgtt atcgaggctg tcagacagaa taggtcgccg accagtgttg 360
ctcccgtctg ccctcggcgt agcattattt acagctttgt tcggtttatc gacctcgttt 420
actatgatgc tcgttctccg ggtttgtgct ggtcttttgg ccggggctac tcctatagtc 480
cattctgttg tgagtgagct cacggacgaa acgaataatg ccctcgtagt accccttac 540 gggttaatta cacctattgg ctttgcgatt ggacctctga ttggtggaac tcttgagcac 600
gctgctacta aatatcccaa cgtatttggt tatgacttcc ttcgaaaata tccatacttt 660
ctaccatcct ttgttccatg ctgcctagct gtcgttggcg tcaccttcgg ctatttcttc 720
ttgcaagaga cgcttcccag tatagtacgg gccaagaaaa gacttgaacg acagaaatct 780
acttcgtcta tttcgtcaag aacctccacc ctatacggtg ctacagatga tcacaataga 840
gatgcatcag aatcaaccgc gttgtctccg gaggaagcgg aagatgaaat tgactctaag 900
cctcaaagca tcaaagcttt aatcgtagac ccttctatgc gggccatcat gggttctggt 960
acctttctga tgttcctcta cacgagttcc gatgttctgt tctcactcta ctgctttact 1020
gctgtcgagg acggaggcgt cggattacct cccgacgaaa tcggttacgc attctctgtt 1080
gccggcgtga tagctatgct tatgcagctt tgcataacac cttgggtcct acgtacattc 1140
gataaggcaa aagtatacaa gttctgcatg ttctcattcc cgcttgtatt tgccctcatg 1200
ggatgtctta atcccctcgc tcaaaccggg tataatgaag tctctaagac tatccaccct 1260
accacaacgg gacttcttta cgctgctatt gctgtgttgc tactgttggc acgggtctgc 1320
gtcatggcgt tcccgatcag catgatgttg attaagcaga atgccgataa aaactcactc 1380
gccactgcga acgggcttgt gcaagtgtcg atgaccattg ctagagcact ctgccccacg 1440
gtctctagtt cgctcttcgc ttattccacg agcaacaata ttctgggtgg tcatctctgg 1500
gtccttatta tggtgaccat atccctcgca ggcgtctggc agtcgatgag catcgcccgc 1560
gttaccaaaa gaaaggaaga gctataa 1587

<210> SEQ ID NO 13
<211> LENGTH: 1416
<212> TYPE: DNA
<213> ORGANISM: Psilocybe cyanescens

<400> SEQUENCE: 13
atgaatccta cgaccgccac cgatgctcat gaacgaacat cgctgttgtc tggaagaccg 60
caatctgctg caaattcgac ggctccatat gagcgacaag ttcaaccatc gcgaaaatcc 120
caatgcttta ctccagtgac cgtgatcacc ataattacgc tcatatatcg tctcgcgaca 180
acgatggtaa tcacgaccaa cattcgggtt ctccacacag ttgcatgcca gctttggtat 240

-continued catgtcaacg atcccgacgt atttccaggg ggaaatatac cagaaaaata ttgtgcgcta 300
cctggtgtag acaagtatta tgctataatg gtgtctatga ccactgtcat agatggtctt 360
ggaggtatac ttgggaccgg catagccagc tacatgtcat ctcgttttgg cagaaagcct 420
gttctcatgt tcctgctttc ctgtaccatg atcgatcacc tcgccatcct gacagtccaa 480
aatgtatacg gatggaagca gttggtaaca tttgggttaa ttatgattgt tgaaaccatt 540
ggaaatgaga acaccacagt atttctggtg agcatgtacg tggttgatgt tactgaggct 600
gagagaagga ccgctgctct gagttcaatt actggctggc ttgttctcgg aggcgccctc 660
gcctattcaa taggcggatc tataacaact tttttacact ccaactctgc cgtatacatt 720
gtatcgttca gtgtcactgg catcgttcta acattcaccg cctttgttct ccctgaatca 780
ttccctgctg aaaaaagaga tctcttgcgg cttgaacgac tggcagaaac ccgtggacac 840
agccagtcct ggacccaaaa aatcaaagct gtggcaactg tcgcattgga acctatggaa 900
ttgctaaaac cgacatttaa ccccataacg gggaaggcaa attggcggct tgtatactgc 960
gccctccact cgtttattgt cactctagca gatgcgtatg ctcttcctgc catgttgata 1020
tttttcacta cccagtattc atatacaccc gctcagatgg gatatgttat gacgacgtac 1080
agtgtctcca gtgtgtttgt tttggcgata gccttacccc tgtttattcg atggttcaag 1140
cccctgtata ataatactca aacgaagtct gtcccagatg aaggggatgg actccgtgcg 1200
accgactctg gagaagcggg tgtgcacaca caagaggtcg ttgtttcgga aacctctgat 1260
cgcatggacg tccatatcac tgtcatatcc tggaccatag agtcattagc atacatagtt 1320
ctcggtactg tgggttcatt ttacgcacaa cttttaggtc ggccgttgcc tctattggct 1380
ttggatctgg acgcattcca ggaattcgaa gcctag 1416

<210> SEQ ID NO 14
<211> LENGTH: 1113
<212> TYPE: DNA
<213> ORGANISM: Psilocybe cyanescens

<400> SEQUENCE: 14
atggcaccca caacacccgc aactcacgat ccagccttgt cccacggagc tcctcctact 60
cagggctcgc aggcaccagc aaatgcggcc ccaaatctta ccccagccga catctctggc 120
atgcaactca acggcctcga tcagtcccag atcatgaacc ttctccgttc attgcccggc 180
atgttcacag gtgctaaaat accagatcaa ggacaaggca atcccaaaga ggatgctgcc 240
caaacactgt ccaacctcgc acaggcttca tcacccttcg gcggccaaca tttgcccatc 300
cactatcaaa ccggcgctgc tggtggtctt ccaggaatca acgacccagg cccgtcaact 360
cacccccgcg gccctcctaa cctcggccag ctgagtgctg tcgcgatgca agcggcccca 420
gcgacgatcc aacaccagga ccagcaacag tctgggcgcc aggaagacgg cgagcaggcc 480
ggaaatacga gcattgatag cccatctgcg aaagatggcg agaatggcac tggggagttt 540
aaccagacgt ctacgagcac tccttcggga ggccgtcggg gtgggcgcag tgccaccatg 600
ggcagcgacg aatggagcag gcagaggaag gataatcata aagaggttga gcgtcggcgc 660
cgcggaaata tcaacgaagg gattaacgag ctgggccgca tcgtaccgag cggatcaggc 720
gagaaagcca aaggcgccat cctctcgcgc gccgtgcagt acatccacca tttgaaagag 780
aatgaagctc ggaacatcga gaagtggacg cttgagaagc tacttatgga tcaggcgatg 840
ggcgacctgc aggcgcaact tgaggagatc aagcggctgt gggaggagga gcgcatggct 900
cgtacgaggc ttgaggctga gctcgaggtg ttgaggaata tgaatggtgt gagtactgcc 960
ggtgcgggtt cgggtgcggc gaaggatgaa agcgctgccg gcacgaagcg gaggagcacg 1020
gatggtgctg atgctgccgg cacaaatgtt gaaggtggta ataacgacaa cgctgaagga 1080
gagagggacg gaaaacgtca gagaactgag tga 1113

<210> SEQ ID NO 15
<211> LENGTH: 17267
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 15
tgagcgtcgc aaaggcgctc ggtcttgcct tgctcgtcgg tgatgtactt caccagctcc 60
gcgaagtcgc tcttcttgat ggagcgcatg gggacgtgct tggcaatcac gcgcaccccc 120
cggccgtttt agcggctaaa aaagtcatgg ctctgccctc gggcggacca cgcccatcat 180
gaccttgcca agctcgtcct gcttctcttc gatcttcgcc agcagggcga ggatcgtggc 240
atcaccgaac cgcgccgtgc gcgggtcgtc ggtgagccag agtttcagca ggccgcccag 300
gcggcccagg tcgccattga tgcgggccag ctcgcggacg tgctcatagt ccacgacgcc 360
cgtgattttg tagccctggc cgacggccag caggtaggcc gacaggctca tgccggccgc 420
cgccgccttt tcctcaatcg ctcttcgttc gtctggaagg cagtacacct tgataggtgg 480
gctgcccttc ctggttggct tggtttcatc agccatccgc ttgccctcat ctgttacgcc 540
ggcggtagcc ggccagcctc gcagagcagg attcccgttg agcaccgcca ggtgcgaata 600
agggacagtg aagaaggaac acccgctcgc gggtgggcct acttcaccta tcctgcccgg 660
ctgacgccgt tggatacacc aaggaaagtc tacacgaacc ctttggcaaa atcctgtata 720
tcgtgcgaaa aaggatggat ataccgaaaa aatcgctata atgaccccga agcagggtta 780
tgcagcggaa aagcgccacg cttcccgaag ggagaaaggc ggacaggtat ccggtaagcg 840
gcagggtcgg aacaggagag cgcacgaggg agcttccagg gggaaacgcc tggtatcttt 900
atagtcctgt cgggtttcgc cacctctgac ttgagcgtcg atttttgtga tgctcgtcag 960
gggggcggag cctatggaaa aacgccagca acgcggcctt tttacggttc ctggcctttt 1020
gctggccttt tgctcacatg ttctttcctg cgttatcccc tgattctgtg gataaccgta 1080
ttaccgcctt tgagtgagct gataccgctc gccgcagccg aacgaccgag cgcagcgagt 1140
cagtgagcga ggaagcggaa gagcgccaga aggccgccag agaggccgag cgcggccgtg 1200
aggcttggac gctagggcag ggcatgaaaa agcccgtagc gggctgctac gggcgtctga 1260
cgcggtggaa agggggaggg gatgttgtct acatggctct gctgtagtga gtgggttgcg 1320
ctccggcagc ggtcctgatc aatcgtcacc ctttctcggt ccttcaacgt tcctgacaac 1380
gagcctcctt ttcgccaatc catcgacaat caccgcgagt ccctgctcga acgctgcgtc 1440
cggaccggct tcgtcgaagg cgtctatcgc ggcccgcaac agcggcgaga gcggagcctg 1500
ttcaacggtg ccgccgcgct cgccggcatc gctgtcgccg gcctgctcct caagcacggc 1560
cccaacagtg aagtagctga ttgtcatcag cgcattgacg gcgtccccgg ccgaaaaacc 1620
cgcctcgcag aggaagcgaa gctgcgcgtc ggccgtttcc atctgcggtg cgcccggtcg 1680
cgtgccggca tggatgcgcg cgccatcgcg gtaggcgagc agcgcctgcc tgaagctgcg 1740
ggcattcccg atcagaaatg agcgccagtc gtcgtcggct ctcggcaccg aatgcgtatg 1800
attctccgcc agcatggctt cggccagtgc gtcgagcagc gcccgcttgt tcctgaagtg 1860

```
ccagtaaagc gccggctgct gaacccccaa ccgttccgcc agtttgcgtg tcgtcagacc   1920
gtctacgccg acctcgttca acaggtccag ggcggcacgg atcactgtat tcggctgcaa   1980
ctttgtcatg cttgacactt tatcactgat aaacataata tgtccaccaa cttatcagtg   2040
ataaagaatc cgcgcgttca atcggaccag cggaggctgg tccggaggcc agacgtgaaa   2100
cccaacatac ccctgatcgt aattctgagc actgtcgcgc tcgacgctgt cggcatcggc   2160
ctgattatgc cggtgctgcc gggcctcctg cgcgatctgg ttcactcgaa cgacgtcacc   2220
gcccactatg gcattctgct ggcgctgtat gcgttggtgc aatttgcctg cgcacctgtg   2280
ctgggcgcgc tgtcggatcg tttcgggcgg cggccaatct tgctcgtctc gctggccggc   2340
gccagatctg gggaaccctg tggttggcat gcacatacaa atggacgaac ggataaacct   2400
tttcacgccc ttttaaatat ccgattattc taataaacgc tcttttctct taggtttacc   2460
cgccaatata tcctgtcaaa cactgatagt ttaaactgaa ggcgggaaac gacaatctga   2520
tcatgagcgg agaattaagg gagtcacgtt atgacccccg ccgatgacgc gggacaagcc   2580
gttttacgtt tggaactgac agaaccgcaa cgttgaagga gccactcagc cgcgggtttc   2640
tggagtttaa tgagctaagc acatacgtca gaaaccatta ttgcgcgttc aaaagtcgcc   2700
taaggtcact atcagctagc aaatatttct tgtcaaaaat gctccactga cgttccataa   2760
attcccctcg gtatccaatt agagtctcat attcactctc aatccaaata atctgcaccg   2820
gatctggatc gtttcgcatg attgaacaag atggattgca cgcaggttct ccggccgctt   2880
gggtggagag gctattcggc tatgactggg cacaacagac aatcggctgc tctgatgccg   2940
ccgtgttccg gctgtcagcg caggggcgcc cggttctttt tgtcaagacc gacctgtccg   3000
gtgccctgaa tgaactgcag gacgaggcag cgcggctatc gtggctggcc acgacgggcg   3060
ttccttgcgc agctgtgctc gacgttgtca ctgaagcggg aagggactgg ctgctattgg   3120
gcgaagtgcc ggggcaggat ctcctgtcat ctcaccttgc tcctgccgag aaagtatcca   3180
tcatggctga tgcaatgcgg cggctgcata cgcttgatcc ggctacctgc ccattcgacc   3240
accaagcgaa acatcgcatc gagcgagcac gtactcggat ggaagccggt cttgtcgatc   3300
aggatgatct ggacgaagag catcaggggc tcgcgccagc cgaactgttc gccaggctca   3360
aggcgcgcat gcccgacggc gatgatctcg tcgtgaccca tggcgatgcc tgcttgccga   3420
atatcatggt ggaaaatggc cgcttttctg gattcatcga ctgtggccgg ctgggtgtgg   3480
cggaccgcta tcaggacata gcgttggcta cccgtgatat tgctgaagag cttggcggcg   3540
aatgggctga ccgcttcctc gtgctttacg gtatcgccgc tcccgattcg cagcgcatcg   3600
ccttctatcg ccttcttgac gagttcttct gagcgggact ctggggttcg aaatgaccga   3660
ccaagcgacg cccaacctgc catcacgaga tttcgattcc accgccgcct tctatgaaag   3720
gttgggcttc ggaatcgttt tccgggacgc cggctggatg atcctccagc gcggggatct   3780
catgctggag ttcttcgccc acgggatctc tgcggaacag gcggtcgaag gtgccgatat   3840
cattacgaca gcaacggccg acaagcacaa cgccacgatc ctgagcgaca atatgatcgg   3900
gcccggcgtc cacatcaacg gcgtcggcgg cgactgccca ggcaagaccg agatgcaccg   3960
cgatatcttg ctgcgttcgg atattttcgt ggagttcccg ccacagaccc ggatgatccc   4020
cgatcgttca aacatttggc aataaagttt cttaagattg aatcctgttg ccggtcttgc   4080
gatgattatc atataatttc tgttgaatta cgttaagcat gtaataatta acatgtaatg   4140
catgacgtta tttatgagat gggtttttat gattagagtc ccgcaattat acatttaata   4200
```

-continued

```
cgcgatagaa aacaaaatat agcgcgcaaa ctaggataaa ttatcgcgcg cggtgtcatc   4260
tatgttacta gatcgggcct cctgtcaatg ctggcggcgg ctctggtggt ggttctggtg   4320
gcggctctga gggtggtggc tctgagggtg gcggttctga gggtggcggc tctgagggag   4380
gcggttccgg tggtggctct ggttccggtg attttgatta tgaaaagatg gcaaacgcta   4440
ataagggggc tatgaccgaa aatgccgatg aaaacgcgct acagtctgac gctaaaggca   4500
aacttgattc tgtcgctact gattacggtg ctgctatcga tggtttcatt ggtgacgttt   4560
ccggccttgc taatggtaat ggtgctactg gtgattttgc tggctctaat tcccaaatgg   4620
ctcaagtcgg tgacggtgat aattcacctt taatgaataa tttccgtcaa tatttacctt   4680
ccctccctca atcggttgaa tgtcgccctt ttgtctttgg cccaatacgc aaaccgcctc   4740
tccccgcgcg ttggccgatt cattaatgca gctggcacga caggtttccc gactggaaag   4800
cgggcagtga gcgcaacgca attaatgtga gttagctcac tcattaggca ccccaggctt   4860
tacactttat gcttccggct cgtatgttgt gtggaattgt gagcggataa caatttcaca   4920
caggaaacag ctatgaccat gattacgcca agcttgcatg cctgcaggtc cccagattag   4980
ccttttcaat ttcagaaaga atgctaaccc acagatggtt agagaggctt acgcagcagg   5040
tctcatcaag acgatctacc cgagcaataa tctccaggaa atcaaatacc ttcccaagaa   5100
ggttaaagat gcagtcaaaa gattcaggac taactgcatc aagaacacag agaaagatat   5160
atttctcaag atcagaagta ctattccagt atggacgatt caaggcttgc ttcacaaacc   5220
aaggcaagta atagagattg gagtctctaa aaaggtagtt cccactgaat caaaggccat   5280
ggagtcaaag attcaaatag aggacctaac agaactcgcc gtaaagactg gcgaacagtt   5340
catacagagt ctcttacgac tcaatgacaa gaagaaaatc ttcgtcaaca tggtggagca   5400
cgacacactt gtctactcca aaaatatcaa agatacagtc tcagaagacc aaagggcaat   5460
tgagactttt caacaaaggg taatatccgg aaacctcctc ggattccatt gcccagctat   5520
ctgtcacttt attgtgaaga tagtggaaaa ggaaggtggc tcctacaaat gccatcattg   5580
cgataaagga aaggccatcg ttgaagatgc ctctgccgac agtggtccca aagatggacc   5640
cccacccacg aggagcatcg tggaaaaaga agacgttcca accacgtctt caaagcaagt   5700
ggattgatgt gatatctcca ctgacgtaag ggatgacgca caatcccact atccttcgca   5760
agacccttcc tctatataag gaagttcatt tcatttggag agaacacggg ggactctaat   5820
caaacaagtt tgtacaaaaa agctgaacga gaaacgtaaa atgatataaa tatcaaatgc   5880
atatcagaaa tccttaccgt acaccaattg actatcaagc actttcagag gccttccctc   5940
ccctcaagcc atttgtgtct gtcaatgcag atggtaccag ttctgttgac ctcactatcc   6000
cagaagccca gagggcgttc acggccgctc ttcttcatcg tgacttcggg ctcaccatga   6060
ccataccaga agaccgtctg tgcccaacag tccccaatag gttgaactac gttctgtgga   6120
ttgaagatat tttcaactac acgaacaaaa ccctcggcct gtcggatgac cgtcctatta   6180
aaggcgttga tattggtaca ggagcctccg caatttatcc tatgcttgcc tgtgctcggt   6240
tcaaggcatg gtctatggtt ggaacagagg tcgagaggaa gtgcattgac acggcccgcc   6300
tcaatgtcgt cgcgaacaat ctccaagacc gtctctcgat attagagaca tccattgatg   6360
gtcctattct cgtccccatt ttcgaggcga ctgaagaata cgaatacgag tttactatgt   6420
gtaaccctcc attctacgac ggtgctgccg atatgcagac ttcggatgct gccaaaggat   6480
ttggatttgg cgtgggcgct ccccattctg gaacagtcat cgaaatgtcg actgagggag   6540
gtgaatcggc tttcgtcgct cagatggtcc gtgagagctt gaagcttcga acacgatgca   6600
```

```
gatggtacac gagtaacttg ggaaagctga aatccttgaa agaaatagtg gggctgctga   6660

aagaacttga gataagcaac tatgccatta acgaatacgt tcaggggtcc acacgtcgtt   6720

atgccgttgc gtggtctttc actgatattc aactgcctga ggagctttct cgtccctcta   6780

accccgagct cagctctctt ttctagcatt ttacgtttct cgttcagctt tcttgtacaa   6840

agtggttcga tctagaggat ccatggtgag caagggcgag gagctgttca ccggggtggt   6900

gcccatcctg gtcgagctgg acggcgacgt gaacggccac aagttcagcg tgtccggcga   6960

gggcgagggc gatgccacct acggcaagct gaccctgaag ttcatctgca ccaccggcaa   7020

gctgcccgtg ccctggccca ccctcgtgac caccttcacc tacggcgtgc agtgcttcag   7080

ccgctacccc gaccacatga agcagcacga cttcttcaag tccgccatgc ccgaaggcta   7140

cgtccaggag cgcaccatct tcttcaagga cgacggcaac tacaagaccc gcgccgaggt   7200

gaagttcgag ggcgacaccc tggtgaaccg catcgagctg aagggcatcg acttcaagga   7260

ggacggcaac atcctggggc acaagctgga gtacaactac aacagccaca acgtctatat   7320

catggccgac aagcagaaga acggcatcaa ggtgaacttc aagatccgcc acaacatcga   7380

ggacggcagc gtgcagctcg ccgaccacta ccagcagaac acccccatcg gcgacggccc   7440

cgtgctgctg cccgacaacc actacctgag cacccagtcc gccctgagca aagaccccaa   7500

cgagaagcgc gatcacatgg tcctgctgga gttcgtgacc gccgccggga tcactcacgg   7560

catggacgag ctgtacaagt aaagcggccc gagctcgaat ttccccgatc gttcaaacat   7620

ttggcaataa agtttcttaa gattgaatcc tgttgccggt cttgcgatga ttatcatata   7680

atttctgttg aattacgtta agcatgtaat aattaacatg taatgcatga cgttatttat   7740

gagatgggtt tttatgatta gagtcccgca attatacatt taatacgcga tagaaaacaa   7800

aatatagcgc gcaaactagg ataaattatc gcgcgcggtg tcatctatgt tactagatcg   7860

ggaattagct tcatcaacgc aagacatgcg cacgaccgtc tgacaggaga ggaatttccg   7920

acgagcacag aaaggacttg ctcttggacg taggcctatt tctcaggcac atgtatcaag   7980

tgttcggacg tgggttttcg atggtgtatc agccgccgcc aactgggaga tgaggaggct   8040

ttcttggggg gcagtcagca gttcatttca caagacagag gaacttgtaa ggagatgcac   8100

tgatttatct tggcgcaaac cagcaggacg aattagtggg aatagcccgc gaatatctaa   8160

gttatgcctg tcggcatgag cagaaacttc caattcgaaa cagtttggag aggttgtttt   8220

tgggcatacc ttttgttagt cagcctctcg attgctcatc gtcattacac agtaccgaag   8280

tttgatcgat ctagtaacat agatgacacc gcgcgcgata atttatccta gtttgcgcgc   8340

tatattttgt tttctatcgc gtattaaatg tataattgcg ggactctaat cataaaaacc   8400

catctcataa ataacgtcat gcattacatg ttaattatta catgcttaac gtaattcaac   8460

agaaattata tgataatcat cgcaagaccg gcaacaggat tcaatcttaa gaaactttat   8520

tgccaaatgt ttgaacgatc tgcttcgacg cactccttct ttactccacc atctcgtcct   8580

tattgaaaac gtgggtagca ccaaaacgaa tcaagtcgct ggaactgaag ttaccaatca   8640

cgctggatga tttgccagtt ggattaatct tgcctttccc cgcatgaata atattgatga   8700

atgcatgcgt gaggggtatt tcgattttgg caatagctgc aattgccgcg acatcctcca   8760

acgagcataa ttcttcagaa aaatagcgat gttccatgtt gtcagggcat gcatgatgca   8820

cgttatgagg tgacggtgct aggcagtatt ccctcaaagt ttcatagtca gtatcatatt   8880

catcattgca ttcctgcaag agagaattga gacgcaatcc acacgctgcg gcaaccttcc   8940
```

-continued

```
ggcgttcgtg gtctatttgc tcttggacgt tgcaaacgta agtgttggat cccggtcggc   9000
atctactcta ttcctttgcc ctcggacgag tgctggggcg tcggtttcca ctatcggcga   9060
gtacttctac acagccatcg gtccagacgg ccgcgcttct gcgggcgatt tgtgtacgcc   9120
cgacagtccc ggctccggat cggacgattg cgtcgcatcg accctgcgcc caagctgcat   9180
catcgaaatt gccgtcaacc aagctctgat agagttggtc aagaccaatg cggagcatat   9240
acgcccggag ccgcggcgat cctgcaagct ccggatgcct ccgctcgaag tagcgcgtct   9300
gctgctccat acaagccaac cacggcctcc agaagaagat gttggcgacc tcgtattggg   9360
aatccccgaa catcgcctcg ctccagtcaa tgaccgctgt tatgcggcca ttgtccgtca   9420
ggacattgtt ggagccgaaa tccgcgtgca cgaggtgccg gacttcgggg cagtcctcgg   9480
cccaaagcat cagctcatcg agagcctgcg cgacggacgc actgacggtg tcgtccatca   9540
cagtttgcca gtgatacaca tggggatcag caatcgcgca tatgaaatca cgccatgtag   9600
tgtattgacc gattccttgc ggtccgaatg ggccgaaccc gctcgtctgg ctaagatcgg   9660
ccgcagcgat cgcatccatg gcctccgcga ccggctgcag aacagcgggc agttcggttt   9720
caggcaggtc ttgcaacgtg acaccctgtg cacggcggga gatgcaatag gtcaggctct   9780
cgctgaattc cccaatgtca agcacttccg gaatcgggag cgcggccgat gcaaagtgcc   9840
gataaacata acgatctttg tagaaaccat cggcgcagct atttacccgc aggacatatc   9900
cacgccctcc tacatcgaag ctgaaagcac gagattcttc gccctccgag agctgcatca   9960
ggtcggagac gctgtcgaac ttttcgatca gaaacttctc gacagacgtc gcggtgagtt  10020
caggcttttt catatcgggg tcgtcctctc caaatgaaat gaacttcctt atatagagga  10080
agggtcttgc gaaggatagt gggattgtgc gtcatccctt acgtcagtgg agatatcaca  10140
tcaatccact tgctttgaag acgtggttgg aacgtcttct ttttccacga tgctcctcgt  10200
gggtgggggt ccatctttgg gaccactgtc ggcagaggca tcttgaacga tagcctttcc  10260
tttatcgcaa tgatggcatt tgtaggtgcc accttccttt tctactgtcc ttttgatgaa  10320
gtgacagata gctgggcaat ggaatccgag gaggtttccc gatattaccc tttgttgaaa  10380
agtctcaata gccctttggt cttctgagac tgtatctttg atattcttgg agtagacgag  10440
agtgtcgtgc tccaccatgt tgacggatct ctaggacgcg tcctagaagc taattcactg  10500
gccgtcgttt tacaacgtcg tgactgggaa aaccctggcg ttacccaact taatcgcctt  10560
gcagcacatc ccccctttcgc cagctggcgt aatagcgaag aggcccgcac cgatcgccct  10620
tcccaacagt tgcgcagcct gaatggcgcc cgctcctttc gctttcttcc cttcctttct  10680
cgccacgttc gccggctttc cccgtcaagc tctaaatcgg gggctccctt tagggttccg  10740
atttagtgct ttacggcacc tcgaccccaa aaaacttgat ttgggtgatg gttcacgtag  10800
tgggccatcg ccctgataga cggtttttcg ccctttgacg ttggagtcca cgttctttaa  10860
tagtggactc ttgttccaaa ctggaacaac actcaaccct atctcgggct attcttttga  10920
tttataaggg attttgccga tttcggaacc accatcaaac aggattttcg cctgctgggg  10980
caaaccagcg tggaccgctt gctgcaactc tctcagggcc aggcggtgaa gggcaatcag  11040
ctgttgcccg tctcactggt gaaaagaaaa accaccccag tacattaaaa acgtccgcaa  11100
tgtgttatta agttgtctaa gcgtcaattt gtttacacca caatatatcc tgccaccagc  11160
cagccaacag ctccccgacc ggcagctcgg cacaaaatca ccactcgata caggcagccc  11220
atcagtccgg gacggcgtca gcgggagagc cgttgtaagg cggcagactt tgctcatgtt  11280
accgatgcta ttcggaagaa cggcaactaa gctgccgggt ttgaaacacg gatgatctcg  11340
```

```
cggagggtag catgttgatt gtaacgatga cagagcgttg ctgcctgtga tcaaatatca  11400
tctccctcgc agagatccga attatcagcc ttcttattca tttctcgctt aaccgtgaca  11460
ggctgtcgat cttgagaact atgccgacat aataggaaat cgctggataa agccgctgag  11520
gaagctgagt ggcgctattt ctttagaagt gaacgttgac gatatcaact cccctatcca  11580
ttgctcaccg aatggtacag gtcggggacc cgaagttccg actgtcggcc tgatgcatcc  11640
ccggctgatc gaccccagat ctggggctga gaaagcccag taaggaaaca actgtaggtt  11700
cgagtcgcga gatcccccgg aaccaaagga agtaggttaa acccgctccg atcaggccga  11760
gccacgccag gccgagaaca ttggttcctg taggcatcgg gattggcgga tcaaacacta  11820
aagctactgg aacgagcaga agtcctccgg ccgccagttg ccaggcggta aaggtgagca  11880
gaggcacggg aggttgccac ttgcgggtca gcacggttcc gaacgccatg gaaaccgccc  11940
ccgccaggcc cgctgcgacg ccgacaggat ctagcgctgc gtttggtgtc aacaccaaca  12000
gcgccacgcc cgcagttccg caaatagccc ccaggaccgc catcaatcgt atcgggctac  12060
ctagcagagc ggcagagatg aacacgacca tcagcggctg cacagcgcct accgtcgccg  12120
cgaccccgcc cggcaggcgg tagaccgaaa taaacaacaa gctccagaat agcgaaatat  12180
taagtgcgcc gaggatgaag atgcgcatcc accagattcc cgttggaatc tgtcggacga  12240
tcatcacgag caataaaccc gccggcaacg cccgcagcag cataccggcg acccctcggc  12300
ctcgctgttc gggctccacg aaaacgccgg acagatgcgc cttgtgagcg tccttggggc  12360
cgtcctcctg tttgaagacc gacagcccaa tgatctcgcc gtcgatgtag gcgccgaatg  12420
ccacggcatc tcgcaaccgt tcagcgaacg cctccatggg ctttttctcc tcgtgctcgt  12480
aaacggaccc gaacatctct ggagctttct tcagggccga caatcggatc tcgcggaaat  12540
cctgcacgtc ggccgctcca agccgtcgaa tctgagcctt aatcacaatt gtcaatttta  12600
atcctctgtt tatcggcagt tcgtagagcg cgccgtgcgt cccgagcgat actgagcgaa  12660
gcaagtgcgt cgagcagtgc ccgcttgttc ctgaaatgcc agtaaagcgc tggctgctga  12720
acccccagcc ggaactgacc ccacaaggcc ctagcgtttg caatgcacca ggtcatcatt  12780
gacccaggcg tgttccacca ggccgctgcc tcgcaactct tcgcaggctt cgccgacctg  12840
ctcgcgccac ttcttcacgc gggtggaatc cgatccgcac atgaggcgga aggtttccag  12900
cttgagcggg tacggctccc ggtgcgagct gaaatagtcg aacatccgtc gggccgtcgg  12960
cgacagcttg cggtacttct cccatatgaa tttcgtgtag tggtcgccag caaacagcac  13020
gacgatttcc tcgtcgatca ggacctggca acgggacgtt ttcttgccac ggtccaggac  13080
gcggaagcgg tgcagcagcg acaccgattc caggtgccca acgcggtcgg acgtgaagcc  13140
catcgccgtc gcctgtaggc gcgacaggca ttcctcggcc ttcgtgtaat accggccatt  13200
gatcgaccag cccaggtcct ggcaaagctc gtagaacgtg aaggtgatcg gctcgccgat  13260
aggggtgcgc ttcgcgtact ccaacacctg ctgccacacc agttcgtcat cgtcggcccg  13320
cagctcgacg ccggtgtagg tgatcttcac gtccttgttg acgtggaaaa tgaccttgtt  13380
ttgcagcgcc tcgcgcggga ttttcttgtt gcgcgtggtg aacagggcag agcgggccgt  13440
gtcgtttggc atcgctcgca tcgtgtccgg ccacggcgca atatcgaaca aggaaagctg  13500
catttccttg atctgctgct tcgtgtgttt cagcaacgcg gcctgcttgg cctcgctgac  13560
ctgttttgcc aggtcctcgc cggcggtttt tcgcttcttg gtcgtcatag ttcctcgcgt  13620
gtcgatggtc atcgacttcg ccaaacctgc cgcctcctgt tcgagacgac gcgaacgctc  13680
```

-continued

```
cacggcggcc gatggcgcgg gcagggcagg gggagccagt tgcacgctgt cgcgctcgat  13740
cttggccgta gcttgctgga ccatcgagcc gacggactgg aaggtttcgc ggggcgcacg  13800
catgacggtg cggcttgcga tggtttcggc atcctcggcg gaaaaccccg cgtcgatcag  13860
ttcttgcctg tatgccttcc ggtcaaacgt ccgattcatt caccctcctt gcgggattgc  13920
cccgactcac gccggggcaa tgtgccctta ttcctgattt gacccgcctg gtgccttggt  13980
gtccagataa tccaccttat cggcaatgaa gtcggtcccg tagaccgtct ggccgtcctt  14040
ctcgtacttg gtattccgaa tcttgccctg cacgaatacc agcgacccct tgcccaaata  14100
cttgccgtgg gcctcggcct gagagccaaa acacttgatg cggaagaagt cggtgcgctc  14160
ctgcttgtcg ccggcatcgt tgcgccacat ctaggtacta aaacaattca tccagtaaaa  14220
tataatattt tattttctcc caatcaggct tgatccccag taagtcaaaa aatagctcga  14280
catactgttc ttccccgata tcctccctga tcgaccggac gcagaaggca atgtcatacc  14340
acttgtccgc cctgccgctt ctcccaagat caataaagcc acttactttg ccatctttca  14400
caaagatgtt gctgtctccc aggtcgccgt gggaaaagac aagttcctct tcgggctttt  14460
ccgtctttaa aaaatcatac agctcgcgcg gatctttaaa tggagtgtct tcttcccagt  14520
tttcgcaatc cacatcggcc agatcgttat tcagtaagta atccaattcg gctaagcggc  14580
tgtctaagct attcgtatag ggacaatccg atatgtcgat ggagtgaaag agcctgatgc  14640
actccgcata cagctcgata atcttttcag ggctttgttc atcttcatac tcttccgagc  14700
aaaggacgcc atcggcctca ctcatgagca gattgctcca gccatcatgc cgttcaaagt  14760
gcaggacctt tggaacaggc agctttcctt ccagccatag catcatgtcc ttttcccgtt  14820
ccacatcata ggtggtccct ttataccggc tgtccgtcat ttttaaatat aggttttcat  14880
tttctcccac cagcttatat accttagcag gagacattcc ttccgtatct tttacgcagc  14940
ggtatttttc gatcagtttt ttcaattccg gtgatattct cattttagcc atttattatt  15000
tccttcctct tttctacagt atttaaagat accccaagaa gctaattata acaagacgaa  15060
ctccaattca ctgttccttg cattctaaaa ccttaaatac cagaaaacag ctttttcaaa  15120
gttgttttca aagttggcgt ataacatagt atcgacggag ccgattttga aaccacaatt  15180
atgggtgatg ctgccaactt actgatttag tgtatgatgg tgtttttgag gtgctccagt  15240
ggcttctgtg tctatcagct gtccctcctg ttcagctact gacggggtgg tgcgtaacgg  15300
caaaagcacc gccggacatc agcgctatct ctgctctcac tgccgtaaaa catggcaact  15360
gcagttcact tacaccgctt ctcaacccgg tacgcaccag aaaatcattg atatggccat  15420
gaatggcgtt ggatgccggg caacagcccg cattatgggc gttggcctca acacgatttt  15480
acgtcactta aaaaactcag gccgcagtcg gtaacctcgc gcatacagcc gggcagtgac  15540
gtcatcgtct gcgcggaaat ggacgaacag tggggctatg tcggggctaa atcgcgccag  15600
cgctggctgt tttacgcgta tgacagtctc cggaagacgg ttgttgcgca cgtattcggt  15660
gaacgcacta tggcgacgct ggggcgtctt atgagcctgc tgtcaccctt tgacgtggtg  15720
atatggatga cggatggctg gccgctgtat gaatcccgcc tgaagggaaa gctgcacgta  15780
atcagcaagc gatatacgca gcgaattgag cggcataacc tgaatctgag gcagcacctg  15840
gcacggctgg gacggaagtc gctgtcgttc tcaaaatcgg tggagctgca tgacaaagtc  15900
atcgggcatt atctgaacat aaaacactat caataagttg gagtcattac ccaattatga  15960
tagaatttac aagctataag gttattgtcc tgggtttcaa gcattagtcc atgcaagttt  16020
ttatgctttg cccattctat agatatattg ataagcgcgc tgcctatgcc ttgccccctg  16080
```

```
aaatccttac atacggcgat atcttctata taaaagatat attatcttat cagtattgtc  16140
aatatattca aggcaatctg cctcctcatc ctcttcatcc tcttcgtctt ggtagctttt  16200
taaatatggc gcttcataga gtaattctgt aaaggtccaa ttctcgtttt catacctcgg  16260
tataatctta cctatcacct caaatggttc gctgggttta tcgcaccccc gaacacgagc  16320
acggcacccg cgaccactat gccaagaatg cccaaggtaa aaattgccgg ccccgccatg  16380
aagtccgtga atgccccgac ggccgaagtg aagggcaggc cgccacccag gccgccgccc  16440
tcactgcccg gcacctggtc gctgaatgtc gatgccagca cctgcggcac gtcaatgctt  16500
ccgggcgtcg cgctcgggct gatcgcccat cccgttactg ccccgatccc ggcaatggca  16560
aggactgcca gcgctgccat ttttggggtg aggccgttcg cggccgaggg gcgcagcccc  16620
tggggggatg ggaggcccgc gttagcgggc cgggagggtt cgagaagggg gggcaccccc  16680
cttcggcgtg cgcggtcacg cgcacagggc gcagccctgg ttaaaaacaa ggtttataaa  16740
tattggttta aaagcaggtt aaaagacagg ttagcggtgg ccgaaaaacg ggcggaaacc  16800
cttgcaaatg ctggattttc tgcctgtgga cagcccctca aatgtcaata ggtgcgcccc  16860
tcatctgtca gcactctgcc cctcaagtgt caaggatcgc gcccctcatc tgtcagtagt  16920
cgcgcccctc aagtgtcaat accgcagggc acttatcccc aggcttgtcc acatcatctg  16980
tgggaaactc gcgtaaaatc aggcgttttc gccgatttgc gaggctggcc agctccacgt  17040
cgccggccga aatcgagcct gcccctcatc tgtcaacgcc gcgccgggtg agtcggcccc  17100
tcaagtgtca acgtccgccc ctcatctgtc agtgagggcc aagttttccg cgaggtatcc  17160
acaacgccgg cggccgcggt gtctcgcaca cggcttcgac ggcgtttctg gcgcgtttgc  17220
agggccatag acggccgcca gcccagcggc gagggcaacc agcccgg                17267
```

<210> SEQ ID NO 16
<211> LENGTH: 17420
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 16

```
tgagcgtcgc aaaggcgctc ggtcttgcct tgctcgtcgg tgatgtactt caccagctcc     60
gcgaagtcgc tcttcttgat ggagcgcatg gggacgtgct tggcaatcac gcgcaccccc    120
cggccgtttt agcggctaaa aaagtcatgg ctctgccctc gggcggacca cgcccatcat    180
gaccttgcca agctcgtcct gcttctcttc gatcttcgcc agcagggcga ggatcgtggc    240
atcaccgaac cgcgccgtgc gcgggtcgtc ggtgagccag agtttcagca ggccgcccag    300
gcggcccagg tcgccattga tgcgggccag ctcgcggacg tgctcatagt ccacgacgcc    360
cgtgattttg tagccctggc cgacggccag caggtaggcc gacaggctca tgccggccgc    420
cgccgccttt tcctcaatcg ctcttcgttc gtctggaagg cagtacacct tgataggtgg    480
gctgcccttc ctggttggct tggtttcatc agccatccgc ttgccctcat ctgttacgcc    540
ggcggtagcc ggccagcctc gcagagcagg attcccgttg agcaccgcca ggtgcgaata    600
agggacagtg aagaaggaac acccgctcgc gggtgggcct acttcaccta tcctgcccgg    660
ctgacgccgt tggatacacc aaggaaagtc tacacgaacc ctttggcaaa atcctgtata    720
tcgtgcgaaa aaggatggat ataccgaaaa aatcgctata atgaccccga agcagggtta    780
tgcagcggaa aagcgccacg cttcccgaag ggagaaaggc ggacaggtat ccggtaagcg    840
```

-continued

```
gcagggtcgg aacaggagag cgcacgaggg agcttccagg gggaaacgcc tggtatcttt    900
atagtcctgt cgggtttcgc cacctctgac ttgagcgtcg atttttgtga tgctcgtcag    960
gggggcggag cctatggaaa aacgccagca acgcggcctt tttacggttc ctggcctttt   1020
gctggccttt tgctcacatg ttctttcctg cgttatcccc tgattctgtg gataaccgta   1080
ttaccgcctt tgagtgagct gataccgctc gccgcagccg aacgaccgag cgcagcgagt   1140
cagtgagcga ggaagcggaa gagcgccaga aggccgccag agaggccgag cgcggccgtg   1200
aggcttggac gctagggcag ggcatgaaaa agcccgtagc gggctgctac gggcgtctga   1260
cgcggtggaa agggggaggg gatgttgtct acatggctct gctgtagtga gtgggttgcg   1320
ctccggcagc ggtcctgatc aatcgtcacc ctttctcggt ccttcaacgt tcctgacaac   1380
gagcctcctt ttcgccaatc catcgacaat caccgcgagt ccctgctcga acgctgcgtc   1440
cggaccggct tcgtcgaagg cgtctatcgc ggcccgcaac agcggcgaga gcggagcctg   1500
ttcaacggtg ccgccgcgct cgccggcatc gctgtcgccg gcctgctcct caagcacggc   1560
cccaacagtg aagtagctga ttgtcatcag cgcattgacg gcgtccccgg ccgaaaaacc   1620
cgcctcgcag aggaagcgaa gctgcgcgtc ggccgtttcc atctgcggtg cgcccggtcg   1680
cgtgccggca tggatgcgcg cgccatcgcg gtaggcgagc agcgcctgcc tgaagctgcg   1740
ggcattcccg atcagaaatg agcgccagtc gtcgtcggct ctcggcaccg aatgcgtatg   1800
attctccgcc agcatggctt cggccagtgc gtcgagcagc gcccgcttgt tcctgaagtg   1860
ccagtaaagc gccggctgct gaacccccaa ccgttccgcc agtttgcgtg tcgtcagacc   1920
gtctacgccg acctcgttca acaggtccag ggcggcacgg atcactgtat tcggctgcaa   1980
ctttgtcatg cttgacactt tatcactgat aaacataata tgtccaccaa cttatcagtg   2040
ataaagaatc cgcgcgttca atcggaccag cggaggctgg tccggaggcc agacgtgaaa   2100
cccaacatac ccctgatcgt aattctgagc actgtcgcgc tcgacgctgt cggcatcggc   2160
ctgattatgc cggtgctgcc gggcctcctg cgcgatctgg ttcactcgaa cgacgtcacc   2220
gcccactatg gcattctgct ggcgctgtat gcgttggtgc aatttgcctg cgcacctgtg   2280
ctgggcgcgc tgtcggatcg tttcgggcgg cggccaatct tgctcgtctc gctggccggc   2340
gccagatctg gggaaccctg tggttggcat gcacatacaa atggacgaac ggataaacct   2400
tttcacgccc ttttaaatat ccgattattc taataaacgc tcttttctct taggtttacc   2460
cgccaatata tcctgtcaaa cactgatagt ttaaactgaa ggcgggaaac gacaatctga   2520
tcatgagcgg agaattaagg gagtcacgtt atgacccccg ccgatgacgc gggacaagcc   2580
gttttacgtt tggaactgac agaaccgcaa cgttgaagga gccactcagc cgcgggtttc   2640
tggagtttaa tgagctaagc acatacgtca gaaaccatta ttgcgcgttc aaaagtcgcc   2700
taaggtcact atcagctagc aaatatttct tgtcaaaaat gctccactga cgttccataa   2760
attcccctcg gtatccaatt agagtctcat attcactctc aatccaaata atctgcaccg   2820
gatctggatc gtttcgcatg attgaacaag atggattgca cgcaggttct ccggccgctt   2880
gggtggagag gctattcggc tatgactggg cacaacagac aatcggctgc tctgatgccg   2940
ccgtgttccg gctgtcagcg caggggcgcc cggttctttt tgtcaagacc gacctgtccg   3000
gtgccctgaa tgaactgcag gacgaggcag cgcggctatc gtggctggcc acgacgggcg   3060
ttccttgcgc agctgtgctc gacgttgtca ctgaagcggg aagggactgg ctgctattgg   3120
gcgaagtgcc ggggcaggat ctcctgtcat ctcaccttgc tcctgccgag aaagtatcca   3180
```

-continued

```
tcatggctga tgcaatgcgg cggctgcata cgcttgatcc ggctacctgc ccattcgacc   3240
accaagcgaa acatcgcatc gagcgagcac gtactcggat ggaagccggt cttgtcgatc   3300
aggatgatct ggacgaagag catcaggggc tcgcgccagc cgaactgttc gccaggctca   3360
aggcgcgcat gcccgacggc gatgatctcg tcgtgaccca tggcgatgcc tgcttgccga   3420
atatcatggt ggaaaatggc cgcttttctg gattcatcga ctgtggccgg ctgggtgtgg   3480
cggaccgcta tcaggacata gcgttggcta cccgtgatat tgctgaagag cttggcggcg   3540
aatgggctga ccgcttcctc gtgctttacg gtatcgccgc tcccgattcg cagcgcatcg   3600
ccttctatcg ccttcttgac gagttcttct gagcgggact ctggggttcg aaatgaccga   3660
ccaagcgacg cccaacctgc catcacgaga tttcgattcc accgccgcct tctatgaaag   3720
gttgggcttc ggaatcgttt tccgggacgc cggctggatg atcctccagc gcggggatct   3780
catgctggag ttcttcgccc acgggatctc tgcggaacag gcggtcgaag gtgccgatat   3840
cattacgaca gcaacggccg acaagcacaa cgccacgatc ctgagcgaca atatgatcgg   3900
gcccggcgtc cacatcaacg gcgtcggcgg cgactgccca ggcaagaccg agatgcaccg   3960
cgatatcttg ctgcgttcgg atattttcgt ggagttcccg ccacagaccc ggatgatccc   4020
cgatcgttca aacatttggc aataaagttt cttaagattg aatcctgttg ccggtcttgc   4080
gatgattatc atataatttc tgttgaatta cgttaagcat gtaataatta acatgtaatg   4140
catgacgtta tttatgagat gggtttttat gattagagtc ccgcaattat acatttaata   4200
cgcgatagaa aacaaaatat agcgcgcaaa ctaggataaa ttatcgcgcg cggtgtcatc   4260
tatgttacta gatcgggcct cctgtcaatg ctggcggcgg ctctggtggt ggttctggtg   4320
gcggctctga gggtggtggc tctgagggtg gcggttctga gggtggcggc tctgagggag   4380
gcggttccgg tggtggctct ggttccggtg attttgatta tgaaaagatg gcaaacgcta   4440
ataagggggc tatgaccgaa aatgccgatg aaaacgcgct acagtctgac gctaaaggca   4500
aacttgattc tgtcgctact gattacggtg ctgctatcga tggtttcatt ggtgacgttt   4560
ccggccttgc taatggtaat ggtgctactg gtgattttgc tggctctaat tcccaaatgg   4620
ctcaagtcgg tgacggtgat aattcacctt taatgaataa tttccgtcaa tatttacctt   4680
ccctccctca atcggttgaa tgtcgccctt ttgtctttgg cccaatacgc aaaccgcctc   4740
tccccgcgcg ttggccgatt cattaatgca gctggcacga caggtttccc gactggaaag   4800
cgggcagtga gcgcaacgca attaatgtga gttagctcac tcattaggca ccccaggctt   4860
tacactttat gcttccggct cgtatgttgt gtggaattgt gagcggataa caatttcaca   4920
caggaaacag ctatgaccat gattacgcca agcttgcatg cctgcaggtc cccagattag   4980
ccttttcaat ttcagaaaga atgctaaccc acagatggtt agagaggctt acgcagcagg   5040
tctcatcaag acgatctacc cgagcaataa tctccaggaa atcaaatacc ttcccaagaa   5100
ggttaaagat gcagtcaaaa gattcaggac taactgcatc aagaacacag agaaagatat   5160
atttctcaag atcagaagta ctattccagt atggacgatt caaggcttgc ttcacaaacc   5220
aaggcaagta atagagattg gagtctctaa aaaggtagtt cccactgaat caaaggccat   5280
ggagtcaaag attcaaatag aggacctaac agaactcgcc gtaaagactg gcgaacagtt   5340
catacagagt ctcttacgac tcaatgacaa gaagaaaatc ttcgtcaaca tggtggagca   5400
cgacacactt gtctactcca aaaatatcaa agatacagtc tcagaagacc aaagggcaat   5460
tgagactttt caacaaaggg taatatccgg aaacctcctc ggattccatt gcccagctat   5520
ctgtcacttt attgtgaaga tagtggaaaa ggaaggtggc tcctacaaat gccatcattg   5580
```

-continued

```
cgataaagga aaggccatcg ttgaagatgc ctctgccgac agtggtccca aagatggacc   5640
cccacccacg aggagcatcg tggaaaaaga agacgttcca accacgtctt caaagcaagt   5700
ggattgatgt gatatctcca ctgacgtaag ggatgacgca caatcccact atccttcgca   5760
agacccttcc tctatataag gaagttcatt tcatttggag agaacacggg ggactctaat   5820
caaacaagtt tgtacaaaaa agctgaacga gaaacgtaaa atgatataat ggcgttcgat   5880
ctcaagactg aagacggcct catcacatat ctcactaaac atctttcttt ggacgtcgac   5940
acgagcggag tgaagcgcct tagcggaggc tttgtcaatg taacctggcg cattaagctc   6000
aatgctcctt atcaaggtca tacgagcatc atcctgaagc atgctcagcc gcacatgtct   6060
acggatgagg attttaagat aggtgtagaa cgttcggttt acgaatacca ggctatcaag   6120
ctcatgatgg ccaatcggga ggttctggga ggcgtggatg gcatagtttc tgtgccagaa   6180
ggcctgaact acgacttaga gaataatgca ttgatcatgc aagatgtcgg gaagatgaag   6240
acccttttag attatgtcac cgccaaaccg ccacttgcga cggatatagc ccgccttgtt   6300
gggacagaaa ttggggggtt cgttgccaga ctccataaca taggccgcga gaggcgagac   6360
gatcctgagt tcaaattctt ctctggaaat attgtcggaa ggacgacttc agaccagctg   6420
tatcaaacca tcatacccaa cgcagcgaaa tatggcgtcg atgacccctt gctgcctact   6480
gtggttaagg accttgtgga cgatgtcatg cacagcgaag agacccttgt catggcggac   6540
ctgtggagtg gaaatattct tctccagttg gaggagggaa acccatcgaa gctgcagaag   6600
atatatatcc tggattggga actttgcaag tacggcccag cgtcgttgga cctgggctat   6660
ttcttgggtg actgctattt gatatcccgc tttcaagacg agcaggtcgg tacgacgatg   6720
cggcaagcct acttgcaaag ctatgcgcgt acgagcaagc attcgatcaa ctacgccaaa   6780
gtcactgcag gtattgctgc tcatattgtg atgtggaccg actttatgca gtgggggagc   6840
gaggaagaaa ggataaattt tgtgaaaaag gggtagctg cctttcacga cgccaggggc    6900
aacaacgaca atggggaaat tacgtctacc ttactgaagg aatcatccac tgcgtaaatc   6960
attttacgtt tctcgttcag ctttcttgta caaagtggtt cgatctagag gatccatggt   7020
gagcaagggc gaggagctgt tcaccggggt ggtgcccatc ctggtcgagc tggacggcga   7080
cgtgaacggc cacaagttca gcgtgtccgg cgagggcgag ggcgatgcca cctacggcaa   7140
gctgaccctg aagttcatct gcaccaccgg caagctgccc gtgccctggc ccaccctcgt   7200
gaccaccttc acctacggcg tgcagtgctt cagccgctac cccgaccaca tgaagcagca   7260
cgacttcttc aagtccgcca tgcccgaagg ctacgtccag gagcgcacca tcttcttcaa   7320
ggacgacggc aactacaaga cccgcgccga ggtgaagttc gagggcgaca ccctggtgaa   7380
ccgcatcgag ctgaagggca tcgacttcaa ggaggacggc aacatcctgg ggcacaagct   7440
ggagtacaac tacaacagcc acaacgtcta tatcatggcc gacaagcaga agaacggcat   7500
caaggtgaac ttcaagatcc gccacaacat cgaggacggc agcgtgcagc tcgccgacca   7560
ctaccagcag aacaccccca tcggcgacgg ccccgtgctg ctgcccgaca accactacct   7620
gagcacccag tccgccctga gcaaagaccc caacgagaag cgcgatcaca tggtcctgct   7680
ggagttcgtg accgccgccg ggatcactca cggcatggac gagctgtaca agtaaagcgg   7740
cccgagctcg aatttccccg atcgttcaaa catttggcaa taaagtttct taagattgaa   7800
tcctgttgcc ggtcttgcga tgattatcat ataatttctg ttgaattacg ttaagcatgt   7860
aataattaac atgtaatgca tgacgttatt tatgagatgg gtttttatga ttagagtccc   7920
```

-continued

```
gcaattatac atttaatacg cgatagaaaa caaaatatag cgcgcaaact aggataaatt   7980
atcgcgcgcg gtgtcatcta tgttactaga tcgggaatta gcttcatcaa cgcaagacat   8040
gcgcacgacc gtctgacagg agaggaattt ccgacgagca cagaaaggac ttgctcttgg   8100
acgtaggcct atttctcagg cacatgtatc aagtgttcgg acgtgggttt tcgatggtgt   8160
atcagccgcc gccaactggg agatgaggag gctttcttgg ggggcagtca gcagttcatt   8220
tcacaagaca gaggaacttg taaggagatg cactgattta tcttggcgca aaccagcagg   8280
acgaattagt gggaatagcc cgcgaatatc taagttatgc ctgtcggcat gagcagaaac   8340
ttccaattcg aaacagtttg gagaggttgt ttttgggcat accttttgtt agtcagcctc   8400
tcgattgctc atcgtcatta cacagtaccg aagtttgatc gatctagtaa catagatgac   8460
accgcgcgcg ataatttatc ctagtttgcg cgctatattt tgttttctat cgcgtattaa   8520
atgtataatt gcgggactct aatcataaaa acccatctca taaataacgt catgcattac   8580
atgttaatta ttacatgctt aacgtaattc aacagaaatt atatgataat catcgcaaga   8640
ccggcaacag gattcaatct taagaaactt tattgccaaa tgtttgaacg atctgcttcg   8700
acgcactcct tctttactcc accatctcgt ccttattgaa aacgtgggta gcaccaaaac   8760
gaatcaagtc gctggaactg aagttaccaa tcacgctgga tgatttgcca gttggattaa   8820
tcttgccttt ccccgcatga ataatattga tgaatgcatg cgtgaggggt atttcgattt   8880
tggcaatagc tgcaattgcc gcgacatcct ccaacgagca taattcttca gaaaaatagc   8940
gatgttccat gttgtcaggg catgcatgat gcacgttatg aggtgacggt gctaggcagt   9000
attccctcaa agtttcatag tcagtatcat attcatcatt gcattcctgc aagagagaat   9060
tgagacgcaa tccacacgct gcggcaacct tccggcgttc gtggtctatt tgctcttgga   9120
cgttgcaaac gtaagtgttg gatcccggtc ggcatctact ctattccttt gccctcggac   9180
gagtgctggg gcgtcggttt ccactatcgg cgagtacttc tacacagcca tcggtccaga   9240
cggccgcgct tctgcgggcg atttgtgtac gcccgacagt cccggctccg gatcggacga   9300
ttgcgtcgca tcgaccctgc gcccaagctg catcatcgaa attgccgtca accaagctct   9360
gatagagttg gtcaagacca atgcggagca tatacgcccg gagccgcggc gatcctgcaa   9420
gctccggatg cctccgctcg aagtagcgcg tctgctgctc catacaagcc aaccacggcc   9480
tccagaagaa gatgttggcg acctcgtatt gggaatcccc gaacatcgcc tcgctccagt   9540
caatgaccgc tgttatgcgg ccattgtccg tcaggacatt gttggagccg aaatccgcgt   9600
gcacgaggtg ccggacttcg ggcagtcct cggcccaaag catcagctca tcgagagcct    9660
gcgcgacgga cgcactgacg gtgtcgtcca tcacagtttg ccagtgatac acatggggat   9720
cagcaatcgc gcatatgaaa tcacgccatg tagtgtattg accgattcct tgcggtccga   9780
atgggccgaa cccgctcgtc tggctaagat cggccgcagc gatcgcatcc atggcctccg   9840
cgaccggctg cagaacagcg ggcagttcgg tttcaggcag gtcttgcaac gtgacaccct   9900
gtgcacggcg ggagatgcaa taggtcaggc tctcgctgaa ttccccaatg tcaagcactt   9960
ccggaatcgg gagcgcggcc gatgcaaagt gccgataaac ataacgatct ttgtagaaac  10020
catcggcgca gctatttacc cgcaggacat atccacgccc tcctacatcg aagctgaaag  10080
cacgagattc ttcgccctcc gagagctgca tcaggtcgga gacgctgtcg aacttttcga  10140
tcagaaactt ctcgacagac gtcgcggtga gttcaggctt tttcatatcg ggtcgtcct   10200
ctccaaatga aatgaacttc cttatataga ggaagggtct tgcgaaggat agtgggattg  10260
tgcgtcatcc cttacgtcag tggagatatc acatcaatcc acttgctttg aagacgtggt  10320
```

```
tggaacgtct tctttttcca cgatgctcct cgtgggtggg ggtccatctt tgggaccact  10380
gtcggcagag gcatcttgaa cgatagcctt tcctttatcg caatgatggc atttgtaggt  10440
gccaccttcc ttttctactg tccttttgat gaagtgacag atagctgggc aatggaatcc  10500
gaggaggttt cccgatatta ccctttgttg aaaagtctca atagcccttt ggtcttctga  10560
gactgtatct ttgatattct tggagtagac gagagtgtcg tgctccacca tgttgacgga  10620
tctctaggac gcgtcctaga agctaattca ctggccgtcg ttttacaacg tcgtgactgg  10680
gaaaaccctg gcgttaccca acttaatcgc cttgcagcac atcccccttt cgccagctgg  10740
cgtaatagcg aagaggcccg caccgatcgc ccttcccaac agttgcgcag cctgaatggc  10800
gcccgctcct ttcgctttct tcccttcctt tctcgccacg ttcgccggct ttccccgtca  10860
agctctaaat cgggggctcc ctttagggtt ccgatttagt gctttacggc acctcgaccc  10920
caaaaaactt gatttgggtg atggttcacg tagtgggcca tcgccctgat agacggtttt  10980
tcgccctttg acgttggagt ccacgttctt taatagtgga ctcttgttcc aaactggaac  11040
aacactcaac cctatctcgg gctattcttt tgatttataa gggattttgc cgatttcgga  11100
accaccatca aacaggattt tcgcctgctg gggcaaacca gcgtggaccg cttgctgcaa  11160
ctctctcagg gccaggcggt gaagggcaat cagctgttgc ccgtctcact ggtgaaaaga  11220
aaaaccaccc cagtacatta aaaacgtccg caatgtgtta ttaagttgtc taagcgtcaa  11280
tttgtttaca ccacaatata tcctgccacc agccagccaa cagctccccg accggcagct  11340
cggcacaaaa tcaccactcg atacaggcag cccatcagtc cgggacggcg tcagcgggag  11400
agccgttgta aggcggcaga ctttgctcat gttaccgatg ctattcggaa gaacggcaac  11460
taagctgccg ggtttgaaac acggatgatc tcgcggaggg tagcatgttg attgtaacga  11520
tgacagagcg ttgctgcctg tgatcaaata tcatctccct cgcagagatc cgaattatca  11580
gccttcttat tcatttctcg cttaaccgtg acaggctgtc gatcttgaga actatgccga  11640
cataatagga aatcgctgga taaagccgct gaggaagctg agtggcgcta tttctttaga  11700
agtgaacgtt gacgatatca actcccctat ccattgctca ccgaatggta caggtcgggg  11760
acccgaagtt ccgactgtcg gcctgatgca tccccggctg atcgacccca gatctggggc  11820
tgagaaagcc cagtaaggaa acaactgtag gttcgagtcg cgagatcccc cggaaccaaa  11880
ggaagtaggt taaacccgct ccgatcaggc cgagccacgc caggccgaga acattggttc  11940
ctgtaggcat cgggattggc ggatcaaaca ctaaagctac tggaacgagc agaagtcctc  12000
cggccgccag ttgccaggcg gtaaaggtga gcagaggcac gggaggttgc cacttgcggg  12060
tcagcacggt tccgaacgcc atggaaaccg cccccgccag gcccgctgcg acgccgacag  12120
gatctagcgc tgcgtttggt gtcaacacca acagcgccac gcccgcagtt ccgcaaatag  12180
cccccaggac cgccatcaat cgtatcgggc tacctagcag agcggcagag atgaacacga  12240
ccatcagcgg ctgcacagcg cctaccgtcg ccgcgacccc gcccggcagg cggtagaccg  12300
aaataaacaa caagctccag aatagcgaaa tattaagtgc gccgaggatg aagatgcgca  12360
tccaccagat tcccgttgga atctgtcgga cgatcatcac gagcaataaa cccgccggca  12420
acgcccgcag cagcataccg gcgacccctc ggcctcgctg ttcgggctcc acgaaaacgc  12480
cggacagatg cgccttgtga gcgtccttgg ggccgtcctc ctgtttgaag accgacagcc  12540
caatgatctc gccgtcgatg taggcgccga atgccacggc atctcgcaac cgttcagcga  12600
acgcctccat gggctttttc tcctcgtgct cgtaaacgga cccgaacatc tctggagctt  12660
```

-continued

```
tcttcagggc cgacaatcgg atctcgcgga aatcctgcac gtcggccgct ccaagccgtc  12720
gaatctgagc cttaatcaca attgtcaatt ttaatcctct gtttatcggc agttcgtaga  12780
gcgcgccgtg cgtcccgagc gatactgagc gaagcaagtg cgtcgagcag tgcccgcttg  12840
ttcctgaaat gccagtaaag cgctggctgc tgaacccccca gccggaactg accccacaag  12900
gccctagcgt ttgcaatgca ccaggtcatc attgacccag gcgtgttcca ccaggccgct  12960
gcctcgcaac tcttcgcagg cttcgccgac ctgctcgcgc cacttcttca cgcgggtgga  13020
atccgatccg cacatgaggc ggaaggtttc cagcttgagc gggtacggct cccggtgcga  13080
gctgaaatag tcgaacatcc gtcgggccgt cggcgacagc ttgcggtact tctcccatat  13140
gaatttcgtg tagtggtcgc cagcaaacag cacgacgatt tcctcgtcga tcaggacctg  13200
gcaacgggac gttttcttgc cacggtccag gacgcggaag cggtgcagca gcgacaccga  13260
ttccaggtgc ccaacgcggt cggacgtgaa gcccatcgcc gtcgcctgta ggcgcgacag  13320
gcattcctcg gccttcgtgt aataccggcc attgatcgac cagcccaggt cctggcaaag  13380
ctcgtagaac gtgaaggtga tcggctcgcc gatagggggtg cgcttcgcgt actccaacac  13440
ctgctgccac accagttcgt catcgtcggc ccgcagctcg acgccggtgt aggtgatctt  13500
cacgtccttg ttgacgtgga aaatgacctt gttttgcagc gcctcgcgcg ggattttctt  13560
gttgcgcgtg gtgaacaggg cagagcgggc cgtgtcgttt ggcatcgctc gcatcgtgtc  13620
cggccacggc gcaatatcga acaaggaaag ctgcatttcc ttgatctgct gcttcgtgtg  13680
tttcagcaac gcggcctgct tggcctcgct gacctgtttt gccaggtcct cgccggcggt  13740
ttttcgcttc ttggtcgtca tagttcctcg cgtgtcgatg gtcatcgact tcgccaaacc  13800
tgccgcctcc tgttcgagac gacgcgaacg ctccacggcg gccgatggcg cgggcagggc  13860
agggggagcc agttgcacgc tgtcgcgctc gatcttggcc gtagcttgct ggaccatcga  13920
gccgacggac tggaaggttt cgcggggcgc acgcatgacg gtgcggcttg cgatggtttc  13980
ggcatcctcg gcggaaaacc ccgcgtcgat cagttcttgc ctgtatgcct tccggtcaaa  14040
cgtccgattc attcaccctc cttgcgggat tgccccgact cacgccgggg caatgtgccc  14100
ttattcctga tttgacccgc ctggtgcctt ggtgtccaga taatccacct tatcggcaat  14160
gaagtcggtc ccgtagaccg tctggccgtc cttctcgtac ttggtattcc gaatcttgcc  14220
ctgcacgaat accagcgacc ccttgcccaa atacttgccg tgggcctcgg cctgagagcc  14280
aaaacacttg atgcggaaga agtcggtgcg ctcctgcttg tcgccggcat cgttgcgcca  14340
catctaggta ctaaaacaat tcatccagta aaatataata ttttattttc tcccaatcag  14400
gcttgatccc cagtaagtca aaaaatagct cgacatactg ttcttccccg atatcctccc  14460
tgatcgaccg gacgcagaag gcaatgtcat accacttgtc cgccctgccg cttctcccaa  14520
gatcaataaa gccacttact ttgccatctt tcacaaagat gttgctgtct cccaggtcgc  14580
cgtgggaaaa gacaagttcc tcttcgggct tttccgtctt taaaaaatca tacagctcgc  14640
gcggatcttt aaatggagtg tcttcttccc agttttcgca atccacatcg gccagatcgt  14700
tattcagtaa gtaatccaat tcggctaagc ggctgtctaa gctattcgta tagggacaat  14760
ccgatatgtc gatggagtga aagagcctga tgcactccgc atacagctcg ataatctttt  14820
cagggctttg ttcatcttca tactcttccg agcaaaggac gccatcggcc tcactcatga  14880
gcagattgct ccagccatca tgccgttcaa agtgcaggac ctttggaaca ggcagctttc  14940
cttccagcca tagcatcatg tccttttccc gttccacatc ataggtggtc cctttatacc  15000
ggctgtccgt catttttaaa tataggtttt cattttctcc caccagctta tataccttag  15060
```

-continued

```
caggagacat tccttccgta tcttttacgc agcggtattt ttcgatcagt tttttcaatt  15120
ccggtgatat tctcatttta gccatttatt atttccttcc tcttttctac agtatttaaa  15180
gataccccaa gaagctaatt ataacaagac gaactccaat tcactgttcc ttgcattcta  15240
aaaccttaaa taccagaaaa cagctttttc aaagttgttt tcaaagttgg cgtataacat  15300
agtatcgacg gagccgattt tgaaaccaca attatgggtg atgctgccaa cttactgatt  15360
tagtgtatga tggtgttttt gaggtgctcc agtggcttct gtgtctatca gctgtccctc  15420
ctgttcagct actgacgggg tggtgcgtaa cggcaaaagc accgccggac atcagcgcta  15480
tctctgctct cactgccgta aaacatggca actgcagttc acttacaccg cttctcaacc  15540
cggtacgcac cagaaaatca ttgatatggc catgaatggc gttggatgcc gggcaacagc  15600
ccgcattatg ggcgttggcc tcaacacgat tttacgtcac ttaaaaaact caggccgcag  15660
tcggtaacct cgcgcataca gccgggcagt gacgtcatcg tctgcgcgga aatggacgaa  15720
cagtggggct atgtcggggc taaatcgcgc cagcgctggc tgttttacgc gtatgacagt  15780
ctccggaaga cggttgttgc gcacgtattc ggtgaacgca ctatggcgac gctggggcgt  15840
cttatgagcc tgctgtcacc ctttgacgtg gtgatatgga tgacggatgg ctggccgctg  15900
tatgaatccc gcctgaaggg aaagctgcac gtaatcagca agcgatatac gcagcgaatt  15960
gagcggcata acctgaatct gaggcagcac ctggcacggc tgggacggaa gtcgctgtcg  16020
ttctcaaaat cggtggagct gcatgacaaa gtcatcgggc attatctgaa cataaaacac  16080
tatcaataag ttggagtcat tacccaatta tgatagaatt tacaagctat aaggttattg  16140
tcctgggttt caagcattag tccatgcaag tttttatgct ttgcccattc tatagatata  16200
ttgataagcg cgctgcctat gccttgcccc ctgaaatcct tacatacggc gatatcttct  16260
atataaaaga tatattatct tatcagtatt gtcaatatat tcaaggcaat ctgcctcctc  16320
atcctcttca tcctcttcgt cttggtagct ttttaaatat ggcgcttcat agagtaattc  16380
tgtaaaggtc caattctcgt tttcatacct cggtataatc ttacctatca cctcaaatgg  16440
ttcgctgggt ttatcgcacc cccgaacacg agcacggcac ccgcgaccac tatgccaaga  16500
atgcccaagg taaaaattgc cggccccgcc atgaagtccg tgaatgcccc gacggccgaa  16560
gtgaagggca ggccgccacc caggccgccg ccctcactgc ccggcacctg gtcgctgaat  16620
gtcgatgcca gcacctgcgg cacgtcaatg cttccgggcg tcgcgctcgg gctgatcgcc  16680
catcccgtta ctgccccgat cccggcaatg gcaaggactg ccagcgctgc catttttggg  16740
gtgaggccgt tcgcggccga ggggcgcagc ccctgggggg atgggaggcc cgcgttagcg  16800
ggccgggagg gttcgagaag ggggggcacc ccccttcggc gtgcgcggtc acgcgcacag  16860
ggcgcagccc tggttaaaaa caaggtttat aaatattggt ttaaaagcag gttaaaagac  16920
aggttagcgg tggccgaaaa acgggcggaa acccttgcaa atgctggatt ttctgcctgt  16980
ggacagcccc tcaaatgtca ataggtgcgc ccctcatctg tcagcactct gcccctcaag  17040
tgtcaaggat cgcgcccctc atctgtcagt agtcgcgccc ctcaagtgtc aataccgcag  17100
ggcacttatc cccaggcttg tccacatcat ctgtgggaaa ctcgcgtaaa atcaggcgtt  17160
ttcgccgatt tgcgaggctg gccagctcca cgtcgccggc cgaaatcgag cctgcccctc  17220
atctgtcaac gccgcgccgg gtgagtcggc ccctcaagtg tcaacgtccg cccctcatct  17280
gtcagtgagg gccaagtttt ccgcgaggta tccacaacgc cggcggccgc ggtgtctcgc  17340
acacggcttc gacggcgttt ctggcgcgtt tgcagggcca tagacggccg ccagcccagc  17400
```

-continued ggcgagggca accagcccgg 17420

<210> SEQ ID NO 17
<211> LENGTH: 18494
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 17
tgagcgtcgc aaaggcgctc ggtcttgcct tgctcgtcgg tgatgtactt caccagctcc 60
gcgaagtcgc tcttcttgat ggagcgcatg ggacgtgct tggcaatcac gcgcaccccc 120
cggccgtttt agcggctaaa aaagtcatgg ctctgccctc gggcggacca cgcccatcat 180
gaccttgcca agctcgtcct gcttctcttc gatcttcgcc agcagggcga ggatcgtggc 240
atcaccgaac cgcgccgtgc gcgggtcgtc ggtgagccag agtttcagca ggccgcccag 300
gcggcccagg tcgccattga tgcgggccag ctcgcggacg tgctcatagt ccacgacgcc 360
cgtgattttg tagccctggc cgacggccag caggtaggcc gacaggctca tgccggccgc 420
cgccgccttt tcctcaatcg ctcttcgttc gtctggaagg cagtacacct tgataggtgg 480
gctgcccttc ctggttggct tggtttcatc agccatccgc ttgccctcat ctgttacgcc 540
ggcggtagcc ggccagcctc gcagagcagg attcccgttg agcaccgcca ggtgcgaata 600
agggacagtg aagaaggaac acccgctcgc gggtgggcct acttcaccta tcctgcccgg 660
ctgacgccgt tggatacacc aaggaaagtc tacacgaacc ctttggcaaa atcctgtata 720
tcgtgcgaaa aaggatggat ataccgaaaa aatcgctata atgaccccga agcagggtta 780
tgcagcggaa aagcgccacg cttcccgaag ggagaaaggc ggacaggtat ccggtaagcg 840
gcagggtcgg aacaggagag cgcacgaggg agcttccagg gggaaacgcc tggtatcttt 900
atagtcctgt cgggtttcgc cacctctgac ttgagcgtcg atttttgtga tgctcgtcag 960
gggggcggag cctatggaaa aacgccagca acgcggcctt tttacggttc ctggcctttt 1020
gctggccttt tgctcacatg ttctttcctg cgttatcccc tgattctgtg gataaccgta 1080
ttaccgcctt tgagtgagct gataccgctc gccgcagccg aacgaccgag cgcagcgagt 1140
cagtgagcga ggaagcggaa gagcgccaga aggccgccag agaggccgag cgcggccgtg 1200
aggcttggac gctagggcag ggcatgaaaa agcccgtagc gggctgctac gggcgtctga 1260
cgcggtggaa agggggaggg gatgttgtct acatggctct gctgtagtga gtgggttgcg 1320
ctccggcagc ggtcctgatc aatcgtcacc ctttctcggt ccttcaacgt tcctgacaac 1380
gagcctcctt ttcgccaatc catcgacaat caccgcgagt ccctgctcga acgctgcgtc 1440
cggaccggct tcgtcgaagg cgtctatcgc ggcccgcaac agcggcgaga gcggagcctg 1500
ttcaacggtg ccgccgcgct cgccggcatc gctgtcgccg gcctgctcct caagcacggc 1560
cccaacagtg aagtagctga ttgtcatcag cgcattgacg gcgtccccgg ccgaaaaacc 1620
cgcctcgcag aggaagcgaa gctgcgcgtc ggccgtttcc atctgcggtg cgcccggtcg 1680
cgtgccggca tggatgcgcg cgccatcgcg gtaggcgagc agcgcctgcc tgaagctgcg 1740
ggcattcccg atcagaaatg agcgccagtc gtcgtcggct ctcggcaccg aatgcgtatg 1800
attctccgcc agcatggctt cggccagtgc gtcgagcagc gcccgcttgt tcctgaagtg 1860
ccagtaaagc gccggctgct gaacccccaa ccgttccgcc agtttgcgtg tcgtcagacc 1920
gtctacgccg acctcgttca acaggtccag ggcggcacgg atcactgtat tcggctgcaa 1980

-continued

```
ctttgtcatg cttgacactt tatcactgat aaacataata tgtccaccaa cttatcagtg   2040
ataaagaatc cgcgcgttca atcggaccag cggaggctgg tccggaggcc agacgtgaaa   2100
cccaacatac ccctgatcgt aattctgagc actgtcgcgc tcgacgctgt cggcatcggc   2160
ctgattatgc cggtgctgcc gggcctcctg cgcgatctgg ttcactcgaa cgacgtcacc   2220
gcccactatg gcattctgct ggcgctgtat gcgttggtgc aatttgcctg cgcacctgtg   2280
ctgggcgcgc tgtcggatcg tttcgggcgg cggccaatct tgctcgtctc gctggccggc   2340
gccagatctg gggaaccctg tggttggcat gcacatacaa atggacgaac ggataaacct   2400
tttcacgccc ttttaaatat ccgattattc taataaacgc tcttttctct taggtttacc   2460
cgccaatata tcctgtcaaa cactgatagt ttaaactgaa ggcgggaaac gacaatctga   2520
tcatgagcgg agaattaagg gagtcacgtt atgacccccg ccgatgacgc gggacaagcc   2580
gttttacgtt tggaactgac agaaccgcaa cgttgaagga gccactcagc cgcgggtttc   2640
tggagtttaa tgagctaagc acatacgtca gaaaccatta ttgcgcgttc aaaagtcgcc   2700
taaggtcact atcagctagc aaatatttct tgtcaaaaat gctccactga cgttccataa   2760
attcccctcg gtatccaatt agagtctcat attcactctc aatccaaata atctgcaccg   2820
gatctggatc gtttcgcatg attgaacaag atggattgca cgcaggttct ccggccgctt   2880
gggtggagag gctattcggc tatgactggg cacaacagac aatcggctgc tctgatgccg   2940
ccgtgttccg gctgtcagcg caggggcgcc cggttctttt tgtcaagacc gacctgtccg   3000
gtgccctgaa tgaactgcag gacgaggcag cgcggctatc gtggctggcc acgacgggcg   3060
ttccttgcgc agctgtgctc gacgttgtca ctgaagcggg aagggactgg ctgctattgg   3120
gcgaagtgcc ggggcaggat ctcctgtcat ctcaccttgc tcctgccgag aaagtatcca   3180
tcatggctga tgcaatgcgg cggctgcata cgcttgatcc ggctacctgc ccattcgacc   3240
accaagcgaa acatcgcatc gagcgagcac gtactcggat ggaagccggt cttgtcgatc   3300
aggatgatct ggacgaagag catcaggggc tcgcgccagc cgaactgttc gccaggctca   3360
aggcgcgcat gcccgacggc gatgatctcg tcgtgaccca tggcgatgcc tgcttgccga   3420
atatcatggt ggaaaatggc cgcttttctg gattcatcga ctgtggccgg ctgggtgtgg   3480
cggaccgcta tcaggacata gcgttggcta cccgtgatat tgctgaagag cttggcggcg   3540
aatgggctga ccgcttcctc gtgctttacg gtatcgccgc tcccgattcg cagcgcatcg   3600
ccttctatcg ccttcttgac gagttcttct gagcgggact ctggggttcg aaatgaccga   3660
ccaagcgacg cccaacctgc catcacgaga tttcgattcc accgccgcct tctatgaaag   3720
gttgggcttc ggaatcgttt tccgggacgc cggctggatg atcctccagc gcggggatct   3780
catgctggag ttcttcgccc acgggatctc tgcggaacag gcggtcgaag gtgccgatat   3840
cattacgaca gcaacggccg acaagcacaa cgccacgatc ctgagcgaca atatgatcgg   3900
gcccggcgtc cacatcaacg gcgtcggcgg cgactgccca ggcaagaccg agatgcaccg   3960
cgatatcttg ctgcgttcgg atattttcgt ggagttcccg ccacagaccc ggatgatccc   4020
cgatcgttca aacatttggc aataaagttt cttaagattg aatcctgttg ccggtcttgc   4080
gatgattatc atataatttc tgttgaatta cgttaagcat gtaataatta acatgtaatg   4140
catgacgtta tttatgagat gggtttttat gattagagtc ccgcaattat acatttaata   4200
cgcgatagaa aacaaaatat agcgcgcaaa ctaggataaa ttatcgcgcg cggtgtcatc   4260
tatgttacta gatcgggcct cctgtcaatg ctggcggcgg ctctggtggt ggttctggtg   4320
gcggctctga gggtggtggc tctgagggtg gcggttctga gggtggcggc tctgagggag   4380
```

```
gcggttccgg tggtggctct ggttccggtg attttgatta tgaaaagatg gcaaacgcta   4440
ataagggggc tatgaccgaa aatgccgatg aaaacgcgct acagtctgac gctaaaggca   4500
aacttgattc tgtcgctact gattacggtg ctgctatcga tggtttcatt ggtgacgttt   4560
ccggccttgc taatggtaat ggtgctactg gtgattttgc tggctctaat tcccaaatgg   4620
ctcaagtcgg tgacggtgat aattcacctt taatgaataa tttccgtcaa tatttacctt   4680
ccctccctca atcggttgaa tgtcgccctt ttgtctttgg cccaatacgc aaaccgcctc   4740
tccccgcgcg ttggccgatt cattaatgca gctggcacga caggtttccc gactggaaag   4800
cgggcagtga gcgcaacgca attaatgtga gttagctcac tcattaggca ccccaggctt   4860
tacactttat gcttccggct cgtatgttgt gtggaattgt gagcggataa caatttcaca   4920
caggaaacag ctatgaccat gattacgcca agcttgcatg cctgcaggtc cccagattag   4980
ccttttcaat ttcagaaaga atgctaaccc acagatggtt agagaggctt acgcagcagg   5040
tctcatcaag acgatctacc cgagcaataa tctccaggaa atcaaatacc ttcccaagaa   5100
ggttaaagat gcagtcaaaa gattcaggac taactgcatc aagaacacag agaaagatat   5160
atttctcaag atcagaagta ctattccagt atggacgatt caaggcttgc ttcacaaacc   5220
aaggcaagta atagagattg gagtctctaa aaaggtagtt cccactgaat caaaggccat   5280
ggagtcaaag attcaaatag aggacctaac agaactcgcc gtaaagactg gcgaacagtt   5340
catacagagt ctcttacgac tcaatgacaa gaagaaaatc ttcgtcaaca tggtggagca   5400
cgacacactt gtctactcca aaaatatcaa agatacagtc tcagaagacc aaagggcaat   5460
tgagactttt caacaaaggg taatatccgg aaacctcctc ggattccatt gcccagctat   5520
ctgtcacttt attgtgaaga tagtggaaaa ggaaggtggc tcctacaaat gccatcattg   5580
cgataaagga aaggccatcg ttgaagatgc ctctgccgac agtggtccca aagatggacc   5640
cccacccacg aggagcatcg tggaaaaaga agacgttcca accacgtctt caaagcaagt   5700
ggattgatgt gatatctcca ctgacgtaag ggatgacgca caatcccact atccttcgca   5760
agacccttcc tctatataag gaagttcatt tcatttggag agaacacggg ggactctaat   5820
caaacaagtt tgtacaaaaa agctgaacga gaaacgtaaa atgatataaa tatcatgatc   5880
gctgtactat tctccttcgt cattgcagga tgcatatact acatcgtttc tcgtagagtg   5940
aggcggtcgc gcttgccacc agggccgcct ggcattccta ttcccttcat tgggaacatg   6000
tttgatatgc ctgaagaatc tccatggtta acatttctac aatggggacg ggattacagt   6060
ctgtcttgcc gcgttgactt ctaatatatg aacagctaat atattgtcag acaccgatat   6120
tctctacgtg gatgctggag ggacagaaat ggttattctt aacacgttgg agaccattac   6180
cgatctatta gaaaagcgag ggtccattta ttctggccgg tgagctgatg ttgagttttt   6240
tgcaattgaa tttgtggtca cacgtttcca gacttgagag tacaatggtc aacgaactta   6300
tggggtggga gtttgactta gggttcatca catacggcga caggtggcgc gaagaaaggc   6360
gcatgttcgc caaggagttc agtgagaagg gcatcaagca atttcgccat gctcaagtga   6420
aagctgccca tcagcttgtc caacagctta ccaaaacgcc agaccgctgg gcacaacata   6480
ttcgccagta agtactactt gaggaaaata gcgtacgctt cgctgaccgg tccgtacatc   6540
aaagtcagat agcggcaatg tcactggata ttggttatgg aattgatctt gcagaagacg   6600
acccttggct ggaagcgacc catttggcta atgaaggcct cgccatagca tcagtgccgg   6660
gcaaattttg ggtcgattcg ttcccttctc gtgagcatcc ttcttctatg taggaaggga   6720
```

```
aggagtctaa caagtgttag taaaatacct tcctgcttgg ttcccaggtg ctgtcttcaa   6780
gcgcaaagcg aaggtctggc gagaagccgc cgaccatatg gttgacatgc cttatgaaac   6840
tatgaggaaa ttagcagtta gtcaaatgcg ttctccccgt attttttcaa tactctaact   6900
tcagctcaca gcctcaagga ttgactcgtc cgtcgtatgc ttcagctcgt ctgcaagcca   6960
tggatctcaa cggtgacctt gagcatcaag aacacgtaat caagaacaca gccgcagagg   7020
ttaatgtcgg taagtcaaaa gcgtccgtcg gcaattcaaa attcaggcgc taaagtgggt   7080
cttctcacca aggtggaggc gatactgtaa ggatttctca atcgttagag tataagtgtt   7140
ctaatgcagt acatactcca ccaaccagac tgtctctgct atgtctgcgt tcatcttggc   7200
catggtgaag taccctgagg tccagcgaaa ggttcaagcg gagcttgatg ctctgaccaa   7260
taacggccaa attcctgact atgacgaaga agatgactcc ttgccatacc tcaccgcatg   7320
tatcaaggag cttttccggt ggaatcaaat cgcacccctc gctataccgc acaaattaat   7380
gaaggacgac gtgtaccgcg ggtatctgat tcccaagaac actctagtct tcgcaaacac   7440
ctggtgaggc tgtccattca ttcctagtac atccgttgcc ccactaatag catcttgata   7500
acagggcagt attaaacgat ccagaagtct atccagatcc ctctgtgttc cgcccagaaa   7560
gatatcttgg tcctgacggg aagcctgata acactgtacg cgacccacgt aaagcggcat   7620
ttggctatgg acgacgaaat tggtaagtgc gctttcagaa ccccccctc cgttgactag   7680
tgccatgcgc gcatacaata tcgctattga tctgatataa cttccctgcg gcatttattt   7740
tggcattcct ttagtcccgg aattcatcta gcgcagtcga cggtttggat tgcaggggca   7800
accctcttat cagcgttcaa tatcgagcga cctgtcgatc agaatgggaa gcccattgac   7860
ataccggctg attttactac aggattcttc aggtagctaa tttccgtctt tgtgtgcata   7920
atacccctaa cgacgcacgt ttaccttttt gtaaagacac ccagtgcctt tccagtgcag   7980
gtttgttcct cgaacagagc aagtctcaca gtcggtatcc ggaccctgaa tatcatttta   8040
cgtttctcgt tcagctttct tgtacaaagt ggttcgatct agaggatcca tggtgagcaa   8100
gggcgaggag ctgttcaccg gggtggtgcc catcctggtc gagctggacg gcgacgtgaa   8160
cggccacaag ttcagcgtgt ccggcgaggg cgagggcgat gccacctacg gcaagctgac   8220
cctgaagttc atctgcacca ccggcaagct gcccgtgccc tggcccaccc tcgtgaccac   8280
cttcacctac ggcgtgcagt gcttcagccg ctaccccgac cacatgaagc agcacgactt   8340
cttcaagtcc gccatgcccg aaggctacgt ccaggagcgc accatcttct tcaaggacga   8400
cggcaactac aagacccgcg ccgaggtgaa gttcgagggc gacaccctgg tgaaccgcat   8460
cgagctgaag ggcatcgact tcaaggagga cggcaacatc ctggggcaca agctggagta   8520
caactacaac agccacaacg tctatatcat ggccgacaag cagaagaacg gcatcaaggt   8580
gaacttcaag atccgccaca acatcgagga cggcagcgtg cagctcgccg accactacca   8640
gcagaacacc cccatcggcg acggccccgt gctgctgccc gacaaccact acctgagcac   8700
ccagtccgcc ctgagcaaag accccaacga gaagcgcgat cacatggtcc tgctggagtt   8760
cgtgaccgcc gccgggatca ctcacggcat ggacgagctg tacaagtaaa gcggcccgag   8820
ctcgaatttc cccgatcgtt caaacatttg gcaataaagt ttcttaagat tgaatcctgt   8880
tgccggtctt gcgatgatta tcatataatt tctgttgaat tacgttaagc atgtaataat   8940
taacatgtaa tgcatgacgt tatttatgag atgggttttt atgattagag tcccgcaatt   9000
atacatttaa tacgcgatag aaaacaaaat atagcgcgca aactaggata aattatcgcg   9060
cgcggtgtca tctatgttac tagatcggga attagcttca tcaacgcaag acatgcgcac   9120
```

```
gaccgtctga caggagagga atttccgacg agcacagaaa ggacttgctc ttggacgtag   9180
gcctatttct caggcacatg tatcaagtgt tcggacgtgg gttttcgatg gtgtatcagc   9240
cgccgccaac tgggagatga ggaggctttc ttggggggca gtcagcagtt catttcacaa   9300
gacagaggaa cttgtaagga gatgcactga tttatcttgg cgcaaaccag caggacgaat   9360
tagtgggaat agcccgcgaa tatctaagtt atgcctgtcg gcatgagcag aaacttccaa   9420
ttcgaaacag tttggagagg ttgtttttgg gcataccttt tgttagtcag cctctcgatt   9480
gctcatcgtc attacacagt accgaagttt gatcgatcta gtaacataga tgacaccgcg   9540
cgcgataatt tatcctagtt tgcgcgctat attttgtttt ctatcgcgta ttaaatgtat   9600
aattgcggga ctctaatcat aaaaacccat ctcataaata acgtcatgca ttacatgtta   9660
attattacat gcttaacgta attcaacaga aattatatga taatcatcgc aagaccggca   9720
acaggattca atcttaagaa actttattgc caaatgtttg aacgatctgc ttcgacgcac   9780
tccttcttta ctccaccatc tcgtccttat tgaaaacgtg ggtagcacca aaacgaatca   9840
agtcgctgga actgaagtta ccaatcacgc tggatgattt gccagttgga ttaatcttgc   9900
ctttccccgc atgaataata ttgatgaatg catgcgtgag ggtatttcg attttggcaa    9960
tagctgcaat tgcccgcgaca tcctccaacg agcataattc ttcagaaaaa tagcgatgtt  10020
ccatgttgtc agggcatgca tgatgcacgt tatgaggtga cggtgctagg cagtattccc  10080
tcaaagtttc atagtcagta tcatattcat cattgcattc ctgcaagaga gaattgagac  10140
gcaatccaca cgctgcggca accttccggc gttcgtggtc tatttgctct tggacgttgc  10200
aaacgtaagt gttggatccc ggtcggcatc tactctattc ctttgccctc ggacgagtgc  10260
tggggcgtcg gtttccacta tcggcgagta cttctacaca gccatcggtc cagacggccg  10320
cgcttctgcg ggcgatttgt gtacgcccga cagtcccggc tccggatcgg acgattgcgt  10380
cgcatcgacc ctgcgcccaa gctgcatcat cgaaattgcc gtcaaccaag ctctgataga  10440
gttggtcaag accaatgcgg agcatatacg cccggagccg cggcgatcct gcaagctccg  10500
gatgcctccg ctcgaagtag cgcgtctgct gctccataca agccaaccac ggcctccaga  10560
agaagatgtt ggcgacctcg tattgggaat ccccgaacat cgcctcgctc cagtcaatga  10620
ccgctgttat gcggccattg tccgtcagga cattgttgga gccgaaatcc gcgtgcacga  10680
ggtgccggac ttcggggcag tcctcggccc aaagcatcag ctcatcgaga gcctgcgcga  10740
cggacgcact gacggtgtcg tccatcacag tttgccagtg atacacatgg ggatcagcaa  10800
tcgcgcatat gaaatcacgc catgtagtgt attgaccgat tccttgcggt ccgaatgggc  10860
cgaacccgct cgtctggcta agatcggccg cagcgatcgc atccatggcc tccgcgaccg  10920
gctgcagaac agcgggcagt tcggtttcag gcaggtcttg caacgtgaca ccctgtgcac  10980
ggcgggagat gcaataggtc aggctctcgc tgaattcccc aatgtcaagc acttccggaa  11040
tcgggagcgc ggccgatgca aagtgccgat aaacataacg atctttgtag aaaccatcgg  11100
cgcagctatt tacccgcagg acatatccac gccctcctac atcgaagctg aaagcacgag  11160
attcttcgcc ctccgagagc tgcatcaggt cggagacgct gtcgaacttt tcgatcagaa  11220
acttctcgac agacgtcgcg gtgagttcag gctttttcat atcggggtcg tcctctccaa  11280
atgaaatgaa cttccttata tagaggaagg gtcttgcgaa ggatagtggg attgtgcgtc  11340
atcccttacg tcagtggaga tatcacatca atccacttgc tttgaagacg tggttggaac  11400
gtcttctttt tccacgatgc tcctcgtggg tgggggtcca tctttgggac cactgtcggc  11460
```

```
agaggcatct tgaacgatag cctttccttt atcgcaatga tggcatttgt aggtgccacc  11520
ttccttttct actgtccttt tgatgaagtg acagatagct gggcaatgga atccgaggag  11580
gtttcccgat attacccttt gttgaaaagt ctcaatagcc ctttggtctt ctgagactgt  11640
atctttgata ttcttggagt agacgagagt gtcgtgctcc accatgttga cggatctcta  11700
ggacgcgtcc tagaagctaa ttcactggcc gtcgttttac aacgtcgtga ctgggaaaac  11760
cctggcgtta cccaacttaa tcgccttgca gcacatcccc ctttcgccag ctggcgtaat  11820
agcgaagagg cccgcaccga tcgcccttcc caacagttgc gcagcctgaa tggcgcccgc  11880
tcctttcgct ttcttccctt cctttctcgc cacgttcgcc ggctttcccc gtcaagctct  11940
aaatcggggg ctccctttag ggttccgatt tagtgcttta cggcacctcg accccaaaaa  12000
acttgatttg ggtgatggtt cacgtagtgg gccatcgccc tgatagacgg tttttcgccc  12060
tttgacgttg gagtccacgt tctttaatag tggactcttg ttccaaactg gaacaacact  12120
caaccctatc tcgggctatt cttttgattt ataagggatt ttgccgattt cggaaccacc  12180
atcaaacagg attttcgcct gctggggcaa accagcgtgg accgcttgct gcaactctct  12240
cagggccagg cggtgaaggg caatcagctg ttgcccgtct cactggtgaa aagaaaaacc  12300
accccagtac attaaaaacg tccgcaatgt gttattaagt tgtctaagcg tcaatttgtt  12360
tacaccacaa tatatcctgc caccagccag ccaacagctc cccgaccggc agctcggcac  12420
aaaatcacca ctcgatacag gcagcccatc agtccgggac ggcgtcagcg ggagagccgt  12480
tgtaaggcgg cagactttgc tcatgttacc gatgctattc ggaagaacgg caactaagct  12540
gccgggtttg aaacacggat gatctcgcgg agggtagcat gttgattgta acgatgacag  12600
agcgttgctg cctgtgatca aatatcatct ccctcgcaga gatccgaatt atcagccttc  12660
ttattcattt ctcgcttaac cgtgacaggc tgtcgatctt gagaactatg ccgacataat  12720
aggaaatcgc tggataaagc cgctgaggaa gctgagtggc gctatttctt tagaagtgaa  12780
cgttgacgat atcaactccc ctatccattg ctcaccgaat ggtacaggtc ggggacccga  12840
agttccgact gtcggcctga tgcatccccg gctgatcgac cccagatctg gggctgagaa  12900
agcccagtaa ggaaacaact gtaggttcga gtcgcgagat cccccggaac caaaggaagt  12960
aggttaaacc cgctccgatc aggccgagcc acgccaggcc gagaacattg gttcctgtag  13020
gcatcgggat tggcggatca aacactaaag ctactggaac gagcagaagt cctccggccg  13080
ccagttgcca ggcggtaaag gtgagcagag gcacgggagg ttgccacttg cgggtcagca  13140
cggttccgaa cgccatggaa accgcccccg ccaggcccgc tgcgacgccg acaggatcta  13200
gcgctgcgtt tggtgtcaac accaacagcg ccacgcccgc agttccgcaa atagcccca   13260
ggaccgccat caatcgtatc gggctaccta gcagagcggc agagatgaac acgaccatca  13320
gcggctgcac agcgcctacc gtcgccgcga ccccgcccgg caggcggtag accgaaataa  13380
acaacaagct ccagaatagc gaaatattaa gtgcgccgag gatgaagatg cgcatccacc  13440
agattcccgt tggaatctgt cggacgatca tcacgagcaa taaacccgcc ggcaacgccc  13500
gcagcagcat accggcgacc cctcggcctc gctgttcggg ctccacgaaa acgccggaca  13560
gatgcgcctt gtgagcgtcc ttggggccgt cctcctgttt gaagaccgac agcccaatga  13620
tctcgccgtc gatgtaggcg ccgaatgcca cggcatctcg caaccgttca gcgaacgcct  13680
ccatgggctt tttctcctcg tgctcgtaaa cggacccgaa catctctgga gctttcttca  13740
gggccgacaa tcggatctcg cggaaatcct gcacgtcggc cgctccaagc cgtcgaatct  13800
gagccttaat cacaattgtc aattttaatc ctctgtttat cggcagttcg tagagcgcgc  13860
```

```
cgtgcgtccc gagcgatact gagcgaagca agtgcgtcga gcagtgcccg cttgttcctg  13920
aaatgccagt aaagcgctgg ctgctgaacc cccagccgga actgacccca caaggcccta  13980
gcgtttgcaa tgcaccaggt catcattgac ccaggcgtgt tccaccaggc cgctgcctcg  14040
caactcttcg caggcttcgc cgacctgctc gcgccacttc ttcacgcggg tggaatccga  14100
tccgcacatg aggcggaagg tttccagctt gagcgggtac ggctcccggt gcgagctgaa  14160
atagtcgaac atccgtcggg ccgtcggcga cagcttgcgg tacttctccc atatgaattt  14220
cgtgtagtgg tcgccagcaa acagcacgac gatttcctcg tcgatcagga cctggcaacg  14280
ggacgttttc ttgccacggt ccaggacgcg gaagcggtgc agcagcgaca ccgattccag  14340
gtgcccaacg cggtcggacg tgaagcccat cgccgtcgcc tgtaggcgcg acaggcattc  14400
ctcggccttc gtgtaatacc ggccattgat cgaccagccc aggtcctggc aaagctcgta  14460
gaacgtgaag gtgatcggct cgccgatagg ggtgcgcttc gcgtactcca acacctgctg  14520
ccacaccagt tcgtcatcgt cggcccgcag ctcgacgccg gtgtaggtga tcttcacgtc  14580
cttgttgacg tggaaaatga ccttgttttg cagcgcctcg cgcgggattt tcttgttgcg  14640
cgtggtgaac agggcagagc gggccgtgtc gtttggcatc gctcgcatcg tgtccggcca  14700
cggcgcaata tcgaacaagg aaagctgcat ttccttgatc tgctgcttcg tgtgtttcag  14760
caacgcggcc tgcttggcct cgctgacctg ttttgccagg tcctcgccgg cggtttttcg  14820
cttcttggtc gtcatagttc ctcgcgtgtc gatggtcatc gacttcgcca aacctgccgc  14880
ctcctgttcg agacgacgcg aacgctccac ggcggccgat ggcgcgggca gggcaggggg  14940
agccagttgc acgctgtcgc gctcgatctt ggccgtagct tgctggacca tcgagccgac  15000
ggactggaag gtttcgcggg gcgcacgcat gacggtgcgg cttgcgatgg tttcggcatc  15060
ctcggcggaa aaccccgcgt cgatcagttc ttgcctgtat gccttccggt caaacgtccg  15120
attcattcac cctccttgcg ggattgcccc gactcacgcc ggggcaatgt gcccttattc  15180
ctgatttgac ccgcctggtg ccttggtgtc cagataatcc accttatcgg caatgaagtc  15240
ggtcccgtag accgtctggc cgtccttctc gtacttggta ttccgaatct tgccctgcac  15300
gaataccagc gaccccttgc ccaaatactt gccgtgggcc tcggcctgag agccaaaaca  15360
cttgatgcgg aagaagtcgg tgcgctcctg cttgtcgccg gcatcgttgc gccacatcta  15420
ggtactaaaa caattcatcc agtaaaatat aatattttat tttctcccaa tcaggcttga  15480
tccccagtaa gtcaaaaaat agctcgacat actgttcttc cccgatatcc tccctgatcg  15540
accggacgca gaaggcaatg tcataccact tgtccgccct gccgcttctc ccaagatcaa  15600
taaagccact tactttgcca tctttcacaa agatgttgct gtctcccagg tcgccgtggg  15660
aaaagacaag ttcctcttcg ggcttttccg tctttaaaaa atcatacagc tcgcgcggat  15720
ctttaaatgg agtgtcttct tcccagtttt cgcaatccac atcggccaga tcgttattca  15780
gtaagtaatc caattcggct aagcggctgt ctaagctatt cgtataggga caatccgata  15840
tgtcgatgga gtgaaagagc ctgatgcact ccgcatacag ctcgataatc ttttcagggc  15900
tttgttcatc ttcatactct tccgagcaaa ggacgccatc ggcctcactc atgagcagat  15960
tgctccagcc atcatgccgt tcaaagtgca ggacctttgg aacaggcagc tttccttcca  16020
gccatagcat catgtccttt tcccgttcca catcataggt ggtcccttta taccggctgt  16080
ccgtcatttt taaatatagg ttttcatttt ctcccaccag cttatatacc ttagcaggag  16140
acattccttc cgtatctttt acgcagcggt atttttcgat cagtttttc aattccggtg  16200
```

-continued

```
atattctcat tttagccatt tattatttcc ttcctctttt ctacagtatt taaagatacc  16260
ccaagaagct aattataaca agacgaactc caattcactg ttccttgcat tctaaaacct  16320
taaataccag aaaacagctt tttcaaagtt gttttcaaag ttggcgtata acatagtatc  16380
gacggagccg attttgaaac cacaattatg ggtgatgctg ccaacttact gatttagtgt  16440
atgatggtgt ttttgaggtg ctccagtggc ttctgtgtct atcagctgtc cctcctgttc  16500
agctactgac ggggtggtgc gtaacggcaa aagcaccgcc ggacatcagc gctatctctg  16560
ctctcactgc cgtaaaacat ggcaactgca gttcacttac accgcttctc aacccggtac  16620
gcaccagaaa atcattgata tggccatgaa tggcgttgga tgccgggcaa cagcccgcat  16680
tatgggcgtt ggcctcaaca cgattttacg tcacttaaaa aactcaggcc gcagtcggta  16740
acctcgcgca tacagccggg cagtgacgtc atcgtctgcg cggaaatgga cgaacagtgg  16800
ggctatgtcg gggctaaatc gcgccagcgc tggctgtttt acgcgtatga cagtctccgg  16860
aagacggttg ttgcgcacgt attcggtgaa cgcactatgg cgacgctggg gcgtcttatg  16920
agcctgctgt caccctttga cgtggtgata tggatgacgg atggctggcc gctgtatgaa  16980
tcccgcctga agggaaagct gcacgtaatc agcaagcgat atacgcagcg aattgagcgg  17040
cataacctga atctgaggca gcacctggca cggctgggac ggaagtcgct gtcgttctca  17100
aaatcggtgg agctgcatga caaagtcatc gggcattatc tgaacataaa acactatcaa  17160
taagttggag tcattaccca attatgatag aatttacaag ctataaggtt attgtcctgg  17220
gtttcaagca ttagtccatg caagtttttta tgctttgccc attctataga tatattgata  17280
agcgcgctgc ctatgccttg ccccctgaaa tccttacata cggcgatatc ttctatataa  17340
aagatatatt atcttatcag tattgtcaat atattcaagg caatctgcct cctcatcctc  17400
ttcatcctct tcgtcttggt agctttttaa atatggcgct tcatagagta attctgtaaa  17460
ggtccaattc tcgttttcat acctcggtat aatcttacct atcacctcaa atggttcgct  17520
gggtttatcg cacccccgaa cacgagcacg gcacccgcga ccactatgcc aagaatgccc  17580
aaggtaaaaa ttgccggccc cgccatgaag tccgtgaatg ccccgacggc cgaagtgaag  17640
ggcaggccgc cacccaggcc gccgccctca ctgcccggca cctggtcgct gaatgtcgat  17700
gccagcacct gcggcacgtc aatgcttccg ggcgtcgcgc tcgggctgat cgcccatccc  17760
gttactgccc cgatcccggc aatggcaagg actgccagcg ctgccatttt tggggtgagg  17820
ccgttcgcgg ccgaggggcg cagcccctgg ggggatggga ggcccgcgtt agcgggccgg  17880
gagggttcga gaaggggggg caccccccctt cggcgtgcgc ggtcacgcgc acagggcgca  17940
gccctggtta aaaacaaggt ttataaatat tggtttaaaa gcaggttaaa agacaggtta  18000
gcggtggccg aaaaacgggc ggaaaccctt gcaaatgctg gattttctgc ctgtggacag  18060
cccctcaaat gtcaataggt gcgcccctca tctgtcagca ctctgcccct caagtgtcaa  18120
ggatcgcgcc cctcatctgt cagtagtcgc gcccctcaag tgtcaatacc gcagggcact  18180
tatccccagg cttgtccaca tcatctgtgg gaaactcgcg taaaatcagg cgttttcgcc  18240
gatttgcgag gctggccagc tccacgtcgc cggccgaaat cgagcctgcc cctcatctgt  18300
caacgccgcg ccgggtgagt cggcccctca agtgtcaacg tccgcccctc atctgtcagt  18360
gagggccaag ttttccgcga ggtatccaca acgccggcgg ccgcggtgtc tcgcacacgg  18420
cttcgacggc gtttctggcg cgtttgcagg gccatagacg gccgccagcc cagcggcgag  18480
ggcaaccagc ccgg                                                    18494
```

-continued

<210> SEQ ID NO 18
<211> LENGTH: 17647
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 18

```
tgagcgtcgc aaaggcgctc ggtcttgcct tgctcgtcgg tgatgtactt caccagctcc     60
gcgaagtcgc tcttcttgat ggagcgcatg gggacgtgct tggcaatcac gcgcaccccc    120
cggccgtttt agcggctaaa aaagtcatgg ctctgccctc gggcggacca cgcccatcat    180
gaccttgcca agctcgtcct gcttctcttc gatcttcgcc agcagggcga ggatcgtggc    240
atcaccgaac cgcgccgtgc gcgggtcgtc ggtgagccag agtttcagca ggccgcccag    300
gcggcccagg tcgccattga tgcgggccag ctcgcggacg tgctcatagt ccacgacgcc    360
cgtgattttg tagccctggc cgacggccag caggtaggcc gacaggctca tgccggccgc    420
cgccgccttt tcctcaatcg ctcttcgttc gtctggaagg cagtacacct tgataggtgg    480
gctgcccttc ctggttggct tggtttcatc agccatccgc ttgccctcat ctgttacgcc    540
ggcggtagcc ggccagcctc gcagagcagg attcccgttg agcaccgcca ggtgcgaata    600
agggacagtg aagaaggaac acccgctcgc gggtgggcct acttcaccta tcctgcccgg    660
ctgacgccgt tggatacacc aaggaaagtc tacacgaacc ctttggcaaa atcctgtata    720
tcgtgcgaaa aaggatggat ataccgaaaa aatcgctata atgaccccga agcagggtta    780
tgcagcggaa aagcgccacg cttcccgaag ggagaaaggc ggacaggtat ccggtaagcg    840
gcagggtcgg aacaggagag cgcacgaggg agcttccagg gggaaacgcc tggtatcttt    900
atagtcctgt cgggtttcgc cacctctgac ttgagcgtcg atttttgtga tgctcgtcag    960
gggggcggag cctatggaaa aacgccagca acgcggcctt tttacggttc ctggcctttt   1020
gctggccttt tgctcacatg ttctttcctg cgttatcccc tgattctgtg gataaccgta   1080
ttaccgcctt tgagtgagct gataccgctc gccgcagccg aacgaccgag cgcagcgagt   1140
cagtgagcga ggaagcggaa gagcgccaga aggccgccag agaggccgag cgcggccgtg   1200
aggcttggac gctagggcag ggcatgaaaa agcccgtagc gggctgctac gggcgtctga   1260
cgcggtggaa agggggaggg gatgttgtct acatggctct gctgtagtga gtgggttgcg   1320
ctccggcagc ggtcctgatc aatcgtcacc ctttctcggt ccttcaacgt tcctgacaac   1380
gagcctcctt ttcgccaatc catcgacaat caccgcgagt ccctgctcga acgctgcgtc   1440
cggaccggct tcgtcgaagg cgtctatcgc ggcccgcaac agcggcgaga gcggagcctg   1500
ttcaacggtg ccgccgcgct cgccggcatc gctgtcgccg gcctgctcct caagcacggc   1560
cccaacagtg aagtagctga ttgtcatcag cgcattgacg gcgtccccgg ccgaaaaacc   1620
cgcctcgcag aggaagcgaa gctgcgcgtc ggccgtttcc atctgcggtg cgcccggtcg   1680
cgtgccggca tggatgcgcg cgccatcgcg gtaggcgagc agcgcctgcc tgaagctgcg   1740
ggcattcccg atcagaaatg agcgccagtc gtcgtcggct ctcggcaccg aatgcgtatg   1800
attctccgcc agcatggctt cggccagtgc gtcgagcagc gcccgcttgt tcctgaagtg   1860
ccagtaaagc gccggctgct gaacccccaa ccgttccgcc agtttgcgtg tcgtcagacc   1920
gtctacgccg acctcgttca acaggtccag ggcggcacgg atcactgtat tcggctgcaa   1980
ctttgtcatg cttgacactt tatcactgat aaacataata tgtccaccaa cttatcagtg   2040
ataaagaatc cgcgcgttca atcggaccag cggaggctgg tccggaggcc agacgtgaaa   2100
```

-continued

```
cccaacatac ccctgatcgt aattctgagc actgtcgcgc tcgacgctgt cggcatcggc   2160
ctgattatgc cggtgctgcc gggcctcctg cgcgatctgg ttcactcgaa cgacgtcacc   2220
gcccactatg gcattctgct ggcgctgtat gcgttggtgc aatttgcctg cgcacctgtg   2280
ctgggcgcgc tgtcggatcg tttcgggcgg cggccaatct tgctcgtctc gctggccggc   2340
gccagatctg gggaaccctg tggttggcat gcacatacaa atggacgaac ggataaacct   2400
tttcacgccc ttttaaatat ccgattattc taataaacgc tcttttctct taggtttacc   2460
cgccaatata tcctgtcaaa cactgatagt ttaaactgaa ggcgggaaac gacaatctga   2520
tcatgagcgg agaattaagg gagtcacgtt atgacccccg ccgatgacgc gggacaagcc   2580
gttttacgtt tggaactgac agaaccgcaa cgttgaagga gccactcagc cgcgggtttc   2640
tggagtttaa tgagctaagc acatacgtca gaaaccatta ttgcgcgttc aaaagtcgcc   2700
taaggtcact atcagctagc aaatatttct tgtcaaaaat gctccactga cgttccataa   2760
attcccctcg gtatccaatt agagtctcat attcactctc aatccaaata atctgcaccg   2820
gatctggatc gtttcgcatg attgaacaag atggattgca cgcaggttct ccggccgctt   2880
gggtggagag gctattcggc tatgactggg cacaacagac aatcggctgc tctgatgccg   2940
ccgtgttccg gctgtcagcg caggggcgcc cggttctttt tgtcaagacc gacctgtccg   3000
gtgccctgaa tgaactgcag gacgaggcag cgcggctatc gtggctggcc acgacgggcg   3060
ttccttgcgc agctgtgctc gacgttgtca ctgaagcggg aagggactgg ctgctattgg   3120
gcgaagtgcc ggggcaggat ctcctgtcat ctcaccttgc tcctgccgag aaagtatcca   3180
tcatggctga tgcaatgcgg cggctgcata cgcttgatcc ggctacctgc ccattcgacc   3240
accaagcgaa acatcgcatc gagcgagcac gtactcggat ggaagccggt cttgtcgatc   3300
aggatgatct ggacgaagag catcaggggc tcgcgccagc cgaactgttc gccaggctca   3360
aggcgcgcat gcccgacggc gatgatctcg tcgtgaccca tggcgatgcc tgcttgccga   3420
atatcatggt ggaaaatggc cgcttttctg gattcatcga ctgtggccgg ctgggtgtgg   3480
cggaccgcta tcaggacata gcgttggcta cccgtgatat tgctgaagag cttggcggcg   3540
aatgggctga ccgcttcctc gtgctttacg gtatcgccgc tcccgattcg cagcgcatcg   3600
ccttctatcg ccttcttgac gagttcttct gagcgggact ctggggttcg aaatgaccga   3660
ccaagcgacg cccaacctgc catcacgaga tttcgattcc accgccgcct tctatgaaag   3720
gttgggcttc ggaatcgttt tccgggacgc cggctggatg atcctccagc gcggggatct   3780
catgctggag ttcttcgccc acgggatctc tgcggaacag gcggtcgaag gtgccgatat   3840
cattacgaca gcaacggccg acaagcacaa cgccacgatc ctgagcgaca atatgatcgg   3900
gcccggcgtc cacatcaacg gcgtcggcgg cgactgccca ggcaagaccg agatgcaccg   3960
cgatatcttg ctgcgttcgg atattttcgt ggagttcccg ccacagaccc ggatgatccc   4020
cgatcgttca aacatttggc aataaagttt cttaagattg aatcctgttg ccggtcttgc   4080
gatgattatc atataatttc tgttgaatta cgttaagcat gtaataatta acatgtaatg   4140
catgacgtta tttatgagat gggtttttat gattagagtc ccgcaattat acatttaata   4200
cgcgatagaa aacaaaatat agcgcgcaaa ctaggataaa ttatcgcgcg cggtgtcatc   4260
tatgttacta gatcgggcct cctgtcaatg ctggcggcgg ctctggtggt ggttctggtg   4320
gcggctctga gggtggtggc tctgagggtg gcggttctga gggtggcggc tctgagggag   4380
gcggttccgg tggtggctct ggttccggtg attttgatta tgaaaagatg gcaaacgcta   4440
```

-continued

```
ataagggggc tatgaccgaa aatgccgatg aaaacgcgct acagtctgac gctaaaggca   4500
aacttgattc tgtcgctact gattacggtg ctgctatcga tggtttcatt ggtgacgttt   4560
ccggccttgc taatggtaat ggtgctactg gtgattttgc tggctctaat tcccaaatgg   4620
ctcaagtcgg tgacggtgat aattcacctt taatgaataa tttccgtcaa tatttacctt   4680
ccctccctca atcggttgaa tgtcgccctt ttgtctttgg cccaatacgc aaaccgcctc   4740
tccccgcgcg ttggccgatt cattaatgca gctggcacga caggtttccc gactggaaag   4800
cgggcagtga gcgcaacgca attaatgtga gttagctcac tcattaggca ccccaggctt   4860
tacactttat gcttccggct cgtatgttgt gtggaattgt gagcggataa caatttcaca   4920
caggaaacag ctatgaccat gattacgcca agcttgcatg cctgcaggtc cccagattag   4980
ccttttcaat ttcagaaaga atgctaaccc acagatggtt agagaggctt acgcagcagg   5040
tctcatcaag acgatctacc cgagcaataa tctccaggaa atcaaatacc ttcccaagaa   5100
ggttaaagat gcagtcaaaa gattcaggac taactgcatc aagaacacag agaaagatat   5160
atttctcaag atcagaagta ctattccagt atggacgatt caaggcttgc ttcacaaacc   5220
aaggcaagta atagagattg gagtctctaa aaaggtagtt cccactgaat caaaggccat   5280
ggagtcaaag attcaaatag aggacctaac agaactcgcc gtaaagactg gcgaacagtt   5340
catacagagt ctcttacgac tcaatgacaa gaagaaaatc ttcgtcaaca tggtggagca   5400
cgacacactt gtctactcca aaaatatcaa agatacagtc tcagaagacc aaagggcaat   5460
tgagactttt caacaaaggg taatatccgg aaacctcctc ggattccatt gcccagctat   5520
ctgtcacttt attgtgaaga tagtggaaaa ggaaggtggc tcctacaaat gccatcattg   5580
cgataaagga aaggccatcg ttgaagatgc ctctgccgac agtggtccca aagatggacc   5640
cccacccacg aggagcatcg tggaaaaaga agacgttcca accacgtctt caaagcaagt   5700
ggattgatgt gatatctcca ctgacgtaag ggatgacgca caatcccact atccttcgca   5760
agacccttcc tctatataag gaagttcatt tcatttggag agaacacggg ggactctaat   5820
caaacaagtt tgtacaaaaa agctgaacga gaaacgtaaa atgatataaa tatgcaggtg   5880
atacccgcgt gcaactcggc agcaataaga tcactatgtc ctactcccga gtcttttaga   5940
aacatgggat ggctctctgt cagcgatgcg gtctacagcg agttcatagg agagttggct   6000
acccgcgctt ccaatcgaaa ttactccaac gagttcggcc tcatgcaacc tatccaggaa   6060
ttcaaggctt tcattgaaag cgacccggtg gtgcaccaag aatttattga catgttcgag   6120
ggcattcagg actctccaag gaattatcag gaactatgta atatgttcaa cgatatcttt   6180
cgcaaagctc ccgtctacgg agaccttggc cctcccgttt atatgattat ggccaaatta   6240
atgaacaccc gagcgggctt ctctgcattc acgagacaaa ggttgaacct tcacttcaaa   6300
aaacttttcg atacctgggg attgttcctg tcttcgaaag attctcgaaa tgttcttgtg   6360
gccgaccagt tcgacgacag acattgcggc tggttgaacg agcgggcctt gtctgctatg   6420
gttaaacatt acaatggacg cgcatttgat gaagtcttcc tctgcgataa aaatgcccca   6480
tactacggct tcaactctta cgacgacttc tttaatcgca gatttcgaaa ccgagatatc   6540
gaccgacctg tagtcggtgg agttaacaac accaccctca tttctgctgc ttgcgaatca   6600
ctttcctaca acgtctctta tgacgtccag tctctcgaca ctttagtttt caaaggagag   6660
acttattcgc ttaagcattt gctgaataat gaccctttca ccccacaatt cgagcatggg   6720
agtattctac aaggattctt gaacgtcacc gcttaccacc gatggcacgc acccgtcaat   6780
gggacaatcg tcaaaatcat caacgttcca ggtacctact ttgcgcaagc cccgagcacg   6840
```

-continued

```
attggcgacc ctatcccgga taacgattac gacccacctc cttaccttaa gtctcttgtc   6900
tacttctcta atattgccgc aaggcaaatt atgtttattg aagccgacaa caaggaaatt   6960
ggcctcattt tccttgtgtt catcggcatg accgaaatct cgacatgtga agccacggtg   7020
tccgaaggtc aacacgtcaa tcgtggcgat gacttgggaa tgttccattt cggtggttct   7080
tcgttcgcgc ttggtctgag gaaggattgc agggcagaga tcgttgaaaa gttcaccgaa   7140
cccggaacag tgatcagaat caacgaagtc gtcgctgctc taaaggctta gtacgtttct   7200
cgttcagctt tcttgtacaa agtggttcga tctagaggat ccatggtgag caagggcgag   7260
gagctgttca ccggggtggt gcccatcctg gtcgagctgg acggcgacgt gaacggccac   7320
aagttcagcg tgtccggcga gggcgagggc gatgccacct acggcaagct gaccctgaag   7380
ttcatctgca ccaccggcaa gctgcccgtg ccctggccca ccctcgtgac caccttcacc   7440
tacggcgtgc agtgcttcag ccgctacccc gaccacatga agcagcacga cttcttcaag   7500
tccgccatgc ccgaaggcta cgtccaggag cgcaccatct tcttcaagga cgacggcaac   7560
tacaagaccc gcgccgaggt gaagttcgag ggcgacaccc tggtgaaccg catcgagctg   7620
aagggcatcg acttcaagga ggacggcaac atcctggggc acaagctgga gtacaactac   7680
aacagccaca acgtctatat catggccgac aagcagaaga acggcatcaa ggtgaacttc   7740
aagatccgcc acaacatcga ggacggcagc gtgcagctcg ccgaccacta ccagcagaac   7800
acccccatcg gcgacggccc cgtgctgctg cccgacaacc actacctgag cacccagtcc   7860
gccctgagca aagaccccaa cgagaagcgc gatcacatgg tcctgctgga gttcgtgacc   7920
gccgccggga tcactcacgg catggacgag ctgtacaagt aaagcggccc gagctcgaat   7980
ttccccgatc gttcaaacat ttggcaataa agtttcttaa gattgaatcc tgttgccggt   8040
cttgcgatga ttatcatata atttctgttg aattacgtta agcatgtaat aattaacatg   8100
taatgcatga cgttatttat gagatgggtt tttatgatta gagtcccgca attatacatt   8160
taatacgcga tagaaaacaa aatatagcgc gcaaactagg ataaattatc gcgcgcggtg   8220
tcatctatgt tactagatcg ggaattagct tcatcaacgc aagacatgcg cacgaccgtc   8280
tgacaggaga ggaatttccg acgagcacag aaaggacttg ctcttggacg taggcctatt   8340
tctcaggcac atgtatcaag tgttcggacg tgggttttcg atggtgtatc agccgccgcc   8400
aactgggaga tgaggaggct ttcttggggg gcagtcagca gttcatttca caagacagag   8460
gaacttgtaa ggagatgcac tgatttatct tggcgcaaac cagcaggacg aattagtggg   8520
aatagcccgc gaatatctaa gttatgcctg tcggcatgag cagaaacttc caattcgaaa   8580
cagtttggag aggttgtttt tgggcatacc ttttgttagt cagcctctcg attgctcatc   8640
gtcattacac agtaccgaag tttgatcgat ctagtaacat agatgacacc gcgcgcgata   8700
atttatccta gtttgcgcgc tatattttgt tttctatcgc gtattaaatg tataattgcg   8760
ggactctaat cataaaaacc catctcataa ataacgtcat gcattacatg ttaattatta   8820
catgcttaac gtaattcaac agaaattata tgataatcat cgcaagaccg gcaacaggat   8880
tcaatcttaa gaaactttat tgccaaatgt ttgaacgatc tgcttcgacg cactccttct   8940
ttactccacc atctcgtcct tattgaaaac gtgggtagca ccaaaacgaa tcaagtcgct   9000
ggaactgaag ttaccaatca cgctggatga tttgccagtt ggattaatct tgcctttccc   9060
cgcatgaata atattgatga atgcatgcgt gaggggtatt tcgattttgg caatagctgc   9120
aattgccgcg acatcctcca acgagcataa ttcttcagaa aaatagcgat gttccatgtt   9180
```

-continued gtcagggcat gcatgatgca cgttatgagg tgacggtgct aggcagtatt ccctcaaagt 9240
ttcatagtca gtatcatatt catcattgca ttcctgcaag agagaattga gacgcaatcc 9300
acacgctgcg gcaaccttcc ggcgttcgtg gtctatttgc tcttggacgt tgcaaacgta 9360
agtgttggat cccggtcggc atctactcta ttcctttgcc ctcggacgag tgctggggcg 9420
tcggtttcca ctatcggcga gtacttctac acagccatcg gtccagacgg ccgcgcttct 9480
gcgggcgatt tgtgtacgcc cgacagtccc ggctccggat cggacgattg cgtcgcatcg 9540
accctgcgcc caagctgcat catcgaaatt gccgtcaacc aagctctgat agagttggtc 9600
aagaccaatg cggagcatat acgcccggag ccgcggcgat cctgcaagct ccggatgcct 9660
ccgctcgaag tagcgcgtct gctgctccat acaagccaac cacggcctcc agaagaagat 9720
gttggcgacc tcgtattggg aatccccgaa catcgcctcg ctccagtcaa tgaccgctgt 9780
tatgcggcca ttgtccgtca ggacattgtt ggagccgaaa tccgcgtgca cgaggtgccg 9840
gacttcgggg cagtcctcgg cccaaagcat cagctcatcg agagcctgcg cgacggacgc 9900
actgacggtg tcgtccatca cagtttgcca gtgatacaca tggggatcag caatcgcgca 9960
tatgaaatca cgccatgtag tgtattgacc gattccttgc ggtccgaatg ggccgaaccc 10020
gctcgtctgg ctaagatcgg ccgcagcgat cgcatccatg gcctccgcga ccggctgcag 10080
aacagcgggc agttcggttt caggcaggtc ttgcaacgtg acaccctgtg cacggcggga 10140
gatgcaatag gtcaggctct cgctgaattc cccaatgtca agcacttccg gaatcgggag 10200
cgcggccgat gcaaagtgcc gataaacata acgatctttg tagaaaccat cggcgcagct 10260
atttacccgc aggacatatc cacgccctcc tacatcgaag ctgaaagcac gagattcttc 10320
gccctccgag agctgcatca ggtcggagac gctgtcgaac ttttcgatca gaaacttctc 10380
gacagacgtc gcggtgagtt caggcttttt catatcgggg tcgtcctctc caaatgaaat 10440
gaacttcctt atatagagga agggtcttgc gaaggatagt gggattgtgc gtcatccctt 10500
acgtcagtgg agatatcaca tcaatccact tgctttgaag acgtggttgg aacgtcttct 10560
ttttccacga tgctcctcgt gggtgggggt ccatctttgg gaccactgtc ggcagaggca 10620
tcttgaacga tagcctttcc tttatcgcaa tgatggcatt tgtaggtgcc accttccttt 10680
tctactgtcc ttttgatgaa gtgacagata gctgggcaat ggaatccgag gaggtttccc 10740
gatattaccc tttgttgaaa agtctcaata gccctttggt cttctgagac tgtatctttg 10800
atattcttgg agtagacgag agtgtcgtgc tccaccatgt tgacggatct ctaggacgcg 10860
tcctagaagc taattcactg gccgtcgttt tacaacgtcg tgactgggaa aaccctggcg 10920
ttacccaact taatcgcctt gcagcacatc ccccttttcgc cagctggcgt aatagcgaag 10980
aggcccgcac cgatcgccct tcccaacagt tgcgcagcct gaatggcgcc cgctcctttc 11040
gctttcttcc cttcctttct cgccacgttc gccggctttc cccgtcaagc tctaaatcgg 11100
gggctccctt tagggttccg atttagtgct ttacggcacc tcgaccccaa aaaacttgat 11160
ttgggtgatg gttcacgtag tgggccatcg ccctgataga cggtttttcg ccctttgacg 11220
ttggagtcca cgttctttaa tagtggactc ttgttccaaa ctggaacaac actcaaccct 11280
atctcgggct attcttttga tttataaggg attttgccga tttcggaacc accatcaaac 11340
aggattttcg cctgctgggg caaaccagcg tggaccgctt gctgcaactc tctcagggcc 11400
aggcggtgaa gggcaatcag ctgttgcccg tctcactggt gaaaagaaaa accaccccag 11460
tacattaaaa acgtccgcaa tgtgttatta agttgtctaa gcgtcaattt gtttacacca 11520
caatatatcc tgccaccagc cagccaacag ctccccgacc ggcagctcgg cacaaaatca 11580

-continued

```
ccactcgata caggcagccc atcagtccgg gacggcgtca gcgggagagc cgttgtaagg  11640
cggcagactt tgctcatgtt accgatgcta ttcggaagaa cggcaactaa gctgccgggt  11700
ttgaaacacg gatgatctcg cggagggtag catgttgatt gtaacgatga cagagcgttg  11760
ctgcctgtga tcaaatatca tctccctcgc agagatccga attatcagcc ttcttattca  11820
tttctcgctt aaccgtgaca ggctgtcgat cttgagaact atgccgacat aataggaaat  11880
cgctggataa agccgctgag gaagctgagt ggcgctattt ctttagaagt gaacgttgac  11940
gatatcaact cccctatcca ttgctcaccg aatggtacag gtcggggacc cgaagttccg  12000
actgtcggcc tgatgcatcc ccggctgatc gaccccagat ctggggctga gaaagcccag  12060
taaggaaaca actgtaggtt cgagtcgcga gatcccccgg aaccaaagga agtaggttaa  12120
acccgctccg atcaggccga gccacgccag gccgagaaca ttggttcctg taggcatcgg  12180
gattggcgga tcaaacacta aagctactgg aacgagcaga agtcctccgg ccgccagttg  12240
ccaggcggta aaggtgagca gaggcacggg aggttgccac ttgcgggtca gcacggttcc  12300
gaacgccatg gaaaccgccc ccgccaggcc cgctgcgacg ccgacaggat ctagcgctgc  12360
gtttggtgtc aacaccaaca gcgccacgcc cgcagttccg caaatagccc ccaggaccgc  12420
catcaatcgt atcgggctac ctagcagagc ggcagagatg aacacgacca tcagcggctg  12480
cacagcgcct accgtcgccg cgaccccgcc cggcaggcgg tagaccgaaa taaacaacaa  12540
gctccagaat agcgaaatat taagtgcgcc gaggatgaag atgcgcatcc accagattcc  12600
cgttggaatc tgtcggacga tcatcacgag caataaaccc gccggcaacg cccgcagcag  12660
cataccggcg accccctcggc ctcgctgttc gggctccacg aaaacgccgg acagatgcgc  12720
cttgtgagcg tccttggggc cgtcctcctg tttgaagacc gacagcccaa tgatctcgcc  12780
gtcgatgtag gcgccgaatg ccacggcatc tcgcaaccgt tcagcgaacg cctccatggg  12840
ctttttctcc tcgtgctcgt aaacggaccc gaacatctct ggagctttct tcagggccga  12900
caatcggatc tcgcggaaat cctgcacgtc ggccgctcca agccgtcgaa tctgagcctt  12960
aatcacaatt gtcaatttta atcctctgtt tatcggcagt tcgtagagcg cgccgtgcgt  13020
cccgagcgat actgagcgaa gcaagtgcgt cgagcagtgc ccgcttgttc ctgaaatgcc  13080
agtaaagcgc tggctgctga acccccagcc ggaactgacc ccacaaggcc ctagcgtttg  13140
caatgcacca ggtcatcatt gacccaggcg tgttccacca ggccgctgcc tcgcaactct  13200
tcgcaggctt cgccgacctg ctcgcgccac ttcttcacgc gggtggaatc cgatccgcac  13260
atgaggcgga aggtttccag cttgagcggg tacggctccc ggtgcgagct gaaatagtcg  13320
aacatccgtc gggccgtcgg cgacagcttg cggtacttct cccatatgaa tttcgtgtag  13380
tggtcgccag caaacagcac gacgatttcc tcgtcgatca ggacctggca acgggacgtt  13440
ttcttgccac ggtccaggac gcggaagcgg tgcagcagcg acaccgattc caggtgccca  13500
acgcggtcgg acgtgaagcc catcgccgtc gcctgtaggc gcgacaggca ttcctcggcc  13560
ttcgtgtaat accggccatt gatcgaccag cccaggtcct ggcaaagctc gtagaacgtg  13620
aaggtgatcg gctcgccgat aggggtgcgc ttcgcgtact ccaacacctg ctgccacacc  13680
agttcgtcat cgtcggcccg cagctcgacg ccggtgtagg tgatcttcac gtccttgttg  13740
acgtggaaaa tgaccttgtt ttgcagcgcc tcgcgcggga ttttcttgtt gcgcgtggtg  13800
aacagggcag agcgggccgt gtcgtttggc atcgctcgca tcgtgtccgg ccacggcgca  13860
atatcgaaca aggaaagctg catttccttg atctgctgct tcgtgtgttt cagcaacgcg  13920
```

-continued gcctgcttgg cctcgctgac ctgttttgcc aggtcctcgc cggcggtttt tcgcttcttg 13980
gtcgtcatag ttcctcgcgt gtcgatggtc atcgacttcg ccaaacctgc cgcctcctgt 14040
tcgagacgac gcgaacgctc cacggcggcc gatggcgcgg gcagggcagg gggagccagt 14100
tgcacgctgt cgcgctcgat cttggccgta gcttgctgga ccatcgagcc gacggactgg 14160
aaggtttcgc ggggcgcacg catgacggtg cggcttgcga tggtttcggc atcctcggcg 14220
gaaaaccccg cgtcgatcag ttcttgcctg tatgccttcc ggtcaaacgt ccgattcatt 14280
caccctcctt gcgggattgc cccgactcac gccggggcaa tgtgccctta ttcctgattt 14340
gacccgcctg gtgccttggt gtccagataa tccaccttat cggcaatgaa gtcggtcccg 14400
tagaccgtct ggccgtcctt ctcgtacttg gtattccgaa tcttgccctg cacgaatacc 14460
agcgacccct tgcccaaata cttgccgtgg gcctcggcct gagagccaaa acacttgatg 14520
cggaagaagt cggtgcgctc ctgcttgtcg ccggcatcgt tgcgccacat ctaggtacta 14580
aaacaattca tccagtaaaa tataatattt tattttctcc caatcaggct tgatccccag 14640
taagtcaaaa aatagctcga catactgttc ttccccgata tcctccctga tcgaccggac 14700
gcagaaggca atgtcatacc acttgtccgc cctgccgctt ctcccaagat caataaagcc 14760
acttactttg ccatctttca caaagatgtt gctgtctccc aggtcgccgt gggaaaagac 14820
aagttcctct tcgggctttt ccgtctttaa aaaatcatac agctcgcgcg gatctttaaa 14880
tggagtgtct tcttcccagt tttcgcaatc cacatcggcc agatcgttat tcagtaagta 14940
atccaattcg gctaagcggc tgtctaagct attcgtatag ggacaatccg atatgtcgat 15000
ggagtgaaag agcctgatgc actccgcata cagctcgata atcttttcag ggctttgttc 15060
atcttcatac tcttccgagc aaaggacgcc atcggcctca ctcatgagca gattgctcca 15120
gccatcatgc cgttcaaagt gcaggacctt tggaacaggc agctttcctt ccagccatag 15180
catcatgtcc ttttcccgtt ccacatcata ggtggtccct ttataccggc tgtccgtcat 15240
ttttaaatat aggttttcat ttctcccac cagcttatat accttagcag gagacattcc 15300
ttccgtatct tttacgcagc ggtatttttc gatcagtttt ttcaattccg gtgatattct 15360
cattttagcc atttattatt tccttcctct tttctacagt atttaaagat accccaagaa 15420
gctaattata acaagacgaa ctccaattca ctgttccttg cattctaaaa ccttaaatac 15480
cagaaaacag ctttttcaaa gttgttttca aagttggcgt ataacatagt atcgacggag 15540
ccgattttga aaccacaatt atgggtgatg ctgccaactt actgatttag tgtatgatgg 15600
tgtttttgag gtgctccagt ggcttctgtg tctatcagct gtccctcctg ttcagctact 15660
gacggggtgg tgcgtaacgg caaaagcacc gccggacatc agcgctatct ctgctctcac 15720
tgccgtaaaa catggcaact gcagttcact tacaccgctt ctcaacccgg tacgcaccag 15780
aaaatcattg atatggccat gaatggcgtt ggatgccggg caacagcccg cattatgggc 15840
gttggcctca acacgatttt acgtcactta aaaaactcag gccgcagtcg gtaacctcgc 15900
gcatacagcc gggcagtgac gtcatcgtct gcgcggaaat ggacgaacag tggggctatg 15960
tcggggctaa atcgcgccag cgctggctgt tttacgcgta tgacagtctc cggaagacgg 16020
ttgttgcgca cgtattcggt gaacgcacta tggcgacgct ggggcgtctt atgagcctgc 16080
tgtcaccctt tgacgtggtg atatggatga cggatggctg gccgctgtat gaatcccgcc 16140
tgaagggaaa gctgcacgta atcagcaagc gatatacgca gcgaattgag cggcataacc 16200
tgaatctgag gcagcacctg gcacggctgg gacggaagtc gctgtcgttc tcaaaatcgg 16260
tggagctgca tgacaaagtc atcgggcatt atctgaacat aaaacactat caataagttg 16320

```
gagtcattac ccaattatga tagaatttac aagctataag gttattgtcc tgggtttcaa  16380

gcattagtcc atgcaagttt ttatgctttg cccattctat agatatattg ataagcgcgc  16440

tgcctatgcc ttgcccctg aaatccttac atacggcgat atcttctata taaaagatat  16500

attatcttat cagtattgtc aatatattca aggcaatctg cctcctcatc ctcttcatcc  16560

tcttcgtctt ggtagctttt taaatatggc gcttcataga gtaattctgt aaaggtccaa  16620

ttctcgtttt catacctcgg tataatctta cctatcacct caaatggttc gctgggttta  16680

tcgcaccccc gaacacgagc acggcacccg cgaccactat gccaagaatg cccaaggtaa  16740

aaattgccgg ccccgccatg aagtccgtga atgccccgac ggccgaagtg aagggcaggc  16800

cgccacccag gccgccgccc tcactgcccg gcacctggtc gctgaatgtc gatgccagca  16860

cctgcggcac gtcaatgctt ccgggcgtcg cgctcgggct gatcgcccat cccgttactg  16920

ccccgatccc ggcaatggca aggactgcca gcgctgccat ttttggggtg aggccgttcg  16980

cggccgaggg gcgcagcccc tggggggatg ggaggcccgc gttagcgggc cgggagggtt  17040

cgagaagggg gggcaccccc cttcggcgtg cgcggtcacg cgcacagggc gcagccctgg  17100

ttaaaaacaa ggtttataaa tattggttta aaagcaggtt aaaagacagg ttagcggtgg  17160

ccgaaaaacg ggcggaaacc cttgcaaatg ctggattttc tgcctgtgga cagcccctca  17220

aatgtcaata ggtgcgcccc tcatctgtca gcactctgcc cctcaagtgt caaggatcgc  17280

gcccctcatc tgtcagtagt cgcgcccctc aagtgtcaat accgcagggc acttatcccc  17340

aggcttgtcc acatcatctg tgggaaactc gcgtaaaatc aggcgttttc gccgatttgc  17400

gaggctggcc agctccacgt cgccggccga aatcgagcct gcccctcatc tgtcaacgcc  17460

gcgccgggtg agtcggcccc tcaagtgtca acgtccgccc ctcatctgtc agtgagggcc  17520

aagttttccg cgaggtatcc acaacgccgg cggccgcggt gtctcgcaca cggcttcgac  17580

ggcgtttctg gcgcgtttgc agggccatag acggccgcca gcccagcggc gagggcaacc  17640

agcccgg                                                            17647
```

<210> SEQ ID NO 19
<211> LENGTH: 9462
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 19

```
agatctctaa ttccggggat cggaaatcca gaagcccgag aggttgccgc ctttcgggct     60

ttttcttttt caaaaaaaaa aatttataaa acgatctgtt gcggccggcc gccgggttgt    120

gggcaaaggc gctggcgctc gacggtgggc aaccgcttgc ggttgtccac gggcggagcc    180

ggtgcgcgta gcgcattgtc cacaagccaa gggcgaccaa taattgatat atatattcat    240

aattgaaaag ctaattgaac atactacttg ctgtaactac ttgccggagc gaggggtgtt    300

tgcaagctgt tgatctgaaa gggctattag cgttctcacg tgcctttttg attagcgatt    360

tcacgtgacc ttattagcga tttcacgtac tccgattagc gatttcacgt accctgatta    420

gcgatttcac gtggatagtt tttggagcgg gccggaaagc cccgtgaatc aaggctttgc    480

ggggcattag cggtttcacg tggataacta ccctctatcc acaggcttcc ggggataaaa    540

aagcccgctc gacggcgggc tgttggatgg ggatcgcctg aatcgcccca tcatccagcc    600

agaaagtgag ggagccacgg ttgatgagag ctttgttgta ggtggaccag ttggtgattt    660
```

-continued

```
tgaacttttg ctttgccacg gaacggtctg cgttgtcggg aagatgcgtg atctgatcct    720
tcaactcagc aaaagttcga tttattcaac aaagccacgt tgtgtctcaa aatctctgat    780
gttacattgc acaagataaa aatatatcat catgaacaat aaaactgtct gcttacataa    840
acagtaatac aaggggtgtt atgagccata ttcaacggga aacgtcttgc tcaaggccgc    900
gattaaattc caacatggat gctgatttat atgggtataa atgggctcgc gataatgtcg    960
ggcaatcagg tgcgacaatc taccgattgt atgggaagcc cgatgcgcca gagttgtttc   1020
tgaaacatgg caaaggtagc gttgccaatg ttgttacaga tgagatggtc agactaaact   1080
ggctgacgga atttatgcct cttccgacca tcaagcattt tatccgtact cctgatgatg   1140
catggttact caccactgcg atccccggga aaacagcatt ccaggtatta gaagaatatc   1200
ctgattcagg tgaaaatatt gttgatgcgc tggcagtgtt cctgcgccgg ttgcattcga   1260
ttcctgtttg taattgtcct tttaacagcg atcgcgtatt tcgtctcgct caggcgcaat   1320
cacgaatgaa taacggtttg gttgatgcga gtgattttga tgacgagcgt aatggctggc   1380
ctgttgaaca agtctggaaa gaaatgcata aacttttgcc attctcaccg gattcagtcg   1440
tcactcatgg tgatttctca cttgataacc ttatttttga cgaggggaaa ttaataggtt   1500
gtattgatgt tggacgagtc ggaatcgcag accgatacca ggatcttgcc atcctatgga   1560
actgcctcgg tgagttttct ccttcattac agaaacggct ttttcaaaaa tatggtattg   1620
ataatcctga tatgaataaa ttgcagtttc atttgatgct cgatgagttt ttctaatcac   1680
tagaccaatg ttacacatat atactttaga ttgatttaaa acttcatttt taatttaaaa   1740
ggatctaggt gaagatcctt tttgataatc tcatgaccaa aatcccttaa cgtgagtttt   1800
cgttccactg agcgtcagac cccgtagaaa agatcaaagg atcttcttga gatccttttt   1860
ttctgcgcgt aatctgctgc ttgcaaacaa aaaaaccacc gctaccagcg gtggtttgtt   1920
tgccggatca agagctacca actctttttc cgaaggtaac tggcttcagc agagcgcaga   1980
taccaaatac tgttcttcta gtgtagccgt agttaggcca ccacttcaag aactctgtag   2040
caccgcctac atacctcgct ctgctaatcc tgttaccagt ggctgctgcc agtggcgata   2100
agtcgtgtct taccgggttg gactcaagac gatagttacc ggataaggcg cagcggtcgg   2160
gctgaacggg gggttcgtgc acacagccca gcttggagcg aacgacctac accgaactga   2220
gatacctaca gcgtgagcta tgagaaagcg ccacgcttcc cgaagggaga aaggcggaca   2280
ggtatccggt aagcggcagg gtcggaacag gagagcgcac gagggagctt ccagggggaa   2340
acgcctggta tctttatagt cctgtcgggt ttcgccacct ctgacttgag cgtcgatttt   2400
tgtgatgctc gtcagggggg cggagcctat ggaaaaacgc cagcaacgcg gcctttttac   2460
ggttcctggc cttttgctgg ccttttgctc acatgagatc tcaaacaaac acatacagcg   2520
acttagttta cccgccaata tatcctgtca aggatcgtac ccctactcca aaaatgtcaa   2580
agatacagtc tcagaagacc aaagggctat tgagactttt caacaaaggg taatttcggg   2640
aaacctcctc ggattccatt gcccagctat ctgtcacttc atcgaaagga cagtagaaaa   2700
ggaaggtggc tcctacaaat gccatcattg cgataaagga aaggctatca ttcaagatgc   2760
ctctgccgac agtggtccca aagatggacc cccacccacg aggagcatcg tggaaaaaga   2820
agacgttcca accacgtctt caaagcaagt ggattgatgt gacatctcca ctgacgtaag   2880
ggatgacgca caatcccact atccttcgca agacccttcc tctatataag gaagttcatt   2940
tcatttggag aggacagccc aagctgatcc ctatgaaaaa gcctgaactc accgcgacgt   3000
```

-continued

```
ctgtcgagaa gtttctgatc gaaaagttcg acagcgtctc cgacctgatg cagctctcgg   3060
agggcgaaga atctcgtgct ttcagcttcg atgtaggagg gcgtggatat gtcctgcggg   3120
taaatagctg cgccgatggt ttctacaaag atcgttatgt ttatcggcac tttgcatcgg   3180
ccgcgctccc gattccggaa gtgcttgaca ttggggagtt cagcgagagc ctgacctatt   3240
gcatctcccg ccgtgcacag ggtgtcacgt tgcaagacct gcctgaaacc gaactgcccg   3300
ctgttcttca gccggtcgcg gaggctatgg atgcgatcgc tgcggccgat cttagccaga   3360
cgagcgggtt cggcccattc ggaccgcaag gaatcggtca atacactaca tggcgtgatt   3420
tcatatgcgc gattgctgat ccccatgtgt atcactggca aactgtgatg gacgacaccg   3480
tcagtgcgtc cgtcgcgcag gctctcgatg agctgatgct ttgggccgag gactgccccg   3540
aagtccggca cctcgtgcac gcggatttcg gctccaacaa tgtcctgacg gacaatggcc   3600
gcataacagc ggtcattgac tggagcgagg cgatgttcgg ggattcccaa tacgaggtcg   3660
ccaacatctt cttctggagg ccgtggttgg cttgtatgga gcagcagacg cgctacttcg   3720
agcggaggca tccggagctt gcaggatcgc cacgcctccg ggcgtatatg ctccgcattg   3780
gtcttgacca actctatcag agcttggttg acggcaattt cgatgatgca gcttgggcgc   3840
agggtcgatg cgacgcaatc gtccgatccg gagccgggac tgtcgggcgt acacaaatcg   3900
cccgcagaag cgcggccgtc tggaccgatg gctgtgtaga agtactcgcc gatagtggaa   3960
accgacgccc cagcactcgt ccgagggcaa aggaatagag tagatgccga ccgaacaaga   4020
gctgatttcg agaacgcctc agccagcaac tcgcgcgagc ctagcaaggc aaatgcgaga   4080
gaacggcctt acgcttggtg gcacagttct cgtccacagt tcgctaagct cgctcggctg   4140
gtcgcgggag aattaattcg gtacgctgaa atcaccagtc tctctctaca aatctatctc   4200
tctctatttt ctccataaat aatgtgtgag tagtttcccg ataagggaaa ttagggttct   4260
tatagggttt cgctcatgtg ttgagcatat aagaaaccct tagtatgtat ttgtatttgt   4320
aaaatacttc tatcaataaa atttctaatt cctaaaacca aaatccagta ctaaaatcca   4380
gatcgatcct tcatgttctt tcctgcgtta tcccctgatt ctgtggataa ccgtattacc   4440
gcctttgagt gagctgatac cgctcgccgc agccgaacga ccgagcgcag cgagtcagtg   4500
agcgaggaag cggaagagcg cccaatacgc aaaccgcctc tccccgcgcg ttggccgatt   4560
cattaatgca gctggcacga caggtttccc gactggaaag cgggcagtga gcgcaacgca   4620
attaatgtga gttagctcac tcattaggca ccccaggctt tacactttat gacttccggc   4680
tcgtatgttg tgtggaattg tgagcggata acaatttcac acaggaaaca gctatgacca   4740
tgattacgcc aagctcggaa ttaaccctca ctaaagggaa caaaagctgg agctctggtc   4800
ccgcaggggc ggcggctgaa acatctgcac aagctactgc cacggcgcag agtagtggac   4860
gggcgacgcc gcaggcgact gcgaacccct ctagtgcagc ttcgcaacaa tctgtcgctg   4920
ctgcggcagc gacgccatct tctgcgaggg cgagtccgat gcctgctatg cacgcccaac   4980
agaatcccac tcagtcgcaa caagcccagc aagcgaatgc ggccatactt caagctgcga   5040
ttcaacaaca acaactacag cgacaacagc aacaatacca gcgcacgttg acccccattc   5100
agccacagaa gacgaactct caaggagggc aggtgcagat gcaggttcag ccgcaattgg   5160
ccgcaaatgg acaatatacg ttcacgacgc cgttcaatgc tgccgcattg cgagccgcaa   5220
cgccccttgac cgctagtcag caagctgctg ctcaacggat ggctgctgcc caagcaaatg   5280
cagctaaaat gagcgcgggg accccctgcac agaatgcagg cagtaacatt cacgtacagc   5340
cgtcaccgca acaagcccag gctcaaatcc aggtacagca gcagcagacg cttcaggtcc   5400
```

-continued

```
cgcaacagca acaggcgagg acaccacaaa tgcaaacgca gcagctacgg acgcctcaaa   5460
ttcaggctca gcaattacgg acgccacaga tgcaaacgca acagcttcag cgaacgcctc   5520
agatgcagac gcaacaactt caaccgacgc cgcagatgca gcctcagcag ctccagtctc   5580
aaatggggca gatgcaacgc cagccgactc ctcagcaaca tacgcctcag caacaacatg   5640
ctcaacttca gcctgtgcag gctcagcagt tagcgatggc ccagcagcaa cagcaacagc   5700
agcaaatgca ggctcaaatt cagcagcaac aaccacaaca agcgcatctg actccgcaac   5760
agtatcagca gtatcagatg tatagcaatt attatcaagc tgcggcggca atgcaacaac   5820
acgggggaca gagactgact ccgcaacaac aacaggcaat ttggaacgcg cagttccagc   5880
gtgctgctgc tgctgctggt atgcaggggc agcatggcgg ggtacctatg aaccaggtac   5940
aacaggctgc gctggccgca cacatagcga aacagcagca acaacagcaa cagcatcaag   6000
gtcaaggtcc acggtgaatg ggtttagctt cgtagatagt gtattagtat tttgtaatgg   6060
acattgggat tgggtgaaga caaacccgag aacgtcatct ttgtggagtg tttgttcgga   6120
tttggtgtga ggccgtgcaa gcttagtcag cagttagtgg aaaaggtgga ggtagaaaga   6180
gggcaaggga agttttcgtc tcctttctga tctggtacca ccatcatcac cccagcaaaa   6240
ctctctactc tcttagacct tcactttatc cttcactttt attctttttc aactcttttc   6300
gtttctcaag ttctactccc aaagtcgctc gtttctttcg aatttcacga aagactgcac   6360
aaaaagacgt atctttgcta gccctgcaag catcgaccac cgatatccac agcgattcaa   6420
gaacgattcg agttcaacaa atcttcaact aatgtaattc tctttctttt gggataagtt   6480
gaaacccgaa cgaggaacta atctttcact cggtgtagaa gcttatcgat accgtcgacc   6540
tcgagggggg gcccggtacc caccggatcc acaagtttgt acaaaaaagc tgaacgagaa   6600
acgtaaaatg atataaatat caatatatta aattagattt tgcataaaaa acagactaca   6660
taatactgta aaacacaaca tatccagtca ctatggcggc cgcattaggc accccaggct   6720
ttacacttta tgcttccggc tcgtataatg tgtggatttt gagttaggat ccggcgagat   6780
tttcaggagc taaggaagct aaaatggaga aaaaaatcac tggatatacc accgttgata   6840
tatcccaatg gcatcgtaaa gaacattttg aggcatttca gtcagttgct caatgtacct   6900
ataaccagac cgttcagctg gatattacgg cctttttaaa gaccgtaaag aaaaataagc   6960
acaagtttta tccggccttt attcacattc ttgcccgcct gatgaatgct catccggaat   7020
tccgtatggc aatgaaagac ggtgagctgg tgatatggga tagtgttcac ccttgttaca   7080
ccgttttcca tgagcaaact gaaacgtttt catcgctctg gagtgaatac cacgacgatt   7140
tccggcagtt tctacacata tattcgcaag atgtggcgtg ttacggtgaa aacctggcct   7200
atttccctaa agggtttatt gagaatatgt ttttcgtctc agccaatccc tgggtgagtt   7260
tcaccagttt tgatttaaac gtggccaata tggacaactt cttcgccccc gttttcacca   7320
tgggcaaata ttatacgcaa ggcgacaagg tgctgatgcc gctggcgatt caggttcatc   7380
atgccgtctg tgatggcttc catgtcggca gaatgcttaa tgaattacaa cagtactgcg   7440
atgagtggca gggcggggcg taaacgcgtg gatccggctt actaaaagcc agataacagt   7500
atgcgtattt gcgcgctgat ttttgcggta taagaatata tactgatatg tatacccgaa   7560
gtatgtcaaa aagaggtgtg ctatgaagca gcgtattaca gtgacagttg acagcgacag   7620
ctatcagttg ctcaaggcat atatgatgtc aatatctccg gtctggtaag cacaaccatg   7680
cagaatgaag cccgtcgtct gcgtgccgaa cgctggaaag cggaaaatca ggaagggatg   7740
```

-continued gctgaggtcg cccggtttat tgaaatgaac ggctcttttg ctgacgagaa cagggactgg 7800
tgaaatgcag tttaaggttt acacctataa aagagagagc cgttatcgtc tgtttgtgga 7860
tgtacagagt gatattattg acacgcccgg gcgacggatg gtgatccccc tggccagtgc 7920
acgtctgctg tcagataaag tctcccgtga actttacccg gtggtgcata tcggggatga 7980
aagctggcgc atgatgacca ccgatatggc cagtgtgccg gtctccgtta tcggggaaga 8040
agtggctgat ctcagccacc gcgaaaatga catcaaaaac gccattaacc tgatgttctg 8100
gggaatataa atgtcaggct cccttataca cagccagtct gcaggtcgac catagtgact 8160
ggatatgttg tgttttacag tattatgtag tctgtttttt atgcaaaatc taatttaata 8220
tattgatatt tatatcattt tacgtttctc gttcagcttt cttgtacaaa gtggtgctcg 8280
agatggtgag caagggcgag gagctgttca ccggggtggt gcccatcctg gtcgagctgg 8340
acggcgacgt aaacggccac aagttcagcg tgtccggcga gggcgagggc gatgccacct 8400
acggcaagct gaccctgaag ctgatctgca ccaccggcaa gctgcccgtg ccctggccca 8460
ccctcgtgac caccctgggc tacggcctgc agtgcttcgc ccgctacccc gaccacatga 8520
agcagcacga cttcttcaag tccgccatgc ccgaaggcta cgtccaggag cgcaccatct 8580
tcttcaagga cgacggcaac tacaagaccc gcgccgaggt gaagttcgag ggcgacaccc 8640
tggtgaaccg catcgagctg aagggcatcg acttcaagga ggacggcaac atcctggggc 8700
acaagctgga gtacaactac aacagccaca acgtctatat caccgccgac aagcagaaga 8760
acggcatcaa ggccaacttc aagatccgcc acaacatcga ggacggcggc gtgcagctcg 8820
ccgaccacta ccagcagaac acccccatcg gcgacggccc cgtgctgctg cccgacaacc 8880
actacctgag ctaccagtcc gccctgagca aagaccccaa cgagaagcgc gatcacatgg 8940
tcctgctgga gttcgtgacc gccgccggga tcactctcgg catggacgag ctgtacaagt 9000
aagtcgacct gcaggcatgc gctgaaatca ccagtctctc tctacaaatc tatctctctc 9060
tataataatg tgtgagtagt tcccagataa gggaattagg gttcttatag ggtttcgctc 9120
atgtgttgag catataagaa acccttagta tgtatttgta tttgtaaaat acttctatca 9180
ataaaatttc taattcctaa aaccaaaatc cagtgggtac ccaattcgcc ctatagtgag 9240
tcgtattaca attcactggc cgtcgtttta caacgtcgtg actgggaaaa ccctggcgtt 9300
acccaactta atcgccttgc agcacatccc cctttcgcca gctggcgtaa tagcgaagag 9360
gcccgcaccg atcgcccttc ccaacagttg cgcagcctga atggcgaatg gcgcgaaatt 9420
gtaaacgtta atgttaacgt tacaccacaa tatatcctgc ca 9462

<210> SEQ ID NO 20
<211> LENGTH: 8067
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 20
agatctctaa ttccggggat cggaaatcca gaagcccgag aggttgccgc ctttcgggct 60
ttttcttttt caaaaaaaaa aatttataaa acgatctgtt gcggccggcc gccgggttgt 120
gggcaaaggc gctggcgctc gacggtgggc aaccgcttgc ggttgtccac gggcggagcc 180
ggtgcgcgta gcgcattgtc cacaagccaa gggcgaccaa taattgatat atatattcat 240
aattgaaaag ctaattgaac atactacttg ctgtaactac ttgccggagc gaggggtgtt 300

-continued

```
tgcaagctgt tgatctgaaa gggctattag cgttctcacg tgccttttg attagcgatt    360
tcacgtgacc ttattagcga tttcacgtac tccgattagc gatttcacgt accctgatta    420
gcgatttcac gtggatagtt tttggagcgg gccggaaagc cccgtgaatc aaggctttgc    480
ggggcattag cggtttcacg tggataacta ccctctatcc acaggcttcc ggggataaaa    540
aagcccgctc gacggcgggc tgttggatgg ggatcgcctg aatcgcccca tcatccagcc    600
agaaagtgag ggagccacgg ttgatgagag ctttgttgta ggtggaccag ttggtgattt    660
tgaacttttg ctttgccacg gaacggtctg cgttgtcggg aagatgcgtg atctgatcct    720
tcaactcagc aaaagttcga tttattcaac aaagccacgt tgtgtctcaa aatctctgat    780
gttacattgc acaagataaa aatatatcat catgaacaat aaaactgtct gcttacataa    840
acagtaatac aaggggtgtt atgagccata ttcaacggga aacgtcttgc tcaaggccgc    900
gattaaattc caacatggat gctgatttat atgggtataa atgggctcgc gataatgtcg    960
ggcaatcagg tgcgacaatc taccgattgt atgggaagcc cgatgcgcca gagttgtttc   1020
tgaaacatgg caaaggtagc gttgccaatg ttgttacaga tgagatggtc agactaaact   1080
ggctgacgga atttatgcct cttccgacca tcaagcattt tatccgtact cctgatgatg   1140
catggttact caccactgcg atccccggga aaacagcatt ccaggtatta gaagaatatc   1200
ctgattcagg tgaaaatatt gttgatgcgc tggcagtgtt cctgcgccgg ttgcattcga   1260
ttcctgtttg taattgtcct tttaacagcg atcgcgtatt tcgtctcgct caggcgcaat   1320
cacgaatgaa taacggtttg gttgatgcga gtgattttga tgacgagcgt aatggctggc   1380
ctgttgaaca agtctggaaa gaaatgcata aacttttgcc attctcaccg gattcagtcg   1440
tcactcatgg tgatttctca cttgataacc ttatttttga cgaggggaaa ttaataggtt   1500
gtattgatgt tggacgagtc ggaatcgcag accgatacca ggatcttgcc atcctatgga   1560
actgcctcgg tgagttttct ccttcattac agaaacggct ttttcaaaaa tatggtattg   1620
ataatcctga tatgaataaa ttgcagtttc atttgatgct cgatgagttt ttctaatcac   1680
tagaccaatg ttacacatat atactttaga ttgatttaaa acttcatttt taatttaaaa   1740
ggatctaggt gaagatcctt tttgataatc tcatgaccaa aatcccttaa cgtgagtttt   1800
cgttccactg agcgtcagac cccgtagaaa agatcaaagg atcttcttga gatccttttt   1860
ttctgcgcgt aatctgctgc ttgcaaacaa aaaaaccacc gctaccagcg gtggtttgtt   1920
tgccggatca agagctacca actctttttc cgaaggtaac tggcttcagc agagcgcaga   1980
taccaaatac tgttcttcta gtgtagccgt agttaggcca ccacttcaag aactctgtag   2040
caccgcctac atacctcgct ctgctaatcc tgttaccagt ggctgctgcc agtggcgata   2100
agtcgtgtct taccgggttg gactcaagac gatagttacc ggataaggcg cagcggtcgg   2160
gctgaacggg gggttcgtgc acacagccca gcttggagcg aacgacctac accgaactga   2220
gatacctaca gcgtgagcta tgagaaagcg ccacgcttcc cgaagggaga aaggcggaca   2280
ggtatccggt aagcggcagg gtcggaacag gagagcgcac gagggagctt ccagggggaa   2340
acgcctggta tctttatagt cctgtcgggt ttcgccacct ctgacttgag cgtcgatttt   2400
tgtgatgctc gtcagggggg cggagcctat ggaaaaacgc cagcaacgcg gcctttttac   2460
ggttcctggc cttttgctgg ccttttgctc acatgagatc tcaaacaaac acatacagcg   2520
acttagttta cccgccaata tatcctgtca aggatcgtac ccctactcca aaaatgtcaa   2580
agatacagtc tcagaagacc aaagggctat tgagactttt caacaaaggg taatttcggg   2640
aaacctcctc ggattccatt gcccagctat ctgtcacttc atcgaaagga cagtagaaaa   2700
```

-continued

```
ggaaggtggc tcctacaaat gccatcattg cgataaagga aaggctatca ttcaagatgc   2760
ctctgccgac agtggtccca aagatggacc cccacccacg aggagcatcg tggaaaaaga   2820
agacgttcca accacgtctt caaagcaagt ggattgatgt gacatctcca ctgacgtaag   2880
ggatgacgca caatcccact atccttcgca agacccttcc tctatataag gaagttcatt   2940
tcatttggag aggacagccc aagctgatcc ctatgaaaaa gcctgaactc accgcgacgt   3000
ctgtcgagaa gtttctgatc gaaaagttcg acagcgtctc cgacctgatg cagctctcgg   3060
agggcgaaga atctcgtgct ttcagcttcg atgtaggagg gcgtggatat gtcctgcggg   3120
taaatagctg cgccgatggt ttctacaaag atcgttatgt ttatcggcac tttgcatcgg   3180
ccgcgctccc gattccggaa gtgcttgaca ttggggagtt cagcgagagc ctgacctatt   3240
gcatctcccg ccgtgcacag ggtgtcacgt tgcaagacct gcctgaaacc gaactgcccg   3300
ctgttcttca gccggtcgcg gaggctatgg atgcgatcgc tgcggccgat cttagccaga   3360
cgagcgggtt cggcccattc ggaccgcaag gaatcggtca atacactaca tggcgtgatt   3420
tcatatgcgc gattgctgat ccccatgtgt atcactggca aactgtgatg gacgacaccg   3480
tcagtgcgtc cgtcgcgcag gctctcgatg agctgatgct ttgggccgag gactgccccg   3540
aagtccggca cctcgtgcac gcggatttcg gctccaacaa tgtcctgacg gacaatggcc   3600
gcataacagc ggtcattgac tggagcgagg cgatgttcgg ggattcccaa tacgaggtcg   3660
ccaacatctt cttctggagg ccgtggttgg cttgtatgga gcagcagacg cgctacttcg   3720
agcggaggca tccggagctt gcaggatcgc cacgcctccg ggcgtatatg ctccgcattg   3780
gtcttgacca actctatcag agcttggttg acggcaattt cgatgatgca gcttgggcgc   3840
agggtcgatg cgacgcaatc gtccgatccg gagccgggac tgtcgggcgt acacaaatcg   3900
cccgcagaag cgcggccgtc tggaccgatg gctgtgtaga agtactcgcc gatagtggaa   3960
accgacgccc cagcactcgt ccgagggcaa aggaatagag tagatgccga ccgaacaaga   4020
gctgatttcg agaacgcctc agccagcaac tcgcgcgagc ctagcaaggc aaatgcgaga   4080
gaacggcctt acgcttggtg gcacagttct cgtccacagt tcgctaagct cgctcggctg   4140
gtcgcgggag aattaattcg gtacgctgaa atcaccagtc tctctctaca aatctatctc   4200
tctctatttt ctccataaat aatgtgtgag tagtttcccg ataagggaaa ttagggttct   4260
tatagggttt cgctcatgtg ttgagcatat aagaaaccct tagtatgtat ttgtatttgt   4320
aaaatacttc tatcaataaa atttctaatt cctaaaacca aaatccagta ctaaaatcca   4380
gatcgatcct tcatgttctt tcctgcgtta tcccctgatt ctgtggataa ccgtattacc   4440
gcctttgagt gagctgatac cgctcgccgc agccgaacga ccgagcgcag cgagtcagtg   4500
agcgaggaag cggaagagcg cccaatacgc aaaccgcctc tccccgcgcg ttggccgatt   4560
cattaatgca gctggcacga caggtttccc gactggaaag cgggcagtga gcgcaacgca   4620
attaatgtga gttagctcac tcattaggca ccccaggctt tacactttat gacttccggc   4680
tcgtatgttg tgtggaattg tgagcggata acaatttcac acaggaaaca gctatgacca   4740
tgattacgcc aagctcggaa ttaaccctca ctaaagggaa caaaagctgg agctcgaggt   4800
ccgcaagtag attgaaagtt cagtacgttt ttaacaatag agcattctcg aggcttgcgt   4860
cattctgtgt caggctagca gtttataagc gttgaggatc tagagctgct gtttccgcgt   4920
ctcgaatgtt ctcggtgttt aggggttagc aatctgatat gataataatt tgtgatgaca   4980
tcgatagtac aaaaacccca attccggtca catccacctc tccgttttct cccatctaca   5040
```

```
cacaacaagc ttatcgccgt aattctcttt cttttgggat aagttgaaac ccgaacgagg   5100
aactaatctt tcactcggtg tagaagctta tcgataccgt cgacctcgag ggggggcccg   5160
gtacccaccg gatccacaag tttgtacaaa aaagctgaac gagaaacgta aaatgatata   5220
aatatcaata tattaaatta gattttgcat aaaaaacaga ctacataata ctgtaaaaca   5280
caacatatcc agtcactatg gcggccgcat taggcacccc aggctttaca ctttatgctt   5340
ccggctcgta taatgtgtgg attttgagtt aggatccggc gagattttca ggagctaagg   5400
aagctaaaat ggagaaaaaa atcactggat ataccaccgt tgatatatcc caatggcatc   5460
gtaaagaaca ttttgaggca tttcagtcag ttgctcaatg tacctataac cagaccgttc   5520
agctggatat tacggccttt ttaaagaccg taaagaaaaa taagcacaag ttttatccgg   5580
cctttattca cattcttgcc cgcctgatga atgctcatcc ggaattccgt atggcaatga   5640
aagacggtga gctggtgata tgggatagtg ttcacccttg ttacaccgtt ttccatgagc   5700
aaactgaaac gttttcatcg ctctggagtg aataccacga cgatttccgg cagtttctac   5760
acatatattc gcaagatgtg gcgtgttacg gtgaaaacct ggcctatttc cctaaagggt   5820
ttattgagaa tatgtttttc gtctcagcca atccctgggt gagtttcacc agttttgatt   5880
taaacgtggc caatatggac aacttcttcg cccccgtttt caccatgggc aaatattata   5940
cgcaaggcga caaggtgctg atgccgctgg cgattcaggt tcatcatgcc gtctgtgatg   6000
gcttccatgt cggcagaatg cttaatgaat tacaacagta ctgcgatgag tggcagggcg   6060
gggcgtaaac gcgtggatcc ggcttactaa aagccagata acagtatgcg tatttgcgcg   6120
ctgatttttg cggtataaga atatatactg atatgtatac ccgaagtatg tcaaaaagag   6180
gtgtgctatg aagcagcgta ttacagtgac agttgacagc gacagctatc agttgctcaa   6240
ggcatatatg atgtcaatat ctccggtctg gtaagcacaa ccatgcagaa tgaagcccgt   6300
cgtctgcgtg ccgaacgctg gaaagcggaa aatcaggaag ggatggctga ggtcgcccgg   6360
tttattgaaa tgaacggctc ttttgctgac gagaacaggg actggtgaaa tgcagtttaa   6420
ggtttacacc tataaaagag agagccgtta tcgtctgttt gtggatgtac agagtgatat   6480
tattgacacg cccgggcgac ggatggtgat ccccctggcc agtgcacgtc tgctgtcaga   6540
taaagtctcc cgtgaacttt acccggtggt gcatatcggg gatgaaagct ggcgcatgat   6600
gaccaccgat atggccagtg tgccggtctc cgttatcggg gaagaagtgg ctgatctcag   6660
ccaccgcgaa aatgacatca aaaacgccat taacctgatg ttctggggaa tataaatgtc   6720
aggctccctt atacacagcc agtctgcagg tcgaccatag tgactggata tgttgtgttt   6780
tacagtatta tgtagtctgt tttttatgca aaatctaatt taatatattg atatttatat   6840
cattttacgt ttctcgttca gctttcttgt acaaagtggt gctcgagatg gtgagcaagg   6900
gcgaggagct gttcaccggg gtggtgccca tcctggtcga gctggacggc gacgtaaacg   6960
gccacaagtt cagcgtgtcc ggcgagggcg agggcgatgc cacctacggc aagctgaccc   7020
tgaagctgat ctgcaccacc ggcaagctgc ccgtgccctg gcccaccctc gtgaccaccc   7080
tgggctacgg cctgcagtgc ttcgcccgct accccgacca catgaagcag cacgacttct   7140
tcaagtccgc catgcccgaa ggctacgtcc aggagcgcac catcttcttc aaggacgacg   7200
gcaactacaa gacccgcgcc gaggtgaagt tcgagggcga caccctggtg aaccgcatcg   7260
agctgaaggg catcgacttc aaggaggacg gcaacatcct ggggcacaag ctggagtaca   7320
actacaacag ccacaacgtc tatatcaccg ccgacaagca gaagaacggc atcaaggcca   7380
acttcaagat ccgccacaac atcgaggacg gcggcgtgca gctcgccgac cactaccagc   7440
```

-continued

```
agaacacccc catcggcgac ggccccgtgc tgctgcccga caaccactac ctgagctacc   7500

agtccgccct gagcaaagac cccaacgaga agcgcgatca catggtcctg ctggagttcg   7560

tgaccgccgc cgggatcact ctcggcatgg acgagctgta caagtaagtc gacctgcagg   7620

catgcgctga aatcaccagt ctctctctac aaatctatct ctctctataa taatgtgtga   7680

gtagttccca gataagggaa ttagggttct tatagggttt cgctcatgtg ttgagcatat   7740

aagaaaccct tagtatgtat ttgtatttgt aaaatacttc tatcaataaa atttctaatt   7800

cctaaaacca aaatccagtg ggtacccaat tcgccctata gtgagtcgta ttacaattca   7860

ctggccgtcg ttttacaacg tcgtgactgg gaaaaccctg gcgttaccca acttaatcgc   7920

cttgcagcac atcccccttt cgccagctgg cgtaatagcg aagaggcccg caccgatcgc   7980

ccttcccaac agttgcgcag cctgaatggc gaatggcgcg aaattgtaaa cgttaatgtt   8040

aacgttacac cacaatatat cctgcca                                      8067

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gly Val Asp Ile Gly Thr Gly Ala Ser
1               5
```

GENETIC ENGINEERING OF FUNGI TO MODULATE TRYPTAMINE EXPRESSION

CROSS REFERENCE TO RELATED APPLICATIONS

This application is a continuation of International Application No. PCT/US20/53842, filed Oct. 1, 2020, which claims the benefit of U.S. Provisional Application No. 62/909,159, filed on Oct. 1, 2019, which is incorporated by reference herein in its entirety.

SEQUENCE LISTING

The instant application contains a Sequence Listing which has been submitted electronically in ASCII format and is hereby incorporated by reference in its entirety. Said ASCII copy, created on Nov. 11, 2020, is named 200021-707301 SL.txt and is 142,223 bytes in size.

BACKGROUND

Tryptamine-derived substance, such as psilocybin and psilocin in fungi is natural drugs that have known psychedelic and other medicinal effects. The pharmacological effects are caused by modified tryptamines, with psilocybin being the major chemical constituent of these fungi. This prodrug-like natural product becomes rapidly dephosphorylated following oral ingestion to yield the actual psychotropic agent psilocin, which is also produced in a small amount by fungi. Tryptamine-derived substance has attracted pharmaceutical attention, as clinical studies show a positive trend in the treatment of existential anxiety with advanced-stage cancer patients and for nicotine addiction. Recently, researches have been underway to investigate the use of psilocybin for the treatment of depression. Fungi having a modified therapeutic component(s) profile may be useful in the production of tryptamine-derived substance and/or may also be useful in the production of genetically modified fungi providing a desired drug profile.

SUMMARY

Provided herein is a genetically modified organism or cell or tissue thereof, comprising a genetic modification that results in an increased production of a compound selected from:

(Formula I)

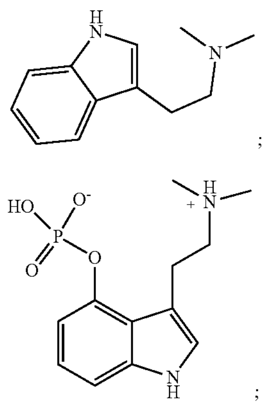

;

(Formula II)

;

-continued (Formula III)

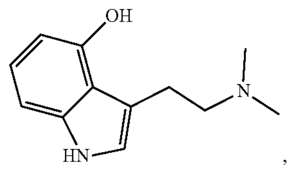

, (Formula IV)

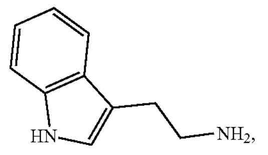

derivatives or analogs thereof, as compared to production of the same compound in a comparable control organism without the genetic modification. Provided herein is also a genetically modified organism, comprising an endonuclease mediated genetic modification that results in an increased amount of a compound (Formula IV)

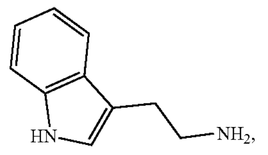

derivatives or analogs thereof, as compared to an amount of the same compound in a comparable control organism without the genetic modification. In some cases, the organism is fungus, yeast, bacterium, animal, or insect. In embodiments described herein, the compound of Formula I is Dimethyltryptamine (DMT), the compound of Formula II is psilocybin, the compound of Formula III is psilocin, and the compound of Formula IV is tryptamine.

Provided here in is a method for increasing production of (Formula I, DMT)

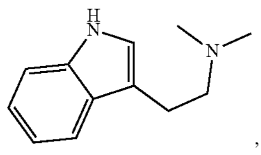

, (Formula III, Psilocin)

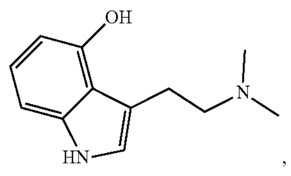

, or derivatives or analogs thereof in an organism, said method comprising introducing a genetic modification to said organism, wherein said genetic modification results in an increased production of the same compound as compared to a comparable control organism without said modification. Provided herein is a method for increasing production of (Formula I, DMT)

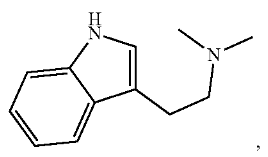

, (Formula II, Psilocybin)

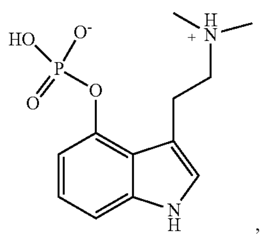

, (Formula III, Psilocin)

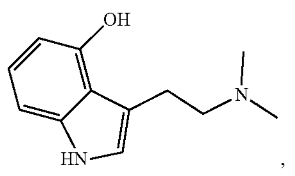

, (Formula IV, Tryptamine)

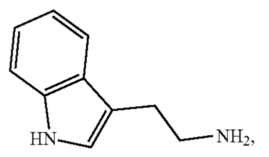

or derivatives or analogs thereof in an organism, said method comprising introducing a genetic modification of said organism, wherein said genetic modification results in an increased production of the same compound as compared to a comparable control organism without said modification, wherein said organism is a fungus and wherein the fungus is from division Basidiomycota.

In some cases, a genetically modified organism described herein is a plant. In some cases, a genetically modified organism described herein is a bacterium. In some cases, a bacterium is an *Agrobacterium*. In some cases, a genetically modified organism provided herein is a fungus. In some cases, the fungus is a Basidiomycota fungus. In some cases the basidiomycota fungus can be selected from the group consisting of *Psilocybe, Conocybe, Gymnopilus, Panaeolus, Pluteus*, and *Stropharia*. In some cases, a fungus is *Panaeolus cyanescecens*. In some cases, a fungus is *Panaeolus cubensis*. In some cases, a fungus is *Pleurotus nebrodensis*.

In an aspect, a the genetically modified organism described herein comprises a genetic modification that is an alteration in or adjacent to a gene or a promoter or enhancer of a gene, and wherein the gene encodes PLP-independent phosphatidylserine decarboxylase, a tryptophan decarboxylase (TDC), a 5-methylthionribose family small molecule kinase, 4-hydroxytryptamine kinase, a class I methyltransferase, facilitator-type transporter PsiT1 or facilitator-type transporter PsiT2.

In an aspect, a genetic modification in an organism described herein results in at least one of: (a) increased tryptophan decarboxylation, (b) increased tryptamine 4-hydroxylation, (c) increased 4-hydroxytryptaine O-phosphorylation, and (d) increased psilocybin via sequential N-methylations with reduced expression of a psilocin intermediate in the genetically modified organism compared to a comparable control organism without the genetic modification. In some cases, a genetic modification results in (i) upregulated expression of a tryptophan decarboxylase gene, a psilocybin-related hydroxylase gene, a psilocybin-related N-methyltransferase gene, or a psilocybin-related phosphotransferase gene; (ii) reduced synthesis of non-psilocybin tryptamines; or (iii) increased production of tryptophan in the genetically modified organism compared to a comparable control organism without the genetic modification.

In an aspect, a genetic modification can be in a promoter or enhancer region of a gene of interest, or associated with a gene of interest. In some cases, the genetic modification results in upregulated expression of a gene. In an aspect, a gene of interest described herein encodes a PLP-independent phosphatidylserine decarboxylase, a tryptophan decarboxylase (TDC), a 5-methylthionribose family small molecule kinase, 4-hydroxytryptamine kinase, or a class I methyltransferase. In some cases, a gene of interest described herein comprises at least 75%, at least 85%, at least 90%, at least 95%, or at least 99% identity to SEQ ID NO: 1. In some cases, a gene of interest described herein comprises at least 75%, at least 85%, at least 90%, at least 95%, or at least 99% identity to SEQ ID NO: 2. In some cases, a gene of interest described herein comprises at least 75%, at least 85%, at least 90%, at least 95%, or at least 99% identity to SEQ ID NO: 3. In some cases, a gene of interest described herein encodes a class I methyltransferase. In some cases, a class I methyltransferase comprises a Rossmann-fold. In some cases, a class I methyltransferase can be norbaeocystin methyltransferase. In some cases, a gene of interest described herein comprises at least 75%, at least 85%, at least 90%, at least 95%, or at least 99% identity to SEQ ID NO: 4. In some cases, a gene of interest described herein comprises at least 75%, at least 85%, at least 90%, at least 95%, or at least 99% identity to SEQ ID NO: 5. In some cases, a gene of interest described herein comprises at least 75%, at least 85%, at least 90%, at least 95%, or at least 99% identity to SEQ ID NO: 6. In some cases, a gene of interest described herein comprises at least 75%, at least 85%, at least 90%, at least 95%, or at least 99% identity to SEQ ID NO: 7. In some cases, a gene of interest described herein comprises at least 75%, at least 85%, at least 90%, at least 95%, or at least 99% identity to SEQ ID NO: 8. In some cases, a gene of interest described herein comprises at least 75%, at least 85%, at least 90%, at least 95%, or at least 99% identity to SEQ ID NO: 9. In some cases, a gene of interest described herein comprises at least 75%, at least 85%, at least 90%, at least 95%, or at least 99% identity to SEQ ID NO: 10. In some cases, a gene of interest described herein comprises at least 75%, at least 85%, at least 90%, at least 95%, or at least 99% identity to SEQ ID NO: 11. In some cases, a gene of interest described herein comprises at least 75%, at least 85%, at least 90%, at least 95%, or at least 99% identity to SEQ ID NO: 12. In some cases, a gene of interest described herein comprises at least 75%, at least 85%, at least 90%, at least 95%, or at least 99% identity to SEQ ID NO: 13. In some cases, a gene of interest described herein comprises at least 75%, at least 85%, at least 90%, at least 95%, or at least 99% identity to SEQ ID NO: 14.

In some cases, a gene can be a PsiD gene, a PsiM gene, a PsiH gene, a PsiK gene, a PsiR gene, a PsiT1 gene, or a PsiT2 gene, or any portions thereof. In some cases, expression of a gene is upregulated by at least 1.1, at least 1.2, at least 1.5, at least 2, at least 2.5, at least 3, at least 3.5, at least 4, or at least 5 folds in a genetically modified organism compared to a comparable control organism without the genetic modification. In some cases, a genetic modification in a genetically modified organism described herein comprises an alteration in a gene selected from the group consisting of Indoleamine 2,3-dioxygenase (IDO), tryptophan 2,3-dioxygenase (TDO), and TrpM. In some cases, a genetic modification can be in a coding region of the gene. In some cases, a genetic modification comprises an alteration in a gene selected from the group consisting of phospho-2-dehydro-3-deoxyheptonate aldolase, 3-dehydroquinate synthase, 3-dehydroquinate dehydratase, shikimate dehydrogenase, 3-phosphoshikimate 1-carboxyvinyltransferase, shikimate kinase 1, shikimate kinase 2, chorismate synthase, tryptophan synthase alpha chain, tryptophan synthase beta chain, anthranilate phosphoribosyltransferase, and anthranilate synthase.

In an aspect, a genetic modification can be in a promoter region of a gene. In some cases, a genetically modified organism comprises 25% more (Formula IV)

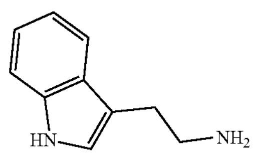

as measured by dry weight compared to a comparable control organism without the genetic modification. In some cases, a genetically modified organism comprises 25% more psilocybin as measured by dry weight compared to a comparable control organism without the genetic modification. In some cases, a genetically modified organism comprises 10% more psilocin as measured by dry weight compared to a comparable control organism without the genetic modification.

In some cases, a genetic modification can be conducted by contacting a cell of an organism with an endonuclease system. In an aspect, an endonuclease system comprises a CRISPR enzyme, TALE-Nuclease, transposon-based nuclease, Zinc finger nuclease, meganuclease, argonaute, Mega-TAL or DNA guided nuclease. In an aspect, a DNA-guided nuclease comprises an argonaute. In some cases, an endonuclease system comprises a CRISPR enzyme and a guide polynucleotide that hybridizes with a target sequence in, or adjacent to the gene or the promoter or enhancer associated therewith. In some cases, a target sequence can be at least 18 nucleotides, at least 19 nucleotides, at least 20 nucleotides, at least 21 nucleotides, or at least 22 nucleotides in length. In some cases, a target sequence is at most 17 nucleotides in length. In some cases, a target sequence can hybridize with at least one of SEQ ID NOs: 1-14 or the complementary thereof. In some cases, a guide polynucleotide can be chemically modified. In an aspect, a guide polynucleotide is a single guide RNA (sgRNA). In an aspect, a guide polynucleotide can be a chimeric single guide comprising RNA and DNA. In some cases, a guide polynucleotide can hybridize with at least one of SEQ ID NOs: 1-14 or a complement thereof.

In some cases, a CRISPR enzyme can be a Cas protein or variant or derivative thereof. In some cases, a Cas protein comprises Cas1, Cas1B, Cas2, Cas3, Cas4, Cas5, Cas5d, Cas5t, Cas5h, Cas5a, Cash, Cas7, Cas8, Cas9, Cas10, Csy1, Csy2, Csy3, Csy4, Cse1, Cse2, Cse3, Cse4, Cse5e, Csc1, Csc2, Csa5, Csn1, Csn2, Csm1, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx1S, Csf1, Csf2, CsO, Csf4, Csd1, Csd2, Cst1, Cst2, Csh1, Csh2, Csa1, Csa2, Csa3, Csa4, Csa5, C2c1, C2c2, C2c3, Cpf1, CARF, DinG, homologues thereof, or modified versions thereof. In some cases, a Cas protein can be a Cas9. In some cases, Cas9 is a modified Cas9 that binds to a canonical PAM. In some cases, Cas9 recognizes a non-canonical PAM. In some cases, a guide polynucleotide binds a target sequence 3-10 nucleotides from a PAM. In some cases, a CRISPR enzyme coupled with a guide polynucleotide can be delivered into a genetically modified organism as an RNP. In some cases, a CRISPR enzyme coupled with a guide polynucleotide can be delivered into a genetically modified organism by a mRNA encoding the CRISPR enzyme and the guide polynucleotide.

In some cases, a CRISPR enzyme coupled with a guide polynucleotide can be delivered into a genetically modified organism by a vector comprising a nucleic acid encoding the CRISPR enzyme and the guide polynucleotide. In an aspect, a vector can be a binary vector or a Ti plasmid. In an aspect, a vector further comprises a selection marker or a reporter gene. In some cases, a RNP, complex, or vector can be delivered via electroporation, microinjection, mechanical cell deformation, lipid nanoparticles, AAV, lentivirus, *Agrobacterium* mediated transformation, biolistic particle bombardment, or protoplast transformation. In some cases, a RNP, mRNA, or vector further comprises a donor polynucleotide or a nucleic acid encoding the donor polynucleotide. In an aspect, a donor polynucleotide comprises homology to sequences flanking a target sequence. In an aspect, a donor polynucleotide further comprises a barcode, a reporter gene, or a selection marker.

In another aspect, the genetically modified organism comprises an exogenous nucleotide. In some cases, the exogenous nucleotide comprises a cis-acting promoter sequence. In some cases, the exogenous nucleotide results in increased tryptophan decarboxylation, tryptamine 4-hydroxylation, 4-hydroxytryptaine O-phosphorylation, or psilocybin production via sequential N-methylations without a psilocin intermediate in said genetically modified organism compared to a comparable control organism without said exogenous nucleotide. In some cases, the exogenous nucleotide results in (i) upregulated expression of a tryptophan decarboxylase gene, a psilocybin-related hydroxylase gene, a psilocybin-related N-methyltransferase gene, or a psilocybin-related phosphotransferase gene; (ii) reduced synthesis of non-psilocybin tryptamines; or (iii) increased production of tryptophan in said genetically modified organism compared to a comparable control organism without said exogenous nucleotide. In some cases, the exogenous nucleotide encodes a PLP-independent phosphatidylserine decarboxylase, a tryptophan decarboxylase (TDC), a putative monooxygenase, a 5-methylthionribose family small molecule kinases, or a 4-hydroxytryptamine kinase.

In some cases, the nucleotide is incorporated in a plasmid. In some cases, the plasmid is pGWB5 or pGHGWY. In some cases, the plasmid is delivered into said genetically modified organism via electroporation, microinjection, mechanical cell deformation, lipid nanoparticles, AAV, lentivirus, *Agrobacterium* mediated transformation, biolistic particle bombardment, or protoplast transformation. In some cases, the plasmid further comprises a barcode, a reporter gene, or a selection marker. In some cases, the plasmid further comprises a promoter. In some cases, the promoter is 35S, GPD, EF1a, Actin or CcDED1.

In embodiments described herein, a genetically modified organism can be a multicellular or unicellular organism. In certain embodiments, the organism can be a single plant or fungal cell. Embodiments described herein also include populations of cells, for instance a population of cells from fungal species described herein.

Provided herein is a kit for genome editing comprising compositions provided herein. Provided herein is also a cell comprising a composition provided herein. A cell can be a plant cell. In some cases, a cell is a fungal cell. In some cases, a cell is a bacterial cell. In some cases, a cell is an animal cell. In some cases, a cell is an insect cell. Provide herein is a pharmaceutical composition comprising an extract of a genetically modified organism, a genetically modified cells, a composition, or a cell. In an aspect, a pharmaceutical composition, further comprises a pharmaceutically acceptable excipient, diluent, or carrier. In some cases, a pharmaceutically acceptable excipient is a lipid.

Provided herein is a nutraceutical composition comprising an extract of a genetically modified organism, a genetically modified cell, a composition, or a cell. Provided herein is a food supplement composition comprising an extract of a genetically modified organism, a genetically modified cell, a composition, or a cell. In an aspect, a nutraceutical composition, or a food supplement can be in an oral form, a transdermal form, an oil formulation, an edible food, a food substrate, an aqueous dispersion, an emulsion, a solution, a suspension, an elixir, a gel, a syrup, an aerosol, a mist, a powder, a tablet, a lozenge, a gel, a lotion, a paste, a formulated stick, a balm, a cream, or an ointment.

Provided herein is a method of treating a disease or condition comprising administering a pharmaceutical composition, a nutraceutical composition, or a food supplement to a subject. In an aspect, a disease or condition is selected from the group consisting of depression, anxiety, post-traumatic stress disorder, addiction, or secession related side-effects, psychological distress, and mental disorders and conditions.

In certain embodiments, a genetically modified organism as described herein can be fungus, yeast, plant, animal, bacterium. In some cases, a fungus is a mushroom. In some cases, a mushroom can produce at least one of: Dimethyltryptamine (DMT), Psilocybin, Psilocin, and/or any combination thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 3A-3D illustrate representative vectors constructs for genetically modified organisms and cells described herein, over-expressing Psi genes under the control of the 35S promoter: FIG. 3A shows a representative vector over-expressing PsiD gene under the control of the 35S promoter; FIG. 3B shows a representative vector over-expressing PsiH gene under the control of the 35S promoter; FIG. 3C shows a representative vector over-expressing PsiK gene under the control of the 35S promoter; FIG. 3D shows a representative vector over-expressing PsiM gene under the control of the 35S promoter.

FIG. 4A shows a representative vector with the CcDED1 promoter; FIG. 4B shows a representative vector with the GPD promoter.

FIG. 5A illustrates a panel of expression vectors with different promoters of varying strengths. FIG. 5B illustrates isolated protoplasts and extract gill tissues. FIG. 5C illustrates selecting transformation with the plasmid DNA or *Agrobacterium* incorporation. FIG. 5D illustrates regeneration of adult mushroom. FIG. 5E illustrates analyzing the psilocybin content of the genetically modified mushroom.

DETAILED DESCRIPTION

Figure 1:
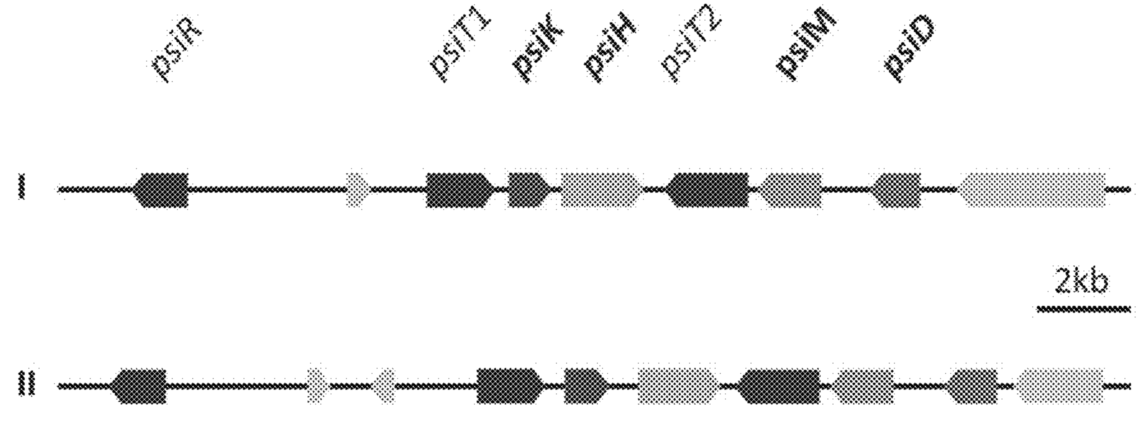
FIG. 1 shows a schematic of the syntenic loci (Psi) for biosynthesis in *P. cubensis* (I) and *P. cyanescens* (II). Genes involved in enzymatic synthesis are labeled in bold font. Clusters include genes for a kinase (PsiK), a methyltransferase (PsiM), a tryptophan decarboxylase (PsiD), and a P450 monooxygenase (PsiH). Additionally, two facilitator-type transporters (PsiT1 and PsiT2) and a putative transcriptional regulator (PsiR) are encoded and shown. Hypothetical genes are shown in light gray. Introns are not shown.
Figure 2:
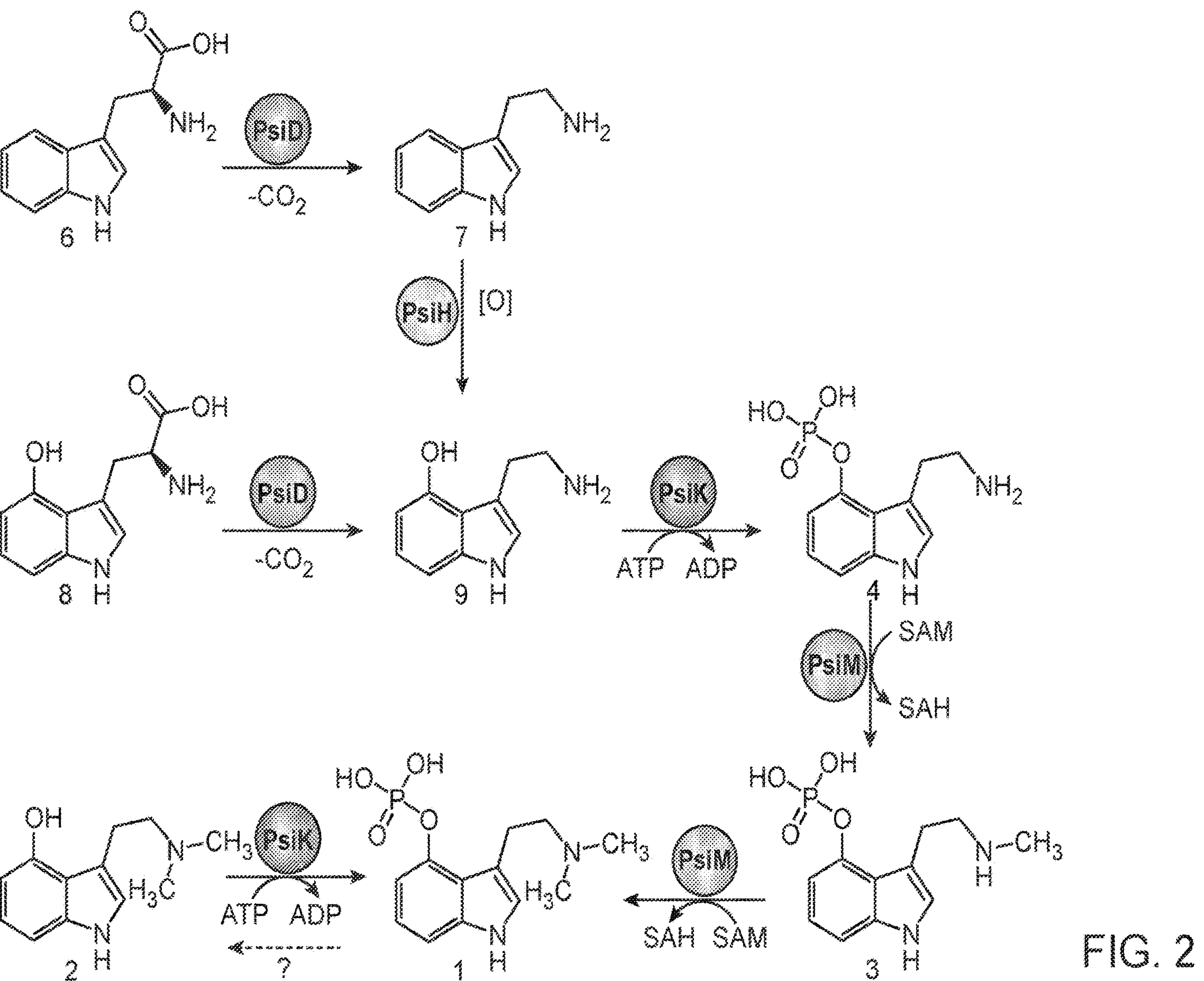
FIG. 2 depicts representative psilocybin biosynthesis pathway in vitro.

As used in the specification and claims, the singular forms "a," "an," and "the" include plural references unless the context clearly dictates otherwise. For example, the term "a chimeric transmembrane receptor polypeptide" includes a plurality of chimeric transmembrane receptor polypeptides.

The term "about" or "approximately" means within an acceptable error range for the particular value as determined by one of ordinary skill in the art, which can depend in part on how the value can be measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated, the term "about" meaning within an acceptable error range for the particular value should be assumed.

As used herein, a "cell" can generally refer to a biological cell. A cell can be the basic structural, functional and/or biological unit of a living organism. A cell can originate from any organism having one or more cells. Some non-limiting examples include: a prokaryotic cell, eukaryotic cell, a bacterial cell, an archaeal cell, a cell of a single-cell eukaryotic organism, a protozoa cell, a cell from a plant, an algal cell, seaweeds, a fungal cell, an animal cell, a cell from an invertebrate animal, a cell from a vertebrate animal, a cell from a mammal, and the like. Sometimes a cell is not originating from a natural organism (e.g. a cell can be a synthetically made, sometimes termed an artificial cell).

The term "gene," as used herein, refers to a nucleic acid (e.g., DNA such as genomic DNA and cDNA) and its corresponding nucleotide sequence that can be involved in encoding an RNA transcript. The term as used herein with reference to genomic DNA includes intervening, non-coding regions as well as regulatory regions and can include 5' and 3' ends. In some uses, the term encompasses the transcribed sequences, including 5' and 3' untranslated regions (5'-UTR and 3'-UTR), exons and introns. In some genes, the transcribed region can contain "open reading frames" that encode polypeptides. In some uses of the term, a "gene" comprises only the coding sequences (e.g., an "open reading frame" or "coding region") necessary for encoding a polypeptide. In some cases, genes do not encode a polypeptide, for example, ribosomal RNA genes (rRNA) and transfer RNA (tRNA) genes. In some cases, the term "gene" includes not only the transcribed sequences, but in addition, also includes non-transcribed regions including upstream and downstream regulatory regions, enhancers and promoters. A gene can refer to an "endogenous gene" or a native gene in its natural location in the genome of an organism. A gene can refer to an "exogenous gene" or a non-native gene. A non-native gene can refer to a gene not normally found in the host organism but which can be introduced into the host organism by gene transfer. A non-native gene can also refer to a gene not in its natural location in the genome of an organism. A non-native gene can also refer to a naturally occurring nucleic acid or polypeptide sequence that comprises mutations, insertions and/or deletions (e.g., non-native sequence).

The term "nucleotide," as used herein, generally refers to a base-sugar-phosphate combination. A nucleotide can comprise a synthetic nucleotide. A nucleotide can comprise a synthetic nucleotide analog. Nucleotides can be monomeric units of a nucleic acid sequence (e.g. deoxyribonucleic acid (DNA) and ribonucleic acid (RNA)). The term nucleotide can include ribonucleoside triphosphates adenosine triphosphate (ATP), uridine triphosphate (UTP), cytosine triphosphate (CTP), guanosine triphosphate (GTP) and deoxyribonucleoside triphosphates such as dATP, dCTP, dITP, dUTP, dGTP, dTTP, or derivatives thereof. Such derivatives can include, for example, [αS]dATP, 7-deaza-dGTP and 7-deaza-dATP, and nucleotide derivatives that confer nuclease resistance on the nucleic acid molecule containing them. The term nucleotide as used herein can refer to dideoxyribonucleoside triphosphates (ddNTPs) and their derivatives. Illustrative examples of dideoxyribonucleoside triphosphates can include, but are not limited to, ddATP, ddCTP, ddGTP, ddITP, and ddTTP. A nucleotide can be unlabeled or detectably labeled by well-known techniques. Labeling can also be carried out with quantum dots. Detectable labels can include, for example, radioactive isotopes, fluorescent labels, chemiluminescent labels, bioluminescent labels and enzyme labels. Fluorescent labels of nucleotides can include but are not limited fluorescein, 5-carboxyfluorescein (FAM), 2'7'-dimethoxy-4'5-dichloro-6-carboxyfluorescein (JOE), rhodamine, 6-carboxyrhodamine (R6G), N,N,N',N'-tetramethyl-6-carboxyrhodamine (TAMRA), 6-carboxy-X-rhodamine (ROX), 4-(4'dimethylaminophenylazo) benzoic acid (DABCYL), Cascade Blue, Oregon Green, Texas Red, Cyanine and 5-(2'-aminoethyl)aminonaphthalene-1-sulfonic acid (EDANS). Specific examples of fluorescently labeled nucleotides can include [R6G]dUTP, [TAMRA]dUTP, [R110]dCTP, [R6G]dCTP, [TAMRA]dCTP, [JOE]ddATP, [R6G]ddATP, [FAM]ddCTP, [R110]ddCTP, [TAMRA]ddGTP, [ROX]ddTTP, [dR6G]ddATP, [dR110]ddCTP, [dTAMRA]ddGTP, and [dROX]ddTTP available from Perkin Elmer, Foster City, Calif.; FluoroLink DeoxyNucleotides, FluoroLink Cy3-dCTP, FluoroLink Cy5-dCTP, FluoroLink Fluor X-dCTP, FluoroLink Cy3-dUTP, and FluoroLink Cy5-dUTP available from Amersham, Arlington Heights, Ill.; Fluorescein-15-dATP, Fluorescein-12-dUTP, Tetramethyl-rodamine-6-dUTP, IR770-9-dATP, Fluorescein-12-ddUTP, Fluorescein-12-UTP, and Fluorescein-15-2'-dATP available from Boehringer Mannheim, Indianapolis, Ind.; and Chromosome Labeled Nucleotides, BODIPY-FL-14-UTP, BODIPY-FL-4-UTP, BODIPY-TMR-14-UTP, BODIPY-TMR-14-dUTP, BODIPY-TR-14-UTP, BODIPY-TR-14-dUTP, Cascade Blue-7-UTP, Cascade Blue-7-dUTP, fluorescein-12-UTP, fluorescein-12-dUTP, Oregon Green 488-5-dUTP, Rhodamine Green-5-UTP, Rhodamine Green-5-dUTP, tetramethylrhodamine-6-UTP, tetramethylrhodamine-6-dUTP, Texas Red-5-UTP, Texas Red-5-dUTP, and Texas Red-12-dUTP available from Molecular Probes, Eugene, Oreg. Nucleotides can also be labeled or marked by chemical modification. A chemically-modified single nucleotide can be biotin-dNTP. Some non-limiting examples of biotinylated dNTPs can include, biotin-dATP (e.g., bio-N6-ddATP, biotin-14-dATP), biotin-dCTP (e.g., biotin-11-dCTP, biotin-14-dCTP), and biotin-dUTP (e.g. biotin-11-dUTP, biotin-16-dUTP, biotin-20-dUTP).

References to a percentage sequence identity between two nucleotide sequences means that, when aligned, that percentage of nucleotides are the same in comparing the two sequences. This alignment and the percent homology or sequence identity can be determined using software programs known in the art, for example those described in section 7.7.18 of Current Protocols in Molecular Biology (F. M. Ausubel et al., eds., 1987) Supplement 30 (incorporated by reference). A preferred alignment is determined by the Smith-Waterman homology search algorithm using an affine gap search with a gap open penalty of 12 and a gap extension penalty of 2, BLOSUM matrix of 62. The Smith-Waterman homology search algorithm is disclosed in Smith & Waterman (1981) Adv. Appl. Math. 2: 482-489 (incorporated by reference).

As used herein, the term "plant" includes a whole plant and any descendant, cell, tissue, or part of a plant. A class of plant that can be used in the present disclosure can be generally as broad as the class of higher and lower plants amenable to mutagenesis including angiosperms (monocotyledonous and dicotyledonous plants), gymnosperms, ferns and multicellular algae. Thus, "plant" includes dicot and monocot plants. The term "plant parts" include any part(s) of a plant, including, for example and without limitation: seed (including mature seed and immature seed); a plant cutting; a plant cell; a plant cell culture; a plant organ (e.g., pollen, embryos, flowers, fruits, shoots, leaves, roots, stems, and explants). A plant tissue or plant organ may be a seed, protoplast, callus, or any other group of plant cells that can be organized into a structural or functional unit. A plant cell or tissue culture may be capable of regenerating a plant having the physiological and morphological characteristics of the plant from which the cell or tissue was obtained, and of regenerating a plant having substantially the same genotype as the plant. In contrast, some plant cells are not capable of being regenerated to produce plants. Regenerable cells in a plant cell or tissue culture may be embryos, protoplasts, meristematic cells, callus, pollen, leaves, anthers, roots, root tips, silk, flowers, kernels, ears, cobs, husks, or stalks.

As used herein, the term "transgene" refers to a segment of DNA which has been incorporated into a host genome or is capable of autonomous replication in a host cell and is capable of causing the expression of one or more coding sequences. Exemplary transgenes will provide the host cell, or plants regenerated therefrom, with a novel phenotype relative to the corresponding non-transformed cell or plant. Transgenes may be directly introduced into a plant by genetic transformation, or may be inherited from a plant of any previous generation which was transformed with the DNA segment. In some cases, a transgene can be a barcode. In some cases, a transgene can be a marker.

As used herein, transgenic organisms, generally refer to recombinant organisms in which a desired DNA sequence or genetic locus within the genome of an organism is modified by insertion, deletion, substitution, or other manipulation of nucleotide sequences.

As used herein, the term "transgenic plant" refers to a plant or progeny plant of any subsequent generation derived therefrom, wherein the DNA of the plant or progeny thereof contains an introduced exogenous DNA segment not naturally present in a non-transgenic plant of the same strain. The transgenic plant may additionally contain sequences which are native to the plant being transformed, but wherein the "exogenous" gene has been altered in order to alter the level or pattern of expression of the gene, for example, by use of one or more heterologous regulatory or other elements.

A vector can be a polynucleotide (e.g., DNA or RNA) used as a vehicle to artificially carry genetic material into a cell, where it can be replicated and/or expressed. In some aspects, a vector is a binary vector or a Ti plasmid. Such a polynucleotide can be in the form of a plasmid, YAC, cosmid, phagemid, BAC, virus, or linear DNA (e.g., linear PCR product), for example, or any other type of construct useful for transferring a polynucleotide sequence into another cell. A vector (or portion thereof) can exist transiently (i.e., not integrated into the genome) or stably (i.e., integrated into the genome) in the target cell. In some aspects, a vector can further comprise a selection marker or a reporter.

The practice of some methods disclosed herein employ, unless otherwise indicated, conventional techniques of immunology, biochemistry, chemistry, molecular biology, microbiology, cell biology, genomics and recombinant DNA, which are within the skill of the art. See for example Sambrook and Green, Molecular Cloning: A Laboratory Manual, 4th Edition (2012); the series Current Protocols in Molecular Biology (F. M. Ausubel, et al. eds.); the series Methods In Enzymology (Academic Press, Inc.), PCR 2: A Practical Approach (M. J. MacPherson, B. D. Hames and G. R. Taylor eds. (1995)), Harlow and Lane, eds. (1988) Antibodies, A Laboratory Manual, and Culture of Animal Cells: A Manual of Basic Technique and Specialized Applications, 6th Edition (R. I. Freshney, ed. (2010)).

The present disclosure provides genetically modified organisms producing an increased amount of tryptamine-derived substance, such as psilocybin and psilocin, as well as expression cassettes, vectors, compositions, and materials and methods for producing the same. Provided herein are also methods of making genetically modified organisms utilizing Clustered Regularly Interspaced Short Palindromic Repeats (CRISPR), Argonaut, zinc-finger, TALEN or other nuclease based technologies and reagents for generating the genetically modified organisms. Compositions and methods provided herein can be utilized for the generation of fungi or plants with increased tryptamine-derived substance production. Compositions provided herein can be utilized for various uses including but not limited to therapeutic uses, preventative uses, palliative uses, and recreational uses.

*Psilocybe* mushrooms contain psilocybin in trace amounts (0.1-1.7%) (Table 1). Production of psilocybin is expensive, due to rarity in mushrooms and the expensive synthetic production process. Research price of psilocybin is $7,000 to $10,000 per gram.

TABLE 1

Psilocybin occurs in trace amounts (0.1-1.7%) in *Psilocybe* mushrooms.

| | Alkaloidal content (%)[a] | | |
|---|---|---|---|
| Species | Psilocybin | Psilocin | Bacocystin |
| *P. azurescens* | 1.70 | 0.38 | 0.35 |
| *P. baeocystis* | 0.85 | 0.59 | 0.10 |
| *P. bohemica* | 1.34 | 0.11 | 0.02 |
| *P. cubensis* | 0.63 | 0.60 | 0.025 |
| *P. cyanescens* | 0.85 | 0.36 | 0.03 |
| *P. cyanofibrillosa* | 0.21 | 0.04 | 0.00 |
| *P. hoogshagenii* | 0.60 | 0.10 | 0.00 |
| *P. liniformans* | 0.16 | 0.00 | 0.005 |
| *P. pelliculosa* | 0.12 | 0.00 | 0.00 |
| *P. samuiensis* | 0.36 | 0.21 | 0.02 |
| *P. semilanceata* | 0.98 | 0.02 | 0.36 |
| *P. semperviva* | 0.30 | 0.07 | 0.00 |
| *P. subcubensis* | 0.80 | 0.02 | 0.00 |
| *P. stuntzii* | 0.36 | 0.12 | 0.02 |
| *P. tampanensis* | 0.68 | 0.32 | 0.00 |
| *P. weilii* | 0.61 | 0.27 | 0.05 |

[a]Average content and may vary in different regions due to environmental condit The structure of psilocybin has been known for 60 years but only recently have the psilocybin biosynthesis enzymes have been identified. This has facilitated the opportunity to now enhance the production of this Psychotropic compound within the mushroom to advance research into psilocybin's medical uses. The yields, potency and efficacy of psilocybin production may be improved by state-of-art plant CRISPR engineering platform. A demonstrated 10-fold increase in Psilocybin production in mushrooms from 1 to 10% (% dry mycelial mass) would be of significant value to the industry.

Genetically Modified Organisms

Provided herein are methods and compositions to modify biosynthesis pathways in organisms to increase production of psilocybin and psilocin in said organism. In embodiments provided herein, using gene editing, the production of early, intermediate, and/or late precursor compounds such as tryptamine and tryptamine derivatives such as dimethyl tryptamine is increased to generate desired end products such as psilocybin and psilocin.

Additionally, provided are methods and compositions for switching off specific pathways of tryptophan consumption using gene editing to generate genetically modified organisms with a higher expression levels of tryptamine and/or tryptamine related substances such as psilocybin and psilocin.

A genetically modified organism as described herein can be a plant, animal, bacteria, yeast or fungus. In some cases, the fungus is a mushroom. Specific mushrooms of the genus *Psilocybe, Conocybe, Gymnopilus, Panaeolus, Pluteus*, and *Stropharia* produce psychotropically active tryptamine-derived substance, for instance psilocybin or psilocin as described herein, the production of which is enhanced by the genetic modifications described herein. In some cases, a genetically modified organism as described herein is a mushroom selected from *Panaeolus cyanescecens, Panaeolus cubensis* and *Pleurotus nebrodensis*.

In embodiments described herein, are genetically modified cells or organisms that enhance the conversion of L-tryptophan or 4-hydroxy-L-tryptophan to tryptamine. In some cases, the genetically modified cell or organism comprises a genetic modification that suppresses or minimizes alternate pathways of consumption of either 4-hydroxy-L-tryptophan or tryptophan, thereby enhancing the formation of tryptamine and optionally downstream derivatives of tryptamine such as psilocybin and psilocin. In some cases this enhancement is achieved by introducing or upregulating genes associated with the expression or activity of tryptophan decarboxylase PsiD.

In some cases are genetically modified cells or organisms in which an enhancement in the production of psilocin or psilocybin is achieved by introducing or upregulating genes associated with the conversion of tryptamine to 4-hydroxytryptamine, for instance P450 monooxygenase PsiH. In some cases, are genetically modified cells or organisms with an enhanced production of norbaeocystin by upregulation of genes associated with the conversion of tryptamine, tryptophan or 4-hydroxytryptamine to norbaeocystin. In some cases, such an upregulation is achieved by upregulation or introduction of 4-hydroxytryptamine kinase, PsiK, by modifying a promoter or enhancer sequence associated with the gene or knocking-in the gene into the cell or organism.

In some cases are genetically modified cells or organisms in which an enhancement in the production of psilocin or psilocybin is achieved by introducing or upregulating genes associated with the conversion of norbaeocystin to baeocystin, or by increasing production of baeocystin. In some cases the upregulation is achieved by increasing synthesis of a norbaeocystin methyltransferase gene by modifying a promoter or enhancer sequence associated with the gene or knocking-in the gene into the cell or organism.

In certain embodiments, a tryptophan decarboxylase gene as described herein can be PsiD (a representative mRNA sequence is provided in Table 3). In some cases, a gene encoding the tryptophan decarboxylase may comprises a sequence identity from about 50%, 60%, 70%, 80%, 90%, 95%, 96%, 97%, 98%, 99%, or up to about 100% to: SEQ ID NO: 1. Enzyme PsiD may be a 49.6 kDa enzyme and belongs to the PLP-independent phosphatidylserine decarboxylase family. In certain embodiments, PsiD is upregulated in a cell or organism by genetically editing a promoter or enhancer sequence in the gene or associated with the gene. In certain embodiments, PsiD is upregulated or synthesized in a genetically modified cell or organism by introducing a PsiD gene in said cell or organism by use of a gene editing technique described herein.

In some cases a genetically modified cell or organism described herein comprises an upregulation in expression of a P450 monooxygenase PsiH gene (a representative mRNA sequence is provided in Table 3). In some cases, a gene encoding the monooxygenase may comprises a sequence identity from about 50%, 60%, 70%, 80%, 90%, 95%, 96%, 97%, 98%, 99%, or up to about 100% to: SEQ ID NO: 2. In certain embodiments PsiH is upregulated in a cell or organism by genetically editing a promoter or enhancer sequence in the gene or associated with the gene. In certain embodiments, PsiH is upregulated or synthesized in a genetically modified cell or organism by introducing a PsiH gene in said cell or organism by use of a gene editing technique described herein.

In some cases a genetically modified cell or organism described herein comprises an upregulation in expression of 4-hydroxytryptamine kinase PsiK gene (a representative mRNA sequence is provided in Table 3). In some cases, a gene encoding the 4-hydroxytryptamine kinase may comprises a sequence identity from about 50%, 60%, 70%, 80%, 90%, 95%, 96%, 97%, 98%, 99%, or up to about 100% to: SEQ ID NO: 3. In certain embodiments PsiK is upregulated in a cell or organism by genetically editing a promoter or enhancer sequence in the gene or associated with the gene. In certain embodiments, PsiK is upregulated or synthesized in a genetically modified cell or organism by introducing a PsiK gene, for instance the gene of Seq ID NO: 3 in said cell or organism by use of a gene editing technique described herein.

In some cases a genetically modified cell or organism described herein comprises an upregulation in expression of norbaeocystin methyltransferase PsiM gene (a representative mRNA sequence is provided in Table 3). In some cases, a gene encoding the methyltransferase may comprises a sequence identity from about 50%, 60%, 70%, 80%, 90%, 95%, 96%, 97%, 98%, 99%, or up to about 100% to any one of: SEQ ID NO: 4. In certain embodiments PsiM is upregulated in a cell or organism by genetically editing a promoter or enhancer sequence in the gene or associated with the gene. In certain embodiments, PsiM is upregulated or synthesized in a genetically modified cell or organism by introducing a PsiM gene, for instance the gene of Seq ID NO: 4 in said cell or organism by use of a gene editing technique described herein. In certain cases, a class I methyltransferase gene or a derivative thereof comprising a Rossmann-fold, with the amino sequence GVDIGTGAS (SEQ ID NO: 21) is introduced in the cell or organism to increase psilocybin production.

Other putative transcriptional regulators and transporter that affect the production and accumulation of produced psilocybin in fungi or other organisms can be modified in organisms and cells described herein. In some cases, the putative transcriptional regulators may promote the transcription or translation of a methyltransferase, hydroxylase, monooxygenase, kinase, or decarboxylase described herein, for instance PsiD, PsiH, PsiK or PsiM. In some cases, the putative transcriptional regulators can promote down-regulate the transcription or translation of enzymes, such as a methyltransferase, hydroxylase, monooxygenase, kinase, or decarboxylase described herein, for instance PsiD, PsiH, PsiK or PsiM.

In certain embodiments, genetic modification technologies disclosed herein can be used to enhance the expression of facilitator family transporters (PsiT1 and PsiT2, or a helix-loop-helix (HLH)-domain transcriptional regulator (PsiR) by genetically editing a promoter or enhancer sequence in the gene or associated with the gene, or by introducing an additional copy of one or more said gene or homologue thereof. It may also play a role in ensuring that the synthesized psilocybin is transported and localized correctly in fungi and other organisms. In certain embodiments PsiR, PsiT1 or PsiT2 is upregulated in a cell or organism by genetically editing a promoter or enhancer sequence in the gene or associated with the gene. In certain embodiments, PsiR, PsiT1 or PsiT2 is upregulated or synthesized in a genetically modified cell or organism by introducing a PsiR, PsiT1 or PsiT2 gene, for instance the gene of Seq ID NO: 5 in said cell or organism by use of a gene editing technique described herein.

A representative sequence of a gene that encodes PsiT2 is listed in Table 3. In some cases, a gene encoding PsiT2 may comprises a sequence identity from about 50%, 60%, 70%, 80%, 90%, 95%, 96%, 97%, 98%, 99%, or up to about 100% to any one of: SEQ ID NO: 5.

The above-mentioned genes can be modified by the disclosed genetic modification technologies herein to increase the production of enzymes involved in the psilocybin biosynthesis pathway, putative regulators, and putative transporters or produce such enzymes, regulators and transporters de novo in a genetically modified cell or organism described herein.

For example, expression level of specific enzyme along the psilocybin biosynthesis pathway may be increased to increase production of one or more of tryptamine, 4-Hydroxytryptamine, baeocystin, norbaeocystin and psilocybin. In some cases, a genetic modification is in a promoter or enhancer region of or associated with one or more genes described herein.

In certain embodiments, genes associated with pathways that also utilize tryptophan and/or 4-hydroxy-L-tryptophan are modified by a genetic modification technology described herein to down-regulate or knockout these genes, thereby reducing tryptophan consumption and/or 4-hydroxy-L-tryptophan consumption by these pathways. Downregulated or knocked-out genes can include for instance Indoleamine 2,3-dioxygenase (IDO), tryptophan 2,3-dioxygenase (TDO), and TrpM. TrpM is a methyltransferase that has Mono- and dimethylation activity on tryptophan but is not part of psilocybin biosynthesis pathway. Downregulation or knockout of genes such as IDO, TDO, TrpM in a genetically modified organism or cell described herein results in increased availability of tryptophan and/or 4-hydroxy-L-tryptophan for psilocybin production.

In certain embodiments are genetically modified cells or organisms comprising modifications that result in increased production of tryptophan and/or 4-hydroxy-L-tryptophan. These modifications include an upregulation in genes encoding phospho-2-dehydro-3-deoxyheptonate aldolase, 3-dehydroquinate synthase, 3-dehydroquinate dehydratase, shikimate dehydrogenase, 3-phosphoshikimate 1-carboxyvinyltransferase, shikimate kinase 1, shikimate kinase 2, chorismate synthase, tryptophan synthase alpha chain, tryptophan synthase beta chain, anthranilate phosphoribosyltransferase, or anthranilate synthase component. Upregulation of these genes is achieved by increase the production of the gene by modifying a promoter or enhancer in or associated with the gene, or by increasing the copy number of said gene in the organism or cell.

By increasing these enzymes's expression, more substrates tryptophan and/or 4-hydroxy-L-tryptophan is produced, leading to increase psilocybin and/or psilocin production.

Provided herein are methods and compositions to characterize the Psilocybin biosynthesis pathway and enzymes. In embodiments provided herein, candidate psilocybin genes are identified by sequencing three diverse Psilocybin positive ($PS^+$) mushroom homokaryon genomes: *Ps. cyanescens*, Pa. (=*Copelandia*) *cyanescens*, and *Gy. Dilepis*. In certain embodiments, five genes were clustered, all in $PS^+$ genomes: tryptophan decarboxylase (PsiD); psilocybin-related N-methyltransferase (PsiM); psilocybin-related hydroxylase (PsiH); psilocybin-related phosphotransferase (PsiK); psilocybin-related transporter (PsiT). In certain embodiments, PsiD, the first committed step in the reaction and the only one not producing a drug-scheduled compound, has specific decarboxylase activity on tryptophan producing tryptamine. In certain embodiments, gene duplications among the clusters relate to alternate or reticulated pathways for genetic modification.

In embodiments described herein, the coding sequences of the genes within the $PS^+$ cluster have been identified from several Mushrooms and as provided herein. In certain embodiments, information also exists on the intronic or exonic architecture of these genes (a representative list of genes is provided in Table 2).

TABLE 2

Length and number of introns of Psilocybin biosynthetic genes in *P. cubensis* and *P. cyanescens*. If there are two values in a cell, the first value refers to the respective gene of *P. cubensis*, the second to *P. cyanescens*. Values for *P. cyanescens* genes and for PsiR, PsiT1, and PsiT2 of *P. cubensis* are predicted, using the Augustus algorithm.

| gene | length (bp) | number of introns | cDNA length | Predicted or verified function of gene product | GenBank accession number |
|---|---|---|---|---|---|
| PsiD | 1426/1441 | 2/2 | 1320/1320 | L-tryptophan decarboxylase | KY984101/ KY984104 |
| PsiH | 2155/2128 | 10/10 | 1527/1527 | monooxygenase | MF000993/ MF000997 |
| PsiK | 1152/1147 | 1/1 | 1089/1086 | kinase | KY984099/ KY984102 |
| PsiM | 1587/1580 | 11/11 | 930/930 | N-methyltransferase | KY984100/ KY984103 |
| PsiT2 | 2014/2047 | 8/8 | 1572/1587 | transporter | MF000992/ MF000996 |
| PsiT1 | 1696/1696 | 5/5 | 1416/1419 | transporter | MF000991/ MF000995 |
| PsiR | 1556/1619 | 2/2 | 1077/1113 | transcription factor | MF000990/ MF000994 |

TABLE 3

Gene sequences for genes with enhanced expression in genetically modified cells or organisms described herein. Expression is enhanced by modification of a promoter or enhancer in or associated with the gene, or by introducing a copy of the gene in the cell or organism.

| SEQ ID NO | Name | Sequence |
|---|---|---|
| 1 | *Psilocybe cubensis* strain FSU 12409 tryptophan decarboxylase (PsiD) mRNA, complete cds GenBank: KY984101.1 | atgcaggtga tacccgcgtg caactcggca gcaataagat cactatgtcc tactcccgag tcttttagaa acatgggatg gctctctgtc agcgatgcgg tctacagcga gttcatagga gagttggcta cccgcgcttc caatcgaaat tactccaacg agttcggcct catgcaacct atccaggaat tcaaggcttt cattgaaagc gacccggtgg tgcaccaaga atttattgac atgttcgagg gcattcagga ctctccaagg aattatcagg aactatgtaa tatgttcaac gatatctttc gcaaagctcc cgtctacgga gaccttggcc ctcccgttta tatgattatg gccaaattaa tgaacacccg agcgggcttc tctgcattca cgagacaaag gttgaacctt cacttcaaaa aacttttcga tacctgggga ttgttcctgt cttcgaaaga ttctcgaaat gttcttgtgg ccgaccagtt cgacgacaga cattgcggct ggttgaacga gcgggccttg tctgctatgg ttaaacatta caatggacgc gcatttgatg aagtcttcct ctgcgataaa aatgccccat actacggctt caactcttac gacgacttct ttaatcgcag atttcgaaac cgagatatcg accgacctgt agtcggtgga gttaacaaca ccaccctcat ttctgctgct tgcgaatcac tttcctacaa cgtctcttat |

TABLE 3-continued

Gene sequences for genes with enhanced expression in genetically modified cells or organisms described herein. Expression is enhanced by modification of a promoter or enhancer in or associated with the gene, or by introducing a copy of the gene in the cell or organism.

| SEQ ID NO | Name | Sequence |
| --- | --- | --- |
| | | gacgtccagt ctctcgacac tttagttttc<br>aaaggagaga cttattcgct taagcatttg<br>ctgaataatg accctttcac cccacaattc<br>gagcatggga gtattctaca aggattcttg<br>aacgtcaccg cttaccaccg atggcacgca<br>cccgtcaatg ggacaatcgt caaaatcatc<br>aacgttccag gtacctactt tgcgcaagcc<br>ccgagcacga ttggcgaccc tatcccggat<br>aacgattacg acccacctcc ttaccttaag<br>tctcttgtct acttctctaa tattgccgca<br>aggcaaatta tgtttattga agccgacaac<br>aaggaaattg gcctcatttt ccttgtgttc<br>atcggcatga ccgaaatctc gacatgtgaa<br>gccacggtgt ccgaaggtca acacgtcaat<br>cgtggcgatg acttgggaat gttccatttc<br>ggtggttctt cgttcgcgct tggtctgagg<br>aaggattgca gggcagagat cgttgaaaag<br>ttcaccgaac ccggaacagt gatcagaatc<br>aacgaagtcg tcgctgctct aaaggcttag |
| 2 | *Psilocybe cubensis* strain FSU12409 putative monooxygenase (PsiH) gene, complete cds GenBank: MF000993.1 | atgatcgctg tactattctc cttcgtcatt<br>gcaggatgca tatactacat cgtttctcgt<br>agagtgaggc ggtcgcgctt gccaccaggg<br>ccgcctggca ttcctattcc cttcattggg<br>aacatgtttg atatgcctga agaatctcca<br>tggttaacat ttctacaatg gggacgggat<br>tacagtctgt cttgccgcgt tgacttctaa<br>tatatgaaca gctaatatat tgtcagacac<br>cgatattctc tacgtggatg ctggagggac<br>agaaatggtt attcttaaca cgttggagac<br>cattaccgat ctattagaaa agcgagggtc<br>catttattct ggccggtgag ctgatgttga<br>gttttttgca attgaatttg tggtcacacg<br>tttccagact tgagagtaca atggtcaacg<br>aacttatggg gtgggagttt gacttagggt<br>tcatcacata cggcgacagg tggcgcgaag<br>aaaggcgcat gttcgccaag gagttcagtg<br>agaagggcat caagcaattt cgccatgctc<br>aagtgaaagc tgcccatcag cttgtccaac<br>agcttaccaa aacgccagac cgctgggcac<br>aacatattcg ccagtaagta ctacttgagg<br>aaaatagcgt acgcttcgct gaccggtccg<br>tacatcaaag tcagatagcg gcaatgtcac<br>tggatattgg ttatggaatt gatcttgcag<br>aagacgaccc ttggctggaa gcgacccatt<br>tggctaatga aggcctcgcc atagcatcag<br>tgccgggcaa attttgggtc gattcgttcc<br>cttctcgtga gcatccttct tctatgtagg<br>aagggaagga gtctaacaag tgttagtaaa<br>ataccttcct gcttggttcc caggtgctgt<br>cttcaagcgc aaagcgaagg tctggcgaga<br>agccgccgac catatggttg acatgcctta<br>tgaaactatg aggaaattag cagttagtca<br>aatgcgttct ccccgtattt tttcaatact<br>ctaacttcag ctcacagcct caaggattga<br>ctcgtccgtc gtatgcttca gctcgtctgc<br>aagccatgga tctcaacggt gaccttgagc<br>atcaagaaca cgtaatcaag aacacagccg<br>cagaggttaa tgtcggtaag tcaaaagcgt<br>ccgtcggcaa ttcaaaattc aggcgctaaa<br>gtgggtcttc tcaccaaggt ggaggcgata<br>ctgtaaggat ttctcaatcg ttagagtata<br>agtgttctaa tgcagtacat actccaccaa<br>ccagactgtc tctgctatgt ctgcgttcat<br>cttggccatg gtgaagtacc ctgaggtcca<br>gcgaaaggtt caagcggagc ttgatgctct<br>gaccaataac ggccaaattc ctgactatga<br>cgaagaagat gactccttgc catacctcac |

TABLE 3-continued

Gene sequences for genes with enhanced expression in genetically modified cells or organisms described herein. Expression is enhanced by modification of a promoter or enhancer in or associated with the gene, or by introducing a copy of the gene in the cell or organism.

| SEQ ID NO | Name | Sequence |
| --- | --- | --- |
| | | cgcatgtatc aaggagcttt tccggtggaa<br>tcaaatcgca cccctcgcta taccgcacaa<br>attaatgaag gacgacgtgt accgcgggta<br>tctgattccc aagaacactc tagtcttcgc<br>aaacacctgg tgaggctgtc cattcattcc<br>tagtacatcc gttgccccac taatagcatc<br>ttgataacag ggcagtatta aacgatccag<br>aagtctatcc agatccctct gtgttccgcc<br>cagaaagata tcttggtcct gacgggaagc<br>ctgataacac tgtacgcgac ccacgtaaag<br>cggcatttgg ctatggacga cgaaattggt<br>aagtgcgctt tcagaacccc cccttccgtt<br>gactagtgcc atgcgcgcat acaatatcgc<br>tattgatctg atataacttc cctgcggcat<br>ttattttggc attcctttag tcccggaatt<br>catctagcgc agtcgacggt ttggattgca<br>ggggcaaccc tcttatcagc gttcaatatc<br>gagcgacctg tcgatcagaa tgggaagccc<br>attgacatac cggctgattt tactacagga<br>ttcttcaggt agctaatttc cgtctttgtg<br>tgcataatac ccctaacgac gcacgtttac<br>ctttttgtaa agacacccag tgcctttcca<br>gtgcaggttt gttcctcgaa cagagcaagt<br>ctcacagtcg gtatccggac cctga |
| 3 | *Psilocybe cubensis* strain FSU 12409 4-hydroxy-tryptamine kinase (PsiK) mRNA, complete cds GenBank: KY984099.1 | atggcgttcg atctcaagac tgaagacggc<br>ctcatcacat atctcactaa acatctttct<br>ttggacgtcg acacgagcgg agtgaagcgc<br>cttagcggag gctttgtcaa tgtaacctgg<br>cgcattaagc tcaatgctcc ttatcaaggt<br>catacgagca tcatcctgaa gcatgctcag<br>ccgcacatgt ctacggatga ggattttaag<br>ataggtgtag aacgttcggt ttacgaatac<br>caggctatca agctcatgat ggccaatcgg<br>gaggttctgg gaggcgtgga tggcatagtt<br>tctgtgccag aaggcctgaa ctacgactta<br>gagaataatg cattgatcat gcaagatgtc<br>gggaagatga agaccctttt agattatgtc<br>accgccaaac cgccacttgc gacggatata<br>gcccgccttg ttgggacaga aattgggggg<br>ttcgttgcca gactccataa cataggccgc<br>gagaggcgag acgatcctga gttcaaattc<br>ttctctggaa atattgtcgg aaggacgact<br>tcagaccagc tgtatcaaac catcataccc<br>aacgcagcga aatatggcgt cgatgacccc<br>ttgctgccta ctgtggttaa ggaccttgtg<br>gacgatgtca tgcacagcga agagaccctt<br>gtcatggcgg acctgtggag tggaaatatt<br>cttctccagt tggaggaggg aaacccatcg<br>aagctgcaga agatatatat cctggattgg<br>gaactttgca agtacggccc agcgtcgttg<br>gacctgggct atttcttggg tgactgctat<br>ttgatatccc gctttcaaga cgagcaggtc<br>ggtacgacga tgcggcaagc ctacttgcaa<br>agctatgcgc gtacgagcaa gcattcgatc<br>aactacgcca aagtcactgc aggtattgct<br>gctcatattg tgatgtggac cgactttatg<br>cagtggggga gcgaggaaga aaggataaat<br>tttgtgaaaa agggggtagc tgcctttcac<br>gacgccaggg gcaacaacga caatggggaa<br>attacgtcta ccttactgaa ggaatcatcc<br>actgcgtaa |

TABLE 3-continued

Gene sequences for genes with enhanced expression in genetically modified cells or organisms described herein. Expression is enhanced by modification of a promoter or enhancer in or associated with the gene, or by introducing a copy of the gene in the cell or organism.

| SEQ ID NO | Name | Sequence |
|---|---|---|
| 4 | *Psilocybe cubensis* strain FSU12409 norbaeocystin methyl transferase (PsiM) mRNA, complete cds GenBank: KY984100.1 | atgcatatca gaaatcctta ccgtacacca<br>attgactatc aagcactttc agaggccttc<br>cctcccctca agccatttgt gtctgtcaat<br>gcagatggta ccagttctgt tgacctcact<br>atcccagaag cccagagggc gttcacggcc<br>gctcttcttc atcgtgactt cgggctcacc<br>atgaccatac cagaagaccg tctgtgccca<br>acagtcccca ataggttgaa ctacgttctg<br>tggattgaag atattttcaa ctacacgaac<br>aaaaccctcg gcctgtcgga tgaccgtcct<br>attaaaggcg ttgatattgg tacaggagcc<br>tccgcaattt atcctatgct tgcctgtgct<br>cggttcaagg catggtctat ggttggaaca<br>gaggtcgaga ggaagtgcat tgacacggcc<br>cgcctcaatg tcgtcgcgaa caatctccaa<br>gaccgtctct cgatattaga gacatccatt<br>gatggtccta ttctcgtccc cattttcgag<br>gcgactgaag aatacgaata cgagtttact<br>atgtgtaacc ctccattcta cgacggtgct<br>gccgatatgc agacttcgga tgctgccaaa<br>ggatttggat ttggcgtggg cgctccccat<br>tctggaacag tcatcgaaat gtcgactgag<br>ggaggtgaat cggctttcgt cgctcagatg<br>gtccgtgaga gcttgaagct tcgaacacga<br>tgcagatggt acacgagtaa cttgggaaag<br>ctgaaatcct tgaaagaaat agtggggctg<br>ctgaaagaac ttgagataag caactatgcc<br>attaacgaat acgttcaggg gtccacacgt<br>cgttatgccg ttgcgtggtc tttcactgat<br>attcaactgc ctgaggagct ttctcgtccc<br>tctaaccccg agctcagctc tcttttctag |
| 5 | *Psilocybe cubensis* strain FSU12409 putative transporter (PsiT2) gene, complete cds GenBank: MF000992.1 | atgtctctggagcgctcaacaagtccaaatcct<br>accgagcgtacatctcttctatctgacactgcg<br>tctaccatttcatccagagatgacgttgaacag<br>tcaagtctgaagcaaaggcgcacgcctatacca<br>actggacaacttggcggtaaggtctcaatgcat<br>tcaattattataaacgctgagggtcatttatgg<br>ccttatattaaccagtttgtgaatgatatcggc<br>gtctctgatgggaatccacgtaatgttgggttc<br>tacagtgggttgatcgaaagtgtatttgcttgc<br>ggagaagtttgctctatcttcatgctgtcgagg<br>ctttcagatagaataggtcgtcgaccggtgcta<br>ctcccatctgcactgggtattgcagtgtttact<br>gctctgtttggtttatcaagctcgtttaccatg<br>atgttgactcttcgagtttgcgctggtctctta<br>gccggagcgacgcctatagtacactccattgtc<br>agcgaacttactgatgataccaataatgcactc<br>gttgtaccattatatggcctcataactcccatc<br>ggatttgccattgggcccctgatcgggggaacc<br>cttgaacacgctgcaactaagtatcccaacgtc<br>tttggatatgagctttttcgaaagtacccctac<br>ttcttaccatcgtttgttccatgctgcatggct<br>atcgtgggcgtcacattcggctacttcttttta<br>aaagaaacgcttcctagtttagtcaagtctaaa<br>aaaagacttgaacgtcaacggtcctcctcttct<br>atatcatcagagaactctactctatacggtgcc<br>acagagcatatcagggactcaacagaagaaacc<br>gcggcggacgaggaacccgattccaagccgaag<br>ggtattactgagttaattcgggatccttctata<br>cgggctataatggcttctggtacattttgatg<br>tttctatacacgagttccgatgtgatattctca<br>ctctactgctttactgctgttgaggatggaggc<br>gttggattgcctcccgagaagatcggttatgca<br>ttctccgttgcaggcctcatagctatgctcatg<br>cagctttgcataacgccatgggtgctccgtact<br>tttgacaaggctaaagtataccacttctgcatg<br>tgctcgttccctctcgtgtttgcactcatggga<br>tgcctgaatcccctcgctcaaactgggtacagt<br>gaaattaacaaaacacttcatccgaccactacg<br>ggactgctctatgctgcaatagccatcttgctc<br>cttctagcccgtgtctgcgttatggcattccct<br>atcagcatgatgctggttaaacaaacggccgat<br>aagcattcgcttgccactgcgaatggcctcgtg<br>caagtggccatgacccttgcaagagcattctgc<br>cctacaatctcaagctcggtgtttgcttattct<br>actagccataatatcctgggtggacatttctgg<br>gtggtagtgatggtattcatttccctggttggg<br>gtatggcaatctacgaaaattgccagggtcaca<br>aaaacaaaagagcaattgtga |
| 6 | *Psilocybe cubensis* strain FSU12409 putative transporter (PsiT1) gene, complete cds GenBank: MF000991.1 | atgaatcctacgaccgccaccgatgctcatgaa<br>cgaacatcgctgttgtctggaagaccgcaatct<br>gctgcaaattcgacggctccatatgagcgacaa<br>gttcaaccatcgcgaaaatcccaatgctttact<br>ccagtgaccgtgatcaccataattacgctcata<br>tatcgtctcgcgacaacgatggtaatcacgacc<br>aacattcgggttctccacacagttgcatgccag<br>ctttggtatcatgtcaacgatcccgacgtattt<br>ccagggggaaatataccagaaaaatattgtgcg<br>ctacctggtgtagacaagtattatgctataatg<br>gtgtctatgaccactgtcatagatggtcttgga<br>ggtatacttgggaccggcatagccagctacatg<br>tcatctcgttttggcagaaagcctgttctcatg<br>ttcctgctttcctgtaccatgatcgatcacctc<br>gccatcctgacagtccaaaatgtatacggatgg<br>aagcagttggtaacatttgggttaattatgatt<br>gttgaaaccattggaaatgagaacaccacagta<br>tttctggtgagcatgtacgtggttgatgttact<br>gaggctgagagaaggaccgctgctctgagttca<br>attactggctggcttgttctcggaggcgccctc<br>gcctattcaataggcggatctataacaactttt<br>ttacactccaactctgccgtatacattgtatcg<br>ttcagtgtcactggcatcgttctaacattcacc<br>gcctttgttctccctgaatcattccctgctgaa<br>aaaagagatctcttgcggcttgaacgactggca<br>gaaacccgtggacacagccagtcctggacccaa<br>aaaatcaaagctgtggcaactgtcgcattggaa<br>cctatggaattgctaaaaccgacatttaacccc<br>ataacggggaaggcaaattggcggcttgtatac<br>tgcgccctccactcgtttattgtcactctagca<br>gatgcgtatgctcttcctgccatgttgatattt<br>ttcactacccagtattcatatacacccgctcag<br>atgggatatgttatgacgacgtacagtgtctcc<br>agtgtgtttgttttggcgatagccttacccctg<br>tttattcgatggttcaagcccctgtataataat<br>actcaaacgaagtctgtcccagatgaaggggat<br>ggactccgtgcgaccgactctggagaagcgggt<br>gtgcacacacaagaggtcgttgtttcggaaacc<br>tctgatcgcatggacgtccatatcactgtcata<br>tcctggaccatagagtcattagcatacatagtt<br>ctcggtactgtgggttcattttacgcacaactt<br>ttaggtcggccgttgcctctattggctttggat<br>ctggacgcattccaggaattcgaagcctag |

TABLE 3-continued

Gene sequences for genes with enhanced expression in genetically modified cells or organisms described herein. Expression is enhanced by modification of a promoter or enhancer in or associated with the gene, or by introducing a copy of the gene in the cell or organism.

| SEQ ID NO | Name | Sequence |
| --- | --- | --- |
| 7 | *Psilocybe cubensis* strain FSU12409 putative transcrip-tional regulator (PsiR) gene, complete cds GenBank: MF000990.1 | atggcacccgcaacacccgcaactcacgatcct gccttgtcccacggagcccctcctgctccaggt gctccagctcctgcaaatgctcctccaaacgcc tcaggagacattgctggaatgcagctcagcgga ctcgatcagtcccagatcatgaaccttcttcgt tcattgcctggcatgttctcgggcggtaaaata cccgaccaaggccaaggcaacaaagaggatgct gctcaaacgctgtccaaccttgcccaagctcaa ccgtatggacaacaattaccccttcactaccaa gctggcggcccaggaggtctgccaggaattaac gacccaggcccgtccacacatccccgcggccct cccaaccttggccaactgagtgctgtggcaatg caagccgcccccgctccaattcagcatccagac cagcaaacgaaccgcaacgatggcgagcaggct ggcaatgcgagtgcaagtacctccggaaaggat ggtgacaatgcagaattcgttcccccacctgct cctgctcctacaactggtcgccgtggtggacg cagcgccaccatgggaagtgacgaatggagcag acagaggaaggataatcataaagaggttgagcg tcgacgccgcggcaatatcaacgagggcatcaa cgagcttggccgcattgtacccagtgggtctgg cgagaaggccaaaggcgccatcctttctcgagc tgtgcagtacatccatcatttgaaagagaacga agctcgcaatatcgagaagtggacccttgagaa gcttctcatggaccaggccatgggtgacctgca ggcgcaactcgaagaggtcaagcgtctgtggga agaagagcgtatggcgcgcacaagactcgaggc cgagctcgaagtgttgagaaatatgaacggcgt gaatgctggctcggccccggcctcgaaagatga gagtgctgcaggtactaagaggaggagtaccga tggagcagaggccgccaccgccgccactgaaag cagcaccgccaatgccgagggcgaacgcgacgg caagcgacaaagaaccgagtga |
| 8 | *Psilocybe cyanescens* strain FSU 12416 tryptophan decarboxylase (PsiD) mRNA, complete cds GenBank: KY984104.1 | atgcaggtactgcccgcgtgccaatcttccgcg cttaaaacattgtgcccatcccccgaggccttt cgaaagctcggttggctccctactagcgacgag gtttacaacgaattcatcgatgacttgaccggt cgcacgtgcaatgaaaagtactccagccaggtt acacttttgaagcctatccaagatttcaagaca ttcatcgagaatgatcccatagtgtatcaagaa tttatctctatgtttgaaggaatcgagcagtct cccaccaactaccacgagctatgtaacatgttc aacgacatctttcgcaaagccccactctacggc gatcttggtcctccggtttacatgatcatggcc agaataatgaatacgcaggcgggtttctctgcg ttcacaaaagagagcttgaacttccatttcaaa aagctcttcgacacctgggggctattcctttcc tcgaaaaactctcgaaacgtgcttgttgcagac cagtttgacgataagcattacgggtggttcagc gagcgagccaagactgccatgatgattaattat ccagggcgtacattcgagaaagtcttcatctgc gacgagcacgttccataccatggcttcacttcc tatgacgatttcttcaatcgcaggttcagggac aaggatacagatcggcccgtagtcggtggggtt actgacaccactttaatcggggctgcctgtgaa tcgttgtcatataacgtctctcacaacgtccag tctcttgacacgctagtcatcaagggagaggcc tattcacttaaacatctacttcataacgacccc ttcacaccgcaattcgaacatgggagcatcatt caaggattcctaaatgtcaccgcttaccaccgc tggcactcccccgtcaatggcacgattgtgaag atcgtcaacgttccaggtacctacttcgctcaa gctccatatacaattggatctcctatccccgat aacgaccgcgacccgcctccttacctcaagtca ctcgtatacttctccaacatcgctgcacggcaa attatgttcatcgaggccgacaacaaagacatc ggcctcatttcttggtcttcattggaatgact gagatctcgacttgcgaggcgacggtgtgcgaa ggtcagcatgtcaaccgcggtgacgatttgggc atgttccatttcggtggttcatcttttgccctt ggcttgcggaaggactcgaaggcgaagatttg gaaaagttcgcgaaaccggggaccgttattagg atcaacgagctagttgcatctgtaaggaagtag |
| 9 | *Psilocybe cyanescens* strain FSU 12416 putative monooxygenase (PsiH) gene, partial cds GenBank: MF000997.1 | atgattgttctattggtctcgctcgtccttgca ggatgcatatactacgccaacgctcgtagagta aggcgctcgcgcttaccaccgggcccgcctggc ataccactgcccttcattgggaatatgtttgat atgccttcagagtcaccgtggttaagatttctt caatggggacgggactatcacactgatatcctt tacttgaatgctggcggaacggaaataattatt ctgaacacactggatgctataaccgacttgttg gaaaagcgagggtcgatgtattcgggtcgactc gagagcaccatggtgaacgaactcatggggtgg gagttcgacttgggattcataacctatggtgaa agatggcgcgaagaaagacgcatgttcgccaag gagttcagcgaaaaaaacatcaggcaattccgc cacgcccaaattaaagctgccaatcagcttgtt cggcagctgatcaaaacgccagatcgttggtcg cagcacatccggcatcagatagcagccatgtct ctagacattggttatggaattgatctcgcagag gatgacccctggattgcagcaacccagctagct aacgaagggctcgccgaagcttcagtaccgggc agtttctgggtcgactcattccccgccctcaaa taccttccttcatggcttcctggtgcaggattc aagcgcaaagcaaaggtatggaaggaaggtgct gaccatatggtgaacatgccgtatgaaacgatg aaaaaattgactgttcaaggcttggcccgacct tcatatgcctcagctcgtctgcaggccatggac cccgatggcgatctcgagcatcaggaacacgtg atcagaaacacagcgactgaggtcaatgtcggc ggaggtgatacgactgtttctgctgtgtcagcc tttattttggccatggtcaaatatccagaagtt caacgccaagtccaagcagaactggatgcactc accagcaaaggagttgtcccaaactatgacgaa gaagacgactccttgccataccttacggcttgc gtcaaggaaatctttcgatggaaccaaatagca ccccttgctatccctcatcggctgatcaaagac gatgtttatcgtgggtatctcataccaaagaat gctttggtctacgccaactcatgggctgtgttg aatgacccagaggagtacccaaatccctctgag ttccgaccagaacgatatttgagctctgacgga aagcccgacccaacggtccgtgatccccgcaaa gcagcatttggctatggtcgacgcaactgtccc ggaatccacctggcacaatcgacggtatggatt gctggagccactcttctctcggtattcaatatc gaacgtcctgttgatgggaatggaaaacccatc gacatcccggcgacgttcactaccggattcttc agacatcccgagcctttccagtgcagatttgtc cctcgcactcaggagattctaaaatccgtttcc ggt |
| 10 | *Psilocybe cyanescens* strain FSU 12416 4-hydroxy-tryptamine kinase (PsiK) mRNA, complete cds GenBank: KY984102.1 | atgactttcgatctcaagactgaagaaggcctg ctctcatacctcacaaagcacctatcgctggac gttgctcccaacggggtgaaacgtcttagtgga ggcttcgtcaacgttacctggcgggtcgggctc aatgccccttatcatggtcacacgagcattatt ctgaagcatgctcaaccgcacctgtcttcagac atagatttcaagataggtgttgaacgatcggcg tacgagtatcaagcgctcaaaatcgtgtcagcc aatagctcccttctaggcagcagcgatattcgg gtctctgtaccagaaggtcttcactacgacgtc gttaataacgcattgatcatgcaagatgtcggg acaatgaagaccctgttggactatgtcactgcc |

TABLE 3-continued

Gene sequences for genes with enhanced expression in genetically modified cells or organisms described herein. Expression is enhanced by modification of a promoter or enhancer in or associated with the gene, or by introducing a copy of the gene in the cell or organism.

| SEQ ID NO | Name | Sequence |
| --- | --- | --- |
| | | aaaccaccaatttctgcagagatcgccagtctc<br>gtaggcagtcaaattggtgcatttatcgctagg<br>ctgcacaacctcggccgcgagaataaagacaag<br>gacgacttcaagttcttctctggaaacatcgtc<br>gggagaacaaccgcagaccagttgtatcaaacc<br>atcatacctaatgccgctaaatacggtatcgac<br>gatccaattctcccaattgtggtaaaggagttg<br>gtggaggaggtcatgaat<br>agtgaagaaacgcttatcatggcggatttatgg<br>agtggcaatattcttctccagtttgatgaaaac<br>tcgacggaattgacgaggatatggctggtagac<br>tgggagttgtgcaaatatggtccaccgtctttg<br>gacatggggtacttcttaggcgactgtttcctg<br>gtcgctcgatttcaagatcagctcgtagggaca<br>tcaatgcgacaggcctacttgaagagctacgca<br>aggaatgtcaaggagccaatcaattatgcaaaa<br>gccaccgcaggcatcggcgcgcatctcgtcatg<br>tggactgatttcatgaagtgggggaacgatgaa<br>gagagggaagagtttgttaagaaaggcgtggaa<br>gccttccatgaagcaaatgaggacaatagaaac<br>ggggagattacgtctatacttgtgaaggaagca<br>tcgcgcacttag |
| 11 | *Psilocybe cyanescens* strain FSU 12416 norbaeocystin methyl transferase (PsiM) mRNA, complete cds GenBank: KY984103.1 | atgcatatcaggaacccataccgcgatggtgtt<br>gactaccaagcactcgctgaagcatttccggct<br>ctcaaaccacatgtcacagtaaattcagacaat<br>acgacctccatcgactttgctgtgccagaagcc<br>caaagactgtatacagctgcccttctacaccgg<br>gatttcggtcttacgatcacactcccggaagac<br>cgtctttgtccgacagtgcctaatcggctcaac<br>tatgtcctttgggttgaagatatccttaaagtc<br>acttctgatgctctcggtcttccggataatcgt<br>caagttaaggggatcgatatcggaactggcgca<br>tcagcgatatatcccatgctcgcatgctctcgt<br>tttaagacatggtccatggttgcaacagaggta<br>gaccagaagtgtattgacactgctcgtctcaac<br>gtcattgccaacaacctccaagaacgtctcgca<br>attatagccacctccgtcgatggtcctatactt<br>gtccccctcttgcaggcgaattctgattttgag<br>tacgattttacgatgtgtaatccgcccttctac<br>gatggggcatccgacatgcagacatcggatgct<br>gcgaaggggtttggattcggtgtgaacgctccg<br>cataccggcacggtgctcgagatggccaccgag<br>ggaggtgaatcggccttcgtagcccaaatggtc<br>cgcgaaagtttgaatcttcaaacacgatgcagg<br>tggttcacgagtaatttggggaaattgaagtcc<br>ttgtacgaaattgtggggctgctgcgagaacat<br>cagataagtaactacgcaatcaacgaatacgtc<br>caaggagccactcgtcgatatgcgattgcatgg<br>tcgttcatcgatgttcgactgcctgatcatttg<br>tcccgtccatctaaccccgacctaagctctctt<br>ttctag |
| 12 | *Psilocybe cyanescens* strain FSU 12416 putative transporter (PsiT2) gene, complete cds GenBank: MF000996.1 | atgtcgccagagcgctcagcaagtcttgaacca<br>gatgagcattcgtctctgctctccgatacggcc<br>tcctacatctcgagagatgacttagaagactca<br>aaagcgaagcaaatcccgacgcctataccaaag<br>aaacaacttggagttttattttccatcagattc<br>acagaacctataatttacagtcatttgtggcct<br>tatatcaaccaattcgttaatgatatcggggtc<br>gccgacgggaaccctcgctatgttggattttac<br>agtggtttgatcgaaagtgtatttgcttgtgga<br>gaagtgtgttctatcttcatgttatcgaggctg<br>tcagacagaataggtcgccgaccagtgttgctc<br>ccgtctgccctcggcgtagcattatttacagct<br>ttgttcggtttatcgacctcgtttactatgatg<br>ctcgttctccgggtttgtgctggtcttttggcc<br>ggggctactcctatagtccattctgttgtgagt<br>gagctcacggacgaaacgaataatgccctcgta<br>gtacccctttacgggttaattacacctattggc<br>tttgcgattggacctctgattggtggaactctt<br>gagcacgctgctactaaatatcccaacgtattt<br>ggttatgacttccttcgaaaatatccatacttt<br>ctaccatcctttgttccatgctgcctagctgtc<br>gttggcgtcaccttcggctatttcttcttgcaa<br>gagacgcttcccagtatagtacgggccaagaaa<br>agacttgaacgacagaaatctacttcgtctatt<br>tcgtcaagaacctccaccctatacggtgctaca<br>gatgatcacaatagagatgcatcagaatcaacc<br>gcgttgtctccggaggaagcggaagatgaaatt<br>gactctaagcctcaaagcatcaaagctttaatc<br>gtagacccttctatgcgggccatcatgggttct<br>ggtacctttctgatgttcctctacacgagttcc<br>gatgttctgttctcactctactgctttactgct<br>gtcgaggacggaggcgtcggattacctcccgac<br>gaaatcggttacgcattctctgttgccggcgtg<br>atagctatgcttatgcagctttgcataacacct<br>tgggtcctacgtacattcgataaggcaaaagta<br>tacaagttctgcatgttctcattcccgcttgta<br>tttgccctcatgggatgtcttaatcccctcgct<br>caaaccgggtataatgaagtctctaagactatc<br>caccctaccacaacgggacttctttacgctgct<br>attgctgtgttgctactgttggcacgggtctgc<br>gtcatggcgttcccgatcagcatgatgttgatt<br>aagcagaatgccgataaaaactcactcgccact<br>gcgaacgggcttgtgcaagtgtcgatgaccatt<br>gctagagcactctgccccacggtctctagttcg<br>ctcttcgcttattccacgagcaacaatattctg<br>ggtggtcatctctgggtccttattatggtgacc<br>atatccctcgcaggcgtctggcagtcgatgagc<br>atcgcccgcgttaccaaaagaaaggaagagcta<br>taa |
| 13 | *Psilocybe cyanescens* strain FSU 12416 putative transporter (PsiT1) gene, complete cds GenBank: MF000995.1 | atgaatcctacgaccgccaccgatgctcatgaa<br>cgaacatcgctgttgtctggaagaccgcaatct<br>gctgcaaattcgacggctccatatgagcgacaa<br>gttcaaccatcgcgaaaatcccaatgctttact<br>ccagtgaccgtgatcaccataattacgctcata<br>tatcgtctcgcgacaacgatggtaatcacgacc<br>aacattcgggttctccacacagttgcatgccag<br>ctttggtatcatgtcaacgatcccgacgtattt<br>ccagggggaaatataccagaaaaatattgtgcg<br>ctacctggtgtagacaagtattatgctataatg<br>gtgtctatgaccactgtcatagatggtcttgga<br>ggtatacttgggaccggcatagccagctacatg<br>tcatctcgttttggcagaaagcctgttctcatg<br>ttcctgctttcctgtaccatgatcgatcacctc<br>gccatcctgacagtccaaaatgtatacggatgg<br>aagcagttggtaacatttgggttaattatgatt<br>gttgaaaccattggaaatgagaacaccacagta<br>tttctggtgagcatgtacgtggttgatgttact<br>gaggctgagagaaggaccgctgctctgagttca<br>attactggctggcttgttctcggaggcgccctc<br>gcctattcaataggcggatctataacaactttt<br>ttacactccaactctgccgtatacattgtatcg<br>ttcagtgtcactggcatcgttctaacattcacc<br>gcctttgttctccctgaatcattccctgctgaa<br>aaaagagatctcttgcggcttgaacgactggca<br>gaaacccgtggacacagccagtcctggacccaa<br>aaaatcaaagctgtggcaactgtcgcattggaa<br>cctatggaattgctaaaaccgacatttaacccc<br>ataacggggaaggcaaattggcggcttgtatac<br>tgcgccctccactcgtttattgtcactctagca<br>gatgcgtatgctcttcctgccatgttgatattt<br>ttcactacccagtattcatatacacccgctcag<br>atgggatatgttatgacgacgtacagtgtctcc |

TABLE 3-continued

Gene sequences for genes with enhanced expression in genetically modified cells or organisms described herein. Expression is enhanced by modification of a promoter or enhancer in or associated with the gene, or by introducing a copy of the gene in the cell or organism.

| SEQ ID NO | Name | Sequence |
|---|---|---|
| | | agtgtgtttgttttggcgatagccttaccccctg<br>tttattcgatggttcaagcccctgtataataat<br>actcaaacgaagtctgtcccagatgaaggggat<br>ggactccgtgcgaccgactctggagaagcgggt<br>gtgcacacacaagaggtcgttgtttcggaaacc<br>tctgatcgcatggacgtccatatcactgtcata<br>tcctggaccatagagtcattagcatacatagtt<br>ctcggtactgtgggttcattttacgcacaactt<br>ttaggtcggccgttgcctctattggctttggat<br>ctggacgcattccaggaattcgaagcctag |
| 14 | *Psilocybe cyanescens* strain FSU 12416 putative transcrip-tional regulator (PsiR) gene, complete cds GenBank: MF000994.1 | atggcacccacaacacccgcaactcacgatcca<br>gccttgtcccacggagctcctcctactcagggc<br>tcgcaggcaccagcaaatgcggccccaaatctt<br>accccagccgacatctctggcatgcaactcaac<br>ggcctcgatcagtcccagatcatgaaccttctc<br>cgttcattgcccggcatgttcacaggtgctaaa<br>ataccagatcaaggacaaggcaatcccaaagag<br>gatgctgcccaaacactgtccaacctcgcacag<br>gcttcatcacccttcggcggccaacatttgccc<br>atccactatcaaaccggcgctgctggtggtctt<br>ccaggaatcaacgacccaggcccgtcaactcac<br>ccccgcggccctcctaacctcggccagctgagt<br>gctgtcgcgatgcaagcggccccagcgacgatc<br>caacaccaggaccagcaacagtctgggcgccag<br>gaagacggcgagcaggccggaaatacgagcatt<br>gatagcccatctgcgaaagatggcgagaatggc<br>actggggagtttaaccagacgtctacgagcaci<br>ccttcgggaggccgtcggggtgggcgcagtgcc<br>accatgggcagcgacgaatggagcaggcagagg<br>aaggataatcataaagaggttgagcgtcggcgc<br>cgcggaaatatcaacgaagggattaacgagctg<br>ggccgcatcgtaccgagcggatcaggcgagaaa<br>gccaaaggcgccatcctctcgcgcgccgtgcag<br>tacatccaccatttgaaagagaatgaagctcgg<br>aacatcgagaagtggacgcttgagaagctactt<br>atggatcaggcgatgggcgacctgcaggcgcaa<br>cttgaggagatcaagcggctgtgggaggaggag<br>cgcatggctcgtacgaggcttgaggctgagctc<br>gaggtgttgaggaatatgaatggtgtgagtact<br>gccggtgcgggttcgggtgcggcgaaggatgaa<br>agcgctgccggcacgaagcggaggagcacggat<br>ggtgctgatgctgccggcacaaatgttgaaggt<br>ggtaataacgacaacgctgaaggagagagggac<br>ggaaaacgtcagagaactgagtga |

In some cases, the efficiency of genomic disruption of a fungus or any other organism, including but not limited to a cell, with any of the nucleic acid delivery platforms described herein, can result in disruption of a gene or portion thereof at about 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, 99.5%, 99.9%, or up to about 100% as measured by nucleic acid or protein analysis.

In some cases, the genetically modified fungi and other organisms comprises about 10%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, 100%, 125%, 150%, 175%, 200%, and up to 400% percent more of a compound of any one of Formula I-IV measured by dry weight of a fungus compared to a comparable control without genetic modification.

In some cases, the genetically modified fungi and other organisms comprises about 10%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, 100%, 125%, 150%, 175%, 200%, and up to 400% percent more dimethyltryptamine (DMT) measured by dry weight of a fungus compared to a comparable control without genetic modification.

In some cases, the genetically modified fungi and other organisms comprises about 10%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, 100%, 125%, 150%, 175%, 200%, and up to 400% percent more psilocybin measured by dry weight of a fungus compared to a comparable control without genetic modification.

In some cases, the genetically modified fungi and other organisms comprises about 10%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, 100%, 125%, 150%, 175%, 200%, and up to 400% percent more psilocin measured by dry weight of a fungus compared to a comparable control without genetic modification.

Various methods may be utilized to identify potential targets for gene editing in a psilocybin and/or psilocin biosynthesis pathway. In some cases, any one of: bioinformatics, gRNA design, CRISPR reagent construction, plant transformation, plant regeneration, and/or genotyping can be utilized. Bioinformatics can comprise gene mapping, gene alignment and copy number analysis, and gene annotation. gRNA design can comprise gRNA grouping to design clusters of guides for intended function, rank and selection of guides based on target gene specificity and off-targets within the cannabis genome. CRISPR reagent construction can comprise generation of infection-ready AGRO reagents to co-deliver Cas9 that has been cannabis codon optimized and gRNA. Plant transformation and regeneration can comprise infecting plant tissue with CRISPR AGRO (for example callus), techniques to isolate cannabis protoplasts and transform RNP reagents, and/or development of techniques to obtain growing plantlets from transformed tissue. Genotyping can comprise isolating plant DNA and analyzing a target sequence. Functional analysis can comprise analyzing cannabinoid content in plant tissue and quantifying relevant cannabinoids.

The above disclosed different approaches of genetic modification could be use on other organisms, such as different plants, *E. coli* and other suitable bacteria, or yeast to produce end products of psilocybin and/or psilocin. In the disclosed genetically engineered fungi and other organisms, the amount of psilocybin and/or psilocin is increased about by 5%, 10%, 15%, 20%, 25%, 30%, 35%, 40%, 45%, 50%, 55%, 60%, 65%, 70%, 75%, 80%, 85%, 90%, 95%, 100%, 125%, 150%, 175%, 200%, 300%, or up to 400% more compared to a comparable control fungus or organism without such disclosed genetic modification.

Genetic Engineering

Provided herein can be systems of genomic engineering. Systems of genomic engineering can include any one of clustered regularly interspaced short palindromic repeats (CRISPR) enzyme, transcription activator-like effector (TALE)-nuclease, transposon-based nuclease, Zinc finger nuclease, meganuclease, argonaute, or Mega-TAL. In some aspects, a genome editing system can utilize a guiding polynucleic acid comprising DNA, RNA, or combinations thereof. In some cases, a guide can be a guide DNA or a guide RNA.

I. Clustered Regularly Interspaced Short Palindromic Repeats (CRISPR)

In some cases, genetic engineering can be performed using a CRISPR system or portion thereof. A CRISPR system can be a multicomponent system comprising a guide polynucleotide or a nucleic acid encoding the guide polynucleotide and a CRISPR enzyme or a nucleic acid encoding the CRISPR enzyme. A CRISPR system can also comprise any modification of the CRISPR components or any portions of any of the CRISPR components.

Methods described herein can take advantage of a CRISPR system. There are at least five types of CRISPR systems which all incorporate guide RNAs and Cas proteins and encoding polynucleic acids. The general mechanism and recent advances of CRISPR system is discussed in Cong, L. et al., "Multiplex genome engineering using CRISPR systems," Science, 339(6121): 819-823 (2013); Fu, Y. et al., "High-frequency off-target mutagenesis induced by CRISPR-Cas nucleases in human cells," Nature Biotechnology, 31, 822-826 (2013); Chu, V T et al. "Increasing the efficiency of homology-directed repair for CRISPR-Cas9-induced precise gene editing in mammalian cells," Nature Biotechnology 33, 543-548 (2015); Shmakov, S. et al., "Discovery and functional characterization of diverse Class 2 CRISPR-Cas systems," Molecular Cell, 60, 1-13 (2015); Makarova, K S et al., "An updated evolutionary classification of CRISPR-Cas systems,", Nature Reviews Microbiology, 13, 1-15 (2015). Site-specific cleavage of a target DNA occurs at locations determined by both 1) base-pairing complementarity between the guide RNA and the target DNA (also called a protospacer) and 2) a short motif in the target DNA referred to as the protospacer adjacent motif (PAM). A PAM can be a canonical PAM or a non-canonical PAM. For example, an engineered cell, such as a plant cell, can be generated using a CRISPR system, e.g., a type II CRISPR system. A Cas enzyme used in the methods disclosed herein can be Cas9, which catalyzes DNA cleavage. Enzymatic action by Cas9 derived from *Streptococcus pyogenes* or any closely related Cas9 can generate double stranded breaks at target site sequences which hybridize to about 20 nucleotides of a guide sequence and that have a protospacer-adjacent motif (PAM) following the about 20 nucleotides of the target sequence. In some aspects, less than 20 nucleotides can be hybridized. In some aspects, more than 20 nucleotides can be hybridized. Provided herein can be genomically disrupting activity of a THCA synthase comprising introducing into a cannabis and/or hemp plant or a cell thereof at least one RNA-guided endonuclease comprising at least one nuclear localization signal or nucleic acid encoding at least one RNA-guided endonuclease comprising at least one nuclear localization signal, at least one guiding nucleic acid encoding at least one guide RNA. In some aspects, a modified plant or portion thereof can be cultured.

Clustered Regularly Interspaced Short Palindromic Repeats (CRISPR) Enzyme

A CRISPR enzyme can comprise or can be a Cas enzyme. In some aspects, a nucleic acid that encodes a Cas protein or portion thereof can be utilized in embodiments provided herein. Non-limiting examples of Cas enzymes can include Cas1, Cas1B, Cas2, Cas3, Cas4, Cas5, Cas5d, Cas5t, Cas5h, Cas5a, Cash, Cas7, Cas8, Cas9, Cas10, Csy1, Csy2, Csy3, Csy4, Cse1, Cse2, Cse3, Cse4, Cse5e, Csc1, Csc2, Csa5, Csn1, Csn2, Csm1, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx1S, Csf1, Csf2, CsO, Csf4, Csd1, Csd2, Cst1, Cst2, Csh1, Csh2, Csa1, Csa2, Csa3, Csa4, Csa5, C2c1, C2c2, C2c3, Cpf1, CARF, DinG, homologues thereof, or modified versions thereof. In some cases, a catalytically dead Cas protein can be used, for example a dCas9. An unmodified CRISPR enzyme can have DNA cleavage activity, such as Cas9. A CRISPR enzyme can direct cleavage of one or both strands at a target sequence, such as within a target sequence and/or within a complement of a target sequence. In some aspects, a target sequence is at least about 18 nucleotides, at least 19 nucleotides, at least 20 nucleotides, at least 21 nucleotides, or at least 22 nucleotides in length. In some cases, a target sequence is at most 17 nucleotides in length. In some aspects, a target can be selected from a sequence comprising homology from about 50%, 60%, 70%, 80%, 90%, 95%, 96%, 97%, 98%, 99%, or up to about 100% to any one of: SEQ ID NO: 1 to SEQ ID NO: 7.

In some aspects, a target sequence can be found within an intron or exon of a gene. In some cases, a CRISPR system can target an exon of a gene involved in a cannabinoid biosynthesis pathway. For example, a CRISPR enzyme can direct cleavage of one or both strands within or within about 1, 2, 3, 4, 5, 6, 7, 8, 9, 10, 15, 20, 25, 50, 100, 200, 500, or more base pairs from the first or last nucleotide of a target sequence. For example, a CRISPR enzyme can direct cleavage of one or both strands within or within about 1, 2, 3, 4, 5, 6, 7, 8, 9, 10, 15, 20, 25, 50, 100, 200, 500, or more base pairs from a PAM sequence. In some cases, a guide polynucleotide binds a target sequence from 3 to 10 nucleotides from a PAM. A vector that encodes a CRISPR enzyme that is mutated with respect to a corresponding wild-type enzyme such that the mutated CRISPR enzyme lacks the ability to cleave one or both strands of a target polynucleotide containing a target sequence can be used. A Cas protein can be a high-fidelity Cas protein such as Cas9HiFi. In some cases, a Cas protein can be modified. For example, a Cas protein modification can comprise N7-Methyl-Gppp (2'-O-Methyl-A).

Cas9 can refer to a polypeptide with at least or at least about 50%, 60%, 70%, 80%, 90%, 100% sequence identity and/or sequence similarity to a wild type exemplary Cas9 polypeptide (e.g., Cas9 from *S. pyogenes*). Cas9 can refer to a polypeptide with at most or at most about 50%, 60%, 70%, 80%, 90%, 100% sequence identity and/or sequence similarity to a wild type exemplary Cas9 polypeptide (e.g., from *S. pyogenes*). Cas9 can refer to the wild type or a modified form of the Cas9 protein that can comprise an amino acid change such as a deletion, insertion, substitution, variant, mutation, fusion, chimera, or any combination thereof. In some cases, a CRISPR enzyme, such as Cas, can be codon optimized for expression in a plant.

A polynucleotide encoding an endonuclease (e.g., a Cas protein such as Cas9) can be codon optimized for expression in particular cells, such as plant cells. This type of optimization can entail the mutation of foreign-derived (e.g., recombinant) DNA to mimic the codon preferences of the intended host organism or cell while encoding the same protein.

An endonuclease can comprise an amino acid sequence having at least or at least about 50%, 60%, 70%, 75%, 80%, 85%, 90%, 95%, 99%, or 100%, amino acid sequence identity to the nuclease domain of a wild type exemplary site-directed polypeptide (e.g., Cas9 from *S. pyogenes*).

*S. pyogenes* Cas9 (SpCas9), can be used as a CRISPR endonuclease for genome engineering. In some cases, a different endonuclease may be used to target certain genomic targets. In some cases, synthetic SpCas9-derived variants with non-NGG PAM sequences may be used. Additionally, other Cas9 orthologues from various species have been identified and these "non-SpCas9s" bind a variety of PAM sequences that could also be useful for the present invention. For example, the relatively large size of SpCas9 (approximately 4 kb coding sequence) means that plasmids carrying the SpCas9 cDNA may not be efficiently expressed in a cell. Conversely, the coding sequence for *Staphylococcus aureus* Cas9 (SaCas9) is approximately 1 kilobase shorter than SpCas9, possibly allowing it to be efficiently expressed in a cell.

Alternatives to *S. pyogenes* Cas9 may include RNA-guided endonucleases from the Cpf1 family. Unlike Cas9 nucleases, the result of Cpf1-mediated DNA cleavage is a double-strand break with a short 3' overhang. Cpf1's staggered cleavage pattern may open up the possibility of directional gene transfer, analogous to traditional restriction enzyme cloning, which may increase the efficiency of gene editing. Like the Cas9 variants and orthologues described above, Cpf1 may also expand the number of sites that can be targeted by CRISPR to AT-rich regions or AT-rich genomes that lack the NGG PAM sites favored by SpCas9.

In some aspects Cas sequence can contain a nuclear localization sequence (NLS). A nuclear localization sequence can be from SV40. An NLS can be from at least one of: SV40, nucleoplasmin, importin alpha, C-myc, EGL-13, TUS, hnRNPA1, Mata2, or PY-NLS. An NLS can be on a C-terminus or an N-terminus of a Cas protein. In some cases, a Cas protein may contain from 1 to 5 NLS sequences. A Cas protein can contain 1, 2, 3, 4, 5, 6, 7, 8, 9, or up to 10 NLS sequences. A Cas protein, such as Cas9, may contain two NLS sequences. A Cas protein may contain a SV40 and nuceloplasmin NLS sequence. A Cas protein may also contain at least one untranslated region.

In some aspects, a vector that encodes a CRISPR enzyme can contain a nuclear localization sequences (NLS) sequence. In some cases, a vector can comprise one or more NLSs. In some cases, a vector can contain about 1, 2, 3, 4, 5, 6, 7, 8, 9, or 10 NLSs. For example, a CRISPR enzyme can comprise more than or more than about 1, 2, 3, 4, 5, 6, 7, 8, 9, 10 NLSs at or near the ammo-terminus, more than or more than about 1, 2, 3, 4, 5, 6, 7, 8, 9, 10, NLSs at or near the carboxyl-terminus, or any combination of these (e.g., one or more NLS at the ammo-terminus and one or more NLS at the carboxyl terminus). When more than one NLS is present, each can be selected independently of others, such that a single NLS can be present in more than one copy and/or in combination with one or more other NLSs present in one or more copies.

An NLS can be monopartite or bipartite. In some cases, a bipartite NLS can have a spacer sequence as opposed to a monopartite NLS. An NLS can be from at least one of: SV40, nucleoplasmin, importin alpha, C-myc, EGL-13, TUS, hnRNPA1, Mata2, or PY-NLS. An NLS can be located anywhere within the polypeptide chain, e.g., near the N- or C-terminus. For example, the NLS can be within or within about 1, 2, 3, 4, 5, 10, 15, 20, 25, 30, 40, 50 amino acids along a polypeptide chain from the N- or C-terminus. Sometimes the NLS can be within or within about 50 amino acids or more, e.g., 100, 200, 300, 400, 500, 600, 700, 800, 900, or 1000 amino acids from the N- or C-terminus.

Any functional concentration of Cas protein can be introduced to a cell. For example, 15 micrograms of Cas mRNA can be introduced to a cell. In other cases, a Cas mRNA can be introduced from 0.5 micrograms to 100 micrograms. A Cas mRNA can be introduced from 0.5, 5, 10, 15, 20, 25, 30, 35, 40, 45, 50, 55, 60, 65, 70, 75, 80, 85, 90, 95, or 100 micrograms.

In some cases, a dual nickase approach may be used to introduce a double stranded break or a genomic break. Cas proteins can be mutated at known amino acids within either nuclease domains, thereby deleting activity of one nuclease domain and generating a nickase Cas protein capable of generating a single strand break. A nickase along with two distinct guide RNAs targeting opposite strands may be utilized to generate a double stranded break (DSB) within a target site (often referred to as a "double nick" or "dual nickase" CRISPR system). This approach may dramatically increase target specificity, since it is unlikely that two off-target nicks will be generated within close enough proximity to cause a DSB.

A nuclease, such as Cas9, can be tested for identity and potency prior to use. For example, identity and potency can be determined using at least one of spectrophotometric analysis, RNA agarose gel analysis, LC-MS, endotoxin analysis, and sterility testing. In some cases, a nuclease sequence, such as a Cas9 sequence can be sequenced to confirm its identity. In some cases, a Cas protein, such as a Cas9 protein, can be sequenced prior to clinical or therapeutic use. For example, a purified in vitro transcription product can be assessed by polyacrylamide gel electrophoresis to verify no other mRNA species exist or substantially no other mRNA species exist within a clinical product other than Cas9. Additionally, purified mRNA encoding a Cas protein, such as Cas9, can undergo validation by reverse-transcription followed by a sequencing step to verify identity at a nucleotide level. A purified in vitro transcription product can be assessed by polyacrylamide gel electrophoresis (PAGE) to verify that an mRNA is the size expected for Cas9 and substantially no other mRNA species exist within a clinical or therapeutic product.

In some cases, an endotoxin level of a nuclease, such as Cas9, can be determined. A clinically/therapeutically acceptable level of an endotoxin can be less than 3 EU/mL. A clinically/therapeutically acceptable level of an endotoxin can be less than 2 EU/mL. A clinically/therapeutically acceptable level of an endotoxin can be less than 1 EU/mL. A clinically/therapeutically acceptable level of an endotoxin can be less than 0.5 EU/mL.

In some cases, a nuclease, such as Cas9, can undergo sterility testing. A clinically/therapeutically acceptable level of a sterility testing can be 0 or denoted by no growth on a culture. A clinically/therapeutically acceptable level of a sterility testing can be less than 0.5%, 0.3%, 0.1%, or 0.05% growth.

Guiding Polynucleic Acid

A guiding polynucleic acid can be DNA or RNA. A guiding polynucleic acid can be single stranded or double stranded. In some cases, a guiding polynucleic acid can contains regions of single stranded areas and double stranded areas. A guiding polynucleic acid can also form secondary structures. As used herein, the term "guide RNA (gRNA)," and its grammatical equivalents can refer to an RNA which can be specific for a target DNA and can form a complex with a Cas protein. A guide RNA can comprise a guide sequence, or spacer sequence, that specifies a target site and guides an RNA/Cas complex to a specified target DNA for cleavage. For example, a guide RNA can target a CRISPR complex to a target gene or portion thereof and perform a targeted double strand break. Site-specific cleavage of a target DNA occurs at locations determined by both 1) base-pairing complementarity between a guide RNA and a target DNA (also called a protospacer) and 2) a short motif in a target DNA referred to as a protospacer adjacent motif (PAM). In some cases, gRNAs can be designed using an algorithm which can identify gRNAs located in early exons within commonly expressed transcripts.

In some cases, a guide polynucleotide can be complementary to a target sequence of a gene encoding: methyltransferase, hydroxylase, monooxygenase, kinase, decarboxylase, transcriptional regulators, transporters, Indoleamine 2,3-dioxygenase (IDO), tryptophan 2,3-dioxygenase (TDO), TrpM, phospho-2-dehydro-3-deoxyheptonate aldolase, 3-dehydroquinate synthase, 3-dehydroquinate dehydratase, shikimate dehydrogenase, 3-phosphoshikimate 1-carboxyvinyltransferase, shikimate kinase 1, shikimate kinase 2, chorismate synthase, tryptophan synthase alpha chain, tryptophan synthase beta chain, anthranilate phosphoribosyltransferase, and anthranilate synthase component. In some cases, a gRNA or gDNA can bind a target sequence that is homologous or complimentary to SEQ ID NOS: 1-5 or any of the genes mentioned above.

Functional gene copies, gene variants and pseudogenes are mapped and aligned to produce a sequence template for CRISPR design. In some cases, multiple guide RNAs targeting sequences conserved across aligned copies of THCA synthase are designed to disrupt the early coding sequence and introduce mutations in the coding sequence, such as frameshift mutation indels. In some cases, a guide RNAs can be selected that has a low occurrence of off-target sites elsewhere in the Cannabis and hemp genome.

In an aspect, a CRISPR gRNA library may be generated and utilized to screen variant plants by DNA analysis. Multiplex CRISPR engineering can generate diverse genotypes of novel cannabinoid-producing cannabis plants. In some cases, these plants produce elevated levels of minor, rare, and/or poorly researched cannabinoids.

In some cases, a gRNA can be designed to target at exon of a gene involved in a cannabinoid biosynthesis pathway. In some cases, gRNAs can be designed to disrupt an early coding sequence. In an aspect, subject guide RNAs can be clustered into two categories: those intended to disrupt the production of functional proteins by targeting coding sequences having early positions within these genes to introduce frameshift mutation indels (KO Guides); and those which target sequences spread within gene regulatory regions (Expression modulating guides). Additionally, guide RNAs can be selected that have the lowest occurrence of off-target sites elsewhere in the cannabis and hemp genome.

In some cases, a gRNA can be selected based on the pattern of indels it inserts into a target gene. Candidate gRNAs can be ranked by off-target potential using a scoring system that can take into account: (a) the total number of mismatches between the gRNA sequence and any closely matching genomic sequences; (b) the mismatch position(s) relative to the PAM site which correlate with a negative effect on activity for mismatches falling close to the PAM site; (c) the distance between mismatches to account for the cumulative effect of neighboring mismatches in disrupting guide-DNA interactions; and any combination thereof. In some cases, a greater number of mismatches between a gRNA and a genomic target site can yield a lower potential for CRISPR-mediated cleavage of that site. In some cases, a mismatch position is directly adjacent to a PAM site. In other cases, a mismatch position can be from 1 nucleotide up to 100 kilobases away from a PAM site. Candidate gRNAs comprising mismatches may not be adjacent to a PAM in some cases. In other cases, at least two candidate gRNAs comprising mismatches may bind a genome from 1 nucleotide up to 100 kilobases away from each other. A mismatch can be a substitution of a nucleotide. For example, in some cases a G will be substituted for a T. Mismatches between a gRNA and a genome may allow for reduced fidelity of CRISPR gene editing. In some cases, a positive scoring gRNA can be about 110 nucleotides in length and may contain no mismatches to a complementary genome sequence. In other cases, a positive scoring gRNA can be about 110 nucleotides in length and may contain up to 3 mismatches to a complementary genome sequence. In other cases, a positive scoring gRNA can be about 110 nucleotides in length and may contain up to 20 mismatches to a complementary genome sequence. In some cases, a guiding polynucleic acid can contain internucleotide linkages that can be phosphorothioates. Any number of phosphorothioates can exist. For example from 1 to about 100 phosphorothioates can exist in a guiding polynucleic acid sequence. In some cases, from 1 to 10 phosphorothioates are present. In some cases, 8 phosphorothioates exist in a guiding polynucleic acid sequence.

In some cases, top scoring gRNAs can be designed and selected and an on-target editing efficiency of each can be assessed experimentally in plant cells. In some cases, an editing efficiency as determined by TiDE analysis can exceed at least about 20%. In other cases, editing efficiency can be from about 20% to from about 50%, from about 50% to from about 80%, from about 80% to from about 100%. In some cases, a percent indel can be determined in a trial GMP run. For example, a final cellular product can be analyzed for on-target indel formation by Sanger sequencing and TIDE analysis. Genomic DNA can be extracted from about $1\times10^6$ cells from both a control and experimental sample and subjected to PCR using primers flanking a gene that has been disrupted, such as a gene involved in a cannabinoid biosynthesis pathway. Sanger sequencing chromatograms can be analyzed using a TIDE software program that can quantify indel frequency and size distribution of indels by comparison of control and knockout samples.

A method disclosed herein also can comprise introducing into a cell or plant embryo at least one guide RNA or nucleic acid, e.g., DNA encoding at least one guide RNA. A guide RNA can interact with a RNA-guided endonuclease to direct the endonuclease to a specific target site, at which site the 5' end of the guide RNA base pairs with a specific protospacer sequence in a chromosomal sequence.

A guide RNA can comprise two RNAs, e.g., CRISPR RNA (crRNA) and transactivating crRNA (tracrRNA). A guide RNA can sometimes comprise a single-guide RNA (sgRNA) formed by fusion of a portion (e.g., a functional portion) of crRNA and tracrRNA. A guide RNA can also be a dual RNA comprising a crRNA and a tracrRNA. A guide RNA can comprise a crRNA and lack a tracrRNA. Furthermore, a crRNA can hybridize with a target DNA or protospacer sequence.

As discussed above, a guide RNA can be an expression product. For example, a DNA that encodes a guide RNA can be a vector comprising a sequence coding for the guide RNA. A guide RNA can be transferred into a cell or organism by transfecting the cell or plant embryo with an isolated guide RNA or plasmid DNA comprising a sequence coding for the guide RNA and a promoter. In some aspects, a promoter can be selected from the group consisting of a leaf-specific promoter, a flower-specific promoter, a THCA synthase promoter, a CaMV35S promoter, a FMV35S promoter, and a tCUP promoter. A guide RNA can also be transferred into a cell or plant embryo in other way, such as using particle bombardment.

A guide RNA can be isolated. For example, a guide RNA can be transfected in the form of an isolated RNA into a cell or plant embryo. A guide RNA can be prepared by in vitro transcription using any in vitro transcription system. A guide RNA can be transferred to a cell in the form of isolated RNA rather than in the form of plasmid comprising encoding sequence for a guide RNA.

A guide RNA can comprise a DNA-targeting segment and a protein binding segment. A DNA-targeting segment (or DNA-targeting sequence, or spacer sequence) comprises a nucleotide sequence that can be complementary to a specific sequence within a target DNA (e.g., a protospacer). A protein-binding segment (or protein-binding sequence) can interact with a site-directed modifying polypeptide, e.g. an RNA-guided endonuclease such as a Cas protein. By "segment" it is meant a segment/section/region of a molecule, e.g., a contiguous stretch of nucleotides in an RNA. A segment can also mean a region/section of a complex such that a segment may comprise regions of more than one molecule. For example, in some cases a protein-binding segment of a DNA-targeting RNA is one RNA molecule and the protein-binding segment therefore comprises a region of that RNA molecule. In other cases, the protein-binding segment of a DNA-targeting RNA comprises two separate molecules that are hybridized along a region of complementarity.

A guide RNA can comprise two separate RNA molecules or a single RNA molecule. An exemplary single molecule guide RNA comprises both a DNA-targeting segment and a protein-binding segment.

An exemplary two-molecule DNA-targeting RNA can comprise a crRNA-like ("CRISPR RNA" or "targeter-RNA" or "crRNA" or "crRNA repeat") molecule and a corresponding tracrRNA-like ("trans-acting CRISPR RNA" or "activator-RNA" or "tracrRNA") molecule. A first RNA molecule can be a crRNA-like molecule (targeter-RNA), that can comprise a DNA-targeting segment (e.g., spacer) and a stretch of nucleotides that can form one half of a double-stranded RNA (dsRNA) duplex comprising the protein-binding segment of a guide RNA. A second RNA molecule can be a corresponding tracrRNA-like molecule (activator-RNA) that can comprise a stretch of nucleotides that can form the other half of a dsRNA duplex of a protein-binding segment of a guide RNA. In other words, a stretch of nucleotides of a crRNA-like molecule can be complementary to and can hybridize with a stretch of nucleotides of a tracrRNA-like molecule to form a dsRNA duplex of a protein-binding domain of a guide RNA. As such, each crRNA-like molecule can be said to have a corresponding tracrRNA-like molecule. A crRNA-like molecule additionally can provide a single stranded DNA-targeting segment, or spacer sequence. Thus, a crRNA-like and a tracrRNA-like molecule (as a corresponding pair) can hybridize to form a guide RNA. A subject two-molecule guide RNA can comprise any corresponding crRNA and tracrRNA pair.

A DNA-targeting segment or spacer sequence of a guide RNA can be complementary to sequence at a target site in a chromosomal sequence, e.g., protospacer sequence such that the DNA-targeting segment of the guide RNA can base pair with the target site or protospacer. In some cases, a DNA-targeting segment of a guide RNA can comprise from or from about 10 nucleotides to from or from about 25 nucleotides or more. For example, a region of base pairing between a first region of a guide RNA and a target site in a chromosomal sequence can be or can be about 10, 11, 12, 13, 14, 15, 16, 17, 18, 19, 20, 22, 23, 24, 25, or more than 25 nucleotides in length. Sometimes, a first region of a guide RNA can be or can be about 19, 20, or 21 nucleotides in length.

A guide RNA can target a nucleic acid sequence of or of about 20 nucleotides. A target nucleic acid can be less than or less than about 20 nucleotides. A target nucleic acid can be at least or at least about 5, 10, 15, 16, 17, 18, 19, 20, 21, 22, 23, 24, 25, 30 or more nucleotides. A target nucleic acid can be at most or at most about 5, 10, 15, 16, 17, 18, 19, 20, 21, 22, 23, 24, 25, 30 or more nucleotides. A target nucleic acid sequence can be or can be about 20 bases immediately 5' of the first nucleotide of the PAM. A guide RNA can target a nucleic acid sequence of a gene that encodes a protein involved in the cannabinoid biosynthesis pathway. In some cases, a guiding polynucleic acid, such as a guide RNA, can bind a genomic region from about 1 base pair to about 20 base pairs away from a PAM. A guide can bind a genomic region from about 1, 2, 3, 4, 5 6, 7, 8, 9, 10, 11, 12, 13, 14, 15, 16, 17, 18, 19, or up to about 20 base pairs away from a PAM.

A guide nucleic acid, for example, a guide RNA, can refer to a nucleic acid that can hybridize to another nucleic acid, for example, the target nucleic acid or protospacer in a genome of a cell. A guide nucleic acid can be RNA. A guide nucleic acid can be DNA. The guide nucleic acid can be programmed or designed to bind to a sequence of nucleic acid site-specifically. A guide nucleic acid can comprise a polynucleotide chain and can be called a single guide nucleic acid. A guide nucleic acid can comprise two polynucleotide chains and can be called a double guide nucleic acid.

A guide nucleic acid can comprise one or more modifications to provide a nucleic acid with a new or enhanced feature. A guide nucleic acid can comprise a nucleic acid affinity tag. A guide nucleic acid can comprise synthetic nucleotide, synthetic nucleotide analog, nucleotide derivatives, and/or modified nucleotides. A guide nucleic acid can comprise a nucleotide sequence (e.g., a spacer), for example, at or near the 5' end or 3' end, that can hybridize to a sequence in a target nucleic acid (e.g., a protospacer). A spacer of a guide nucleic acid can interact with a target nucleic acid in a sequence-specific manner via hybridization (i.e., base pairing). A spacer sequence can hybridize to a target nucleic acid that is located 5' or 3' of a protospacer adjacent motif (PAM). The length of a spacer sequence can be at least or at least about 5, 10, 15, 16, 17, 18, 19, 20, 21, 22, 23, 24, 25, 30 or more nucleotides. The length of a spacer sequence can be at most or at most about 5, 10, 15, 16, 17, 18, 19, 20, 21, 22, 23, 24, 25, 30 or more nucleotides.

A guide RNA can also comprise a dsRNA duplex region that forms a secondary structure. For example, a secondary structure formed by a guide RNA can comprise a stem (or hairpin) and a loop. A length of a loop and a stem can vary. For example, a loop can range from about 3 to about 10 nucleotides in length, and a stem can range from about 6 to about 20 base pairs in length. A stem can comprise one or more bulges of 1 to about 10 nucleotides. The overall length of a second region can range from about 16 to about 60 nucleotides in length. For example, a loop can be or can be about 4 nucleotides in length and a stem can be or can be about 12 base pairs. A dsRNA duplex region can comprise a protein-binding segment that can form a complex with an RNA-binding protein, such as an RNA-guided endonuclease, e.g. Cas protein.

A guide RNA can also comprise a tail region at the 5' or 3' end that can be essentially single-stranded. For example, a tail region is sometimes not complementarity to any chromosomal sequence in a cell of interest and is sometimes not complementarity to the rest of a guide RNA. Further, the length of a tail region can vary. A tail region can be more than or more than about 4 nucleotides in length. For example, the length of a tail region can range from or from about 5 to from or from about 60 nucleotides in length.

A guide RNA can be introduced into a cell or embryo as an RNA molecule. For example, an RNA molecule can be transcribed in vitro and/or can be chemically synthesized. A guide RNA can then be introduced into a cell or embryo as an RNA molecule. A guide RNA can also be introduced into a cell or embryo in the form of a non-RNA nucleic acid molecule, e.g., DNA molecule. For example, a DNA encoding a guide RNA can be operably linked to promoter control sequence for expression of the guide RNA in a cell or embryo of interest. A RNA coding sequence can be operably linked to a promoter sequence that is recognized by RNA polymerase III (Pol III).

A DNA molecule encoding a guide RNA can also be linear. A DNA molecule encoding a guide RNA can also be circular. A DNA sequence encoding a guide RNA can also be part of a vector. Some examples of vectors can include plasmid vectors, phagemids, cosmids, artificial/mini-chromosomes, transposons, and viral vectors. For example, a DNA encoding a RNA-guided endonuclease is present in a plasmid vector. Other non-limiting examples of suitable plasmid vectors include pUC, pBR322, pET, pBluescript, and variants thereof. Further, a vector can comprise additional expression control sequences (e.g., enhancer sequences, Kozak sequences, polyadenylation sequences, transcriptional termination sequences, etc.), selectable marker sequences (e.g., antibiotic resistance genes), origins of replication, and the like.

When both a RNA-guided endonuclease and a guide RNA are introduced into a cell as DNA molecules, each can be part of a separate molecule (e.g., one vector containing fusion protein coding sequence and a second vector containing guide RNA coding sequence) or both can be part of a same molecule (e.g., one vector containing coding (and regulatory) sequence for both a fusion protein and a guide RNA).

A Cas protein, such as a Cas9 protein or any derivative thereof, can be pre-complexed with a guide RNA to form a ribonucleoprotein (RNP) complex. The RNP complex can be introduced into plant cells. Introduction of the RNP complex can be timed. The cell can be synchronized with other cells at G1, S, and/or M phases of the cell cycle. The RNP complex can be delivered at a cell phase such that HDR is enhanced. The RNP complex can facilitate homology directed repair.

A guide RNA can also be modified. The modifications can comprise chemical alterations, synthetic modifications, nucleotide additions, and/or nucleotide subtractions. The modifications can also enhance CRISPR genome engineering. A modification can alter chirality of a gRNA. In some cases, chirality may be uniform or stereopure after a modification. A guide RNA can be synthesized. The synthesized guide RNA can enhance CRISPR genome engineering. A guide RNA can also be truncated. Truncation can be used to reduce undesired off-target mutagenesis. The truncation can comprise any number of nucleotide deletions. For example, the truncation can comprise 1, 2, 3, 4, 5, 10, 15, 20, 25, 30, 40, 50 or more nucleotides. A guide RNA can comprise a region of target complementarity of any length. For example, a region of target complementarity can be less than 20 nucleotides in length. A region of target complementarity can be more than 20 nucleotides in length. A region of target complementarity can target from about 5 bp to about 20 bp directly adjacent to a PAM sequence. A region of target complementarity can target about 13 bp directly adjacent to a PAM sequence. The polynucleic acids as described herein can be modified. A modification can be made at any location of a polynucleic acid. More than one modification can be made to a single polynucleic acid. A polynucleic acid can undergo quality control after a modification. In some cases, quality control may include PAGE, HPLC, MS, or any combination thereof. A modification can be a substitution, insertion, deletion, chemical modification, physical modification, stabilization, purification, or any combination thereof. A polynucleic acid can also be modified by 5' adenylate, 5' guanosine-triphosphate cap, 5'$N^7$-Methylguanosine-triphosphate cap, 5'triphosphate cap, 3'phosphate, 3'thiophosphate, 5'phosphate, 5'thiophosphate, Cis-Syn thymidine dimer, trimers, C12 spacer, C3 spacer, C6 spacer, dSpacer, PC spacer, rSpacer, Spacer 18, Spacer 9,3'-3' modifications, 5'-5' modifications, abasic, acridine, azobenzene, biotin, biotin BB, biotin TEG, cholesteryl TEG, desthiobiotin TEG, DNP TEG, DNP-X, DOTA, dT-Biotin, dual biotin, PC biotin, psoralen C2, psoralen C6, TINA, 3'DABCYL, black hole quencher 1, black hole quencher 2, DABCYL SE, dT-DABCYL, IRDye QC-1, QSY-21, QSY-35, QSY-7, QSY-9, carboxyl linker, thiol linkers, 2'deoxyribonucleoside analog purine, 2'deoxyribonucleoside analog pyrimidine, ribonucleoside analog, 2'-O-methyl ribonucleoside analog, sugar modified analogs, wobble/universal bases, fluorescent dye label, 2'fluoro RNA, 2'O-methyl RNA, methylphosphonate, phosphodiester DNA, phosphodiester RNA, phosphothioate DNA, phosphorothioate RNA, UNA, pseudouridine-5'-triphosphate, 5-methylcytidine-5'-triphosphate, or any combination thereof. In some cases, a modification can be permanent. In other cases, a modification can be transient. In some cases, multiple modifications are made to a polynucleic acid. A polynucleic acid modification may alter physio-chemical properties of a nucleotide, such as their conformation, polarity, hydrophobicity, chemical reactivity, base-pairing interactions, or any combination thereof. In some aspects a gRNA can be modified. In some cases, a modification is on a 5' end, a 3' end, from a 5' end to a 3' end, a single base modification, a 2'-ribose modification, or any combination thereof. A modification can be selected from a group consisting of base substitutions, insertions, deletions, chemical modifications, physical modifications, stabilization, purification, and any combination thereof. In some cases, a modification is a chemical modification.

In some cases, a modification is a 2-O-methyl 3 phosphorothioate addition denoted as "m". A phosphothioate backbone can be denoted as "(ps)." A 2-O-methyl 3 phosphorothioate addition can be performed from 1 base to 150 bases. A 2-O-methyl 3 phosphorothioate addition can be performed from 1 base to 4 bases. A 2-O-methyl 3 phosphorothioate addition can be performed on 2 bases. A 2-O-methyl 3 phosphorothioate addition can be performed on 4 bases. A modification can also be a truncation. A truncation can be a 5-base truncation. In some cases, a modification may be at C terminus and N terminus nucleotides.

A modification can also be a phosphorothioate substitute. In some cases, a natural phosphodiester bond may be susceptible to rapid degradation by cellular nucleases and; a modification of internucleotide linkage using phosphorothioate (PS) bond substitutes can be more stable towards hydrolysis by cellular degradation. A modification can increase stability in a polynucleic acid. A modification can also enhance biological activity. In some cases, a phosphorothioate enhanced RNA polynucleic acid can inhibit RNase A, RNase T1, calf serum nucleases, or any combinations thereof. These properties can allow the use of PS-RNA polynucleic acids to be used in applications where exposure to nucleases is of high probability in vivo or in vitro. For example, phosphorothioate (PS) bonds can be introduced between the last 3-5 nucleotides at the 5'- or 3'-end of a polynucleic acid which can inhibit exonuclease degradation. In some cases, phosphorothioate bonds can be added throughout an entire polynucleic acid to reduce attack by endonucleases.

In another embodiment, genetically modifying fungi comprises introducing into a fungus to increase tryptamine derived substance, such as dimethyltryptamine, psilocybin, or psilocin, or a cell thereof (i) at least one RNA-guided endonuclease comprising at least one nuclear localization signal or nucleic acid encoding at least one RNA-guided endonuclease comprising at least one nuclear localization signal, (ii) at least one guide RNA or DNA encoding at least one guide RNA, and, optionally, (iii) at least one donor polynucleotide such as a barcode; and culturing the fungus or cell thereof such that each guide RNA directs an RNA-guided endonuclease to a targeted site in the chromosomal sequence where the RNA-guided endonuclease introduces a double-stranded break in the targeted site, and the double-stranded break is repaired by a DNA repair process such that the chromosomal sequence is modified, wherein the targeted site is located in any of the genes that encode methyltransferase, hydroxylase, monooxygenase, kinase, decarboxylase, putative transcriptional regulators, and putative transporters and the chromosomal modification interrupts or interferes with transcription and/or translation of said gene.

In some cases, a GUIDE-Seq analysis can be performed to determine the specificity of engineered guide RNAs. The general mechanism and protocol of GUIDE-Seq profiling of off-target cleavage by CRISPR system nucleases is discussed in Tsai, S. et al., "GUIDE-Seq enables genome-wide profiling of off-target cleavage by CRISPR system nucleases," Nature, 33: 187-197 (2015). To assess off-target frequencies by next generation sequencing cells can be transfected with Cas9 mRNA and a guiding RNA. Genomic DNA can be isolated from transfected cells from about 72 hours post transfection and PCR amplified at potential off-target sites. A potential off-target site can be predicted using the Wellcome Trust Sanger Institute Genome Editing database (WGE) algorithm. Candidate off-target sites can be chosen based on sequence homology to an on-target site. In some cases, sites with about 4 or less mismatches between a gRNA and a genomic target site can be utilized. For each candidate off-target site, two primer pairs can be designed. PCR amplicons can be obtained from both untreated (control) and Cas9/gRNA-treated cells. PCR amplicons can be pooled. NGS libraries can be prepared using TruSeq Nano DNA library preparation kit (Illumina). Samples can be analyzed on an Illumina HiSeq machine using a 250 bp paired-end workflow. In some cases, from about 40 million mappable NGS reads per gRNA library can be acquired. This can equate to an average number of about 450,000 reads for each candidate off-target site of a gRNA. In some cases, detection of CRISPR-mediated disruption can be at a frequency as low as 0.1% at any genomic locus.

Computational predictions can be used to select candidate gRNAs likely to be the safest choice for a targeted gene. Candidate gRNAs can then tested empirically using a focused approach steered by computational predictions of potential off-target sites. In some cases, an assessment of gRNA off-target safety can employ a next-generation deep sequencing approach to analyze the potential off-target sites predicted by the CRISPR design tool for each gRNA. In some cases, gRNAs can be selected with fewer than 3 mismatches to any sequence in the genome (other than the perfect matching intended target). In some cases, a gRNA can be selected with fewer than 50, 40, 30, 20, 10, 5, 4, 3, 2, or 1 mismatch(es) to any sequence in a genome. In some cases, a computer system or software can be utilized to provide recommendations of candidate gRNAs with predictions of low off-target potential.

In some cases, potential off-target sites can be identified with at least one of: GUIDE-Seq and targeted PCR amplification, and next generation sequencing. In addition, modified cells, such as Cas9/gRNA-treated cells can be subjected to karyotyping to identify any chromosomal re-arrangements or translocations.

A gRNA can be introduced at any functional concentration. For example, a gRNA can be introduced to a cell at 10 micrograms. In other cases, a gRNA can be introduced from 0.5 micrograms to 100 micrograms. A gRNA can be introduced from 0.5, 5, 10, 15, 20, 25, 30, 35, 40, 45, 50, 55, 60, 65, 70, 75, 80, 85, 90, 95, or 100 micrograms.

A guiding polynucleic acid can have any frequency of bases. For example, a guiding polynucleic acid can have 29 As, 17 Cs, 23 Gs, 23 Us, 3 mGs, 1 mCs, and 4 mUs. A guiding polynucleic acid can have from about 1 to about 100 nucleotides. A guiding polynucleic acid can have from about 1 to 30 of a single polynucleotide. A guiding polynucleic acid can have from about 1 to 10, 10 to 20, or from 20 to 30 of a single nucleotide.

A guiding polynucleic acid can be tested for identity and potency prior to use. For example, identity and potency can be determined using at least one of spectrophotometric analysis, RNA agarose gel analysis, LC-MS, endotoxin analysis, and sterility testing. In some cases, identity testing can determine an acceptable level for clinical/therapeutic use. For example, an acceptable spectrophotometric analysis result can be 14±2 μL/vial at 5.0±0.5 mg/mL. an acceptable spectrophotometric analysis result can also be from about 10-20±2 μL/vial at 5.0±0.5 mg/mL or from about 10-20±2 μL/vial at about 3.0 to 7.0±0.5 mg/mL. An acceptable clinical/therapeutic size of a guiding polynucleic acid can be about 100 bases. A clinical/therapeutic size of a guiding polynucleic acid can be from about 5 bases to about 150 bases. A clinical/therapeutic size of a guiding polynucleic acid can be from about 20 bases to about 150 bases. A clinical/therapeutic size of a guiding polynucleic acid can be from about 40 bases to about 150 bases. A clinical/therapeutic size of a guiding polynucleic acid can be from about 60 bases to about 150 bases. A clinical/therapeutic size of a guiding polynucleic acid can be from about 80 bases to about 150 bases. A clinical/therapeutic size of a guiding polynucleic acid can be from about 100 bases to about 150 bases. A clinical/therapeutic size of a guiding polynucleic acid can be from about 110 bases to about 150 bases. A clinical/therapeutic size of a guiding polynucleic acid can be from about 120 bases to about 150 bases.

In some cases, a mass of a guiding polynucleic acid can be determined. A mass can be determined by LC-MS assay. A mass can be about 32,461.0 amu. A guiding polynucleic acid can have a mass from about 30,000 amu to about 50,000 amu. A guiding polynucleic acid can have a mass from about 30,000 amu to 40,000 amu, from about 40,000 amu to about 50,000 amu. A mass can be of a sodium salt of a guiding polynucleic acid.

In some cases, an endotoxin level of a guiding polynucleic acid can be determined. A clinically/therapeutically acceptable level of an endotoxin can be less than 3 EU/mL. A clinically/therapeutically acceptable level of an endotoxin can be less than 2 EU/mL. A clinically/therapeutically acceptable level of an endotoxin can be less than 1 EU/mL. A clinically/therapeutically acceptable level of an endotoxin can be less than 0.5 EU/mL.

In some cases, a guiding polynucleic acid can go sterility testing. A clinically/therapeutically acceptable level of a sterility testing can be 0 or denoted by no growth on a culture. A clinically/therapeutically acceptable level of a sterility testing can be less than 0.5% growth.

Guiding polynucleic acids can be assembled by a variety of methods, e.g., by automated solid-phase synthesis. A polynucleic acid can be constructed using standard solid-phase DNA/RNA synthesis. A polynucleic acid can also be constructed using a synthetic procedure. A polynucleic acid can also be synthesized either manually or in a fully automated fashion. In some cases, a synthetic procedure may comprise 5'-hydroxyl oligonucleotides can be initially transformed into corresponding 5'-H-phosphonate mono esters, subsequently oxidized in the presence of imidazole to activated 5'-phosphorimidazolidates, and finally reacted with pyrophosphate on a solid support. This procedure may include a purification step after the synthesis such as PAGE, HPLC, MS, or any combination thereof.

Donor Sequences

In some cases, a donor sequence may be introduced to a genome of a fungus, yeast, plant or portion thereof. In some cases, a donor is inserted into a genomic break. In some aspects, a donor comprises homology to sequencing flanking a target sequence. Methods of introducing a donor sequence are known to the skilled artisan but may include the use of homology arms. For example, a donor sequence can comprise homology arms to at least a portion of a genome that comprises a genomic break. In some cases, a donor sequence is randomly inserted into a genome of a cannabis or hemp plant cell genome.

In some cases, a donor sequence can be introduced in a site directed fashion using homologous recombination. Homologous recombination permits site specific modifications in endogenous genes and thus inherited or acquired mutations may be corrected, and/or novel alterations may be engineered into the genome. Homologous recombination and site-directed integration in plants are discussed in, for example, U.S. Pat. Nos. 5,451,513, 5,501,967 and 5,527,695.

In some aspects, a donor sequence comprises a promoter sequence. Increasing expression of designed gene products may be achieved by synthetically increasing expression by modulating promoter regions or inserting stronger promoters upstream of desired gene sequences. In some aspects, a promoter such as 35s and Ubi10 that are highly functional in *Arabidopsis* and other plants may be introduced. In some cases, a promoter that is highly functional in cannabis and/or hemp is introduced.

In some cases, a barcode can comprise a non-natural sequence. In some aspects, a barcode contains natural sequences. In some aspects, a barcode can be utilized to allow for identification of transgenic organism via genotyping. In some aspects, a donor sequence can be a marker. Selectable marker genes can include, for example, photosynthesis (atpB, tscA, psaA/B, petB, petA, ycf3, rpoA, rbcL), antibiotic resistance (rrnS, rrnL, aadA, nptII, aphA-6), herbicide resistance (psbA, bar, AHAS (ALS), EPSPS, HPPD, sul) and metabolism (BADH, codA, ARG8, ASA2) genes. The sul gene from bacteria has herbicidal sulfonamide-insensitive dihydropteroate synthase activity and can be used as a selectable marker when the protein product is targeted to plant mitochondria (U.S. Pat. No. 6,121,513). In some embodiments, the sequence encoding the marker can be incorporated into the genetically modified cell or organism, for instance fungus, yeast or plant described herein. In some embodiments, the incorporated sequence encoding the marker may by subsequently removed from the transformed genome. Removal of a sequence encoding a marker may be facilitated by the presence of direct repeats before and after the region encoding the marker. Removal of the sequence encoding the marker can occur via the endogenous homologous recombination system of the organelle or by use of a site-specific recombinase system such as cre-lox or FLP/FRT.

In some cases, a marker can refer to a label capable of detection, such as, for example, a radioisotope, fluorescent compound, bioluminescent compound, a chemiluminescent compound, metal chelator, or enzyme. Examples of detectable markers include, but are not limited to, the following: fluorescent labels (e.g., FITC, rhodamine, lanthanide phosphors), enzymatic labels (e.g., horseradish peroxidase, β-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags).

Selectable or detectable markers normally comprise DNA segments that allow a cell, or a molecule marked with a "tag" inside a cell of interest, to be identified, often under specific conditions. Such markers can encode an activity, selected from, but not limited to, the production of RNA, peptides, or proteins, or the marker can provide a bonding site for RNA, peptides, proteins, inorganic and organic compounds or composites, etc. By way of example, selectable markers comprise, without being limited thereto, DNA segments that comprise restriction enzyme cleavage points, DNA segments comprising a fluorescent probe, DNA segments that encode products that provide resistance to otherwise toxic compounds, comprising antibiotics, e.g. spectinomycin, ampicillin, kanamycin, tetracycline, BASTA, neomycin-phosphotransferase II (NEO) and hygromycin-phosphotransferase (HPT), DNA segments that encode products that a plant target cell of interest would not have under natural conditions, e.g. tRNA genes, auxotrophic markers and the like, DNA segments that encode products that can be readily identified, in particular optically observable markers, e.g. phenotype markers such as—galactosidases, GUS, fluorescent proteins, e.g. green fluorescent protein (GFP) and other fluorescent proteins, e.g. blue (CFP), yellow (YFP) or red (RFP) fluorescent proteins, and surface proteins, wherein those fluorescent proteins that exhibit a high fluorescence intensity are of particular interest, because these proteins can also be identified in deeper tissue layers if, instead of a single cell, a complex plant target structure or a plant material or a plant comprising numerous types of tissues or cells can be to be analyzed, new primer sites for PCR, the recording of DNA sequences that cannot be modified in accordance with the present disclosure by restriction endonucleases or other DNA modified enzymes or effector domains, DNA sequences that are used for specific modifications, e.g. epigenetic modifications, e.g. methylations, and DNA sequences that carry a PAM motif, which can be identified by a suitable CRISPR system in accordance with the present disclosure, and also DNA sequences that do not have a PAM motif, such as can be naturally present in an endogenous plant genome sequence.

In one embodiment, a donor comprises a selectable, screenable, or scoreable marker gene or portion thereof. In some cases, a marker serves as a selection or screening device may function in a regenerable genetically modified organism to produce a compound that would confer upon a tissue in said organism resistance to an otherwise toxic compound. Genes of interest for use as a selectable, screenable, or scoreable marker would include but are not limited to gus, green fluorescent protein (gfp), luciferase (lux), genes conferring tolerance to antibiotics like kanamycin (Dekeyser et al., 1989) or spectinomycin (e.g. spectinomycin aminoglycoside adenyltransferase (aadA), genes that encode enzymes that give tolerance to herbicides like glyphosate (e.g. 5-enolpyruvylshikimate-3-phosphate synthase (EPSPS); glyphosate oxidoreductase (GOX); glyphosate decarboxylase; or glyphosate N-acetyltransferase (GAT), dalapon (e.g. dehI encoding 2,2-dichloropropionic acid dehalogenase conferring tolerance to 2,2-dichloropropionic acid, bromoxynil (haloarylnitrilase (Bxn) for conferring tolerance to bromoxynil, sulfonyl herbicides (e.g. acetohydroxyacid synthase or acetolactate synthase conferring tolerance to acetolactate synthase inhibitors such as sulfonylurea, imidazolinone, triazolopyrimidine, pyrimidyloxybenzoates and phthalide; encoding ALS, GST-II), bialaphos or phosphinothricin or derivatives (e.g. phosphinothricin acetyltransferase (bar) conferring tolerance to phosphinothricin or glufosinate, atrazine (encoding GST-III), dicamba (dicamba monooxygenase), or sethoxydim (modified acetyl-coenzyme A carboxylase for conferring tolerance to cyclohexanedione (sethoxydim) and aryloxyphenoxypropionate (haloxyfop), among others. Other selection procedures can also be implemented including positive selection mechanisms (e.g. use of the manA gene of *E. coli*, allowing growth in the presence of mannose), and dual selection (e.g. simultaneously using 75-100 ppm spectinomycin and 3-10 ppm glufosinate, or 75 ppm spectinomycin and 0.2-0.25 ppm dicamba). Use of spectinomycin at a concentration of about 25-1000 ppm, such as at about 150 ppm, can be also contemplated. In an embodiment, a detectable marker can be attached by spacer arms of various lengths to reduce potential steric hindrance.

In some cases, a donor polynucleotide comprises homology to sequences flanking a target sequence. In some cases, a donor polynucleotide introduces a stop codon into a gene provided herein for example to block synthesis of a non-psilocybin tryptamine. In some cases, a donor polynucleotide comprises a barcode, a reporter, or a selection marker.

Transformation

Appropriate transformation techniques can include but are not limited to: electroporation of fungi protoplasts; liposome-mediated transformation; polyethylene glycol (PEG) mediated transformation; transformation using viruses; micro-injection of cells; micro-projectile bombardment of cells; vacuum infiltration; and *Agrobacterium tumeficiens* mediated transformation. Transformation means introducing a nucleotide sequence into a cell in a manner to cause stable or transient expression of the sequence.

Following transformation, fungi or other organisms may be selected using a dominant selectable marker incorporated into the transformation vector. In certain embodiments, such marker confers antibiotic or herbicide resistance on the transformed fungi or other organisms, and selection of transformants can be accomplished by exposing the fungi and other organisms to appropriate concentrations of the antibiotic or herbicide. After transformed fungi or other organisms are selected and grown to maturity, those fungi and other organisms showing a modified trait are identified. The modified trait can be any of those traits described above. Additionally, expression levels or activity of the polypeptide or polynucleotide of the invention can be determined by analyzing mRNA expression using Northern blots, RT-PCR, RNA seq or microarrays, or protein expression using immunoblots or Western blots or gel shift assays.

Suitable methods for transformation of fungal or other cells for use with the current invention are believed to include virtually any method by which DNA can be introduced into a cell, such as by direct delivery of DNA such as by PEG-mediated transformation of protoplasts, by desiccation/inhibition-mediated DNA uptake, by electroporation, by agitation with silicon carbide fibers, by *Agrobacterium*-mediated transformation and by acceleration of DNA coated particles. Through the application of techniques such as these, the cells of virtually any fungus species may be stably transformed, and these cells developed into transgenic fungi.

*Agrobacterium* Mediated Transformation

*Agrobacterium*-mediated transfer is a widely applicable system for introducing genes into fungal cells because the DNA can be introduced into whole fungal tissues, thereby bypassing the need for regeneration of an intact fungus from a protoplast. The use of *Agrobacterium*-mediated fungal integrating vectors to introduce DNA, for example comprising CRISPR systems or donors sequences, into fungal cells is well known in the art.

Further, *Agrobacterium*-mediated transformation can be efficient in other organisms, such as dicotyledonous plants and can be used for the transformation of dicots, including *Arabidopsis*, tobacco, tomato, alfalfa and potato. Indeed, while *Agrobacterium*-mediated transformation has been routinely used with dicotyledonous plants for a number of years. In some cases, *Agrobacterium*-mediated transformation can be used in monocotyledonous plants. For example, *Agrobacterium*-mediated transformation techniques have now been applied to rice, wheat, barley, alfalfa and maize.

Modern *Agrobacterium* transformation vectors are capable of replication in *E. coli* as well as *Agrobacterium*, allowing for convenient manipulations as described. Moreover, recent technological advances in vectors for *Agrobacterium*-mediated gene transfer have improved the arrangement of genes and restriction sites in the vectors to facilitate the construction of vectors capable of expressing various polypeptide coding genes. In some aspects, a vector can have convenient multi-linker regions flanked by a promoter and a polyadenylation site for direct expression of inserted polypeptide coding genes and are suitable for purposes described herein. In addition, *Agrobacterium* containing both armed and disarmed Ti genes can be used for the transformations.

Electroporation

In some aspects, a fungus, yeast, plant or a cell thereof may be modified using electroporation. To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells, by exposing them to pectin-degrading enzymes (pectolyases) or mechanically wounding in a controlled manner.

Any transfection system can be utilized. In some cases, a Neon transfection system may be utilized. A Neon system can be a three-component electroporation apparatus comprising a central control module, an electroporation chamber that can be connected to a central control module by a 3-foot-long electrical cord, and a specialized pipette. In some cases, a specialized pipette can be fitted with exchangeable and/or disposable sterile tips. In some cases, an electroporation chamber can be fitted with exchangeable/disposable sterile electroporation cuvettes. In some cases, standard electroporation buffers supplied by a manufacturer of a system, such as a Neon system, can be replaced with GMP qualified solutions and buffers. In some cases, a standard electroporation buffer can be replaced with GMP grade phosphate buffered saline (PBS). A self-diagnostic system check can be performed on a control module prior to initiation of sample electroporation to ensure the Neon system is properly functioning. In some cases, a transfection can be performed in a class 1,000 biosafety cabinet within a class 10,000 clean room in a cGMP facility. In some cases, electroporation pulse voltage may be varied to optimize transfection efficiency and/or cell viability. In some cases, electroporation pulse width may be varied to optimize transfection efficiency and/or cell viability. In some cases, the number of electroporation pulses may be varied to optimize transfection efficiency and/or cell viability. In some cases, electroporation may comprise a single pulse. In some cases, electroporation may comprise more than one pulse. In some cases, electroporation may comprise 2 pulses, 3 pulses, 4 pulses, 5 pulses 6 pulses, 7 pulses, 8 pulses, 9 pulses, or 10 or more pulses.

In some aspects, protoplasts of fungi and/or plants may be used for electroporation transformation.

Microprojectile Bombardment

Another method for delivering transforming DNA segments to fungal cells and cells derived from other organisms in accordance with the invention is microprojectile bombardment. In this method, particles may be coated with nucleic acids and delivered into cells by a propelling force. Exemplary particles include those comprised of tungsten, platinum, and preferably, gold. It is contemplated that in some instances DNA precipitation onto metal particles would not be necessary for DNA delivery to a recipient cell using microprojectile bombardment. However, it is contemplated that particles may contain DNA rather than be coated with DNA. In some aspects, DNA-coated particles may increase the level of DNA delivery via particle bombardment. For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into fungal cells by acceleration is the Biolistics Particle Delivery System, which can be used to propel particles coated with DNA or cells through a screen, such as a stainless steel or Nytex screen, onto a filter surface covered with monocot plant cells cultured in suspension. The screen disperses the particles so that they are not delivered to the recipient cells in large aggregates.

Other Transformation Methods

Additional transformation methods include but are not limited to calcium phosphate precipitation, polyethylene glycol treatment, electroporation, and combinations of these treatments.

To transform fungi that cannot be successfully regenerated from protoplasts, other ways to introduce DNA into intact cells or tissues can be utilized. For example, regeneration of plants from immature embryos or explants can be affected as described. Also, silicon carbide fiber-mediated transformation may be used with or without protoplasting. Transformation with this technique can be accomplished by agitating silicon carbide fibers together with cells in a DNA solution. DNA passively enters as the cells are punctured.

In some cases, a starting cell density for genomic editing may be varied to optimize editing efficiency and/or cell viability. In some cases, the starting cell density for genomic editing may be less than about $1\times10^5$ cells. In some cases, the starting cell density for electroporation may be at least about $1\times10^5$ cells, at least about $2\times10^5$ cells, at least about $3\times10^5$ cells, at least about $4\times10^5$ cells, at least about $5\times10^5$ cells, at least about $6\times10^5$ cells, at least about $7\times10^5$ cells, at least about $8\times10^5$ cells, at least about $9\times10^5$ cells, at least about $1\times10^6$ cells, at least about $1.5\times10^6$ cells, at least about $2\times10^6$ cells, at least about $2.5\times10^6$ cells, at least about $3\times10^6$ cells, at least about $3.5\times10^6$ cells, at least about $4\times10^6$ cells, at least about $4.5\times10^6$ cells, at least about $5\times10^6$ cells, at least about $5.5\times10^6$ cells, at least about $6\times10^6$ cells, at least about $6.5\times10^6$ cells, at least about $7\times10^6$ cells, at least about $7.5\times10^6$ cells, at least about $8\times10^6$ cells, at least about $8.5\times10^6$ cells, at least about $9\times10^6$ cells, at least about $9.5\times10^6$ cells, at least about $1\times10^7$ cells, at least about $1.2\times10^7$ cells, at least about $1.4\times10^7$ cells, at least about $1.6\times10^7$ cells, at least about $1.8\times10^7$ cells, at least about $2\times10^7$ cells, at least about $2.2\times10^7$ cells, at least about $2.4\times10^7$ cells, at least about $2.6\times10^7$ cells, at least about $2.8\times10^7$ cells, at least about $3\times10^7$ cells, at least about $3.2\times10^7$ cells, at least about $3.4\times10^7$ cells, at least about $3.6\times10^7$ cells, at least about $3.8\times10^7$ cells, at least about $4\times10^7$ cells, at least about $4.2\times10^7$ cells, at least about $4.4\times10^7$ cells, at least about $4.6\times10^7$ cells, at least about $4.8\times10^7$ cells, or at least about $5\times10^7$ cells.

The efficiency of genomic disruption of plants or any part thereof, including but not limited to a cell, with any of the nucleic acid delivery platforms described herein, can result in disruption of a gene or portion thereof at about 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, 99.5%, 99.9%, or up to about 100% as measured by nucleic acid or protein analysis.

Organism Breeding

In some embodiments, fungi, yeast or plants of the present disclosure can be used to produce new plant varieties. In some embodiments, the plants are used to develop new, unique and superior varieties or hybrids with desired phenotypes. In some embodiments, selection methods, e.g., molecular marker assisted selection, can be combined with breeding methods to accelerate the process. In some embodiments, a method comprises (i) crossing any organism provided herein comprising the expression cassette as a donor to a recipient organism line to create a FI population; (ii) selecting offspring that have expression cassette. Optionally, the offspring can be further selected by testing the expression of the gene of interest. In some embodiments, complete chromosomes of a donor organism are transferred. For example, the transgenic organism with an expression cassette can serve as a male or female parent in a cross pollination to produce offsprings by receiving a transgene from a donor thereby generating offsprings having an expression cassette. In a method for producing organisms having the expression cassette, protoplast fusion can also be used for the transfer of the transgene from a donor to a recipient. Protoplast fusion is an induced or spontaneous union, such as a somatic hybridization, between two or more protoplasts (cells in which the cell walls are removed by enzymatic treatment) to produce a single bi- or multinucleate cell. The fused cell that may even be obtained with species that cannot be interbred in nature is tissue cultured into a hybrid organism exhibiting the desirable combination of traits. More specifically, a first protoplast can be obtained from an organism having the expression cassette. A second protoplast can be obtained from a second organism, optionally from another species or variety, or from the same species or variety, that comprises commercially desirable characteristics, such as, but not limited to disease resistance, insect resistance etc. The protoplasts are then fused using traditional protoplast fusion procedures, which are known in the art to produce the cross. Alternatively, embryo rescue may be employed in the transfer of the expression cassette from a donor to a recipient. Embryo rescue can be used as a procedure to isolate embryos and tissue culture the same.

In some cases, population improvement methods may be utilized. Population improvement methods fall naturally into two groups, those based on purely phenotypic selection, normally called mass selection, and those based on selection with progeny testing. Interpopulation improvement utilizes the concept of open breeding populations; allowing genes to flow from one population to another. Selection can be applied to improve one (or sometimes both) population(s) by isolating plants comprising desirable traits from both sources.

In another aspect, mass selection can be utilized. In mass selection, desirable individual plants are chosen, harvested, and the seed composited without progeny testing to produce the following generation. Since selection is based on the maternal parent only, and there is no control over pollination, mass selection amounts to a form of random mating with selection. As stated herein, the purpose of mass selection is to increase the proportion of superior genotypes m the population. While mass selection is sometimes used, progeny testing is generally preferred for poly crosses, because of their operational simplicity and obvious relevance to the objective, namely exploitation of general combining ability in a synthetic.

In some embodiments, breeding may utilize molecular markers. Molecular markers are designed and made, based on the genome of the plants of the present application. In some embodiments, the molecular markers are selected from Isozyme Electrophoresis, Restriction Fragment Length Polymorphisms (RFLPs), Randomly-Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs). Amplified Fragment Length Polymorphisms (AFLPs), and Simple Sequence Repeats (SSRs) which are also referred to as Microsatellites, etc. Methods of developing molecular markers and their applications are described by Avise (Molecular markers, natural history, and evolution, Publisher: Sinauer Associates, 2004, ISBN 0878930418, 9780878930418), Snvastava et al. (Plant biotechnology and molecular markers, Publisher: Springer, 2004, ISBN1402019114, 9781402019111), and Vienne (Molecular markers in plant genetics and biotechnology, Publisher: Science Publishers, 2003), each of winch is incorporated by reference in its entirety for all purposes. The molecular markers can be used in molecular marker assisted breeding. Provided herein can also be methods for generating transgenic fungi. In some aspects, methods provided herein can comprise (a) contacting a fungus cell with an endonuclease or a polypeptide encoding an endonuclease. In some cases, an endonuclease introduces a genetic modification in a genome of a fungal cell resulting in an increased amount of one of Formula I-IV, derivatives or analogs thereof, as compared to an amount of the same compound in a comparable control without a genetic modification. In some aspects, a method can further comprise culturing a fungal cell that has been genetically modified as previously described to generate a transgenic fungus. Methods of making transgenic fungi can include electroporation, *Agrobacterium* mediated transformation, biolistic particle bombardment, or protoplast transformation. In some aspects, a method can further comprise culturing a fungal cell to generate a fungus.

In some aspects, provided herein can also be a method for generating transgenic plants comprising contacting a plant cell with an endonuclease or a polypeptide encoding an endonuclease. An endonuclease can introduce a genetic modification resulting in an increased amount of a psilocybin, psilocin, or dimethyltryptamine (DMT), a derivative, or analogue thereof as compared to an amount of the same compound in a comparable control absent a genetic modification.

In some aspects, provided herein can also be a method for generating transgenic animals comprising contacting an animal cell with an endonuclease or a polypeptide encoding an endonuclease. An endonuclease can introduce a genetic modification resulting in an increased amount of a psilocybin, psilocin, or dimethyltryptamine (DMT), a derivative, or analogue thereof as compared to an amount of the same compound in a comparable control absent a genetic modification.

In some aspects, provided herein can also be a method for generating transgenic insects comprising contacting an insect cell with an endonuclease or a polypeptide encoding an endonuclease. An endonuclease can introduce a genetic modification resulting in an increased amount of a psilocybin, psilocin, or dimethyltryptamine (DMT), a derivative, or analogue thereof as compared to an amount of the same compound in a comparable control absent a genetic modification.

In some aspects, provided herein can also be a method for generating transgenic yeast comprising contacting a yeast cell with an endonuclease or a polypeptide encoding an endonuclease. An endonuclease can introduce a genetic modification resulting in an increased amount of a psilocybin, psilocin, or dimethyltryptamine (DMT), a derivative, or analogue thereof as compared to an amount of the same compound in a comparable control absent a genetic modification.

In some aspects, provided herein can also be a method for generating transgenic *E. coli* comprising contacting an *E. coli* cell with an endonuclease or a polypeptide encoding an endonuclease. An endonuclease can introduce a genetic modification resulting in an increased amount of a psilocybin, psilocin, or dimethyltryptamine (DMT), a derivative, or analogue thereof as compared to an amount of the same compound in a comparable control absent a genetic modification.

Methods comprising modifications of fungal cell genomes can result in: 5%, 10%, 15%, 20%, 25%, 30%, 35%, 40%, 45%, 50%, 55%, 60%, 65%, 70%, 75%, or up to about 80% more (Formula IV)

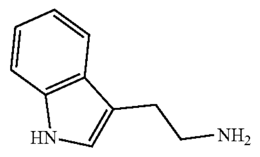

as measured by dry weight in a transgenic fungus as compared to a comparable control without a genomic modification. Further, methods comprising modifications can also result in from about 1%, 5%, 10%, 15%, 20%, 25%, 30%, 35%, 40%, 45%, 50%, 55%, 60%, 65%, 70%, 80%, 90%, 100%, or up to about 200% more (Formula I)

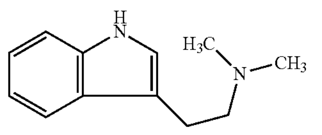

as measured by dry weight in a transgenic as compared to a comparable control without a modification. Moreover, methods comprising modifications can also result in from about 1%, 5%, 10%, 15%, 20%, 25%, 30%, 35%, 40%, 45%, 50%, 55%, 60%, 65%, 70%, 80%, 90%, 100%, or up to about 200% more psilocybin or psilocin as measured by dry weight in a transgenic as compared to a comparable control without a modification.

Provided herein can also be genetically modified cells comprising a disruption in a gene that results in an increased amount of a compound (Formula IV)

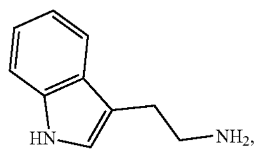

derivatives or analogs thereof, compared to an amount of the same compound in a comparable control cell without said genetic modification. Further, provided herein can also be genetically modified cells comprising a disruption in a gene that results in an increased amount of a compound (Formula I)

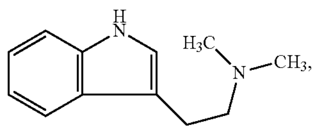

derivatives or analogs thereof, compared to an amount of the same compound in a comparable control cell without said genetic modification. In addition, provided herein can also be genetically modified cells comprising a disruption in a gene that results in an increased amount of psilocybin and/or psilocin, derivatives or analogs thereof, compared to an amount of the same compound in a comparable control cell without said genetic modification. Alternatively, the genetically modified cells are plant cells, fungal cells, bacterial cells, animal cells, or insect cells.

Additionally, provided herein can also be compositions comprising an endonuclease or polynucleotide encoding said endonuclease capable of introducing a genetic modification, wherein said genetic modification results in an increased amount of psilocybin or psilocin, their derivatives or analogs compared to a comparable control cell without said genetic modification.

Psilocybin Synthesis Genes Transgene Methods and Compositions

Provided herein can be methods of transforming mushrooms with Psilocybin synthesis genes. In some embodiments, the coding sequences of the 4 major Psilocybin Synthesis genes are synthesized and cloned into an overexpression vector system pGWB5 under the control of the 35S promoter. In some embodiments, additional vectors with different promoters driving expression of these genes are also produced (including Gpd, EF1a and Actin).

In some cases, Basidiomycete fungi are transformed using pGWB5 to test transformation efficiency and develop protocols. In some cases, transformations including the different Psi genes individually and in combination to observe potential for increase in psilocybin production. In some cases, an all-in-one expression vector of the four Psi genes in tandem within a polycistronic vector is generated and tested.

In some embodiments, propagation and growth of *Psilocybe cubensis* is enabled on different substrates to generate both mature fruiting mushrooms and mycelia. In some embodiments, tissue is extracted from the mushroom gills and is transformed of the Psi genes by *Agrobacterium*-mediated transformation. In some embodiments, protoplasts are generated from Mycelia and PEG-mediated transformation of the Psi genes, along with *Agrobacterium*-mediated transformation of the mycelia. In some embodiments, *Psilocybe cubensis* is grown in PDA agar or in a barley-perlite compost at room temperature for 7 days. In some cases, Mycelia and fruiting bodies are harvested for tissue extraction and cell isolation prior to transformation.

In some embodiments, Psi gene overexpression is under the control of two distinct promoter types, the 35S promoter, a widely used plant over-expression promoter, and two fungal specific over-expression promoters, GPD and CcDED1 (Table 4, FIGS. 3A-3D, FIGS. 4A-4B).

TABLE 4

Gene Expression Vectors

| Vector | Gene Promoter | Gene Inserted | Promoter characteristics |
| --- | --- | --- | --- |
| pGWB5 | 35S | PsiH/PsiD/PsiK/PsiH | Cauliflower mosaic virus 35S promoter |
| pGHGWY | GPD | PsiH/PsiD/PsiK/PsiH | Fungal specific promoters |
| pGHGWY | CcDED1 | PsiH/PsiD/PsiK/PsiH | Fungal specific promoters |

Figure 3B:
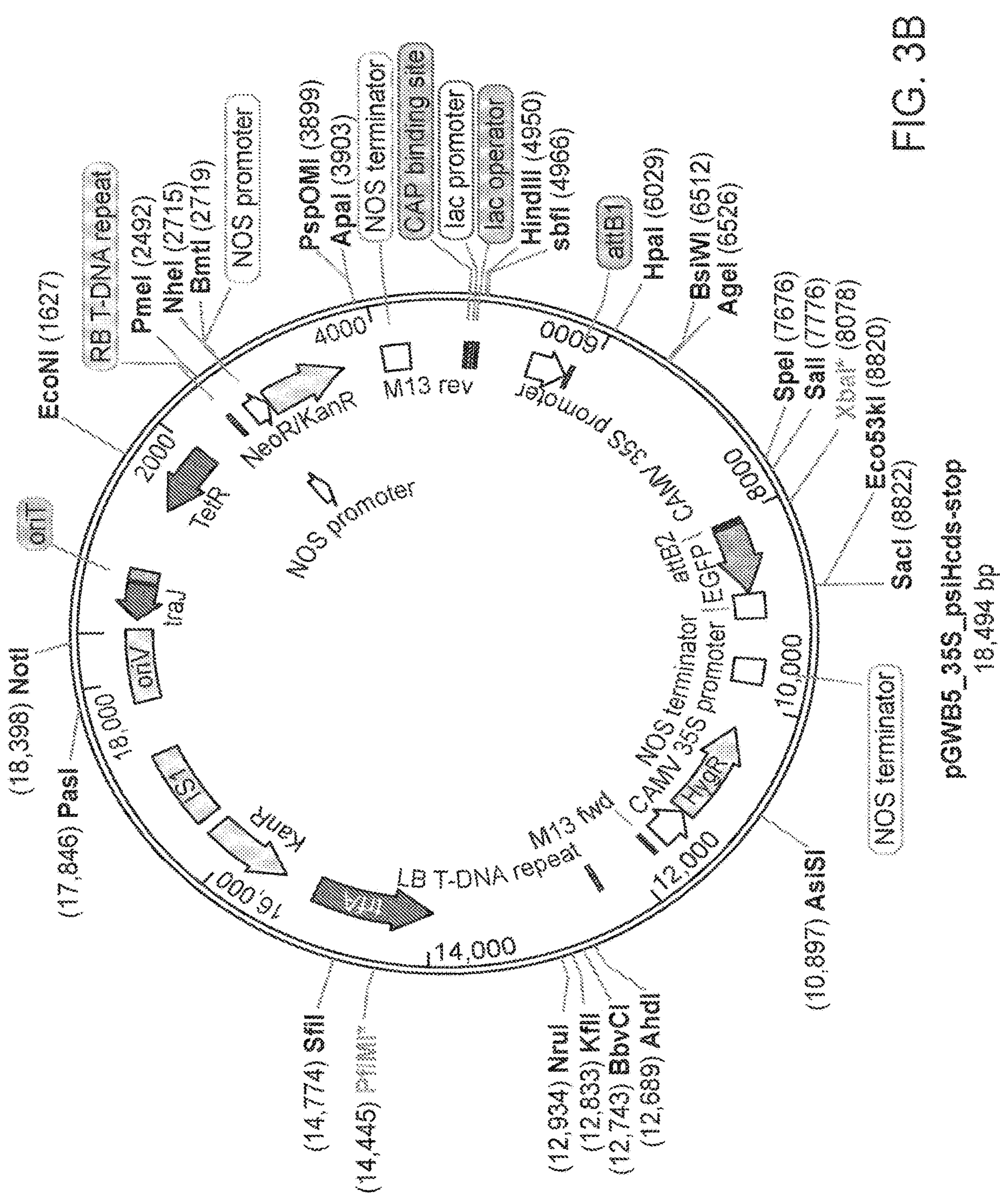
Figure 3C:
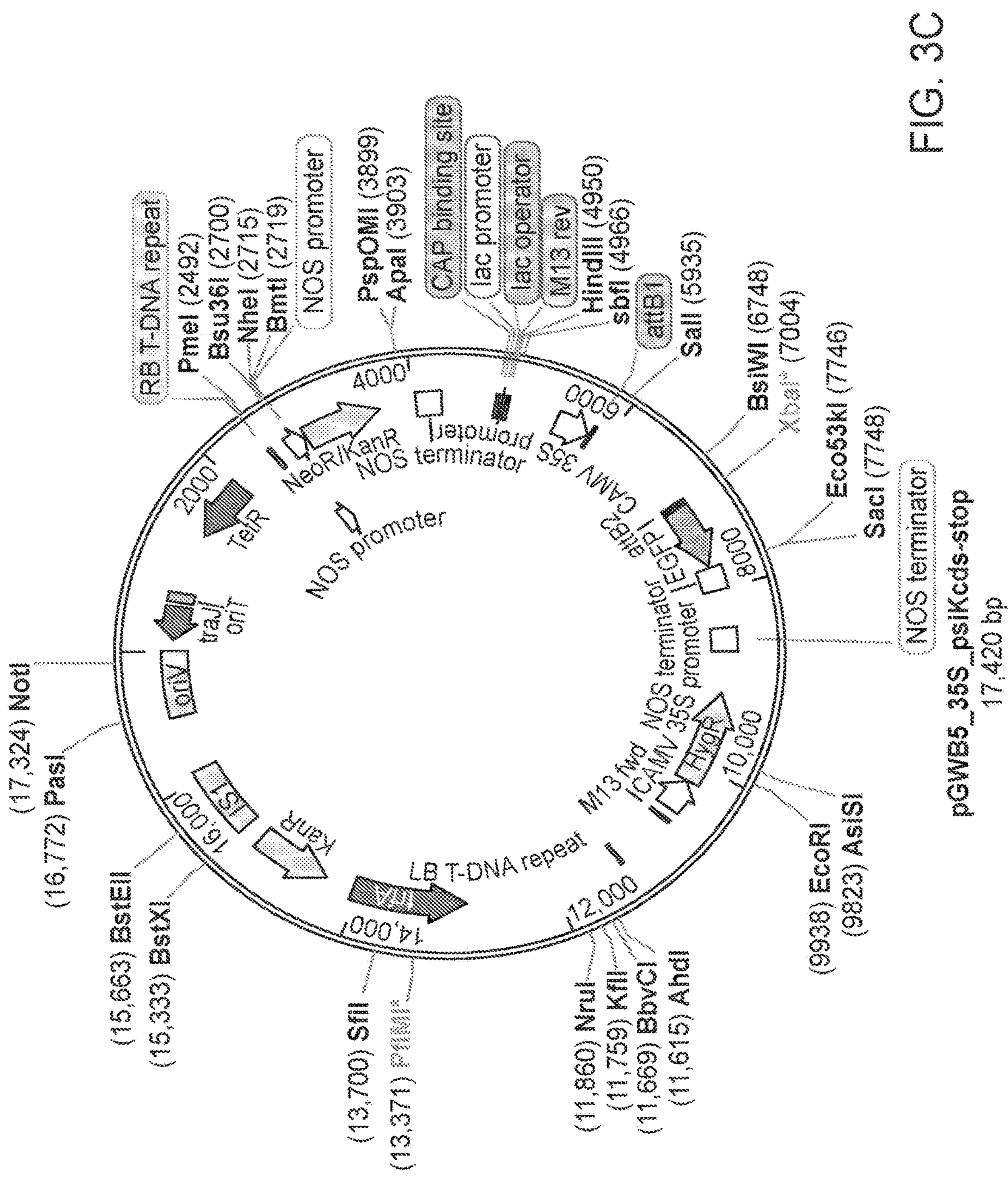
Figure 3D:
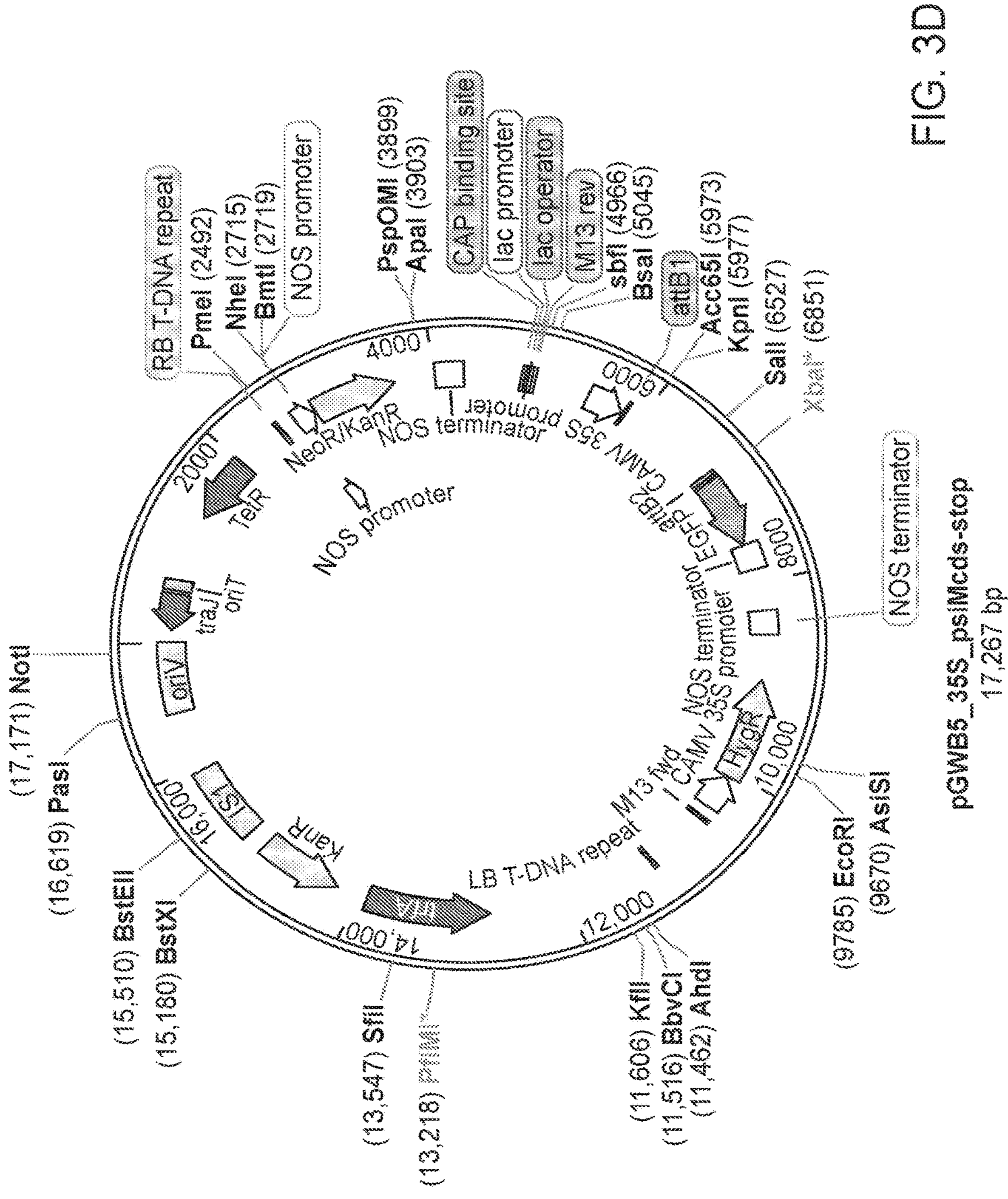

In some embodiments, PsiD gene over-expression comprises a vector expressing PsiD gene under the control of a 35S promoter (Table 5: SEQ ID NO: 18, 17,647 bp; FIG. 3A). In some embodiments, PsiH gene over-expression comprises a vector expressing PsiH gene under the control of a 35S promoter (Table 5: SEQ ID NO: 17, 18,494 bp; FIG. 3B). In some embodiments, PsiK gene over-expression comprises a vector expressing PsiK gene under the control of a 35S promoter (Table 5: SEQ ID NO: 16, 17,420 bp; FIG. 3C). In some embodiments, PsiM gene over-expression comprises a vector expressing PsiM gene under the control of a 35S promoter (Table 5: SEQ ID NO: 15, 17,267 bp; FIG. 3D).

Figure 4A:
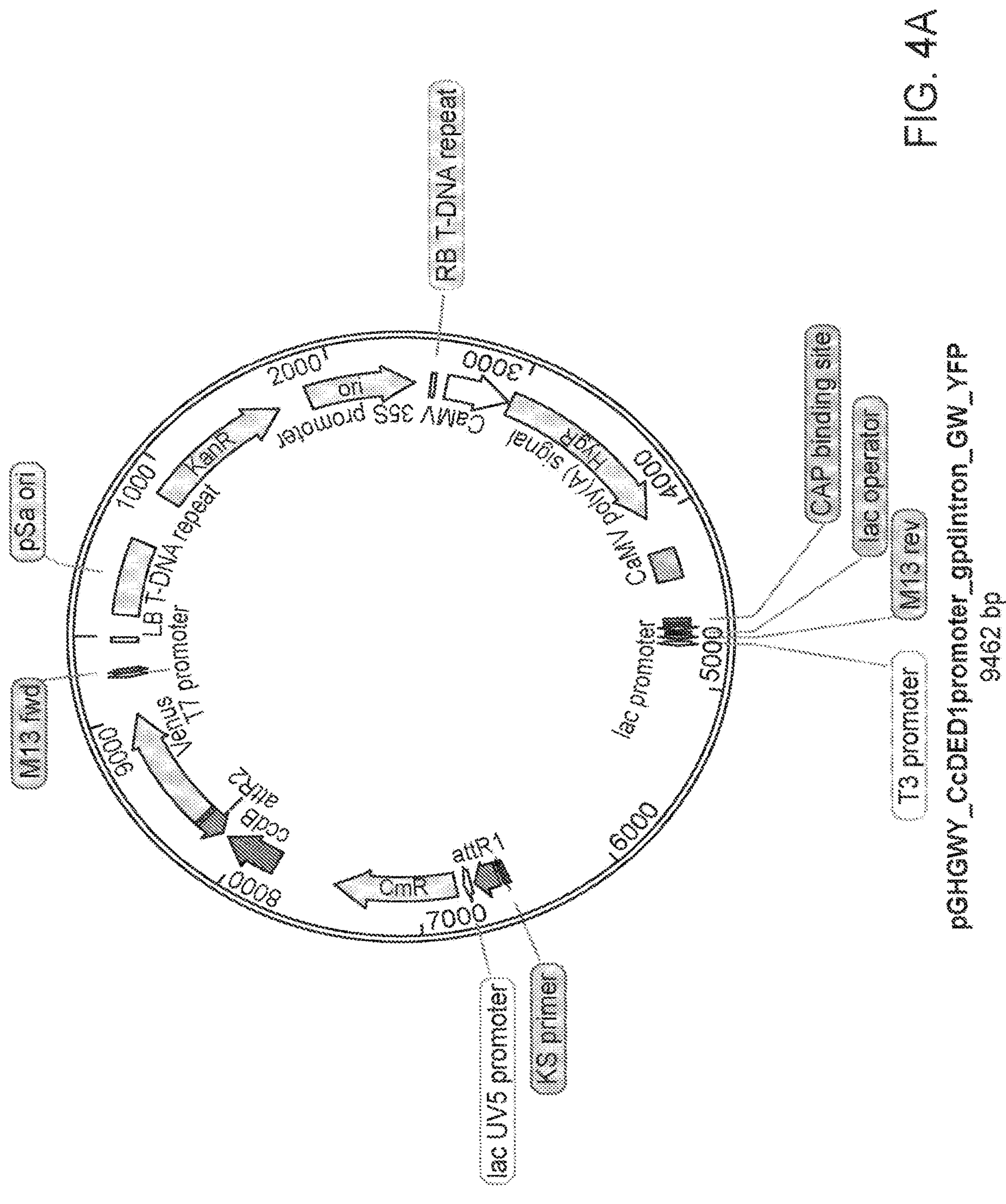
FIGS. 4A-4B illustrate representative vectors constructs for genetically modified organisms and cells described herein, over-expressing genes under the control of fungal specific over-expression promoters.
Figure 4B:
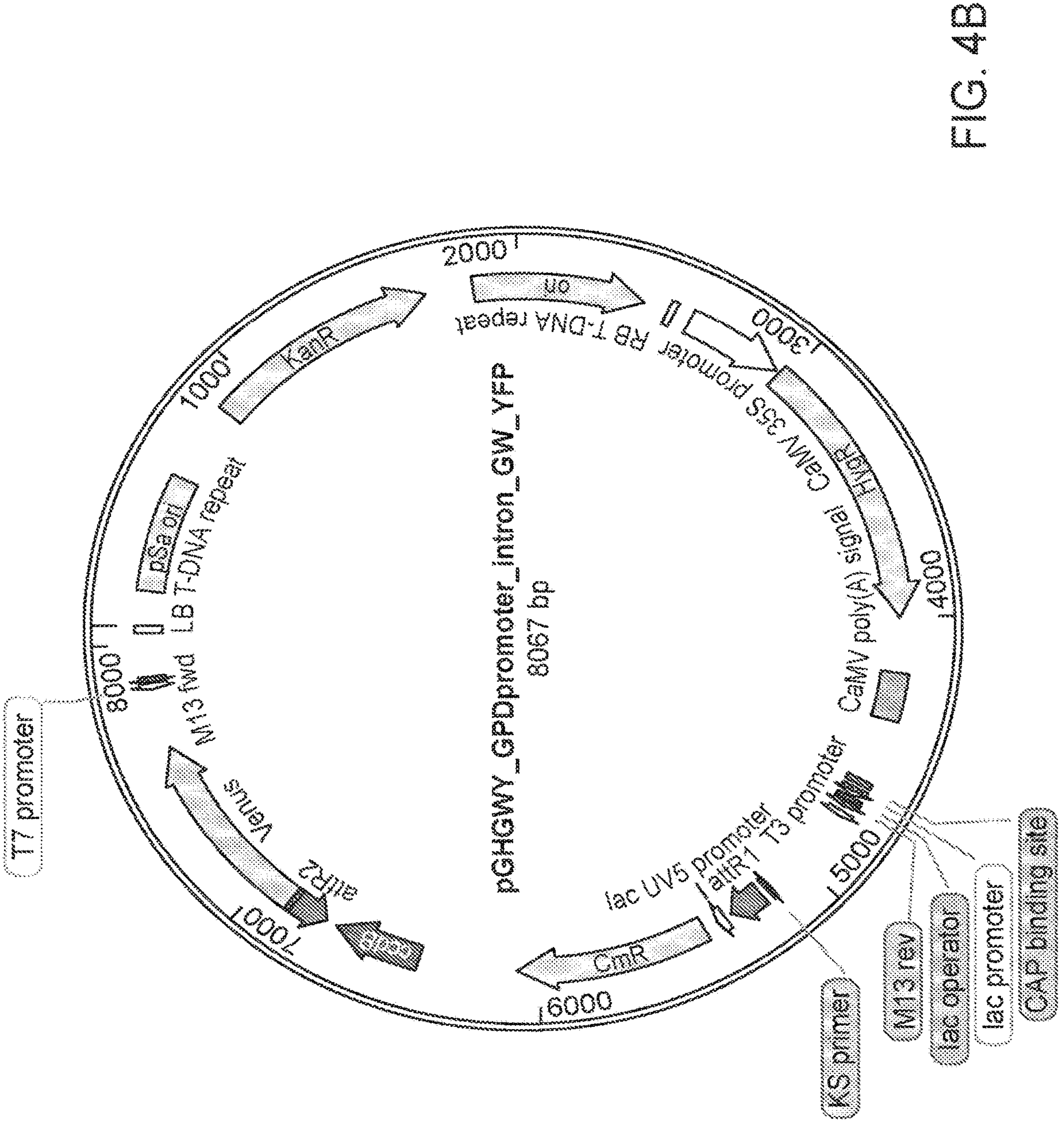

In some embodiments, Psi genes over-expression comprises a vector expressing Psi genes under the control of a GcDED1 promoter (Table 5: SEQ ID NO: 19, 9,462 bp; FIG. 4A). In some embodiments, Psi genes over-expression comprises a vector expressing Psi genes under the control of a GPD promoter (Table 5: SEQ ID NO: 20, 8,067 bp; FIG. 4B).

Pharmaceutical and Nutraceutical Compositions and Methods

Provided herein can be pharmaceutical or nutraceutical compositions comprising genetically modified cells, organisms, fungi or plants described herein or an extract, derivative or product thereof. Provided herein can also be pharmaceutical or nutraceutical reagents, methods of using the same, and method of making pharmaceutical or nutraceutical compositions comprising genetically modified cells, organisms, fungi or plants described herein or an extract or product thereof. Provided herein are also pharmaceutically and nutraceutical-suitable cells, organisms, or plants described herein or an extract, derivative or product thereof.

In some cases, a genetically modified cells, organisms, fungi or plants described herein or an extract or product thereof can be used as a pharmaceutical or nutraceutical agent. In some cases, a composition comprising such a pharmaceutical or nutraceutical agents can be used for treating or stabilizing conditions or symptoms associated with conditions such as depression, anxiety, post-traumatic stress, addiction or cessation related side-effects such as smoking cessation, and psychological distress including cancer-related psychological distress. Specifically genetically modified cells, organisms, fungi or plants described herein or an extract, derivative or product thereof can be used to alleviate various symptoms associated with mental disorders and conditions.

In some aspects, cells, organisms, or plants described herein or an extract or product thereof can be used to treat particular symptoms. For example, pain, nausea, weight loss, wasting, multiple sclerosis, allergies, infection, vasoconstrictor, depression, migraine, hypertension, post-stroke neuroprotection, as well as inhibition of tumor growth, inhibition of angiogenesis, and inhibition of metastasis, antioxidant, and neuroprotectant. In some aspects, cells, organisms, or plants described herein or an extract or product thereof can be used to treat additional symptoms. For instance, persistent muscle spasms, including those that are characteristic of multiple sclerosis, severe arthritis, peripheral neuropathy, intractable pain, migraines, terminal illness requiring end of life care, Hydrocephalus with intractable headaches, Intractable headache syndromes, neuropathic facial pain, shingles, chronic nonmalignant pain, causalgia, chronic inflammatory demyelinating polyneuropathy, bladder pain, myoclonus, post-concussion syndrome, residual limb pain, obstructive sleep apnea, traumatic brain injury (TBI), elevated intraocular pressure, opioids or opiates withdrawal, and/or appetite loss.

In some cases, cells, organisms, or plants described herein or an extract or product thereof may also comprise other pharmaceutically or nutraceutically relevant compounds and extracts, including flavonoids, monoamine oxidase inhibitors and phytosterols (e.g., apigenin, quercetin, cannflavin A, beta.-sitosterol and the like).

In some an extract or product thereof can be subject to methods comprising extractions that preserve the psilocybene, dimethyltryptamine or psilocene. The extracts of the present disclosure are designed to produce products for human or animal consumption via inhalation (via combustion, vaporization and nebulization), buccal absorption within the mouth, oral administration, and topical application delivery methods. The present disclosure teaches an optimized method at which we extract compounds of interest, by extracting at the point when the drying harvested plant or fungus has reached 5, 10, or 15% water weight. Stems are typically still 'cool' and 'rubbery' from evaporation taking place. This timeframe (or if frozen at this point in process) allow extractor to minimize active agent loss to evaporation. There is a direct correlation between cool/slow, -'dry and preservation of essential oils. Thus, there is a direct correlation to EO loss in flowers that dry too fast, or too hot conditions or simply dry out too much (<10% H20). The chemical extraction of cells, organisms, or plants described herein or an extract or product thereof can be accomplished employing polar and non-polar solvents in various phases at varying pressures and temperatures to selectively or comprehensively extract other compounds of flavor, fragrance or pharmacological value for use individually or combination in the formulation of products. The extractions can be shaped and formed into single or multiple dose packages, e.g., dabs, pellets and loads. The solvents employed for selective extraction of our cultivars may include water, carbon dioxide, 1,1,1,2-tetrafluoroethane, butane, propane, ethanol, isopropyl alcohol, hexane, and limonene, in combination or series. The extracts of the present disclosure may also be combined with pure compounds of interest to the extractions, e.g. cannabinoids or terpenes to further enhance or modify the resulting formulation's fragrance, flavor or pharmacology. In some embodiments, the extractions are supplemented with terpenes or cannabinoids to adjust for any loss of those compounds during extraction processes.

In some aspects, genetically modified organism, derivative or extracts of the present disclosure can be used for vaporization, production of e-juice or tincture for e-cigarettes, or for the production of other consumable products such as edibles, balms, or topical spreads. In an aspect, a modified composition provided herein can be used as a supplement, for example a food supplement. In some embodiments, the cells, organisms, or plants described herein or an extract or product thereof can be used to make edibles. Edible recipes can begin with the extraction of cannabinoids and terpenes, which are then used as an ingredient in various edible recipes. Extraction methods for edibles include extraction into cooking oil, milk, cream, balms, flour and butter. Lipid rich extraction mediums/edibles are believed to facilitate absorption into the blood stream. Lipids may be utilized as excipients in combination with the various compositions provided herein In other aspects, compositions provided herein can comprise: oral forms, a transdermal forms, an oil formulation, an edible food, or a food substrate, an aqueous dispersion, an emulsion, a solution, a suspension, an elixir, a gel, a syrup, an aerosol, a mist, a powder, a tablet, a lozenge, a gel, a lotion, a paste, a formulated stick, a balm, a cream, or an ointment.

Provided herein are also kits comprising compositions provided herein. Kits can include packaging, instructions, and various compositions provided herein. In some aspects, kits can also contain additional compositions used to generate the various plants and portions of plants provided herein such as pots, soil, fertilizers, water, and culturing tools.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

EXAMPLES

Example 1: Strategy of Overexpressing Psi Genes in *Psliocybe Cubensis*

Step 1. Build Psilocybin Pathway Expression Vectors.

Figure 5A:
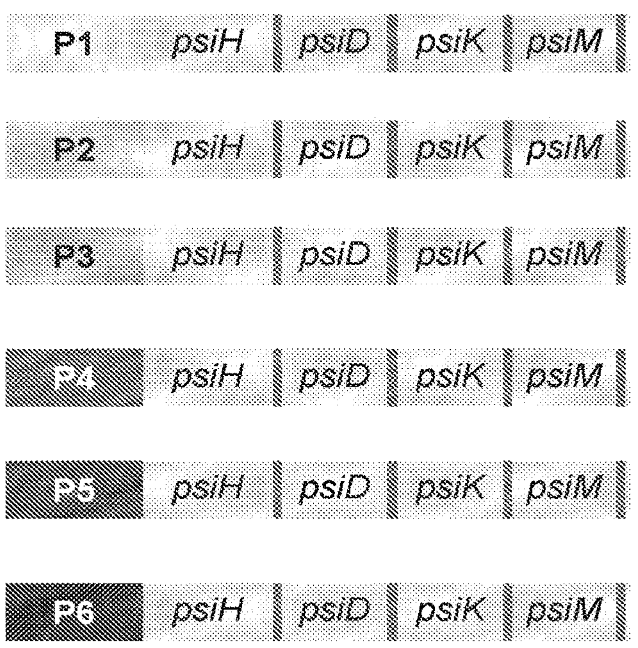
FIGS. 5A-5E illustrate strategy and workflow of Psi genes overexpression in *Psliocybe cubensis*.

Panel of expression vectors with different promoters of varying strengths are being constructed. Some promoters are mushroom specific while other promoters are from high expression plant systems etc. (FIG. 5A). Then *Agrobacterium* will be generated from these expression vectors.

Step 2. Prepare Mushroom Material for Transformation.

Figure 5B:
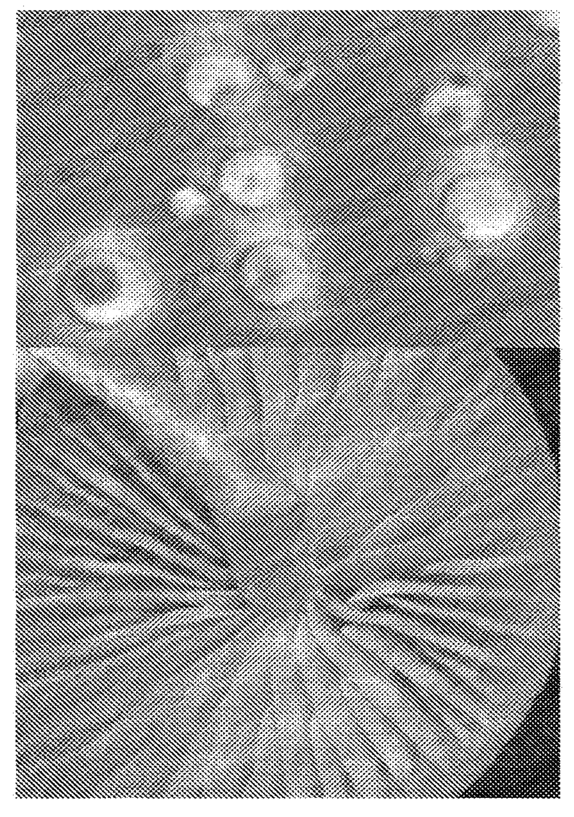

Protoplast, conidia, gill tissue and mycelium were isolated for transformation as illustrated in Examples 3-7. The selection of the appropriate protocol depends on the mushroom to be transformed. Here, protoplasts and extract gill tissue were isolated, as exemplified in Examples 3-5 and FIG. 5B. Protoplasts were extracted from mycelium as illustrated in Example 4. Methods for gill tissue transformation using *Agrobacterium* co-cultivation is illustrated in Example 6.

Step 3. Transformation.

Figure 5C:
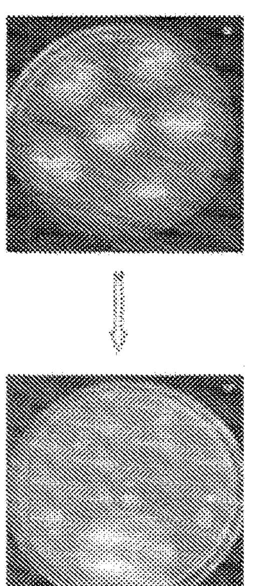

Cultured protoplasts from Step 2 was transfected with plasmid DNA from Step 1 using various protocols. See Examples 3-5. Additionally, gill tissue from Step 2 was transformed with *Agrobacterium* from Step 1 using various protocols. See Examples 6-7. Transformants with the plasmid DNA or *Agrobacterium* incorporation will be selected, as illustrated in FIG. 5C.

Step 4. Regeneration.

Figure 5D:
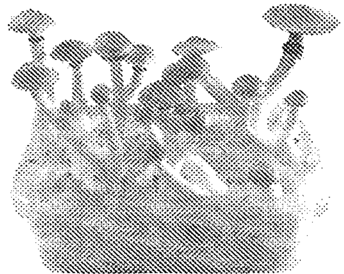

Adult mushrooms from transformants of Step 3 will be regenerated, as illustrated in FIG. 5D.

Step 5. Psilocybin Analysis.

Figure 5E:
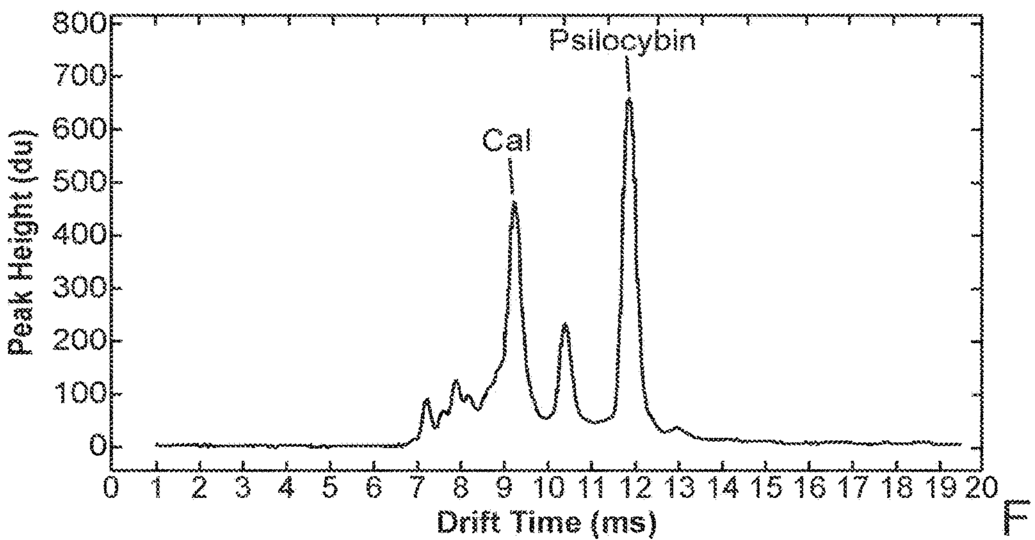

The psilocybin content of the genetically modified mushrooms will be analyzed by gas chromatography/mass spectrometry, as illustrated in FIG. 5E. Psilocybin accounts for 0.63% of dry weight in unmodified *P. Cubensis*. The goal of genetic engineering is to increase the amount of psilocybin to >6%.

Example 2: Vector Constructs Overexpressing Psi Genes

The coding sequences of the 4 major psilocybin synthesis genes (psiD/psiH/psiK/psiM) have been synthesized and cloned into an overexpression vector system (pGWB5) under the control of a 35S promoter. The 35S promoter is a widely used plant over-expression promoter. See Table 4. For example, PsiD gene was cloned into a vector expressing PsiD gene under the control of a 35S promoter (Table 5: SEQ ID NO: 18, 17,647 bp; FIG. 3A), PsiH gene was cloned into a vector expressing PsiH gene under the control of a 35S promoter (Table 5: SEQ ID NO: 17, 18,494 bp; FIG. 3B), PsiK gene was cloned into a vector expressing PsiK gene under the control of a 35S promoter (Table 5: SEQ ID NO: 16, 17,420 bp; FIG. 3C), PsiM gene was cloned into a vector expressing PsiM gene under the control of a 35S promoter (Table 5: SEQ ID NO: 15, 17,267 bp; FIG. 3D).

In addition, an all-in-one expression vector of the four Psi genes in tandem within a polycistronic vector has also been generated and is now being tested.

Other vectors with different promoters (including GPD, EF1a and Actin) were produced, and the 4 major psilocybin synthesis genes (psiD/psiH/psiK/psiM) will be cloned into these vectors. For example, GPD and CcDED1 promoters are two fungi specific over-expression promoters. See Table 4. Psi genes will be cloned into a vector expressing Psi genes under the control of a GcDED1 promoter (vector backbone Table 5: SEQ ID NO: 19, 9,462 bp; FIG. 4A), or cloned into a vector expressing Psi genes under the control of a GPD promoter (Table 5: SEQ ID NO: 20, 8,067 bp; FIG. 4B).

Example 3: Vector Mediated Transfection of Protoplasts: Protocol A

Material

*Pleurotus nebrodensis* strain was grown at 25° C. on PDSA medium (20% potato, 2% dextrose, 0.3% KH2PO4, 0.15% MgSO4, 0.0005% vitamin B1, 2% agar) and kept at 4° C.

Vegetative cultures of mycelia were conducted in PDSB medium (PDSA medium without agar) at 25° C. for 1 week.

Protoplast Extraction.

Collected 1 gr mycelum growing in PDSB medium for 7 days by infiltration through nylon mesh.

Washed in 0.6 M of MgSO4 for two times.

Resuspended in 3 ml of lysis buffer containing 1.5% lywallzyme (Guangdong Institute of Micro-biology) and 0.6 M MgSO4, then incubated at 32° C. for 2.5 h with gently shaking for protoplast release.

Protoplasts were purified by filtration through a glass injector with a layer of 1 mm of loose absorbent cotton and collected by centrifugation at 2000 gf or 20 min at 4° C.

Washed twice with 3 ml MM buffer containing 0.5 M mannitol and 50 mM maleic acid buffer (pH 5.5).

Resuspended in 2-3 ml of MMC buffer (0.5 M mannitol, 50 mM maleic acid buffer with pH 5.5, 5 mM CaCl2) to a concentration of $10^8$-$10^9$ protoplasts $ml^{-1}$.

Protoplast Transformation 3 ug of desired plasmid, 12.5 ul of PTC buffer (25% PEG4000, 10 mM Tris-HCl at pH 7.5, 25 mM CaCl2) were added to 50 ul of chilled protoplast suspension and mixed well.

Mixture was kept on ice for 20 min.

0.5 ml of PTC buffer was added to the mixture and mixed gently, followed by incubation for 5 min at room temperature.

Protoplast mixture was ready for plating on the regeneration and screening medium.

Protoplast Regeneration

The protoplast mixture was diluted with 1 ml STC buffer (18.2% sorbitol, 10 mM Tris-HCl at pH 7.5, 25 mM CaCl2) and plated on the regeneration medium (PDSA plus 1.0 M sorbitol) for 24 h at 25° C.

After regeneration culture for 24 h at 25° C., each plate was added with 20 ml screening medium (PDSA plus 0.8 M sorbitol, 80 ug/ml hygromycin B, 0.8% agar) and incubated at 25° C. in dark for 2 weeks.

Putative transformants appeared on the screening medium were subjected to a further five-round subculture on PDSA medium containing 80 ug/ml hygromycin B for screening of stable transformants. Some regenerating protoplast stops growing at 1-2 mm diameter. Only those that pass the 1-2 mm diameter size were transferred to further selection rounds.

The average transformation efficiency is about 3 transformants per microgram of plasmid pAN7-1 DNA.

DNA Extract and Analysis

Genomic DNA was isolated from mycelia of the putative stable transformants and non-transformed control of *P. nebrodensis* by the fungal DNA extraction (FDE) method. One gram of mycelium was crushed in liquid nitrogen to powder and digested in 10 ml TESN buffer (50 mM Tris-HCl at pH 7.5, 100 mM EDTA at pH 8.0, 0.5% SDS, 300 mM NaOAc at pH 5.2) at 68° C. for 1 h. After the addition of 3.5 ml 3 M NaOAc (pH 5.2) and incubation on ice for 20 min, the digestion mixture was centrifuged at 8000 g for 20 min at 4° C. The DNA in supernatant was extracted by phenol/chloroform extraction method.

Example 4: Vector Mediated Transfection of Protoplasts: Protocol B

Protoplast Extraction and Collection:

Step 1: Small blocks of monokaryon mycelium were inoculated into CYM medium (1% maltose, 2% glucose, 0.2% yeast extract, 0.2% tryptone, 0.05% MgSO47H2O, 0.46% KH2PO4) and allowed to grow for 5 days at 25° C. with shaking at 230 rpm.

Step 2: Mycelia were harvested by centrifugation, washed twice with 0.7 M NaCl, and treated with enzyme solution (50 mg/ml lysing enzymes from *Trichoderma harzianum* [Sigma-Aldrich] in 1 M MgSO4 and 0.6 M phosphate buffer, pH 6.0) at 25° C. for 2.0 to 2.5 h.

Step 3: After incubation, protoplasts were separated from hyphal debris by filtration through a sterile Miracloth and collected by centrifugation at 3,000×g for 10 min.

Step 4: Protoplasts were washed twice with 1 M sorbitol, and the protoplast density was adjusted to 108/ml with the same.

PEG-Mediated Transformation:

Step 1: Fifty microliters of protoplasts (108/ml) was mixed with 10 μg of each plasmid DNA and 12.5 μl of PEG solution (40% PEG 4000, 10 mM Tris-HCl, pH 8.0, 25 mM $CaCl_2$; filter sterilized).

Step 2: Protoplasts were incubated on ice for 20 min.

Step 3: Five hundred microliters of PEG solution was added, gently mixed, and incubated for 5 min at room temperature.

Step 4: One millilitre of ice-cold STC buffer (1 M sorbitol, 10 mM Tris-HCl, pH 8.0, 25 mM $CaCl_2$) was added, and the mixture was then spread on plates containing 20 ml PDAS regeneration agar medium (PDA plus 0.6 M sucrose, pH 6.5).

Step 5: Plates were incubated at 25° C. for 48 h, and then 5 ml of PDAS medium containing 600 μg/ml hygromycin B (Duchefa, The Netherlands), 600 μg/ml phleomycin (Invitrogen), or 60 μg/ml carboxin (Duchefa, The Netherlands) was added as an overlay, and plates were further incubated at 25° C. until the transformants appeared (5 to 7 days).

Protoplast Regeneration:

Step 1: Transformants were individually subcultured onto fresh PDA plates containing 50 μg/ml hygromycin, 50 μg/ml phleomycin, or 5 μg/ml carboxin.

Step 2: Mature fruiting bodies of *Psilocybe cubensis* were obtained following cultivation on MMP medium (1% malt extract, 0.5% mycological peptone, 1.5% agar) at 25° C. for 20 to 22 days with the respective selection agent.

Example 5: *Agrobacterium* Mediated Transformation of Protoplast

Material: Gill Tissue

The veil was cut from the fruiting body of *P. eryngii* and the exposed gill tissue was aseptically excised and sectioned into 1.0×0.5 cm pieces.

*Agrobacterium* Preparation

GV3101 carrying plasmid vector of interest was grown in 50 ml LB medium supplemented with kanamycin (50 μg/ml) at 28° C. for 2 days to an optical density at 600 nm of 1.6. Bacteria was collected by centrifugation for 30 min at 4,000 g and then washed once with 50 ml washing solution containing 100 mM MgCl2 and 100 μM acetosyringone. After centrifugation at 4,000 g for another 30 min, the pellet of bacteria was resuspended in washing solution to an optical density at 600 nm of 1.0.

Transformation (This dark culture method is highly effective for growing mycelium and eliminating *Agrobacterium*).

These pieces (from ##) were vacuum infiltrated in the *Agrobacterium* suspension culture two times for 10 min.

The evacuated tissues were washed with triple distilled water and dried on sterile Whatman filter paper under aseptic condition for 10 min.

The tissues were then transferred to a sterile Petri dish without medium and incubated for 7-14 days in the dark at 25° C.

For selection, the dark-cultured active tissues were transferred to PDA (Potato dextrose agar) medium (20% potato extract, 2% dextrose, and 1.5% Agar) containing 50 μg/ml hygromycin and 100 μg/ml cefotaxime and cultured for 2-3 weeks in the dark at 25° C.

Putative transformants will then be sub-cultured onto PDA medium at 25° C. for 1 week in the dark. Finally, the mycelia will be cultured on liquid medium containing PDB (PDA without agar) for 2 weeks in a shaking incubator at 25° C. and 130 g.

Mycelia will then be separated by filtration through Whatman filter paper and used for further processing.

DNA extraction: Mycelia will be collected from putative transgenic and untransformed mushrooms and grounded in liquid nitrogen using a pre-chilled mortar and pestle. DNA will be isolated from mycelia following the cetyl-trimethyl-ammonium bro-mide (CTAB).

Example 6: *Agrobacterium* Mediated Transformation of Mycelium

*Psilocybe cubensis* mycelia was routinely maintained on potato dextrose agar (PDA) at 25° C. Mature fruiting bodies of *Psilocybe cubensis* were obtained following cultivation on MMP medium (1% malt extract, 0.5% mycological peptone, 1.5% agar) at 25° C. for 20 to 22 days.

*A. tumefaciens* strains AGL1 containing the desired expression vector were grown for 24 h in LB medium supplemented with appropriate antibiotics.

Bacterial cultures were subsequently diluted to an optical density at 660 nm of 0.15 with *Agrobacterium* induction medium (AIM) (Induction medium (IM) [MM containing 0.5% (w/v) glycerol, 0.2 mM acetosyringone (AS), 40 mM 2-(N-morpholino)ethanesulfonicacid (MES), pH 5.3]) in the presence of 200 μM acetosyringone and grown for an additional 5 to 6 h.

5-day-old *Psilocybe cubensis* mycelia obtained from general-purpose growth medium were homogenized using an Ultra-Turrax homogenizer, and hyphal fragments were transferred to fresh general-purpose growth medium and grown for 24 h to give a uniform mycelial slurry.

A 100-μl mycelial suspension was mixed with 100 μl of bacterial culture and then spread on cellophane discs, overlaid on AIM agar plates, and incubated at 25° C. for 48 h.

After cocultivation, cellophane discs were transferred to PDA medium containing 200 μg/ml Timentine to kill residual *Agrobacterium* cells and 100 μg/ml hygromycin to select fungal transformants.

These were incubated at 25° C. until the hygromycin-resistant colonies appeared. Individual colonies were subsequently transferred to PDA medium containing 50 μg/ml hygromycin.

Mature fruiting bodies of *Psilocybe cubensis* were obtained following cultivation on MMP medium (1% malt extract, 0.5% mycological peptone, 1.5% agar) at 25° C. for 20 to 22 days with the respective selection agent.

Example 7: *Agrobacterium* Mediated Transformation of Fruiting Body

*P. cubensis* was routinely maintained on potato dextrose agar (PDA) at 25° C. Mature fruiting bodies of *P. cubensis* were obtained following cultivation on MMP medium (1% malt extract, 0.5% mycological peptone, 1.5% agar) at 25° C. for 20 to 22 days.

*A. tumefaciens* strains AGL-1 containing desired expression vector were grown for 24 h in LB medium supplemented with appropriate antibiotics Bacterial cultures were subsequently diluted to an optical density at 660 nm of 0.15 with *Agrobacterium* induction medium (AIM) in the presence of 200 μM acetosyringone and grown for an additional 5 to 6 h.

Mature fruiting bodies (mature but before gill exposure) were excised from MMP plates using a scalpel and diced into small sections.

Fruiting body gill tissue pieces were mixed with induced *A. tumefaciens* culture and vacuum infiltrated until no more air bubbles emerged.

The infiltrated gill pieces were transferred to cellulose discs overlaid on AIM agar plates. Cocultivation and selection of transformants were carried out as described in Example 6.

After cocultivation, cellophane discs were transferred to PDA medium containing 200 μg/ml Timentine to kill residual *Agrobacterium* cells and 100 μg/ml hygromycin to select fungal transformants.

These were incubated at 25° C. until the hygromycin-resistant colonies appeared. Individual colonies were subsequently transferred to PDA medium containing 50 μg/ml hygromycin.

Mature fruiting bodies of *P. cubensis* were obtained following cultivation on MMP medium (1% malt extract, 0.5% mycological peptone, 1.5% agar) at 25° C. for 20 to 22 days with the respective selection agent.

Example 8: Transformation, Transfection, and Regeneration

Figure 6A:
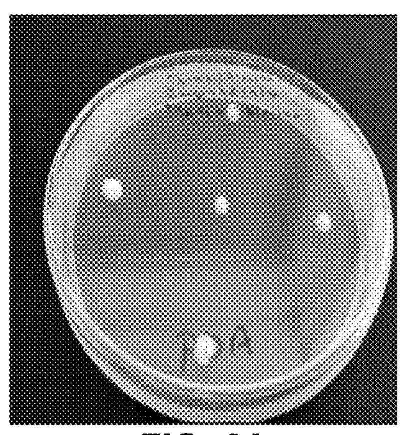
FIGS. 6A-6C show growing *Psilocybe cubensis* for tissue extraction and transformation: *Psilocybe cubensis* was grown in PDA agar (FIG. 6A and FIG. 6B) and also in a barley-perlite compost (FIG. 6C) at room temperature for 7 days.
Figure 6B:
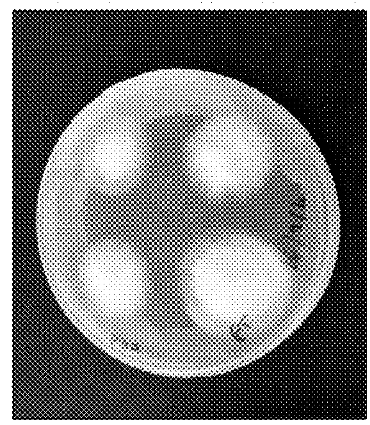
Figure 6C:
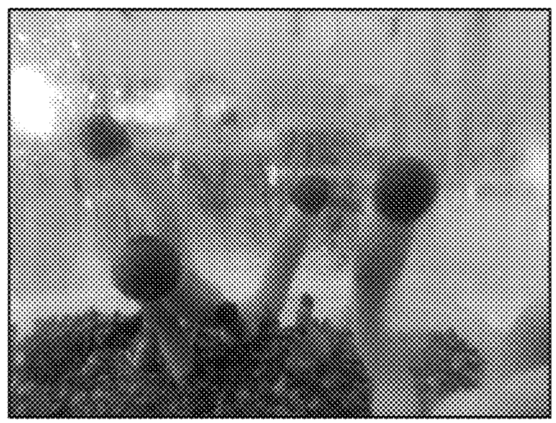

*Psilocybe cubensis* was propagated and grown on different substrates to generate both mature fruiting mushrooms and mycelia, as shown in FIGS. 6A-6C. *Psilocybe cubensis* was grown in PDA agar (FIG. 6A and FIG. 6B) and also in a barley-perlite compost (FIG. 6C) at room temperature for 7 days.

Basidiomycete fungi are transformed using pGWB5 vectors described in Example 2, with transformation or transfection protocol described through Example 3-7. Transformations include the different Psi genes individually and in combination (using multiple different vectors, or a vector with multiple Psi genes).

For example, tissue was extracted from the mushroom gills and was transformed of the Psi genes by *Agrobacterium*-mediated transformation described in Example 3-7.

Protoplasts were generated from mycelia and transformed of the Psi genes with PEG-mediated transfection. Mycelia were transformed with *Agrobacterium*-mediated transformation.

After regeneration of multiple transformed fungi, polynucleotide analysis will be performed to confirm gene integration and to determine RNA expression levels. In addition, mRNA and protein levels of the disrupted gene will be determined. The content of one or more bioactive metabolites, such as terpenes or cannabinoids in plant tissues will also be determined. For example, the content of one or more of psilocybin and/or psilocin will be determined with procedures known to a person with an ordinary skill in the art.

TABLE 5

Psilocybin Expression Vector Sequences.

| SEQ ID NO | Name | Sequence |
|---|---|---|
| 15 | pGWB5: 35S: PsiMcds: stop | tgagcgtcgcaaaggcgctcggtcttgcct<br>tgctcgtcggtgatgtacttcaccagctcc<br>gcgaagtcgctcttcttgatggagcgcatg<br>gggacgtgcttggcaatcacgcgcaccccc<br>cggccgttttagcggctaaaaaagtcatgg<br>ctctgccctcgggcggaccacgcccatcat<br>gaccttgccaagctcgtcctgcttctcttc<br>gatcttcgccagcagggcgaggatcgtggc<br>atcaccgaaccgcgccgtgcgcgggtcgtc<br>ggtgagccagagtttcagcaggccgcccag<br>gcggcccaggtcgccattgatgcgggccag<br>ctcgcggacgtgctcatagtccacgacgcc<br>cgtgattttgtagccctggccgacggccag<br>caggtaggccgacaggctcatgccggccgc<br>cgccgcctttttcctcaatcgctcttcgttc<br>gtctggaaggcagtacaccttgataggtgg<br>gctgcccttcctggttggcttggtttcatc<br>agccatccgcttgccctcatctgttacgcc<br>ggcggtagccggccagcctcgcagagcagg<br>attcccgttgagcaccgccaggtgcgaata<br>agggacagtgaagaaggaacacccgctcgc<br>gggtgggcctacttcacctatcctgcccgg<br>ctgacgccgttggatacaccaaggaaagtc<br>tacacgaaccctttggcaaaatcctgtata<br>tcgtgcgaaaaaggatggatataccgaaaa<br>aatcgctataatgaccccgaagcagggtta<br>tgcagcggaaaagcgccacgcttcccgaag<br>ggagaaaggcggacaggtatccggtaagcg<br>gcagggtcggaacaggagagcgcacgaggg<br>agcttccagggggaaacgcctggtatcttt<br>atagtcctgtcgggtttcgccacctctgac<br>ttgagcgtcgatttttgtgatgctcgtcag<br>gggggcggagcctatggaaaaacgccagca<br>acgcggcctttttacggttcctggcctttt<br>gctggccttttgctcacatgttctttcctg<br>cgttatcccctgattctgtggataaccgta<br>ttaccgcctttgagtgagctgataccgctc<br>gccgcagccgaacgaccgagcgcagcgagt<br>cagtgagcgaggaagcggaagagcgccaga<br>aggccgccagagaggccgagcgcggccgtg<br>aggcttggacgctagggcagggcatgaaaa<br>agcccgtagcgggctgctacgggcgtctga<br>cgcggtggaaagggggaggggatgttgtct<br>acatggctctgctgtagtgagtgggttgcg<br>ctccggcagcggtcctgatcaatcgtcacc<br>ctttctcggtccttcaacgttcctgacaac<br>gagcctccttttcgccaatccatcgacaat<br>caccgcgagtccctgctcgaacgctgcgtc<br>cggaccggcttcgtcgaaggcgtctatcgc<br>ggcccgcaacagcggcgagagcggagcctg<br>ttcaacggtgccgccgcgctcgccggcatc<br>gctgtcgccggcctgctcctcaagcacggc<br>cccaacagtgaagtagctgattgtcatcag<br>cgcattgacggcgtccccggccgaaaaacc<br>cgcctcgcagaggaagcgaagctgcgcgtc<br>ggccgtttccatctgcggtgcgcccggtcg<br>cgtgccggcatggatgcgcgcgccatcgcg<br>gtaggcgagcagcgcctgcctgaagctgcg<br>ggcattcccgatcagaaatgagcgccagtc<br>gtcgtcggctctcggcaccgaatgcgtatg<br>attctccgccagcatggcttcggccagtgc<br>gtcgagcagcgcccgcttgttcctgaagtg<br>ccagtaaagcgccggctgctgaaccccca |

TABLE 5-continued

Psilocybin Expression Vector Sequences.

| SEQ ID NO | Name | Sequence |
|---|---|---|
| | | ccgttccgccagtttgcgtgtcgtcagacc |
| | | gtctacgccgacctcgttcaacaggtccag |
| | | ggcggcacggatcactgtattcggctgcaa |
| | | ctttgtcatgcttgacactttatcactgat |
| | | aaacataatatgtccaccaacttatcagtg |
| | | ataaagaatccgcgcgttcaatcggaccag |
| | | cggaggctggtccggaggccagacgtgaaa |
| | | cccaacatacccctgatcgtaattctgagc |
| | | actgtcgcgctcgacgctgtcggcatcggc |
| | | ctgattatgccggtgctgccgggcctcctg |
| | | cgcgatctggttcactcgaacgacgtcacc |
| | | gcccactatggcattctgctggcgctgtat |
| | | gcgttggtgcaatttgcctgcgcacctgtg |
| | | ctgggcgcgctgtcggatcgtttcgggcgg |
| | | cggccaatcttgctcgtctcgctggccggc |
| | | gccagatctggggaaccctgtggttggcat |
| | | gcacatacaaatggacgaacggataaacct |
| | | tttcacgcccttttaaatatccgattattc |
| | | taataaacgctcttttctcttaggtttacc |
| | | cgccaatatatcctgtcaaacactgatagt |
| | | ttaaactgaaggcgggaaacgacaatctga |
| | | tcatgagcggagaattaagggagtcacgtt |
| | | atgacccccgccgatgacgcgggacaagcc |
| | | gttttacgtttggaactgacagaaccgcaa |
| | | cgttgaaggagccactcagccgcgggtttc |
| | | tggagtttaatgagctaagcacatacgtca |
| | | gaaaccattattgcgcgttcaaaagtcgcc |
| | | taaggtcactatcagctagcaaatatttct |
| | | tgtcaaaaatgctccactgacgttccataa |
| | | attcccctcggtatccaattagagtctcat |
| | | attcactctcaatccaaataatctgcaccg |
| | | gatctggatcgtttcgcatgattgaacaag |
| | | atggattgcacgcaggttctccggccgctt |
| | | gggtggagaggctattcggctatgactggg |
| | | cacaacagacaatcggctgctctgatgccg |
| | | ccgtgttccggctgtcagcgcaggggcgcc |
| | | cggttctttttgtcaagaccgacctgtccg |
| | | gtgccctgaatgaactgcaggacgaggcag |
| | | cgcggctatcgtggctggccacgacgggcg |
| | | ttccttgcgcagctgtgctcgacgttgtca |
| | | ctgaagcgggaagggactggctgctattgg |
| | | gcgaagtgccggggcaggatctcctgtcat |
| | | ctcaccttgctcctgccgagaaagtatcca |
| | | tcatggctgatgcaatgcggcggctgcata |
| | | cgcttgatccggctacctgcccattcgacc |
| | | accaagcgaaacatcgcatcgagcgagcac |
| | | gtactcggatggaagccggtcttgtcgatc |
| | | aggatgatctggacgaagagcatcaggggc |
| | | tcgcgccagccgaactgttcgccaggctca |
| | | aggcgcgcatgcccgacggcgatgatctcg |
| | | tcgtgacccatggcgatgcctgcttgccga |
| | | atatcatggtggaaaatggccgcttttctg |
| | | gattcatcgactgtggccggctgggtgtgg |
| | | cggaccgctatcaggacatagcgttggcta |
| | | cccgtgatattgctgaagagcttggcggcg |
| | | aatgggctgaccgcttcctcgtgctttacg |
| | | gtatcgccgctcccgattcgcagcgcatcg |
| | | ccttctatcgccttcttgacgagttcttct |
| | | gagcgggactctggggttcgaaatgaccga |
| | | ccaagcgacgcccaacctgccatcacgaga |
| | | tttcgattccaccgccgccttctatgaaag |
| | | gttgggcttcggaatcgttttccgggacgc |
| | | cggctggatgatcctccagcgcggggatct |
| | | catgctggagttcttcgcccacgggatctc |
| | | tgcggaacaggcggtcgaaggtgccgatat |
| | | cattacgacagcaacggccgacaagcacaa |
| | | cgccacgatcctgagcgacaatatgatcgg |
| | | gcccggcgtccacatcaacggcgtcggcgg |
| | | cgactgcccaggcaagaccgagatgcaccg |
| | | cgatatcttgctgcgttcggatattttcgt |
| | | ggagttcccgccacagacccggatgatccc |
| | | cgatcgttcaaacatttggcaataaagttt |
| | | cttaagattgaatcctgttgccggtcttgc |
| | | gatgattatcatataatttctgttgaatta |

TABLE 5-continued

Psilocybin Expression Vector Sequences.

| SEQ ID NO | Name | Sequence |
|---|---|---|
| | | cgttaagcatgtaataattaacatgtaatg |
| | | catgacgttatttatgagatgggtttttat |
| | | gattagagtcccgcaattatacatttaata |
| | | cgcgatagaaaacaaaatatagcgcgcaaa |
| | | ctaggataaattatcgcgcgcggtgtcatc |
| | | tatgttactagatcgggcctcctgtcaatg |
| | | ctggcggcggctctggtggtggttctggtg |
| | | gcggctctgagggtggtggctctgagggtg |
| | | gcggttctgagggtggcggctctgagggag |
| | | gcggttccggtggtggctctggttccggtg |
| | | attttgattatgaaaagatggcaaacgcta |
| | | ataagggggctatgaccgaaaatgccgatg |
| | | aaaacgcgctacagtctgacgctaaaggca |
| | | aacttgattctgtcgctactgattacggtg |
| | | ctgctatcgatggtttcattggtgacgttt |
| | | ccggccttgctaatggtaatggtgctactg |
| | | gtgattttgctggctctaattcccaaatgg |
| | | ctcaagtcggtgacggtgataattcacctt |
| | | taatgaataatttccgtcaatatttacctt |
| | | ccctccctcaatcggttgaatgtcgccctt |
| | | ttgtctttggcccaatacgcaaaccgcctc |
| | | tccccgcgcgttggccgattcattaatgca |
| | | gctggcacgacaggtttcccgactggaaag |
| | | cgggcagtgagcgcaacgcaattaatgtga |
| | | gttagctcactcattaggcaccccaggctt |
| | | tacactttatgcttccggctcgtatgttgt |
| | | gtggaattgtgagcggataacaatttcaca |
| | | caggaaacagctatgaccatgattacgcca |
| | | agcttgcatgcctgcaggtccccagattag |
| | | ccttttcaatttcagaaagaatgctaaccc |
| | | acagatggttagagaggcttacgcagcagg |
| | | tctcatcaagacgatctacccgagcaataa |
| | | tctccaggaaatcaaataccttcccaagaa |
| | | ggttaaagatgcagtcaaaagattcaggac |
| | | taactgcatcaagaacacagagaaagatat |
| | | atttctcaagatcagaagtactattccagt |
| | | atggacgattcaaggcttgcttcacaaacc |
| | | aaggcaagtaatagagattggagtctctaa |
| | | aaaggtagttcccactgaatcaaaggccat |
| | | ggagtcaaagattcaaatagaggacctaac |
| | | agaactcgccgtaaagactggcgaacagtt |
| | | catacagagtctcttacgactcaatgacaa |
| | | gaagaaaatcttcgtcaacatggtggagca |
| | | cgacacacttgtctactccaaaaatatcaa |
| | | agatacagtctcagaagaccaaagggcaat |
| | | tgagacttttcaacaaagggtaatatccgg |
| | | aaacctcctcggattccattgcccagctat |
| | | ctgtcactttattgtgaagatagtggaaaa |
| | | ggaaggtggctcctacaaatgccatcattg |
| | | cgataaaggaaaggccatcgttgaagatgc |
| | | ctctgccgacagtggtcccaaagatggacc |
| | | cccacccacgaggagcatcgtggaaaaaga |
| | | agacgttccaaccacgtcttcaaagcaagt |
| | | ggattgatgtgatatctccactgacgtaag |
| | | ggatgacgcacaatcccactatccttcgca |
| | | agacccttcctctatataaggaagttcatt |
| | | tcatttggagagaacacgggggactctaat |
| | | caaacaagtttgtacaaaaaagctgaacga |
| | | gaaacgtaaaatgatataaatatcaaatgc |
| | | atatcagaaatccttaccgtacaccaattg |
| | | actatcaagcactttcagaggccttccctc |
| | | ccctcaagccatttgtgtctgtcaatgcag |
| | | atggtaccagttctgttgacctcactatcc |
| | | cagaagcccagagggcgttcacggccgctc |
| | | ttcttcatcgtgacttcgggctcaccatga |
| | | ccataccagaagaccgtctgtgcccaacag |
| | | tccccaataggttgaactacgttctgtgga |
| | | ttgaagatattttcaactacacgaacaaaa |
| | | ccctcggcctgtcggatgaccgtcctatta |
| | | aaggcgttgatattggtacaggagcctccg |
| | | caatttatcctatgcttgcctgtgctcggt |
| | | tcaaggcatggtctatggttggaacagagg |
| | | tcgagaggaagtgcattgacacggcccgcc |
| | | tcaatgtcgtcgcgaacaatctccaagacc |

TABLE 5-continued

Psilocybin Expression Vector Sequences.

| SEQ ID NO | Name | Sequence |
|---|---|---|
| | | gtctctcgatattagagacatccattgatg |
| | | gtcctattctcgtccccattttcgaggcga |
| | | ctgaagaatacgaatacgagtttactatgt |
| | | gtaaccctccattctacgacggtgctgccg |
| | | atatgcagacttcggatgctgccaaaggat |
| | | ttggatttggcgtgggcgctccccattctg |
| | | gaacagtcatcgaaatgtcgactgagggag |
| | | gtgaatcggctttcgtcgctcagatggtcc |
| | | gtgagagcttgaagcttcgaacacgatgca |
| | | gatggtacacgagtaacttgggaaagctga |
| | | aatccttgaaagaaatagtggggctgctga |
| | | aagaacttgagataagcaactatgccatta |
| | | acgaatacgttcaggggtccacacgtcgtt |
| | | atgccgttgcgtggtctttcactgatattc |
| | | aactgcctgaggagctttctcgtccctcta |
| | | accccgagctcagctctcttttctagcatt |
| | | ttacgtttctcgttcagctttcttgtacaa |
| | | agtggttcgatctagaggatccatggtgag |
| | | caagggcgaggagctgttcaccggggtggt |
| | | gcccatcctggtcgagctggacggcgacgt |
| | | gaacggccacaagttcagcgtgtccggcga |
| | | gggcgagggcgatgccacctacggcaagct |
| | | gaccctgaagttcatctgcaccaccggcaa |
| | | gctgcccgtgccctggcccaccctcgtgac |
| | | caccttcacctacggcgtgcagtgcttcag |
| | | ccgctaccccgaccacatgaagcagcacga |
| | | cttcttcaagtccgccatgcccgaaggcta |
| | | cgtccaggagcgcaccatcttcttcaagga |
| | | cgacggcaactacaagacccgcgccgaggt |
| | | gaagttcgagggcgacaccctggtgaaccg |
| | | catcgagctgaagggcatcgacttcaagga |
| | | ggacggcaacatcctggggcacaagctgga |
| | | gtacaactacaacagccacaacgtctatat |
| | | catggccgacaagcagaagaacggcatcaa |
| | | ggtgaacttcaagatccgccacaacatcga |
| | | ggacggcagcgtgcagctcgccgaccacta |
| | | ccagcagaacacccccatcggcgacggccc |
| | | cgtgctgctgcccgacaaccactacctgag |
| | | cacccagtccgccctgagcaaagaccccaa |
| | | cgagaagcgcgatcacatggtcctgctgga |
| | | gttcgtgaccgccgccgggatcactcacgg |
| | | catggacgagctgtacaagtaaagcggccc |
| | | gagctcgaatttccccgatcgttcaaacat |
| | | ttggcaataaagtttcttaagattgaatcc |
| | | tgttgccggtcttgcgatgattatcatata |
| | | atttctgttgaattacgttaagcatgtaat |
| | | aattaacatgtaatgcatgacgttatttat |
| | | gagatgggtttttatgattagagtcccgca |
| | | attatacatttaatacgcgatagaaaacaa |
| | | aatatagcgcgcaaactaggataaattatc |
| | | gcgcgcggtgtcatctatgttactagatcg |
| | | ggaattagcttcatcaacgcaagacatgcg |
| | | cacgaccgtctgacaggagaggaatttccg |
| | | acgagcacagaaaggacttgctcttggacg |
| | | taggcctatttctcaggcacatgtatcaag |
| | | tgttcggacgtgggttttcgatggtgtatc |
| | | agccgccgccaactgggagatgaggaggct |
| | | ttcttggggggcagtcagcagttcatttca |
| | | caagacagaggaacttgtaaggagatgcac |
| | | tgatttatcttggcgcaaaccagcaggacg |
| | | aattagtgggaatagcccgcgaatatctaa |
| | | gttatgcctgtcggcatgagcagaaacttc |
| | | caattcgaaacagtttggagaggttgtttt |
| | | tgggcataccttttgttagtcagcctctcg |
| | | attgctcatcgtcattacacagtaccgaag |
| | | tttgatcgatctagtaacatagatgacacc |
| | | gcgcgcgataatttatcctagtttgcgcgc |
| | | tatattttgttttctatcgcgtattaaatg |
| | | tataattgcgggactctaatcataaaaacc |
| | | catctcataaataacgtcatgcattacatg |
| | | ttaattattacatgcttaacgtaattcaac |
| | | agaaattatatgataatcatcgcaagaccg |
| | | gcaacaggattcaatcttaagaaactttat |
| | | tgccaaatgtttgaacgatctgcttcgacg |
| | | cactccttctttactccaccatctcgtcct |
| | | tattgaaaacgtgggtagcaccaaaacgaa |
| | | tcaagtcgctggaactgaagttaccaatca |
| | | cgctggatgatttgccagttggattaatct |
| | | tgcctttccccgcatgaataatattgatga |
| | | atgcatgcgtgaggggtatttcgattttgg |
| | | caatagctgcaattgccgcgacatcctcca |
| | | acgagcataattcttcagaaaaatagcgat |
| | | gttccatgttgtcagggcatgcatgatgca |
| | | cgttatgaggtgacggtgctaggcagtatt |
| | | ccctcaaagtttcatagtcagtatcatatt |
| | | catcattgcattcctgcaagagagaattga |
| | | gacgcaatccacacgctgcggcaaccttcc |
| | | ggcgttcgtggtctatttgctcttggacgt |
| | | tgcaaacgtaagtgttggatcccggtcggc |
| | | atctactctattcctttgccctcggacgag |
| | | tgctggggcgtcggtttccactatcggcga |
| | | gtacttctacacagccatcggtccagacgg |
| | | ccgcgcttctgcgggcgatttgtgtacgcc |
| | | cgacagtcccggctccggatcggacgattg |
| | | cgtcgcatcgaccctgcgcccaagctgcat |
| | | catcgaaattgccgtcaaccaagctctgat |
| | | agagttggtcaagaccaatgcggagcatat |
| | | acgcccggagccgcggcgatcctgcaagct |
| | | ccggatgcctccgctcgaagtagcgcgtct |
| | | gctgctccatacaagccaaccacggcctcc |
| | | agaagaagatgttggcgacctcgtattggg |
| | | aatccccgaacatcgcctcgctccagtcaa |
| | | tgaccgctgttatgcggccattgtccgtca |
| | | ggacattgttggagccgaaatccgcgtgca |
| | | cgaggtgccggacttcggggcagtcctcgg |
| | | cccaaagcatcagctcatcgagagcctgcg |
| | | cgacggacgcactgacggtgtcgtccatca |
| | | cagtttgccagtgatacacatggggatcag |
| | | caatcgcgcatatgaaatcacgccatgtag |
| | | tgtattgaccgattccttgcggtccgaatg |
| | | ggccgaacccgctcgtctggctaagatcgg |
| | | ccgcagcgatcgcatccatggcctccgcga |
| | | ccggctgcagaacagcgggcagttcggttt |
| | | caggcaggtcttgcaacgtgacaccctgtg |
| | | cacggcgggagatgcaataggtcaggctct |
| | | cgctgaattccccaatgtcaagcacttccg |
| | | gaatcgggagcgcggccgatgcaaagtgcc |
| | | gataaacataacgatctttgtagaaaccat |
| | | cggcgcagctatttacccgcaggacatatc |
| | | cacgccctcctacatcgaagctgaaagcac |
| | | gagattcttcgccctccgagagctgcatca |
| | | ggtcggagacgctgtcgaacttttcgatca |
| | | gaaacttctcgacagacgtcgcggtgagtt |
| | | caggctttttcatatcggggtcgtcctctc |
| | | caaatgaaatgaacttccttatatagagga |
| | | agggtcttgcgaaggatagtgggattgtgc |
| | | gtcatcccttacgtcagtggagatatcaca |
| | | tcaatccacttgctttgaagacgtggttgg |
| | | aacgtcttcttttttccacgatgctcctcgt |
| | | gggtgggggtccatctttgggaccactgtc |
| | | ggcagaggcatcttgaacgatagcctttcc |
| | | tttatcgcaatgatggcatttgtaggtgcc |
| | | accttccttttctactgtccttttgatgaa |
| | | gtgacagatagctgggcaatggaatccgag |
| | | gaggtttcccgatattaccctttgttgaaa |
| | | agtctcaatagccctttggtcttctgagac |
| | | tgtatctttgatattcttggagtagacgag |
| | | agtgtcgtgctccaccatgttgacggatct |
| | | ctaggacgcgtcctagaagctaattcactg |
| | | gccgtcgttttacaacgtcgtgactgggaa |
| | | aaccctggcgttacccaacttaatcgcctt |
| | | gcagcacatccccctttcgccagctggcgt |
| | | aatagcgaagaggcccgcaccgatcgccct |
| | | tcccaacagttgcgcagcctgaatggcgcc |
| | | cgctcctttcgctttcttcccttcctttct |
| | | cgccacgttcgccggctttccccgtcaagc |
| | | tctaaatcgggggctccctttagggttccg |
| | | atttagtgctttacggcacctcgaccccaa |

TABLE 5-continued

Psilocybin Expression Vector Sequences.

| SEQ ID NO | Name | Sequence |
| --- | --- | --- |
| | | aaaacttgatttgggtgatggttcacgtag |
| | | tgggccatcgccctgatagacggtttttcg |
| | | ccctttgacgttggagtccacgttctttaa |
| | | tagtggactcttgttccaaactggaacaac |
| | | actcaaccctatctcgggctattcttttga |
| | | tttataagggattttgccgatttcggaacc |
| | | accatcaaacaggattttcgcctgctgggg |
| | | caaaccagcgtggaccgcttgctgcaactc |
| | | tctcagggccaggcggtgaagggcaatcag |
| | | ctgttgcccgtctcactggtgaaaagaaaa |
| | | accaccccagtacattaaaaacgtccgcaa |
| | | tgtgttattaagttgtctaagcgtcaattt |
| | | gtttacaccacaatatatcctgccaccagc |
| | | cagccaacagctccccgaccggcagctcgg |
| | | cacaaaatcaccactcgatacaggcagccc |
| | | atcagtccgggacggcgtcagcgggagagc |
| | | cgttgtaaggcggcagactttgctcatgtt |
| | | accgatgctattcggaagaacggcaactaa |
| | | gctgccgggtttgaaacacggatgatctcg |
| | | cggagggtagcatgttgattgtaacgatga |
| | | cagagcgttgctgcctgtgatcaaatatca |
| | | tctccctcgcagagatccgaattatcagcc |
| | | ttcttattcatttctcgcttaaccgtgaca |
| | | ggctgtcgatcttgagaactatgccgacat |
| | | aataggaaatcgctggataaagccgctgag |
| | | gaagctgagtggcgctatttctttagaagt |
| | | gaacgttgacgatatcaactcccctatcca |
| | | ttgctcaccgaatggtacaggtcggggacc |
| | | cgaagttccgactgtcggcctgatgcatcc |
| | | ccggctgatcgaccccagatctggggctga |
| | | gaaagcccagtaaggaaacaactgtaggtt |
| | | cgagtcgcgagatcccccggaaccaaagga |
| | | agtaggttaaacccgctccgatcaggccga |
| | | gccacgccaggccgagaacattggttcctg |
| | | taggcatcgggattggcggatcaaacacta |
| | | aagctactggaacgagcagaagtcctccgg |
| | | ccgccagttgccaggcggtaaaggtgagca |
| | | gaggcacgggaggttgccacttgcgggtca |
| | | gcacggttccgaacgccatggaaaccgccc |
| | | ccgccaggcccgctgcgacgccgacaggat |
| | | ctagcgctgcgtttggtgtcaacaccaaca |
| | | gcgccacgcccgcagttccgcaaatagccc |
| | | ccaggaccgccatcaatcgtatcgggctac |
| | | ctagcagagcggcagagatgaacacgacca |
| | | tcagcggctgcacagcgcctaccgtcgccg |
| | | cgaccccgcccggcaggcggtagaccgaaa |
| | | taaacaacaagctccagaatagcgaaatat |
| | | taagtgcgccgaggatgaagatgcgcatcc |
| | | accagattcccgttggaatctgtcggacga |
| | | tcatcacgagcaataaacccgccggcaacg |
| | | cccgcagcagcataccggcgacccctcggc |
| | | ctcgctgttcgggctccacgaaaacgccgg |
| | | acagatgcgccttgtgagcgtccttggggc |
| | | cgtcctcctgtttgaagaccgacagcccaa |
| | | tgatctcgccgtcgatgtaggcgccgaatg |
| | | ccacggcatctcgcaaccgttcagcgaacg |
| | | cctccatgggctttttctcctcgtgctcgt |
| | | aaacggacccgaacatctctggagctttct |
| | | tcagggccgacaatcggatctcgcggaaat |
| | | cctgcacgtcggccgctccaagccgtcgaa |
| | | tctgagccttaatcacaattgtcaatttta |
| | | atcctctgtttatcggcagttcgtagagcg |
| | | cgccgtgcgtcccgagcgatactgagcgaa |
| | | gcaagtgcgtcgagcagtgcccgcttgttc |
| | | ctgaaatgccagtaaagcgctggctgctga |
| | | acccccagccggaactgaccccacaaggcc |
| | | ctagcgtttgcaatgcaccaggtcatcatt |
| | | gacccaggcgtgttccaccaggccgctgcc |
| | | tcgcaactcttcgcaggcttcgccgacctg |
| | | ctcgcgccacttcttcacgcgggtggaatc |
| | | cgatccgcacatgaggcggaaggtttccag |
| | | cttgagcgggtacggctcccggtgcgagct |
| | | gaaatagtcgaacatccgtcgggccgtcgg |
| | | cgacagcttgcggtacttctcccatatgaa |
| | | tttcgtgtagtggtcgccagcaaacagcac |
| | | gacgatttcctcgtcgatcaggacctggca |
| | | acgggacgttttcttgccacggtccaggac |
| | | gcggaagcggtgcagcagcgacaccgattc |
| | | caggtgcccaacgcggtcggacgtgaagcc |
| | | catcgccgtcgcctgtaggcgcgacaggca |
| | | ttcctcggccttcgtgtaataccggccatt |
| | | gatcgaccagcccaggtcctggcaaagctc |
| | | gtagaacgtgaaggtgatcggctcgccgat |
| | | aggggtgcgcttcgcgtactccaacacctg |
| | | ctgccacaccagttcgtcatcgtcggcccg |
| | | cagctcgacgccggtgtaggtgatcttcac |
| | | gtccttgttgacgtggaaaatgaccttgtt |
| | | ttgcagcgcctcgcgcgggatttcttgtt |
| | | gcgcgtggtgaacagggcagagcgggccgt |
| | | gtcgtttggcatcgctcgcatcgtgtccgg |
| | | ccacggcgcaatatcgaacaaggaaagctg |
| | | catttccttgatctgctgcttcgtgtgttt |
| | | cagcaacgcggcctgcttggcctcgctgac |
| | | ctgttttgccaggtcctcgccggcggtttt |
| | | tcgcttcttggtcgtcatagttcctcgcgt |
| | | gtcgatggtcatcgacttcgccaaacctgc |
| | | cgcctcctgttcgagacgacgcgaacgctc |
| | | cacggcggccgatggcgcgggcagggcagg |
| | | gggagccagttgcacgctgtcgcgctcgat |
| | | cttggccgtagcttgctggaccatcgagcc |
| | | gacggactggaaggtttcgcggggcgcacg |
| | | catgacggtgcggcttgcgatggtttcggc |
| | | atcctcggcggaaaaccccgcgtcgatcag |
| | | ttcttgcctgtatgccttccggtcaaacgt |
| | | ccgattcattcaccctccttgcgggattgc |
| | | cccgactcacgccggggcaatgtgccctta |
| | | ttcctgatttgacccgcctggtgccttggt |
| | | gtccagataatccaccttatcggcaatgaa |
| | | gtcggtcccgtagaccgtctggccgtcctt |
| | | ctcgtacttggtattccgaatcttgccctg |
| | | cacgaataccagcgaccccttgcccaaata |
| | | cttgccgtgggcctcggcctgagagccaaa |
| | | acacttgatgcggaagaagtcggtgcgctc |
| | | ctgcttgtcgccggcatcgttgcgccacat |
| | | ctaggtactaaaacaattcatccagtaaaa |
| | | tataatattttattttctcccaatcaggct |
| | | tgatccccagtaagtcaaaaaatagctcga |
| | | catactgttcttccccgatatcctccctga |
| | | tcgaccggacgcagaaggcaatgtcatacc |
| | | acttgtccgccctgccgcttctcccaagat |
| | | caataaagccacttactttgccatctttca |
| | | caaagatgttgctgtctcccaggtcgccgt |
| | | gggaaaagacaagttcctcttcgggctttt |
| | | ccgtctttaaaaaatcatacagctcgcgcg |
| | | gatctttaaatggagtgtcttcttcccagt |
| | | tttcgcaatccacatcggccagatcgttat |
| | | tcagtaagtaatccaattcggctaagcggc |
| | | tgtctaagctattcgtatagggacaatccg |
| | | atatgtcgatggagtgaaagagcctgatgc |
| | | actccgcatacagctcgataatcttttcag |
| | | ggctttgttcatcttcatactcttccgagc |
| | | aaaggacgccatcggcctcactcatgagca |
| | | gattgctccagccatcatgccgttcaaagt |
| | | gcaggacctttggaacaggcagctttcctt |
| | | ccagccatagcatcatgtccttttcccgtt |
| | | ccacatcataggtggtccctttataccggc |
| | | tgtccgtcatttttaaatataggttttcat |
| | | tttctcccaccagcttatataccttagcag |
| | | gagacattccttccgtatcttttacgcagc |
| | | ggtatttttcgatcagtttttttcaattccg |
| | | gtgatattctcattttagccatttattatt |
| | | tccttcctcttttctacagtatttaaagat |
| | | accccaagaagctaattataacaagacgaa |
| | | ctccaattcactgttccttgcattctaaaa |
| | | ccttaaataccagaaaacagctttttcaaa |
| | | gttgttttcaaagttggcgtataacatagt |
| | | atcgacggagccgattttgaaaccacaatt |
| | | atgggtgatgctgccaacttactgatttag |

TABLE 5-continued

Psilocybin Expression Vector Sequences.

| SEQ ID NO | Name | Sequence |
|---|---|---|
| | | tgtatgatggtgtttttgaggtgctccagt<br>ggcttctgtgtctatcagctgtccctcctg<br>ttcagctactgacggggtggtgcgtaacgg<br>caaaagcaccgccggacatcagcgctatct<br>ctgctctcactgccgtaaaacatggcaact<br>gcagttcacttacaccgcttctcaacccgg<br>tacgcaccagaaaatcattgatatggccat<br>gaatggcgttggatgccgggcaacagcccg<br>cattatgggcgttggcctcaacacgatttt<br>acgtcacttaaaaaactcaggccgcagtcg<br>gtaacctcgcgcatacagccgggcagtgac<br>gtcatcgtctgcgcggaaatggacgaacag<br>tggggctatgtcggggctaaatcgcgccag<br>cgctggctgttttacgcgtatgacagtctc<br>cggaagacggttgttgcgcacgtattcggt<br>gaacgcactatggcgacgctggggcgtctt<br>atgagcctgctgtcaccctttgacgtggtg<br>atatggatgacggatggctggccgctgtat<br>gaatcccgcctgaagggaaagctgcacgta<br>atcagcaagcgatatacgcagcgaattgag<br>cggcataacctgaatctgaggcagcacctg<br>gcacggctgggacggaagtcgctgtcgttc<br>tcaaaatcggtggagctgcatgacaaagtc<br>atcgggcattatctgaacataaaacactat<br>caataagttggagtcattacccaattatga<br>tagaatttacaagctataaggttattgtcc<br>tgggtttcaagcattagtccatgcaagttt<br>ttatgctttgcccattctatagatatattg<br>ataagcgcgctgcctatgccttgcccctg<br>aaatccttacatacggcgatatcttctata<br>taaaagatatattatcttatcagtattgtc<br>aatatattcaaggcaatctgcctcctcatc<br>ctcttcatcctcttcgtcttggtagctttt<br>taaatatggcgcttcatagagtaattctgt<br>aaaggtccaattctcgttttcatacctcgg<br>tataatcttacctatcacctcaaatggttc<br>gctgggtttatcgcacccccgaacacgagc<br>acggcacccgcgaccactatgccaagaatg<br>cccaaggtaaaaattgccggccccgccatg<br>aagtccgtgaatgccccgacggccgaagtg<br>aagggcaggccgccacccaggccgccgccc<br>tcactgcccggcacctggtcgctgaatgtc<br>gatgccagcacctgcggcacgtcaatgctt<br>ccgggcgtcgcgctcgggctgatcgcccat<br>cccgttactgccccgatcccggcaatggca<br>aggactgccagcgctgccatttttggggtg<br>aggccgttcgcggccgaggggcgcagcccc<br>tggggggatgggaggcccgcgttagcgggc<br>cgggagggttcgagaagggggggcaccccc<br>cttcggcgtgcgcggtcacgcgcacagggc<br>gcagccctggttaaaaacaaggtttataaa<br>tattggtttaaaagcaggttaaaagacagg<br>ttagcggtggccgaaaaacgggcggaaacc<br>cttgcaaatgctggattttctgcctgtgga<br>cagcccctcaaatgtcaataggtgcgcccc<br>tcatctgtcagcactctgcccctcaagtgt<br>caaggatcgcgcccctcatctgtcagtagt<br>cgcgcccctcaagtgtcaataccgcagggc<br>acttatccccaggcttgtccacatcatctg<br>tgggaaactcgcgtaaaatcaggcgttttc<br>gccgatttgcgaggctggccagctccacgt<br>cgccggccgaaatcgagcctgcccctcatc<br>tgtcaacgccgcgccgggtgagtcggcccc<br>tcaagtgtcaacgtccgcccctcatctgtc<br>agtgagggccaagttttccgcgaggtatcc<br>acaacgccggcggccgcggtgtctcgcaca<br>cggcttcgacggcgtttctggcgcgtttgc<br>agggccatagacggccgccagcccagcggc<br>gagggcaaccagcccgg |

TABLE 5-continued

Psilocybin Expression Vector Sequences.

| SEQ ID NO | Name | Sequence |
|---|---|---|
| 16 | pGWB5:<br>35S:<br>PsiKcds:<br>stop | tgagcgtcgcaaaggcgctcggtcttgcct<br>tgctcgtcggtgatgtacttcaccagctcc<br>gcgaagtcgctcttcttgatggagcgcatg<br>gggacgtgcttggcaatcacgcgcaccccc<br>cggccgttttagcggctaaaaaagtcatgg<br>ctctgccctcgggcggaccacgcccatcat<br>gaccttgccaagctcgtcctgcttctcttc<br>gatcttcgccagcagggcgaggatcgtggc<br>atcaccgaaccgcgccgtgcgcgggtcgtc<br>ggtgagccagagtttcagcaggccgcccag<br>gcggcccaggtcgccattgatgcgggccag<br>ctcgcggacgtgctcatagtccacgacgcc<br>cgtgattttgtagccctggccgacggccag<br>caggtaggccgacaggctcatgccggccgc<br>cgccgcctttcctcaatcgctcttcgttc<br>gtctggaaggcagtacaccttgataggtgg<br>gctgcccttcctggttggcttggtttcatc<br>agccatccgcttgccctcatctgttacgcc<br>ggcggtagccggccagcctcgcagagcagg<br>attcccgttgagcaccgccaggtgcgaata<br>agggacagtgaagaaggaacacccgctcgc<br>gggtgggcctacttcacctatcctgcccgg<br>ctgacgccgttggatacaccaaggaaagtc<br>tacacgaaccctttggcaaaatcctgtata<br>tcgtgcgaaaaaggatggatataccgaaaa<br>aatcgctataatgaccccgaagcagggtta<br>tgcagcggaaaagcgccacgcttcccgaag<br>ggagaaaggcggacaggtatccggtaagcg<br>gcagggtcggaacaggagagcgcacgaggg<br>agcttccagggggaaacgcctggtatcttt<br>atagtcctgtcgggtttcgccacctctgac<br>ttgagcgtcgatttttgtgatgctcgtcag<br>gggggcggagcctatggaaaaacgccagca<br>acgcggcctttttacggttcctggcctttt<br>gctggccttttgctcacatgttctttcctg<br>cgttatcccctgattctgtggataaccgta<br>ttaccgcctttgagtgagctgataccgctc<br>gccgcagccgaacgaccgagcgcagcgagt<br>cagtgagcgaggaagcggaagagcgccaga<br>aggccgccagagaggccgagcgcggccgtg<br>aggcttggacgctagggcagggcatgaaaa<br>agcccgtagcgggctgctacgggcgtctga<br>cgcggtggaaagggggaggggatgttgtct<br>acatggctctgctgtagtgagtgggttgcg<br>ctccggcagcggtcctgatcaatcgtcacc<br>ctttctcggtccttcaacgttcctgacaac<br>gagcctccttttcgccaatccatcgacaat<br>caccgcgagtccctgctcgaacgctgcgtc<br>cggaccggcttcgtcgaaggcgtctatcgc<br>ggcccgcaacagcggcgagagcggagcctg<br>ttcaacggtgccgccgcgctcgccggcatc<br>gctgtcgccggcctgctcctcaagcacggc<br>cccaacagtgaagtagctgattgtcatcag<br>cgcattgacggcgtccccggccgaaaaacc<br>cgcctcgcagaggaagcgaagctgcgcgtc<br>ggccgtttccatctgcggtgcgcccggtcg<br>cgtgccggcatggatgcgcgcgccatcgcg<br>gtaggcgagcagcgcctgcctgaagctgcg<br>ggcattcccgatcagaaatgagcgccagtc<br>gtcgtcggctctcggcaccgaatgcgtatg<br>attctccgccagcatggcttcggccagtgc<br>gtcgagcagcgcccgcttgttcctgaagtg<br>ccagtaaagcgccggctgctgaacccccaa<br>ccgttccgccagtttgcgtgtcgtcagacc<br>gtctacgccgacctcgttcaacaggtccag<br>ggcggcacggatcactgtattcggctgcaa<br>ctttgtcatgcttgacactttatcactgat<br>aaacataatatgtccaccaacttatcagtg<br>ataaagaatccgcgcgttcaatcggaccag<br>cggaggctggtccggaggccagacgtgaaa<br>cccaacataccctgatcgtaattctgagc<br>actgtcgcgctcgacgctgtcggcatcggc<br>ctgattatgccggtgctgccgggcctcctg |

TABLE 5-continued

Psilocybin Expression Vector Sequences.

| SEQ ID NO | Name | Sequence |
|---|---|---|
| | | cgcgatctggttcactcgaacgacgtcacc |
| | | gcccactatggcattctgctggcgctgtat |
| | | gcgttggtgcaatttgcctgcgcacctgtg |
| | | ctgggcgcgctgtcggatcgtttcgggcgg |
| | | cggccaatcttgctcgtctcgctggccggc |
| | | gccagatctggggaaccctgtggttggcat |
| | | gcacatacaaatggacgaacggataaacct |
| | | tttcacgcccttttaaatatccgattattc |
| | | taataaacgctcttttctcttaggtttacc |
| | | cgccaatatatcctgtcaaacactgatagt |
| | | ttaaactgaaggcgggaaacgacaatctga |
| | | tcatgagcggagaattaagggagtcacgtt |
| | | atgacccccgccgatgacgcgggacaagcc |
| | | gttttacgtttggaactgacagaaccgcaa |
| | | cgttgaaggagccactcagccgcgggtttc |
| | | tggagtttaatgagctaagcacatacgtca |
| | | gaaaccattattgcgcgttcaaaagtcgcc |
| | | taaggtcactatcagctagcaaatatttct |
| | | tgtcaaaaatgctccactgacgttccataa |
| | | attcccctcggtatccaattagagtctcat |
| | | attcactctcaatccaaataatctgcaccg |
| | | gatctggatcgtttcgcatgattgaacaag |
| | | atggattgcacgcaggttctccggccgctt |
| | | gggtggagaggctattcggctatgactggg |
| | | cacaacagacaatcggctgctctgatgccg |
| | | ccgtgttccggctgtcagcgcaggggcgcc |
| | | cggttctttttgtcaagaccgacctgtccg |
| | | gtgccctgaatgaactgcaggacgaggcag |
| | | cgcggctatcgtggctggccacgacgggcg |
| | | ttccttgcgcagctgtgctcgacgttgtca |
| | | ctgaagcgggaagggactggctgctattgg |
| | | gcgaagtgccggggcaggatctcctgtcat |
| | | ctcaccttgctcctgccgagaaagtatcca |
| | | tcatggctgatgcaatgcggcggctgcata |
| | | cgcttgatccggctacctgcccattcgacc |
| | | accaagcgaaacatcgcatcgagcgagcac |
| | | gtactcggatggaagccggtcttgtcgatc |
| | | aggatgatctggacgaagagcatcaggggc |
| | | tcgcgccagccgaactgttcgccaggctca |
| | | aggcgcgcatgcccgacggcgatgatctcg |
| | | tcgtgacccatggcgatgcctgcttgccga |
| | | atatcatggtggaaaatggccgcttttctg |
| | | gattcatcgactgtggccggctgggtgtgg |
| | | cggaccgctatcaggacatagcgttggcta |
| | | cccgtgatattgctgaagagcttggcggcg |
| | | aatgggctgaccgcttcctcgtgctttacg |
| | | gtatcgccgctcccgattcgcagcgcatcg |
| | | ccttctatcgccttcttgacgagttcttct |
| | | gagcgggactctggggttcgaaatgaccga |
| | | ccaagcgacgcccaacctgccatcacgaga |
| | | tttcgattccaccgccgccttctatgaaag |
| | | gttgggcttcggaatcgttttccgggacgc |
| | | cggctggatgatcctccagcgcggggatct |
| | | catgctggagttcttcgcccacgggatctc |
| | | tgcggaacaggcggtcgaaggtgccgatat |
| | | cattacgacagcaacggccgacaagcacaa |
| | | cgccacgatcctgagcgacaatatgatcgg |
| | | gcccggcgtccacatcaacggcgtcggcgg |
| | | cgactgcccaggcaagaccgagatgcaccg |
| | | cgatatcttgctgcgttcggatattttcgt |
| | | ggagttcccgccacagacccggatgatccc |
| | | cgatcgttcaaacatttggcaataaagttt |
| | | cttaagattgaatcctgttgccggtcttgc |
| | | gatgattatcatataatttctgttgaatta |
| | | cgttaagcatgtaataattaacatgtaatg |
| | | catgacgttatttatgagatgggtttttat |
| | | gattagagtcccgcaattatacatttaata |
| | | cgcgatagaaaacaaaatatagcgcgcaaa |
| | | ctaggataaattatcgcgcgcggtgtcatc |
| | | tatgttactagatcgggcctcctgtcaatg |
| | | ctggcggcggctctggtggtggttctggtg |
| | | gcggctctgagggtggtggctctgagggtg |
| | | gcggttctgagggtggcggctctgagggag |
| | | gcggttccggtggtggctctggttccggtg |

TABLE 5-continued

Psilocybin Expression Vector Sequences.

| SEQ ID NO | Name | Sequence |
|---|---|---|
| | | attttgattatgaaaagatggcaaacgcta |
| | | ataagggggctatgaccgaaaatgccgatg |
| | | aaaacgcgctacagtctgacgctaaaggca |
| | | aacttgattctgtcgctactgattacggtg |
| | | ctgctatcgatggtttcattggtgacgttt |
| | | ccggccttgctaatggtaatggtgctactg |
| | | gtgattttgctggctctaattcccaaatgg |
| | | ctcaagtcggtgacggtgataattcacctt |
| | | taatgaataatttccgtcaatatttacctt |
| | | ccctccctcaatcggttgaatgtcgccctt |
| | | ttgtctttggcccaatacgcaaaccgcctc |
| | | tccccgcgcgttggccgattcattaatgca |
| | | gctggcacgacaggtttcccgactggaaag |
| | | cgggcagtgagcgcaacgcaattaatgtga |
| | | gttagctcactcattaggcaccccaggctt |
| | | tacactttatgcttccggctcgtatgttgt |
| | | gtggaattgtgagcggataacaatttcaca |
| | | caggaaacagctatgaccatgattacgcca |
| | | agcttgcatgcctgcaggtccccagattag |
| | | ccttttcaatttcagaaagaatgctaaccc |
| | | acagatggttagagaggcttacgcagcagg |
| | | tctcatcaagacgatctacccgagcaataa |
| | | tctccaggaaatcaaataccttcccaagaa |
| | | ggttaaagatgcagtcaaaagattcaggac |
| | | taactgcatcaagaacacagagaaagatat |
| | | atttctcaagatcagaagtactattccagt |
| | | atggacgattcaaggcttgcttcacaaacc |
| | | aaggcaagtaatagagattggagtctctaa |
| | | aaaggtagttcccactgaatcaaaggccat |
| | | ggagtcaaagattcaaatagaggacctaac |
| | | agaactcgccgtaaagactggcgaacagtt |
| | | catacagagtctcttacgactcaatgacaa |
| | | gaagaaaatcttcgtcaacatggtggagca |
| | | cgacacacttgtctactccaaaaatatcaa |
| | | agatacagtctcagaagaccaaagggcaat |
| | | tgagacttttcaacaaagggtaatatccgg |
| | | aaacctcctcggattccattgcccagctat |
| | | ctgtcactttattgtgaagatagtggaaaa |
| | | ggaaggtggctcctacaaatgccatcattg |
| | | cgataaaggaaaggccatcgttgaagatgc |
| | | ctctgccgacagtggtcccaaagatggacc |
| | | cccacccacgaggagcatcgtggaaaaaga |
| | | agacgttccaaccacgtcttcaaagcaagt |
| | | ggattgatgtgatatctccactgacgtaag |
| | | ggatgacgcacaatcccactatccttcgca |
| | | agacccttcctctatataaggaagttcatt |
| | | tcatttggagagaacacgggggactctaat |
| | | caaacaagtttgtacaaaaaagctgaacga |
| | | gaaacgtaaaatgatataatggcgttcgat |
| | | ctcaagactgaagacggcctcatcacatat |
| | | ctcactaaacatctttctttggacgtcgac |
| | | acgagcggagtgaagcgccttagcggaggc |
| | | tttgtcaatgtaacctggcgcattaagctc |
| | | aatgctccttatcaaggtcatacgagcatc |
| | | atcctgaagcatgctcagccgcacatgtct |
| | | acggatgaggattttaagataggtgtagaa |
| | | cgttcggtttacgaataccaggctatcaag |
| | | ctcatgatggccaatcgggaggttctggga |
| | | ggcgtggatggcatagtttctgtgccagaa |
| | | ggcctgaactacgacttagagaataatgca |
| | | ttgatcatgcaagatgtcgggaagatgaag |
| | | acccttttagattatgtcaccgccaaaccg |
| | | ccacttgcgacggatatagcccgccttgtt |
| | | gggacagaaattgggggttcgttgccaga |
| | | ctccataacataggccgcgagaggcgagac |
| | | gatcctgagttcaaattcttctctggaaat |
| | | attgtcggaaggacgacttcagaccagctg |
| | | tatcaaaccatcatacccaacgcagcgaaa |
| | | tatggcgtcgatgaccccttgctgcctact |
| | | gtggttaaggaccttgtggacgatgtcatg |
| | | cacagcgaagagacccttgtcatggcggac |
| | | ctgtggagtggaaatattcttctccagttg |
| | | gaggagggaaacccatcgaagctgcagaag |
| | | atatatatcctggattgggaactttgcaag |

TABLE 5-continued

Psilocybin Expression Vector Sequences.

| SEQ ID NO | Name | Sequence |
|---|---|---|
| | | tacggcccagcgtcgttggacctgggctat |
| | | ttcttgggtgactgctatttgatatcccgc |
| | | tttcaagacgagcaggtcggtacgacgatg |
| | | cggcaagcctacttgcaaagctatgcgcgt |
| | | acgagcaagcattcgatcaactacgccaaa |
| | | gtcactgcaggtattgctgctcatattgtg |
| | | atgtggaccgactttatgcagtgggggagc |
| | | gaggaagaaaggataaattttgtgaaaaag |
| | | ggggtagctgcctttcacgacgccaggggc |
| | | aacaacgacaatggggaaattacgtctacc |
| | | ttactgaaggaatcatccactgcgtaaatc |
| | | attttacgtttctcgttcagctttcttgta |
| | | caaagtggttcgatctagaggatccatggt |
| | | gagcaagggcgaggagctgttcaccggggt |
| | | ggtgcccatcctggtcgagctggacggcga |
| | | cgtgaacggccacaagttcagcgtgtccgg |
| | | cgagggcgagggcgatgccacctacggcaa |
| | | gctgaccctgaagttcatctgcaccaccgg |
| | | caagctgcccgtgccctggcccaccctcgt |
| | | gaccaccttcacctacggcgtgcagtgctt |
| | | cagccgctaccccgaccacatgaagcagca |
| | | cgacttcttcaagtccgccatgcccgaagg |
| | | ctacgtccaggagcgcaccatcttcttcaa |
| | | ggacgacggcaactacaagacccgcgccga |
| | | ggtgaagttcgagggcgacaccctggtgaa |
| | | ccgcatcgagctgaagggcatcgacttcaa |
| | | ggaggacggcaacatcctggggcacaagct |
| | | ggagtacaactacaacagccacaacgtcta |
| | | tatcatggccgacaagcagaagaacggcat |
| | | caaggtgaacttcaagatccgccacaacat |
| | | cgaggacggcagcgtgcagctcgccgacca |
| | | ctaccagcagaacacccccatcggcgacgg |
| | | ccccgtgctgctgcccgacaaccactacct |
| | | gagcacccagtccgccctgagcaaagaccc |
| | | caacgagaagcgcgatcacatggtcctgct |
| | | ggagttcgtgaccgccgccgggatcactca |
| | | cggcatggacgagctgtacaagtaaagcgg |
| | | cccgagctcgaatttccccgatcgttcaaa |
| | | catttggcaataaagtttcttaagattgaa |
| | | tcctgttgccggtcttgcgatgattatcat |
| | | ataatttctgttgaattacgttaagcatgt |
| | | aataattaacatgtaatgcatgacgttatt |
| | | tatgagatgggtttttatgattagagtccc |
| | | gcaattatacatttaatacgcgatagaaaa |
| | | caaaatatagcgcgcaaactaggataaatt |
| | | atcgcgcgcggtgtcatctatgttactaga |
| | | tcgggaattagcttcatcaacgcaagacat |
| | | gcgcacgaccgtctgacaggagaggaattt |
| | | ccgacgagcacagaaaggacttgctcttgg |
| | | acgtaggcctatttctcaggcacatgtatc |
| | | aagtgttcggacgtgggttttcgatggtgt |
| | | atcagccgccgccaactgggagatgaggag |
| | | gctttcttgggggcagtcagcagttcatt |
| | | tcacaagacagaggaacttgtaaggagatg |
| | | cactgatttatcttggcgcaaaccagcagg |
| | | acgaattagtgggaatagcccgcgaatatc |
| | | taagttatgcctgtcggcatgagcagaaac |
| | | ttccaattcgaaacagtttggagaggttgt |
| | | ttttgggcataccttttgttagtcagcctc |
| | | tcgattgctcatcgtcattacacagtaccg |
| | | aagtttgatcgatctagtaacatagatgac |
| | | accgcgcgcgataatttatcctagtttgcg |
| | | cgctatattttgttttctatcgcgtattaa |
| | | atgtataattgcgggactctaatcataaaa |
| | | acccatctcataaataacgtcatgcattac |
| | | atgttaattattacatgcttaacgtaattc |
| | | aacagaaattatatgataatcatcgcaaga |
| | | ccggcaacaggattcaatcttaagaaactt |
| | | tattgccaaatgtttgaacgatctgcttcg |
| | | acgcactccttctttactccaccatctcgt |
| | | ccttattgaaaacgtgggtagcaccaaaac |
| | | gaatcaagtcgctggaactgaagttaccaa |
| | | tcacgctggatgatttgccagttggattaa |
| | | tcttgcctttccccgcatgaataatattga |

TABLE 5-continued

Psilocybin Expression Vector Sequences.

| SEQ ID NO | Name | Sequence |
|---|---|---|
| | | tgaatgcatgcgtgaggggtatttcgattt |
| | | tggcaatagctgcaattgccgcgacatcct |
| | | ccaacgagcataattcttcagaaaaatagc |
| | | gatgttccatgttgtcagggcatgcatgat |
| | | gcacgttatgaggtgacggtgctaggcagt |
| | | attccctcaaagtttcatagtcagtatcat |
| | | attcatcattgcattcctgcaagagagaat |
| | | tgagacgcaatccacacgctgcggcaacct |
| | | tccggcgttcgtggtctatttgctcttgga |
| | | cgttgcaaacgtaagtgttggatcccggtc |
| | | ggcatctactctattcctttgccctcggac |
| | | gagtgctggggcgtcggtttccactatcgg |
| | | cgagtacttctacacagccatcggtccaga |
| | | cggccgcgcttctgcgggcgatttgtgtac |
| | | gcccgacagtcccggctccggatcggacga |
| | | ttgcgtcgcatcgaccctgcgcccaagctg |
| | | catcatcgaaattgccgtcaaccaagctct |
| | | gatagagttggtcaagaccaatgcggagca |
| | | tatacgcccggagccgcggcgatcctgcaa |
| | | gctccggatgcctccgctcgaagtagcgcg |
| | | tctgctgctccatacaagccaaccacggcc |
| | | tccagaagaagatgttggcgacctcgtatt |
| | | gggaatccccgaacatcgcctcgctccagt |
| | | caatgaccgctgttatgcggccattgtccg |
| | | tcaggacattgttggagccgaaatccgcgt |
| | | gcacgaggtgccggacttcggggcagtcct |
| | | cggcccaaagcatcagctcatcgagagcct |
| | | gcgcgacggacgcactgacggtgtcgtcca |
| | | tcacagtttgccagtgatacacatggggat |
| | | cagcaatcgcgcatatgaaatcacgccatg |
| | | tagtgtattgaccgattccttgcggtccga |
| | | atgggccgaacccgctcgtctggctaagat |
| | | cggccgcagcgatcgcatccatggcctccg |
| | | cgaccggctgcagaacagcgggcagttcgg |
| | | tttcaggcaggtcttgcaacgtgacaccct |
| | | gtgcacggcgggagatgcaataggtcaggc |
| | | tctcgctgaattccccaatgtcaagcactt |
| | | ccggaatcgggagcgcggccgatgcaaagt |
| | | gccgataaacataacgatctttgtagaaac |
| | | catcggcgcagctatttacccgcaggacat |
| | | atccacgccctcctacatcgaagctgaaag |
| | | cacgagattcttcgccctccgagagctgca |
| | | tcaggtcggagacgctgtcgaacttttcga |
| | | tcagaaacttctcgacagacgtcgcggtga |
| | | gttcaggctttttcatatcggggtcgtcct |
| | | ctccaaatgaaatgaacttccttatataga |
| | | ggaagggtcttgcgaaggatagtgggattg |
| | | tgcgtcatcccttacgtcagtggagatatc |
| | | acatcaatccacttgctttgaagacgtggt |
| | | tggaacgtcttctttttccacgatgctcct |
| | | cgtgggtgggggtccatctttgggaccact |
| | | gtcggcagaggcatcttgaacgatagcctt |
| | | tcctttatcgcaatgatggcatttgtaggt |
| | | gccaccttccttttctactgtccttttgat |
| | | gaagtgacagatagctgggcaatggaatcc |
| | | gaggaggtttcccgatattaccctttgttg |
| | | aaaagtctcaatagccctttggtcttctga |
| | | gactgtatctttgatattcttggagtagac |
| | | gagagtgtcgtgctccaccatgttgacgga |
| | | tctctaggacgcgtcctagaagctaattca |
| | | ctggccgtcgttttacaacgtcgtgactgg |
| | | gaaaaccctggcgttacccaacttaatcgc |
| | | cttgcagcacatccccctttcgccagctgg |
| | | cgtaatagcgaagaggcccgcaccgatcgc |
| | | ccttcccaacagttgcgcagcctgaatggc |
| | | gcccgctcctttcgctttcttcccttcctt |
| | | tctcgccacgttcgccggctttccccgtca |
| | | agctctaaatcgggggctccctttagggtt |
| | | ccgatttagtgctttacggcacctcgaccc |
| | | caaaaaacttgatttgggtgatggttcacg |
| | | tagtgggccatcgccctgatagacggtttt |
| | | tcgccctttgacgttggagtccacgttctt |
| | | taatagtggactcttgttccaaactggaac |
| | | aacactcaaccctatctcgggctattcttt |

TABLE 5-continued

Psilocybin Expression Vector Sequences.

| SEQ ID NO | Name | Sequence |
|---|---|---|
| | | tgatttataagggattttgccgatttcgga |
| | | accaccatcaaacaggattttcgcctgctg |
| | | gggcaaaccagcgtggaccgcttgctgcaa |
| | | ctctctcagggccaggcggtgaagggcaat |
| | | cagctgttgcccgtctcactggtgaaaaga |
| | | aaaaccaccccagtacattaaaaacgtccg |
| | | caatgtgttattaagttgtctaagcgtcaa |
| | | tttgtttacaccacaatatatcctgccacc |
| | | agccagccaacagctccccgaccggcagct |
| | | cggcacaaaatcaccactcgatacaggcag |
| | | cccatcagtccgggacggcgtcagcgggag |
| | | agccgttgtaaggcggcagactttgctcat |
| | | gttaccgatgctattcggaagaacggcaac |
| | | taagctgccgggtttgaaacacggatgatc |
| | | tcgcggagggtagcatgttgattgtaacga |
| | | tgacagagcgttgctgcctgtgatcaaata |
| | | tcatctccctcgcagagatccgaattatca |
| | | gccttcttattcatttctcgcttaaccgtg |
| | | acaggctgtcgatcttgagaactatgccga |
| | | cataataggaaatcgctggataaagccgct |
| | | gaggaagctgagtggcgctatttctttaga |
| | | agtgaacgttgacgatatcaactcccctat |
| | | ccattgctcaccgaatggtacaggtcgggg |
| | | acccgaagttccgactgtcggcctgatgca |
| | | tccccggctgatcgaccccagatctggggc |
| | | tgagaaagcccagtaaggaaacaactgtag |
| | | gttcgagtcgcgagatcccccggaaccaaa |
| | | ggaagtaggttaaacccgctccgatcaggc |
| | | cgagccacgccaggccgagaacattggttc |
| | | ctgtaggcatcgggattggcggatcaaaca |
| | | ctaaagctactggaacgagcagaagtcctc |
| | | cggccgccagttgccaggcggtaaaggtga |
| | | gcagaggcacgggaggttgccacttgcggg |
| | | tcagcacggttccgaacgccatggaaaccg |
| | | cccccgccaggcccgctgcgacgccgacag |
| | | gatctagcgctgcgtttggtgtcaacacca |
| | | acagcgccacgcccgcagttccgcaaatag |
| | | cccccaggaccgccatcaatcgtatcgggc |
| | | tacctagcagagcggcagagatgaacacga |
| | | ccatcagcggctgcacagcgcctaccgtcg |
| | | ccgcgaccccgcccggcaggcggtagaccg |
| | | aaataaacaacaagctccagaatagcgaaa |
| | | tattaagtgcgccgaggatgaagatgcgca |
| | | tccaccagattcccgttggaatctgtcgga |
| | | cgatcatcacgagcaataaacccgccggca |
| | | acgcccgcagcagcataccggcgacccctc |
| | | ggcctcgctgttcgggctccacgaaaacgc |
| | | cggacagatgcgccttgtgagcgtccttgg |
| | | ggccgtcctcctgtttgaagaccgacagcc |
| | | caatgatctcgccgtcgatgtaggcgccga |
| | | atgccacggcatctcgcaaccgttcagcga |
| | | acgcctccatgggctttttctcctcgtgct |
| | | cgtaaacggacccgaacatctctggagctt |
| | | tcttcagggccgacaatcggatctcgcgga |
| | | aatcctgcacgtcggccgctccaagccgtc |
| | | gaatctgagccttaatcacaattgtcaatt |
| | | ttaatcctctgtttatcggcagttcgtaga |
| | | gcgcgccgtgcgtcccgagcgatactgagc |
| | | gaagcaagtgcgtcgagcagtgcccgcttg |
| | | ttcctgaaatgccagtaaagcgctggctgc |
| | | tgaaccccagccggaactgaccccacaag |
| | | gccctagcgtttgcaatgcaccaggtcatc |
| | | attgacccaggcgtgttccaccaggccgct |
| | | gcctcgcaactcttcgcaggcttcgccgac |
| | | ctgctcgcgccacttcttcacgcgggtgga |
| | | atccgatccgcacatgaggcggaaggtttc |
| | | cagcttgagcgggtacggctcccggtgcga |
| | | gctgaaatagtcgaacatccgtcgggccgt |
| | | cggcgacagcttgcggtacttctcccatat |
| | | gaatttcgtgtagtggtcgccagcaaacag |
| | | cacgacgatttcctcgtcgatcaggacctg |
| | | gcaacgggacgttttcttgccacggtccag |
| | | gacgcggaagcggtgcagcagcgacaccga |
| | | ttccaggtgcccaacgcggtcggacgtgaa |

TABLE 5-continued

Psilocybin Expression Vector Sequences.

| SEQ ID NO | Name | Sequence |
|---|---|---|
| | | gcccatcgccgtcgcctgtaggcgcgacag |
| | | gcattcctcggccttcgtgtaataccggcc |
| | | attgatcgaccagcccaggtcctggcaaag |
| | | ctcgtagaacgtgaaggtgatcggctcgcc |
| | | gataggggtgcgcttcgcgtactccaacac |
| | | ctgctgccacaccagttcgtcatcgtcggc |
| | | ccgcagctcgacgccggtgtaggtgatctt |
| | | cacgtccttgttgacgtggaaaatgacctt |
| | | gttttgcagcgcctcgcgcgggattttctt |
| | | gttgcgcgtggtgaacagggcagagcgggc |
| | | cgtgtcgtttggcatcgctcgcatcgtgtc |
| | | cggccacggcgcaatatcgaacaaggaaag |
| | | ctgcatttccttgatctgctgcttcgtgtg |
| | | tttcagcaacgcggcctgcttggcctcgct |
| | | gacctgttttgccaggtcctcgccggcggt |
| | | ttttcgcttcttggtcgtcatagttcctcg |
| | | cgtgtcgatggtcatcgacttcgccaaacc |
| | | tgccgcctcctgttcgagacgacgcgaacg |
| | | ctccacggcggccgatggcgcgggcagggc |
| | | agggggagccagttgcacgctgtcgcgctc |
| | | gatcttggccgtagcttgctggaccatcga |
| | | gccgacggactggaaggtttcgcggggcgc |
| | | acgcatgacggtgcggcttgcgatggtttc |
| | | ggcatcctcggcggaaaaccccgcgtcgat |
| | | cagttcttgcctgtatgccttccggtcaaa |
| | | cgtccgattcattcaccctccttgcgggat |
| | | tgccccgactcacgccggggcaatgtgccc |
| | | ttattcctgatttgacccgcctggtgcctt |
| | | ggtgtccagataatccaccttatcggcaat |
| | | gaagtcggtcccgtagaccgtctggccgtc |
| | | cttctcgtacttggtattccgaatcttgcc |
| | | ctgcacgaataccagcgaccccttgcccaa |
| | | atacttgccgtgggcctcggcctgagagcc |
| | | aaaacacttgatgcggaagaagtcggtgcg |
| | | ctcctgcttgtcgccggcatcgttgcgcca |
| | | catctaggtactaaaacaattcatccagta |
| | | aaatataatattttattttctcccaatcag |
| | | gcttgatccccagtaagtcaaaaaatagct |
| | | cgacatactgttcttccccgatatcctccc |
| | | tgatcgaccggacgcagaaggcaatgtcat |
| | | accacttgtccgccctgccgcttctcccaa |
| | | gatcaataaagccacttactttgccatctt |
| | | tcacaaagatgttgctgtctcccaggtcgc |
| | | cgtgggaaaagacaagttcctcttcgggct |
| | | tttccgtctttaaaaaatcatacagctcgc |
| | | gcggatctttaaatggagtgtcttcttccc |
| | | agttttcgcaatccacatcggccagatcgt |
| | | tattcagtaagtaatccaattcggctaagc |
| | | ggctgtctaagctattcgtatagggacaat |
| | | ccgatatgtcgatggagtgaaagagcctga |
| | | tgcactccgcatacagctcgataatctttt |
| | | cagggctttgttcatcttcatactcttccg |
| | | agcaaaggacgccatcggcctcactcatga |
| | | gcagattgctccagccatcatgccgttcaa |
| | | agtgcaggacctttggaacaggcagctttc |
| | | cttccagccatagcatcatgtccttttccc |
| | | gttccacatcataggtggtccctttatacc |
| | | ggctgtccgtcatttttaaatataggtttt |
| | | cattttctcccaccagcttatataccttag |
| | | caggagacattccttccgtatcttttacgc |
| | | agcggtatttttcgatcagtttttcaatt |
| | | ccggtgatattctcattttagccatttatt |
| | | atttccttcctcttttctacagtatttaaa |
| | | gataccccaagaagctaattataacaagac |
| | | gaactccaattcactgttccttgcattcta |
| | | aaaccttaaataccagaaaacagcttttc |
| | | aaagttgttttcaaagttggcgtataacat |
| | | agtatcgacggagccgatttgaaaccaca |
| | | attatgggtgatgctgccaacttactgatt |
| | | tagtgtatgatggtgtttttgaggtgctcc |
| | | agtggcttctgtgtctatcagctgtccctc |
| | | ctgttcagctactgacggggtggtgcgtaa |
| | | cggcaaaagcaccgccggacatcagcgcta |
| | | tctctgctctcactgccgtaaaacatggca |

TABLE 5-continued

Psilocybin Expression Vector Sequences.

| SEQ ID NO | Name | Sequence |
|---|---|---|
| | | actgcagttcacttacaccgcttctcaacc<br>cggtacgcaccagaaaatcattgatatggc<br>catgaatggcgttggatgccgggcaacagc<br>ccgcattatgggcgttggcctcaacacgat<br>tttacgtcacttaaaaaactcaggccgcag<br>tcggtaacctcgcgcatacagccgggcagt<br>gacgtcatcgtctgcgcggaaatggacgaa<br>cagtggggctatgtcggggctaaatcgcgc<br>cagcgctggctgttttacgcgtatgacagt<br>ctccggaagacggttgttgcgcacgtattc<br>ggtgaacgcactatggcgacgctggggcgt<br>cttatgagcctgctgtcaccctttgacgtg<br>gtgatatggatgacggatggctggccgctg<br>tatgaatcccgcctgaagggaaagctgcac<br>gtaatcagcaagcgatatacgcagcgaatt<br>gagcggcataacctgaatctgaggcagcac<br>ctggcacggctgggacggaagtcgctgtcg<br>ttctcaaaatcggtggagctgcatgacaaa<br>gtcatcgggcattatctgaacataaaacac<br>tatcaataagttggagtcattacccaatta<br>tgatagaatttacaagctataaggttattg<br>tcctgggtttcaagcattagtccatgcaag<br>tttttatgctttgcccattctatagatata<br>ttgataagcgcgctgcctatgccttgcccc<br>ctgaaatccttacatacggcgatatcttct<br>atataaaagatatattatcttatcagtatt<br>gtcaatatattcaaggcaatctgcctcctc<br>atcctcttcatcctcttcgtcttggtagct<br>ttttaaatatggcgcttcatagagtaattc<br>tgtaaaggtccaattctcgttttcatacct<br>cggtataatcttacctatcacctcaaatgg<br>ttcgctgggtttatcgcacccccgaacacg<br>agcacggcacccgcgaccactatgccaaga<br>atgcccaaggtaaaaattgccggccccgcc<br>atgaagtccgtgaatgccccgacggccgaa<br>gtgaagggcaggccgccacccaggccgccg<br>ccctcactgcccggcacctggtcgctgaat<br>gtcgatgccagcacctgcggcacgtcaatg<br>cttccgggcgtcgcgctcgggctgatc<br>gcccatcccgttactgccccgatcccggca<br>atggcaaggactgccagcgctgccattttt<br>ggggtgaggccgttcgcggccgaggggcgc<br>agcccctgggggggatgggaggcccgcgtta<br>gcgggccgggagggttcgagaagggggggc<br>acccccccttcggcgtgcgcggtcacgcgca<br>cagggcgcagccctggttaaaaacaaggtt<br>tataaatattggtttaaaagcaggttaaaa<br>gacaggttagcggtggccgaaaaacgggcg<br>gaaacccttgcaaatgctggattttctgcc<br>tgtggacagcccctcaaatgtcaataggtg<br>cgcccctcatctgtcagcactctgcccctc<br>aagtgtcaaggatcgcgcccctcatctgtc<br>agtagtcgcgcccctcaagtgtcaataccg<br>cagggcacttatccccaggcttgtccacat<br>catctgtgggaaactcgcgtaaaatcaggc<br>gttttcgccgatttgcgaggctggccagct<br>ccacgtcgccggccgaaatcgagcctgccc<br>ctcatctgtcaacgccgcgccgggtgagtc<br>ggcccctcaagtgtcaacgtccgcccctca<br>tctgtcagtgagggccaagttttccgcgag<br>gtatccacaacgccggcggccgcggtgtct<br>cgcacacggcttcgacggcgtttctggcgc<br>gtttgcagggccatagacggccgccagccc<br>agcggcgagggcaaccagcccgg |
| 17 | pGWB5:<br>35S:<br>PsiHcds:<br>stop | tgagcgtcgcaaaggcgctcggtcttgcct<br>tgctcgtcggtgatgtacttcaccagctcc<br>gcgaagtcgctcttcttgatggagcgcatg<br>gggacgtgcttggcaatcacgcgcaccccc<br>cggccgttttagcggctaaaaaagtcatgg<br>ctctgccctcgggcggaccacgcccatcat<br>gaccttgccaagctcgtcctgcttctcttc<br>gatcttcgccagcagggcgaggatcgtggc<br>atcaccgaaccgcgccgtgcgcgggtcgtc |

TABLE 5-continued

Psilocybin Expression Vector Sequences.

| SEQ ID NO | Name | Sequence |
|---|---|---|
| | | ggtgagccagagtttcagcaggccgcccag<br>gcggcccaggtcgccattgatgcgggccag<br>ctcgcggacgtgctcatagtccacgacgcc<br>cgtgattttgtagccctggccgacggccag<br>caggtaggccgacaggctcatgccggccgc<br>cgccgcctttttcctcaatcgctcttcgttc<br>gtctggaaggcagtacaccttgataggtgg<br>gctgcccttcctggttggcttggtttcatc<br>agccatccgcttgccctcatctgttacgcc<br>ggcggtagccggccagcctcgcagagcagg<br>attcccgttgagcaccgccaggtgcgaata<br>agggacagtgaagaaggaacacccgctcgc<br>gggtgggcctacttcacctatcctgcccgg<br>ctgacgccgttggatacaccaaggaaagtc<br>tacacgaaccctttggcaaaatcctgtata<br>tcgtgcgaaaaaggatggatataccgaaaa<br>aatcgctataatgaccccgaagcagggtta<br>tgcagcggaaaagcgccacgcttcccgaag<br>ggagaaaggcggacaggtatccggtaagcg<br>gcagggtcggaacaggagagcgcacgaggg<br>agcttccagggggaaacgcctggtatcttt<br>atagtcctgtcgggtttcgccacctctgac<br>ttgagcgtcgatttttgtgatgctcgtcag<br>gggggcggagcctatggaaaaacgccagca<br>acgcggcctttttacggttcctggcctttt<br>gctggccttttgctcacatgttctttcctg<br>cgttatcccctgattctgtggataaccgta<br>ttaccgcctttgagtgagctgataccgctc<br>gccgcagccgaacgaccgagcgcagcgagt<br>cagtgagcgaggaagcggaagagcgccaga<br>aggccgccagagaggccgagcgcggccgtg<br>aggcttggacgctagggcagggcatgaaaa<br>agcccgtagcgggctgctacgggcgtctga<br>cgcggtggaaagggggagggggatgttgtct<br>acatggctctgctgtagtgagtgggttgcg<br>ctccggcagcggtcctgatcaatcgtcacc<br>ctttctcggtccttcaacgttcctgacaac<br>gagcctccttttcgccaatccatcgacaat<br>caccgcgagtccctgctcgaacgctgcgtc<br>cggaccggcttcgtcgaaggcgtctatcgc<br>ggcccgcaacagcggcgagagcggagcctg<br>ttcaacggtgccgccgcgctcgccggcatc<br>gctgtcgccggcctgctcctcaagcacggc<br>cccaacagtgaagtagctgattgtcatcag<br>cgcattgacggcgtccccggccgaaaaacc<br>cgcctcgcagaggaagcgaagctgcgcgtc<br>ggccgtttccatctgcggtgcgcccggtcg<br>cgtgccggcatggatgcgcgcgccatcgcg<br>gtaggcgagcagcgcctgcctgaagctgcg<br>ggcattcccgatcagaaatgagcgccagtc<br>gtcgtcggctctcggcaccgaatgcgtatg<br>attctccgccagcatggcttcggccagtgc<br>gtcgagcagcgcccgcttgttcctgaagtg<br>ccagtaaagcgccggctgctgaacccccaa<br>ccgttccgccagtttgcgtgtcgtcagacc<br>gtctacgccgacctcgttcaacaggtccag<br>ggcggcacggatcactgtattcggctgcaa<br>ctttgtcatgcttgacactttatcactgat<br>aaacataatatgtccaccaacttatcagtg<br>ataaagaatccgcgcgttcaatcggaccag<br>cggaggctggtccggaggccagacgtgaaa<br>cccaacataccccctgatcgtaattctgagc<br>actgtcgcgctcgacgctgtcggcatcggc<br>ctgattatgccggtgctgccgggcctcctg<br>cgcgatctggttcactcgaacgacgtcacc<br>gcccactatggcattctgctggcgctgtat<br>gcgttggtgcaatttgcctgcgcacctgtg<br>ctgggcgcgctgtcggatcgtttcgggcgg<br>cggccaatcttgctcgtctcgctggccggc<br>gccagatctggggaaccctgtggttggcat<br>gcacatacaaatggacgaacggataaacct<br>tttcacgcccttttaaatatccgattattc<br>taataaacgctcttttctcttaggtttacc<br>cgccaatatatcctgtcaaacactgatagt |

TABLE 5-continued

Psilocybin Expression Vector Sequences.

| SEQ ID NO | Name | Sequence |
|---|---|---|
| | | ttaaactgaaggcgggaaacgacaatctga |
| | | tcatgagcggagaattaagggagtcacgtt |
| | | atgacccccgccgatgacgcgggacaagcc |
| | | gttttacgtttggaactgacagaaccgcaa |
| | | cgttgaaggagccactcagccgcgggtttc |
| | | tggagtttaatgagctaagcacatacgtca |
| | | gaaaccattattgcgcgttcaaaagtcgcc |
| | | taaggtcactatcagctagcaaatatttct |
| | | tgtcaaaaatgctccactgacgttccataa |
| | | attcccctcggtatccaattagagtctcat |
| | | attcactctcaatccaaataatctgcaccg |
| | | gatctggatcgtttcgcatgattgaacaag |
| | | atggattgcacgcaggttctccggccgctt |
| | | gggtggagaggctattcggctatgactggg |
| | | cacaacagacaatcggctgctctgatgccg |
| | | ccgtgttccggctgtcagcgcaggggcgcc |
| | | cggttctttttgtcaagaccgacctgtccg |
| | | gtgccctgaatgaactgcaggacgaggcag |
| | | cgcggctatcgtggctggccacgacgggcg |
| | | ttccttgcgcagctgtgctcgacgttgtca |
| | | ctgaagcgggaagggactggctgctattgg |
| | | gcgaagtgccggggcaggatctcctgtcat |
| | | ctcaccttgctcctgccgagaaagtatcca |
| | | tcatggctgatgcaatgcggcggctgcata |
| | | cgcttgatccggctacctgcccattcgacc |
| | | accaagcgaaacatcgcatcgagcgagcac |
| | | gtactcggatggaagccggtcttgtcgatc |
| | | aggatgatctggacgaagagcatcaggggc |
| | | tcgcgccagccgaactgttcgccaggctca |
| | | aggcgcgcatgcccgacggcgatgatctcg |
| | | tcgtgacccatggcgatgcctgcttgccga |
| | | atatcatggtggaaaatggccgcttttctg |
| | | gattcatcgactgtggccggctgggtgtgg |
| | | cggaccgctatcaggacatagcgttggcta |
| | | cccgtgatattgctgaagagcttggcggcg |
| | | aatgggctgaccgcttcctcgtgctttacg |
| | | gtatcgccgctcccgattcgcagcgcatcg |
| | | ccttctatcgccttcttgacgagttcttct |
| | | gagcgggactctggggttcgaaatgaccga |
| | | ccaagcgacgcccaacctgccatcacgaga |
| | | tttcgattccaccgccgccttctatgaaag |
| | | gttgggcttcggaatcgttttccgggacgc |
| | | cggctggatgatcctccagcgcggggatct |
| | | catgctggagttcttcgcccacgggatctc |
| | | tgcggaacaggcggtcgaaggtgccgatat |
| | | cattacgacagcaacggccgacaagcacaa |
| | | cgccacgatcctgagcgacaatatgatcgg |
| | | gcccggcgtccacatcaacggcgtcggcgg |
| | | cgactgcccaggcaagaccgagatgcaccg |
| | | cgatatcttgctgcgttcggatattttcgt |
| | | ggagttcccgccacagacccggatgatccc |
| | | cgatcgttcaaacatttggcaataaagttt |
| | | cttaagattgaatcctgttgccggtcttgc |
| | | gatgattatcatataatttctgttgaatta |
| | | cgttaagcatgtaataattaacatgtaatg |
| | | catgacgttatttatgagatgggtttttat |
| | | gattagagtcccgcaattatacatttaata |
| | | cgcgatagaaaacaaaatatagcgcgcaaa |
| | | ctaggataaattatcgcgcgcggtgtcatc |
| | | tatgttactagatcgggcctcctgtcaatg |
| | | ctggcggcggctctggtggtggttctggtg |
| | | gcggctctgagggtggtggctctgagggtg |
| | | gcggttctgagggtggcggctctgagggag |
| | | gcggttccggtggtggctctggttccggtg |
| | | attttgattatgaaaagatggcaaacgcta |
| | | ataagggggctatgaccgaaaatgccgatg |
| | | aaaacgcgctacagtctgacgctaaaggca |
| | | aacttgattctgtcgctactgattacggtg |
| | | ctgctatcgatggtttcattggtgacgttt |
| | | ccggccttgctaatggtaatggtgctactg |
| | | gtgattttgctggctctaattcccaaatgg |
| | | ctcaagtcggtgacggtgataattcacctt |
| | | taatgaataatttccgtcaatatttacctt |
| | | ccctccctcaatcggttgaatgtcgccctt |
| | | ttgtctttggcccaatacgcaaaccgcctc |
| | | tccccgcgcgttggccgattcattaatgca |
| | | gctggcacgacaggtttcccgactggaaag |
| | | cgggcagtgagcgcaacgcaattaatgtga |
| | | gttagctcactcattaggcaccccaggctt |
| | | tacactttatgcttccggctcgtatgttgt |
| | | gtggaattgtgagcggataacaatttcaca |
| | | caggaaacagctatgaccatgattacgcca |
| | | agcttgcatgcctgcaggtccccagattag |
| | | ccttttcaatttcagaaagaatgctaaccc |
| | | acagatggttagagaggcttacgcagcagg |
| | | tctcatcaagacgatctacccgagcaataa |
| | | tctccaggaaatcaaataccttcccaagaa |
| | | ggttaaagatgcagtcaaaagattcaggac |
| | | taactgcatcaagaacacagagaaagatat |
| | | atttctcaagatcagaagtactattccagt |
| | | atggacgattcaaggcttgcttcacaaacc |
| | | aaggcaagtaatagagattggagtctctaa |
| | | aaaggtagttcccactgaatcaaaggccat |
| | | ggagtcaaagattcaaatagaggacctaac |
| | | agaactcgccgtaaagactggcgaacagtt |
| | | catacagagtctcttacgactcaatgacaa |
| | | gaagaaaatcttcgtcaacatggtggagca |
| | | cgacacacttgtctactccaaaaatatcaa |
| | | agatacagtctcagaagaccaaagggcaat |
| | | tgagacttttcaacaaagggtaatatccgg |
| | | aaacctcctcggattccattgcccagctat |
| | | ctgtcactttattgtgaagatagtggaaaa |
| | | ggaaggtggctcctacaaatgccatcattg |
| | | cgataaaggaaaggccatcgttgaagatgc |
| | | ctctgccgacagtggtcccaaagatggacc |
| | | cccacccacgaggagcatcgtggaaaaaga |
| | | agacgttccaaccacgtcttcaaagcaagt |
| | | ggattgatgtgatatctccactgacgtaag |
| | | ggatgacgcacaatcccactatccttcgca |
| | | agacccttcctctatataaggaagttcatt |
| | | tcatttggagagaacacgggggactctaat |
| | | caaacaagtttgtacaaaaaagctgaacga |
| | | gaaacgtaaaatgatataaatatcatgatc |
| | | gctgtactattctccttcgtcattgcagga |
| | | tgcatatactacatcgtttctcgtagagtg |
| | | aggcggtcgcgcttgccaccagggccgcct |
| | | ggcattcctattcccttcattgggaacatg |
| | | tttgatatgcctgaagaatctccatggtta |
| | | acatttctacaatggggacgggattacagt |
| | | ctgtcttgccgcgttgacttctaatatatg |
| | | aacagctaatatattgtcagacaccgatat |
| | | tctctacgtggatgctggagggacagaaat |
| | | ggttattcttaacacgttggagaccattac |
| | | cgatctattagaaaagcgagggtccattta |
| | | ttctggccggtgagctgatgttgagttttt |
| | | tgcaattgaatttgtggtcacacgtttcca |
| | | gacttgagagtacaatggtcaacgaactta |
| | | tggggtgggagtttgacttagggttcatca |
| | | catacggcgacaggtggcgcgaagaaaggc |
| | | gcatgttcgccaaggagttcagtgagaagg |
| | | gcatcaagcaatttcgccatgctcaagtga |
| | | aagctgcccatcagcttgtccaacagctta |
| | | ccaaaacgccagaccgctgggcacaacata |
| | | ttcgccagtaagtactacttgaggaaaata |
| | | gcgtacgcttcgctgaccggtccgtacatc |
| | | aaagtcagatagcggcaatgtcactggata |
| | | ttggttatggaattgatcttgcagaagacg |
| | | acccttggctggaagcgacccatttggcta |
| | | atgaaggcctcgccatagcatcagtgccgg |
| | | gcaaattttgggtcgattcgttcccttctc |
| | | gtgagcatccttcttctatgtaggaaggga |
| | | aggagtctaacaagtgttagtaaaatacct |
| | | tcctgcttggttcccaggtgctgtcttcaa |
| | | gcgcaaagcgaaggtctggcgagaagccgc |
| | | cgaccatatggttgacatgccttatgaaac |
| | | tatgaggaaattagcagttagtcaaatgcg |
| | | ttctccccgtatttttcaatactctaact |
| | | tcagctcacagcctcaggattgactcgtc |

TABLE 5-continued

Psilocybin Expression Vector Sequences.

| SEQ ID NO | Name | Sequence |
|---|---|---|
| | | cgtcgtatgcttcagctcgtctgcaagcca |
| | | tggatctcaacggtgaccttgagcatcaag |
| | | aacacgtaatcaagaacacagccgcagagg |
| | | ttaatgtcggtaagtcaaaagcgtccgtcg |
| | | gcaattcaaaattcaggcgctaaagtgggt |
| | | cttctcaccaaggtggaggcgatactgtaa |
| | | ggatttctcaatcgttagagtataagtgtt |
| | | ctaatgcagtacatactccaccaaccagac |
| | | tgtctctgctatgtctgcgttcatcttggc |
| | | catggtgaagtaccctgaggtccagcgaaa |
| | | ggttcaagcggagcttgatgctctgaccaa |
| | | taacggccaaattcctgactatgacgaaga |
| | | agatgactccttgccatacctcaccgcatg |
| | | tatcaaggagcttttccggtggaatcaaat |
| | | cgcacccctcgctataccgcacaaattaat |
| | | gaaggacgacgtgtaccgcgggtatctgat |
| | | tcccaagaacactctagtcttcgcaaacac |
| | | ctggtgaggctgtccattcattcctagtac |
| | | atccgttgccccactaatagcatcttgata |
| | | acagggcagtattaaacgatccagaagtct |
| | | atccagatccctctgtgttccgcccagaaa |
| | | gatatcttggtcctgacgggaagcctgata |
| | | acactgtacgcgacccacgtaaagcggcat |
| | | ttggctatggacgacgaaattggtaagtgc |
| | | gctttcagaaccccccttccgttgactag |
| | | tgccatgcgcgcatacaatatcgctattga |
| | | tctgatataacttccctgcggcatttattt |
| | | tggcattcctttagtcccggaattcatcta |
| | | gcgcagtcgacggtttggattgcaggggca |
| | | accctcttatcagcgttcaatatcgagcga |
| | | cctgtcgatcagaatgggaagcccattgac |
| | | ataccggctgattttactacaggattcttc |
| | | aggtagctaatttccgtctttgtgtgcata |
| | | ataccccctaacgacgcacgtttaccttttt |
| | | gtaaagacacccagtgcctttccagtgcag |
| | | gtttgttcctcgaacagagcaagtctcaca |
| | | gtcggtatccggaccctgaatatcatttta |
| | | cgtttctcgttcagctttcttgtacaaagt |
| | | ggttcgatctagaggatccatggtgagcaa |
| | | gggcgaggagctgttcaccggggtggtgcc |
| | | catcctggtcgagctggacggcgacgtgaa |
| | | cggccacaagttcagcgtgtccggcgaggg |
| | | cgagggcgatgccacctacggcaagctgac |
| | | cctgaagttcatctgcaccaccggcaagct |
| | | gcccgtgccctggcccaccctcgtgaccac |
| | | cttcacctacggcgtgcagtgcttcagccg |
| | | ctaccccgaccacatgaagcagcacgactt |
| | | cttcaagtccgccatgcccgaaggctacgt |
| | | ccaggagcgcaccatcttcttcaaggacga |
| | | cggcaactacaagacccgcgccgaggtgaa |
| | | gttcgagggcgacaccctggtgaaccgcat |
| | | cgagctgaagggcatcgacttcaaggagga |
| | | cggcaacatcctggggcacaagctggagta |
| | | caactacaacagccacaacgtctatatcat |
| | | ggccgacaagcagaagaacggcatcaaggt |
| | | gaacttcaagatccgccacaacatcgagga |
| | | cggcagcgtgcagctcgccgaccactacca |
| | | gcagaacacccccatcggcgacggccccgt |
| | | gctgctgcccgacaaccactacctgagcac |
| | | ccagtccgccctgagcaaagaccccaacga |
| | | gaagcgcgatcacatggtcctgctggagtt |
| | | cgtgaccgccgccgggatcactcacggcat |
| | | ggacgagctgtacaagtaaagcggcccgag |
| | | ctcgaatttccccgatcgttcaaacatttg |
| | | gcaataaagtttcttaagattgaatcctgt |
| | | tgccggtcttgcgatgattatcatataatt |
| | | tctgttgaattacgttaagcatgtaataat |
| | | taacatgtaatgcatgacgttatttatgag |
| | | atgggtttttatgattagagtcccgcaatt |
| | | atacatttaatacgcgatagaaaacaaaat |
| | | atagcgcgcaaactaggataaattatcgcg |
| | | cgcggtgtcatctatgttactagatcggga |
| | | attagcttcatcaacgcaagacatgcgcac |
| | | gaccgtctgacaggagaggaatttccgacg |
| | | agcacagaaaggacttgctcttggacgtag |
| | | gcctatttctcaggcacatgtatcaagtgt |
| | | tcggacgtgggttttcgatggtgtatcagc |
| | | cgccgccaactgggagatgaggaggctttc |
| | | ttgggggcagtcagcagttcatttcacaa |
| | | gacagaggaacttgtaaggagatgcactga |
| | | tttatcttggcgcaaaccagcaggacgaat |
| | | tagtgggaatagcccgcgaatatctaagtt |
| | | atgcctgtcggcatgagcagaaacttccaa |
| | | ttcgaaacagtttggagaggttgtttttgg |
| | | gcatacctttttgttagtcagcctctcgatt |
| | | gctcatcgtcattacacagtaccgaagttt |
| | | gatcgatctagtaacatagatgacaccgcg |
| | | cgcgataatttatcctagtttgcgcgctat |
| | | attttgttttctatcgcgtattaaatgtat |
| | | aattgcgggactctaatcataaaaacccat |
| | | ctcataaataacgtcatgcattacatgtta |
| | | attattacatgcttaacgtaattcaacaga |
| | | aattatatgataatcatcgcaagaccggca |
| | | acaggattcaatcttaagaaactttattgc |
| | | caaatgtttgaacgatctgcttcgacgcac |
| | | tccttctttactccaccatctcgtccttat |
| | | tgaaaacgtgggtagcaccaaaacgaatca |
| | | agtcgctggaactgaagttaccaatcacgc |
| | | tggatgatttgccagttggattaatcttgc |
| | | ctttccccgcatgaataatattgatgaatg |
| | | catgcgtgaggggtatttcgattttggcaa |
| | | tagctgcaattgccgcgacatcctccaacg |
| | | agcataattcttcagaaaaatagcgatgtt |
| | | ccatgttgtcagggcatgcatgatgcacgt |
| | | tatgaggtgacggtgctaggcagtattccc |
| | | tcaaagtttcatagtcagtatcatattcat |
| | | cattgcattcctgcaagagagaattgagac |
| | | gcaatccacacgctgcggcaaccttccggc |
| | | gttcgtggtctatttgctcttggacgttgc |
| | | aaacgtaagtgttggatcccggtcggcatc |
| | | tactctattcctttgccctcggacgagtgc |
| | | tggggcgtcggtttccactatcggcgagta |
| | | cttctacacagccatcggtccagacggccg |
| | | cgcttctgcgggcgatttgtgtacgcccga |
| | | cagtcccggctccggatcggacgattgcgt |
| | | cgcatcgaccctgcgcccaagctgcatcat |
| | | cgaaattgccgtcaaccaagctctgataga |
| | | gttggtcaagaccaatgcggagcatatacg |
| | | cccggagccgcggcgatcctgcaagctccg |
| | | gatgcctccgctcgaagtagcgcgtctgct |
| | | gctccatacaagccaaccacggcctccaga |
| | | agaagatgttggcgacctcgtattgggaat |
| | | ccccgaacatcgcctcgctccagtcaatga |
| | | ccgctgttatgcggccattgtccgtcagga |
| | | cattgttggagccgaaatccgcgtgcacga |
| | | ggtgccggacttcggggcagtcctcggccc |
| | | aaagcatcagctcatcgagagcctgcgcga |
| | | cggacgcactgacggtgtcgtccatcacag |
| | | tttgccagtgatacacatggggatcagcaa |
| | | tcgcgcatatgaaatcacgccatgtagtgt |
| | | attgaccgattccttgcggtccgaatgggc |
| | | cgaacccgctcgtctggctaagatcggccg |
| | | cagcgatcgcatccatggcctccgcgaccg |
| | | gctgcagaacagcgggcagttcggtttcag |
| | | gcaggtcttgcaacgtgacaccctgtgcac |
| | | ggcgggagatgcaataggtcaggctctcgc |
| | | tgaattccccaatgtcaagcacttccggaa |
| | | tcgggagcgcggccgatgcaaagtgccgat |
| | | aaacataacgatctttgtagaaaccatcgg |
| | | cgcagctatttacccgcaggacatatccac |
| | | gccctcctacatcgaagctgaaagcacgag |
| | | attcttcgccctccgagagctgcatcaggt |
| | | cggagacgctgtcgaacttttcgatcagaa |
| | | acttctcgacagacgtcgcggtgagttcag |
| | | gctttttcatatcggggtcgtcctctccaa |
| | | atgaaatgaacttccttatatagaggaagg |
| | | gtcttgcgaaggatagtgggattgtgcgtc |
| | | atcccttacgtcagtggagatatcacatca |

TABLE 5-continued

Psilocybin Expression Vector Sequences.

| SEQ ID NO | Name | Sequence |
| --- | --- | --- |
| | | atccacttgctttgaagacgtggttggaac<br>gtcttctttttccacgatgctcctcgtggg<br>tgggggtccatctttgggaccactgtcggc<br>agaggcatcttgaacgatagcctttccttt<br>atcgcaatgatggcatttgtaggtgccacc<br>ttccttttctactgtccttttgatgaagtg<br>acagatagctgggcaatggaatccgaggag<br>gtttcccgatattaccctttgttgaaaagt<br>ctcaatagccctttggtcttctgagactgt<br>atctttgatattcttggagtagacgagagt<br>gtcgtgctccaccatgttgacggatctcta<br>ggacgcgtcctagaagctaattcactggcc<br>gtcgttttacaacgtcgtgactgggaaaac<br>cctggcgttacccaacttaatcgccttgca<br>gcacatccccctttcgccagctggcgtaat<br>agcgaagaggcccgcaccgatcgcccttcc<br>caacagttgcgcagcctgaatggcgcccgc<br>tcctttcgctttcttcccttcctttctcgc<br>cacgttcgccggctttccccgtcaagctct<br>aaatcgggggctccctttagggttccgatt<br>tagtgctttacggcacctcgaccccaaaaa<br>acttgatttgggtgatggttcacgtagtgg<br>gccatcgccctgatagacggtttttcgccc<br>tttgacgttggagtccacgttctttaatag<br>tggactcttgttccaaactggaacaacact<br>caaccctatctcgggctattcttttgattt<br>ataagggattttgccgatttcggaaccacc<br>atcaaacaggattttcgcctgctggggcaa<br>accagcgtggaccgcttgctgcaactctct<br>cagggccaggcggtgaagggcaatcagctg<br>ttgcccgtctcactggtgaaaagaaaaacc<br>accccagtacattaaaaacgtccgcaatgt<br>gttattaagttgtctaagcgtcaatttgtt<br>tacaccacaatatatcctgccaccagccag<br>ccaacagctccccgaccggcagctcggcac<br>aaaatcaccactcgatacaggcagcccatc<br>agtccgggacggcgtcagcgggagagccgt<br>tgtaaggcggcagactttgctcatgttacc<br>gatgctattcggaagaacggcaactaagct<br>gccgggtttgaaacacggatgatctcgcgg<br>agggtagcatgttgattgtaacgatgacag<br>agcgttgctgcctgtgatcaaatatcatct<br>ccctcgcagagatccgaattatcagccttc<br>ttattcatttctcgcttaaccgtgacaggc<br>tgtcgatcttgagaactatgccgacataat<br>aggaaatcgctggataaagccgctgaggaa<br>gctgagtggcgctatttctttagaagtgaa<br>cgttgacgatatcaactcccctatccattg<br>ctcaccgaatggtacaggtcggggacccga<br>agttccgactgtcggcctgatgcatccccg<br>gctgatcgaccccagatctggggctgagaa<br>agcccagtaaggaaacaactgtaggttcga<br>gtcgcgagatcccccggaaccaaaggaagt<br>aggttaaacccgctccgatcaggccgagcc<br>acgccaggccgagaacattggttcctgtag<br>gcatcgggattggcggatcaaacactaaag<br>ctactggaacgagcagaagtcctccggccg<br>ccagttgccaggcggtaaaggtgagcagag<br>gcacgggaggttgccacttgcgggtcagca<br>cggttccgaacgccatggaaaccgcccccg<br>ccaggcccgctgcgacgccgacaggatcta<br>gcgctgcgtttggtgtcaacaccaacagcg<br>ccacgcccgcagttccgcaaatagccccca<br>ggaccgccatcaatcgtatcgggctaccta<br>gcagagcggcagagatgaacacgaccatca<br>gcggctgcacagcgcctaccgtcgccgcga<br>ccccgcccggcaggcggtagaccgaaataa<br>acaacaagctccagaatagcgaaatattaa<br>gtgcgccgaggatgaagatgcgcatccacc<br>agattcccgttggaatctgtcggacgatca<br>tcacgagcaataaacccgccggcaacgccc<br>gcagcagcataccggcgacccctcggcctc<br>gctgttcgggctccacgaaaacgccggaca<br>gatgcgccttgtgagcgtccttggggccgt |

TABLE 5-continued

Psilocybin Expression Vector Sequences.

| SEQ ID NO | Name | Sequence |
| --- | --- | --- |
| | | cctcctgtttgaagaccgacagcccaatga<br>tctcgccgtcgatgtaggcgccgaatgcca<br>cggcatctcgcaaccgttcagcgaacgcct<br>ccatgggctttttctcctcgtgctcgtaaa<br>cggacccgaacatctctggagctttcttca<br>gggccgacaatcggatctcgcggaaatcct<br>gcacgtcggccgctccaagccgtcgaatct<br>gagccttaatcacaattgtcaattttaatc<br>ctctgtttatcggcagttcgtagagcgcgc<br>cgtgcgtcccgagcgatactgagcgaagca<br>agtgcgtcgagcagtgcccgcttgttcctg<br>aaatgccagtaaagcgctggctgctgaacc<br>cccagccggaactgaccccacaaggcccta<br>gcgtttgcaatgcaccaggtcatcattgac<br>ccaggcgtgttccaccaggccgctgcctcg<br>caactcttcgcaggcttcgccgacctgctc<br>gcgccacttcttcacgcgggtggaatccga<br>tccgcacatgaggcggaaggtttccagctt<br>gagcgggtacggctcccggtgcgagctgaa<br>atagtcgaacatccgtcgggccgtcggcga<br>cagcttgcggtacttctcccatatgaattt<br>cgtgtagtggtcgccagcaaacagcacgac<br>gatttcctcgtcgatcaggacctggcaacg<br>ggacgttttcttgccacggtccaggacgcg<br>gaagcggtgcagcagcgacaccgattccag<br>gtgcccaacgcggtcggacgtgaagcccat<br>cgccgtcgcctgtaggcgcgacaggcattc<br>ctcggccttcgtgtaataccggccattgat<br>cgaccagcccaggtcctggcaaagctcgta<br>gaacgtgaaggtgatcggctcgccgatagg<br>ggtgcgcttcgcgtactccaacacctgctg<br>ccacaccagttcgtcatcgtcggcccgcag<br>ctcgacgccggtgtaggtgatcttcacgtc<br>cttgttgacgtggaaaatgaccttgttttg<br>cagcgcctcgcgcgggattttcttgttgcg<br>cgtggtgaacagggcagagcggccgtgtc<br>gtttggcatcgctcgcatcgtgtccggcca<br>cggcgcaatatcgaacaaggaaagctgcat<br>ttccttgatctgctgcttcgtgtgtttcag<br>caacgcggcctgcttggcctcgctgacctg<br>ttttgccaggtcctcgccggcggtttttcg<br>cttcttggtcgtcatagttcctcgcgtgtc<br>gatggtcatcgacttcgccaaacctgccgc<br>ctcctgttcgagacgacgcgaacgctccac<br>ggcggccgatggcgcgggcagggcaggggg<br>agccagttgcacgctgtcgcgctcgatctt<br>ggccgtagcttgctggaccatcgagccgac<br>ggactggaaggtttcgcggggcgcacgcat<br>gacggtgcggcttgcgatggtttcggcatc<br>ctcggcggaaaaccccgcgtcgatcagttc<br>ttgcctgtatgccttccggtcaaacgtccg<br>attcattcaccctccttgcgggattgcccc<br>gactcacgccggggcaatgtgcccttattc<br>ctgatttgacccgcctggtgccttggtgtc<br>cagataatccaccttatcggcaatgaagtc<br>ggtcccgtagaccgtctggccgtccttctc<br>gtacttggtattccgaatcttgccctgcac<br>gaataccagcgaccccttgcccaaatactt<br>gccgtgggcctcggcctgagagccaaaaca<br>cttgatgcggaagaagtcggtgcgctcctg<br>cttgtcgccggcatcgttgcgccacatcta<br>ggtactaaaacaattcatccagtaaaatat<br>aatattttattttctcccaatcaggcttga<br>tccccagtaagtcaaaaaatagctcgacat<br>actgttcttccccgatatcctccctgatcg<br>accggacgcagaaggcaatgtcataccact<br>tgtccgccctgccgcttctcccaagatcaa<br>taaagccacttactttgccatctttcacaa<br>agatgttgctgtctcccaggtcgccgtggg<br>aaaagacaagttcctcttcgggcttttccg<br>tctttaaaaaatcatacagctcgcgcggat<br>ctttaaatggagtgtcttcttcccagtttt<br>cgcaatccacatcggccagatcgttattca<br>gtaagtaatccaattcggctaagcggctgt |

TABLE 5-continued

Psilocybin Expression Vector Sequences.

| SEQ ID NO | Name | Sequence |
| --- | --- | --- |
| | | ctaagctattcgtatagggacaatccgata<br>tgtcgatggagtgaaagagcctgatgcact<br>ccgcatacagctcgataatcttttcagggc<br>tttgttcatcttcatactcttccgagcaaa<br>ggacgccatcggcctcactcatgagcagat<br>tgctccagccatcatgccgttcaaagtgca<br>ggacctttggaacaggcagctttccttcca<br>gccatagcatcatgtccttttcccgttcca<br>catcataggtggtccctttataccggctgt<br>ccgtcatttttaaatataggttttcatttt<br>ctcccaccagcttatataccttagcaggag<br>acattccttccgtatcttttacgcagcggt<br>atttttcgatcagttttttcaattccggtg<br>atattctcattttagccatttattatttcc<br>ttcctcttttctacagtatttaaagatacc<br>ccaagaagctaattataacaagacgaactc<br>caattcactgttccttgcattctaaaacct<br>taaataccagaaaacagctttttcaaagtt<br>gttttcaaagttggcgtataacatagtatc<br>gacggagccgattttgaaaccacaattatg<br>ggtgatgctgccaacttactgatttagtgt<br>atgatggtgtttttgaggtgctccagtggc<br>ttctgtgtctatcagctgtccctcctgttc<br>agctactgacggggtggtgcgtaacggcaa<br>aagcaccgccggacatcagcgctatctctg<br>ctctcactgccgtaaaacatggcaactgca<br>gttcacttacaccgcttctcaacccggtac<br>gcaccagaaaatcattgatatggccatgaa<br>tggcgttggatgccgggcaacagcccgcat<br>tatgggcgttggcctcaacacgattttacg<br>tcacttaaaaaactcaggccgcagtcggta<br>acctcgcgcatacagccgggcagtgacgtc<br>atcgtctgcgcggaaatggacgaacagtgg<br>ggctatgtcggggctaaatcgcgccagcgc<br>tggctgttttacgcgtatgacagtctccgg<br>aagacggttgttgcgcacgtattcggtgaa<br>cgcactatggcgacgctggggcgtcttatg<br>agcctgctgtcaccctttgacgtggtgata<br>tggatgacggatggctggccgctgtatgaa<br>tcccgcctgaagggaaagctgcacgtaatc<br>agcaagcgatatacgcagcgaattgagcgg<br>cataacctgaatctgaggcagcacctggca<br>cggctgggacggaagtcgctgtcgttctca<br>aaatcggtggagctgcatgacaaagtcatc<br>gggcattatctgaacataaaacactatcaa<br>taagttggagtcattacccaattatgatag<br>aatttacaagctataaggttattgtcctgg<br>gtttcaagcattagtccatgcaagtttta<br>tgctttgcccattctatagatatattgata<br>agcgcgctgcctatgccttgccccctgaaa<br>tccttacatacggcgatatcttctatataa<br>aagatatattatcttatcagtattgtcaat<br>atattcaaggcaatctgcctcctcatcctc<br>ttcatcctcttcgtcttggtagctttttaa<br>atatggcgcttcatagagtaattctgtaaa<br>ggtccaattctcgttttcatacctcggtat<br>aatcttacctatcacctcaaatggttcgct<br>gggtttatcgcacccccgaacacgagcacg<br>gcacccgcgaccactatgccaagaatgccc<br>aaggtaaaaattgccggccccgccatgaag<br>tccgtgaatgccccgacggccgaagtgaag<br>ggcaggccgccacccaggccgccgccctca<br>ctgcccggcacctggtcgctgaatgtcgat<br>gccagcacctgcggcacgtcaatgcttccg<br>ggcgtcgcgctcgggctgatcgcccatccc<br>gttactgccccgatcccggcaatggcaagg<br>actgccagcgctgccatttttggggtgagg<br>ccgttcgcggccgaggggcgcagcccctgg<br>ggggatgggaggcccgcgttagcgggccgg<br>gagggttcgagaagggggggcacccccctt<br>cggcgtgcgcggtcacgcgcacagggcgca<br>gccctggttaaaaacaaggtttataaatat<br>tggtttaaaagcaggttaaaagacaggtta<br>gcggtggccgaaaaacgggcggaaaccctt |

TABLE 5-continued

Psilocybin Expression Vector Sequences.

| SEQ ID NO | Name | Sequence |
| --- | --- | --- |
| | | gcaaatgctggattttctgcctgtggacag<br>cccctcaaatgtcaataggtgcgcccctca<br>tctgtcagcactctgcccctcaagtgtcaa<br>ggatcgcgcccctcatctgtcagtagtcgc<br>gcccctcaagtgtcaataccgcagggcact<br>tatccccaggcttgtccacatcatctgtgg<br>gaaactcgcgtaaaatcaggcgttttcgcc<br>gatttgcgaggctggccagctccacgtcgc<br>cggccgaaatcgagcctgcccctcatctgt<br>caacgccgcgccgggtgagtcggcccctca<br>agtgtcaacgtccgcccctcatctgtcagt<br>gagggccaagttttccgcgaggtatccaca<br>acgccggcggccgcggtgtctcgcacacgg<br>cttcgacggcgtttctggcgcgtttgcagg<br>gccatagacggccgccagcccagcggcgag<br>ggcaaccagcccgg |
| 18 | pGWB5:<br>35S:<br>PsiDcds:<br>stop | tgagcgtcgcaaaggcgctcggtcttgcct<br>tgctcgtcggtgatgtacttcaccagctcc<br>gcgaagtcgctcttcttgatggagcgcatg<br>gggacgtgcttggcaatcacgcgcaccccc<br>cggccgttttagcggctaaaaaagtcatgg<br>ctctgccctcgggcggaccacgcccatcat<br>gaccttgccaagctcgtcctgcttctcttc<br>gatcttcgccagcagggcgaggatcgtggc<br>atcaccgaaccgcgccgtgcgcgggtcgtc<br>ggtgagccagagtttcagcaggccgcccag<br>gcggcccaggtcgccattgatgcgggccag<br>ctcgcggacgtgctcatagtccacgacgcc<br>cgtgattttgtagccctggccgacggccag<br>caggtaggccgacaggctcatgccggccgc<br>cgccgccttttcctcaatcgctcttcgttc<br>gtctggaaggcagtacaccttgataggtgg<br>gctgcccttcctggttggcttggtttcatc<br>agccatccgcttgccctcatctgttacgcc<br>ggcggtagccggccagcctcgcagagcagg<br>attcccgttgagcaccgccaggtgcgaata<br>agggacagtgaagaaggaacacccgctcgc<br>gggtgggcctacttcacctatcctgcccgg<br>ctgacgccgttggatacaccaaggaaagtc<br>tacacgaaccctttggcaaaatcctgtata<br>tcgtgcgaaaaaggatggatataccgaaaa<br>aatcgctataatgaccccgaagcagggtta<br>tgcagcggaaaagcgccacgcttcccgaag<br>ggagaaaggcggacaggtatccggtaagcg<br>gcagggtcggaacaggagagcgcacgaggg<br>agcttccagggggaaacgcctggtatcttt<br>atagtcctgtcgggtttcgccacctctgac<br>ttgagcgtcgatttttgtgatgctcgtcag<br>gggggcggagcctatggaaaaacgccagca<br>acgcggcctttttacggttcctggcctttt<br>gctggccttttgctcacatgttctttcctg<br>cgttatcccctgattctgtggataaccgta<br>ttaccgcctttgagtgagctgataccgctc<br>gccgcagccgaacgaccgagcgcagcgagt<br>cagtgagcgaggaagcggaagagcgccaga<br>aggccgccagagaggccgagcgcggccgtg<br>aggcttggacgctagggcagggcatgaaaa<br>agcccgtagcgggctgctacgggcgtctga<br>cgcggtggaaagggggaggggatgttgtct<br>acatggctctgctgtagtgagtgggttgcg<br>ctccggcagcggtcctgatcaatcgtcacc<br>ctttctcggtccttcaacgttcctgacaac<br>gagcctccttttcgccaatccatcgacaat<br>caccgcgagtccctgctcgaacgctgcgtc<br>cggaccggcttcgtcgaaggcgtctatcgc<br>ggcccgcaacagcggcgagagcggagcctg<br>ttcaacggtgccgccgcgctcgccggcatc<br>gctgtcgccggcctgctcctcaagcacggc<br>cccaacagtgaagtagctgattgtcatcag<br>cgcattgacggcgtccccggccgaaaaacc<br>cgcctcgcagaggaagcgaagctgcgcgtc<br>ggccgtttccatctgcggtgcgcccggtcg<br>cgtgccggcatggatgcgcgcgccatcgcg |

TABLE 5-continued

Psilocybin Expression Vector Sequences.

| SEQ ID NO | Name | Sequence |
|---|---|---|
| | | gtaggcgagcagcgcctgcctgaagctgcg ggcattcccgatcagaaatgagcgccagtc gtcgtcggctctcggcaccgaatgcgtatg attctccgccagcatggcttcggccagtgc gtcgagcagcgcccgcttgttcctgaagtg ccagtaaagcgccggctgctgaacccccaa ccgttccgccagtttgcgtgtcgtcagacc gtctacgccgacctcgttcaacaggtccag ggcggcacggatcactgtattcggctgcaa ctttgtcatgcttgacactttatcactgat aaacataatatgtccaccaacttatcagtg ataaagaatccgcgcgttcaatcggaccag cggaggctggtccggaggccagacgtgaaa cccaacatacccctgatcgtaattctgagc actgtcgcgctcgacgctgtcggcatcggc ctgattatgccggtgctgccgggcctcctg cgcgatctggttcactcgaacgacgtcacc gcccactatggcattctgctggcgctgtat gcgttggtgcaatttgcctgcgcacctgtg ctgggcgcgctgtcggatcgtttcgggcgg cggccaatcttgctcgtctcgctggccggc gccagatctggggaaccctgtggttggcat gcacatacaaatggacgaacggataaacct tttcacgcccttttaaatatccgattattc taataaacgctcttttctcttaggtttacc cgccaatatatcctgtcaaacactgatagt ttaaactgaaggcgggaaacgacaatctga tcatgagcggagaattaagggagtcacgtt atgacccccgccgatgacgcgggacaagcc gttttacgtttggaactgacagaaccgcaa cgttgaaggagccactcagccgcgggtttc tggagtttaatgagctaagcacatacgtca gaaaccattattgcgcgttcaaaagtcgcc taaggtcactatcagctagcaaatatttct tgtcaaaaatgctccactgacgttccataa attcccctcggtatccaattagagtctcat attcactctcaatccaaataatctgcaccg gatctggatcgtttcgcatgattgaacaag atggattgcacgcaggttctccggccgctt gggtggagaggctattcggctatgactggg cacaacagacaatcggctgctctgatgccg ccgtgttccggctgtcagcgcaggggcgcc cggttctttttgtcaagaccgacctgtccg gtgccctgaatgaactgcaggacgaggcag cgcggctatcgtggctggccacgacgggcg ttccttgcgcagctgtgctcgacgttgtca ctgaagcgggaagggactggctgctattgg gcgaagtgccggggcaggatctcctgtcat ctcaccttgctcctgccgagaaagtatcca tcatggctgatgcaatgcggcggctgcata cgcttgatccggctacctgcccattcgacc accaagcgaaacatcgcatcgagcgagcac gtactcggatggaagccggtcttgtcgatc aggatgatctggacgaagagcatcaggggc tcgcgccagccgaactgttcgccaggctca aggcgcgcatgcccgacggcgatgatctcg tcgtgacccatggcgatgcctgcttgccga atatcatggtggaaaatggccgcttttctg gattcatcgactgtggccggctgggtgtgg cggaccgctatcaggacatagcgttggcta cccgtgatattgctgaagagcttggcggcg aatgggctgaccgcttcctcgtgctttacg gtatcgccgctcccgattcgcagcgcatcg ccttctatcgccttcttgacgagttcttct gagcgggactctggggttcgaaatgaccga ccaagcgacgcccaacctgccatcacgaga tttcgattccaccgccgccttctatgaaag gttgggcttcggaatcgttttccgggacgc cggctggatgatcctccagcgcggggatct catgctggagttcttcgcccacgggatctc tgcggaacaggcggtcgaaggtgccgatat cattacgacagcaacggccgacaagcacaa cgccacgatcctgagcgacaatatgatcgg gcccggcgtccacatcaacggcgtcggcgg |
| | | cgactgcccaggcaagaccgagatgcaccg cgatatcttgctgcgttcggatattttcgt ggagttcccgccacagacccggatgatccc cgatcgttcaaacatttggcaataaagttt cttaagattgaatcctgttgccggtcttgc gatgattatcatataatttctgttgaatta cgttaagcatgtaataattaacatgtaatg catgacgttatttatgagatgggtttttat gattagagtcccgcaattatacatttaata cgcgatagaaaacaaaatatagcgcgcaaa ctaggataaattatcgcgcgcggtgtcatc tatgttactagatcgggcctcctgtcaatg ctggcggcggctctggtggtggttctggtg gcggctctgagggtggtggctctgagggtg gcggttctgagggtggcggctctgagggag gcggttccggtggtggctctggttccggtg atttgattatgaaaagatggcaaacgcta ataagggggctatgaccgaaaatgccgatg aaaacgcgctacagtctgacgctaaaggca aacttgattctgtcgctactgattacggtg ctgctatcgatggtttcattggtgacgttt ccggccttgctaatggtaatggtgctactg gtgattttgctggctctaattcccaaatgg ctcaagtcggtgacggtgataattcacctt taatgaataatttccgtcaatatttacctt ccctccctcaatcggttgaatgtcgccctt ttgtctttggcccaatacgcaaaccgcctc tccccgcgcgttggccgattcattaatgca gctggcacgacaggtttcccgactggaaag cgggcagtgagcgcaacgcaattaatgtga gttagctcactcattaggcaccccaggctt tacactttatgcttccggctcgtatgttgt gtggaattgtgagcggataacaatttcaca caggaaacagctatgaccatgattacgcca agcttgcatgcctgcaggtccccagattag ccttttcaatttcagaaagaatgctaaccc acagatggttagagaggcttacgcagcagg tctcatcaagacgatctacccgagcaataa tctccaggaaatcaaataccttcccaagaa ggttaaagatgcagtcaaaagattcaggac taactgcatcaagaacacagagaaagatat atttctcaagatcagaagtactattccagt atggacgattcaaggcttgcttcacaaacc aaggcaagtaatagagattggagtctctaa aaaggtagttcccactgaatcaaaggccat ggagtcaaagattcaaatagaggacctaac agaactcgccgtaaagactggcgaacagtt catacagagtctcttacgactcaatgacaa gaagaaaatcttcgtcaacatggtggagca cgacacacttgtctactccaaaaatatcaa agatacagtctcagaagaccaaagggcaat tgagacttttcaacaaagggtaatatccgg aaacctcctcggattccattgcccagctat ctgtcactttattgtgaagatagtggaaaa ggaaggtggctcctacaaatgccatcattg cgataaaggaaaggccatcgttgaagatgc ctctgccgacagtggtcccaaagatggacc cccacccacgaggagcatcgtggaaaaaga agacgttccaaccacgtcttcaaagcaagt ggattgatgtgatatctccactgacgtaag ggatgacgcacaatcccactatccttcgca agacccttcctctatataaggaagttcatt tcatttggagagaacacgggggactctaat caaacaagtttgtacaaaaaagctgaacga gaaacgtaaaatgatataaatatgcaggtg atacccgcgtgcaactcggcagcaataaga tcactatgtcctactcccgagtcttttaga aacatgggatggctctctgtcagcgatgcg gtctacagcgagttcataggagagttggct acccgcgcttccaatcgaaattactccaac gagttcggcctcatgcaacctatccaggaa ttcaaggctttcattgaaagcgacccggtg gtgcaccaagaatttattgacatgttcgag ggcattcaggactctccaaggaattatcag |

TABLE 5-continued

Psilocybin Expression Vector Sequences.

| SEQ ID NO | Name | Sequence |
|---|---|---|
| | | gaactatgtaatatgttcaacgatatcttt |
| | | cgcaaagctcccgtctacggagaccttggc |
| | | cctcccgtttatatgattatggccaaatta |
| | | atgaacacccgagcgggcttctctgcattc |
| | | acgagacaaaggttgaaccttcacttcaaa |
| | | aaacttttcgatacctggggattgttcctg |
| | | tcttcgaaagattctcgaaatgttcttgtg |
| | | gccgaccagttcgacgacagacattgcggc |
| | | tggttgaacgagcgggccttgtctgctatg |
| | | gttaaacattacaatggacgcgcatttgat |
| | | gaagtcttcctctgcgataaaaatgcccca |
| | | tactacggcttcaactcttacgacgacttc |
| | | tttaatcgcagatttcgaaaccgagatatc |
| | | gaccgacctgtagtcggtggagttaacaac |
| | | accaccctcatttctgctgcttgcgaatca |
| | | ctttcctacaacgtctcttatgacgtccag |
| | | tctctcgacactttagttttcaaaggagag |
| | | acttattcgcttaagcatttgctgaataat |
| | | gaccctttcaccccacaattcgagcatggg |
| | | agtattctacaaggattcttgaacgtcacc |
| | | gcttaccaccgatggcacgcacccgtcaat |
| | | gggacaatcgtcaaaatcatcaacgttcca |
| | | ggtacctactttgcgcaagccccgagcacg |
| | | attggcgaccctatcccggataacgattac |
| | | gacccacctccttaccttaagtctcttgtc |
| | | tacttctctaatattgccgcaaggcaaatt |
| | | atgtttattgaagccgacaacaaggaaatt |
| | | ggcctcattttccttgtgttcatcggcatg |
| | | accgaaatctcgacatgtgaagccacggtg |
| | | tccgaaggtcaacacgtcaatcgtggcgat |
| | | gacttgggaatgttccatttcggtggttct |
| | | tcgttcgcgcttggtctgaggaaggattgc |
| | | agggcagagatcgttgaaaagttcaccgaa |
| | | cccggaacagtgatcagaatcaacgaagtc |
| | | gtcgctgctctaaaggcttagtacgtttct |
| | | cgttcagctttcttgtacaaagtggttcga |
| | | tctagaggatccatggtgagcaagggcgag |
| | | gagctgttcaccggggtggtgcccatcctg |
| | | gtcgagctggacggcgacgtgaacggccac |
| | | aagttcagcgtgtccggcgagggcgagggc |
| | | gatgccacctacggcaagctgaccctgaag |
| | | ttcatctgcaccaccggcaagctgcccgtg |
| | | ccctggcccaccctcgtgaccaccttcacc |
| | | tacggcgtgcagtgcttcagccgctacccc |
| | | gaccacatgaagcagcacgacttcttcaag |
| | | tccgccatgcccgaaggctacgtccaggag |
| | | cgcaccatcttcttcaaggacgacggcaac |
| | | tacaagacccgcgccgaggtgaagttcgag |
| | | ggcgacaccctggtgaaccgcatcgagctg |
| | | aagggcatcgacttcaaggaggacggcaac |
| | | atcctggggcacaagctggagtacaactac |
| | | aacagccacaacgtctatatcatggccgac |
| | | aagcagaagaacggcatcaaggtgaacttc |
| | | aagatccgccacaacatcgaggacggcagc |
| | | gtgcagctcgccgaccactaccagcagaac |
| | | acccccatcggcgacggccccgtgctgctg |
| | | cccgacaaccactacctgagcacccagtcc |
| | | gccctgagcaaagaccccaacgagaagcgc |
| | | gatcacatggtcctgctggagttcgtgacc |
| | | gccgccgggatcactcacggcatggacgag |
| | | ctgtacaagtaaagcggcccgagctcgaat |
| | | ttccccgatcgttcaaacatttggcaataa |
| | | agtttcttaagattgaatcctgttgccggt |
| | | cttgcgatgattatcatataatttctgttg |
| | | aattacgttaagcatgtaataattaacatg |
| | | taatgcatgacgttatttatgagatgggtt |
| | | tttatgattagagtcccgcaattatacatt |
| | | taatacgcgatagaaaacaaaatatagcgc |
| | | gcaaactaggataaattatcgcgcgcggtg |
| | | tcatctatgttactagatcgggaattagct |
| | | tcatcaacgcaagacatgcgcacgaccgtc |
| | | tgacaggagaggaatttccgacgagcacag |
| | | aaaggacttgctcttggacgtaggcctatt |
| | | tctcaggcacatgtatcaagtgttcggacg |

TABLE 5-continued

Psilocybin Expression Vector Sequences.

| SEQ ID NO | Name | Sequence |
|---|---|---|
| | | tgggttttcgatggtgtatcagccgccgcc |
| | | aactgggagatgaggaggctttcttggggg |
| | | gcagtcagcagttcatttcacaagacagag |
| | | gaacttgtaaggagatgcactgatttatct |
| | | tggcgcaaaccagcaggacgaattagtggg |
| | | aatagcccgcgaatatctaagttatgcctg |
| | | tcggcatgagcagaaacttccaattcgaaa |
| | | cagtttggagaggttgtttttgggcatacc |
| | | ttttgttagtcagcctctcgattgctcatc |
| | | gtcattacacagtaccgaagtttgatcgat |
| | | ctagtaacatagatgacaccgcgcgcgata |
| | | atttatcctagtttgcgcgctatattttgt |
| | | tttctatcgcgtattaaatgtataattgcg |
| | | ggactctaatcataaaaacccatctcataa |
| | | ataacgtcatgcattacatgttaattatta |
| | | catgcttaacgtaattcaacagaaattata |
| | | tgataatcatcgcaagaccggcaacaggat |
| | | tcaatcttaagaaactttattgccaaatgt |
| | | ttgaacgatctgcttcgacgcactccttct |
| | | ttactccaccatctcgtccttattgaaaac |
| | | gtgggtagcaccaaaacgaatcaagtcgct |
| | | ggaactgaagttaccaatcacgctggatga |
| | | tttgccagttggattaatcttgcctttccc |
| | | cgcatgaataatattgatgaatgcatgcgt |
| | | gaggggtatttcgattttggcaatagctgc |
| | | aattgccgcgacatcctccaacgagcataa |
| | | ttcttcagaaaaatagcgatgttccatgtt |
| | | gtcagggcatgcatgatgcacgttatgagg |
| | | tgacggtgctaggcagtattccctcaaagt |
| | | ttcatagtcagtatcatattcatcattgca |
| | | ttcctgcaagagagaattgagacgcaatcc |
| | | acacgctgcggcaaccttccggcgttcgtg |
| | | gtctatttgctcttggacgttgcaaacgta |
| | | agtgttggatcccggtcggcatctactcta |
| | | ttcctttgccctcggacgagtgctggggcg |
| | | tcggtttccactatcggcgagtacttctac |
| | | acagccatcggtccagacggccgcgcttct |
| | | gcgggcgatttgtgtacgcccgacagtccc |
| | | ggctccggatcggacgattgcgtcgcatcg |
| | | accctgcgcccaagctgcatcatcgaaatt |
| | | gccgtcaaccaagctctgatagagttggtc |
| | | aagaccaatgcggagcatatacgcccggag |
| | | ccgcggcgatcctgcaagctccggatgcct |
| | | ccgctcgaagtagcgcgtctgctgctccat |
| | | acaagccaaccacggcctccagaagaagat |
| | | gttggcgacctcgtattgggaatccccgaa |
| | | catcgcctcgctccagtcaatgaccgctgt |
| | | tatgcggccattgtccgtcaggacattgtt |
| | | ggagccgaaatccgcgtgcacgaggtgccg |
| | | gacttcggggcagtcctcggcccaaagcat |
| | | cagctcatcgagagcctgcgcgacggacgc |
| | | actgacggtgtcgtccatcacagtttgcca |
| | | gtgatacacatggggatcagcaatcgcgca |
| | | tatgaaatcacgccatgtagtgtattgacc |
| | | gattccttgcggtccgaatgggccgaaccc |
| | | gctcgtctggctaagatcggccgcagcgat |
| | | cgcatccatggcctccgcgaccggctgcag |
| | | aacagcgggcagttcggtttcaggcaggtc |
| | | ttgcaacgtgacaccctgtgcacggcggga |
| | | gatgcaataggtcaggctctcgctgaattc |
| | | cccaatgtcaagcacttccggaatcgggag |
| | | cgcggccgatgcaaagtgccgataaacata |
| | | acgatctttgtagaaaccatcggcgcagct |
| | | atttacccgcaggacatatccacgccctcc |
| | | tacatcgaagctgaaagcacgagattcttc |
| | | gccctccgagagctgcatcaggtcggagac |
| | | gctgtcgaacttttcgatcagaaacttctc |
| | | gacagacgtcgcggtgagttcaggcttttt |
| | | catatcggggtcgtcctctccaaatgaaat |
| | | gaacttccttatatagaggaagggtcttgc |
| | | gaaggatagtgggattgtgcgtcatccctt |
| | | acgtcagtggagatatcacatcaatccact |
| | | tgctttgaagacgtggttggaacgtcttct |
| | | ttttccacgatgctcctcgtgggtgggggt |

TABLE 5-continued

Psilocybin Expression Vector Sequences.

| SEQ ID NO | Name | Sequence |
|---|---|---|
| | | ccatctttgggaccactgtcggcagaggca tcttgaacgatagcctttcctttatcgcaa tgatggcatttgtaggtgccaccttccttt tctactgtccttttgatgaagtgacagata gctgggcaatggaatccgaggaggtttccc gatattaccctttgttgaaaagtctcaata gccctttggtcttctgagactgtatctttg atattcttggagtagacgagagtgtcgtgc tccaccatgttgacggatctctaggacgcg tcctagaagctaattcactggccgtcgttt tacaacgtcgtgactgggaaaaccctggcg ttacccaacttaatcgccttgcagcacatc cccctttcgccagctggcgtaatagcgaag aggcccgcaccgatcgcccttcccaacagt tgcgcagcctgaatggcgcccgctcctttc gctttcttcccttcctttctcgccacgttc gccggctttccccgtcaagctctaaatcgg gggctccctttagggttccgatttagtgct ttacggcacctcgaccccaaaaaacttgat ttgggtgatggttcacgtagtgggccatcg ccctgatagacggtttttcgccctttgacg ttggagtccacgttctttaatagtggactc ttgttccaaactggaacaacactcaaccct atctcgggctattcttttgatttataaggg attttgccgatttcggaaccaccatcaaac aggattttcgcctgctggggcaaaccagcg tggaccgcttgctgcaactctctcagggcc aggcggtgaagggcaatcagctgttgcccg tctcactggtgaaaagaaaaaccaccccag tacattaaaaacgtccgcaatgtgttatta agttgtctaagcgtcaatttgtttacacca caatatatcctgccaccagccagccaacag ctccccgaccggcagctcggcacaaaatca ccactcgatacaggcagcccatcagtccgg gacggcgtcagcgggagagccgttgtaagg cggcagactttgctcatgttaccgatgcta ttcggaagaacggcaactaagctgccgggt ttgaaacacggatgatctcgcggagggtag catgttgattgtaacgatgacagagcgttg ctgcctgtgatcaaatatcatctccctcgc agagatccgaattatcagccttcttattca tttctcgcttaaccgtgacaggctgtcgat cttgagaactatgccgacataataggaaat cgctggataaagccgctgaggaagctgagt ggcgctatttctttagaagtgaacgttgac gatatcaactcccctatccattgctcaccg aatggtacaggtcggggacccgaagttccg actgtcggcctgatgcatccccggctgatc gaccccagatctggggctgagaaagcccag taaggaaacaactgtaggttcgagtcgcga gatcccccggaaccaaaggaagtaggttaa acccgctccgatcaggccgagccacgccag gccgagaacattggttcctgtaggcatcgg gattggcggatcaaacactaaagctactgg aacgagcagaagtcctccggccgccagttg ccaggcggtaaaggtgagcagaggcacggg aggttgccacttgcgggtcagcacggttcc gaacgccatggaaaccgcccccgccaggcc cgctgcgacgccgacaggatctagcgctgc gtttggtgtcaacaccaacagcgccacgcc cgcagttccgcaaatagcccccaggaccgc catcaatcgtatcgggctacctagcagagc ggcagagatgaacacgaccatcagcggctg cacagcgcctaccgtcgccgcgaccccgcc cggcaggcggtagaccgaaataaacaacaa gctccagaatagcgaaatattaagtgcgcc gaggatgaagatgcgcatccaccagattcc cgttggaatctgtcggacgatcatcacgag caataaacccgccggcaacgcccgcagcag cataccggcgacccctcggcctcgctgttc gggctccacgaaaacgccggacagatgcgc cttgtgagcgtccttggggccgtcctcctg tttgaagaccgacagcccaatgatctcgcc gtcgatgtaggcgccgaatgccacggcatc |

TABLE 5-continued

Psilocybin Expression Vector Sequences.

| SEQ ID NO | Name | Sequence |
|---|---|---|
| | | tcgcaaccgttcagcgaacgcctccatggg ctttttctcctcgtgctcgtaaacggaccc gaacatctctggagctttcttcagggccga caatcggatctcgcggaaatcctgcacgtc ggccgctccaagccgtcgaatctgagcctt aatcacaattgtcaattttaatcctctgtt tatcggcagttcgtagagcgcgccgtgcgt cccgagcgatactgagcgaagcaagtgcgt cgagcagtgcccgcttgttcctgaaatgcc agtaaagcgctggctgctgaaccccagcc ggaactgaccccacaaggccctagcgtttg caatgcaccaggtcatcattgacccaggcg tgttccaccaggccgctgcctcgcaactct tcgcaggcttcgccgacctgctcgcgccac ttcttcacgcgggtggaatccgatccgcac atgaggcggaaggtttccagcttgagcggg tacggctcccggtgcgagctgaaatagtcg aacatccgtcgggccgtcggcgacagcttg cggtacttctcccatatgaatttcgtgtag tggtcgccagcaaacagcacgacgatttcc tcgtcgatcaggacctggcaacgggacgtt ttcttgccacggtccaggacgcggaagcgg tgcagcagcgacaccgattccaggtgccca acgcggtcggacgtgaagcccatcgccgtc gcctgtaggcgcgacaggcattcctcggcc ttcgtgtaataccggccattgatcgaccag cccaggtcctggcaaagctcgtagaacgtg aaggtgatcggctcgccgataggggtgcgc ttcgcgtactccaacacctgctgccacacc agttcgtcatcgtcggcccgcagctcgacg ccggtgtaggtgatcttcacgtccttgttg acgtggaaaatgaccttgttttgcagcgcc tcgcgcgggattttcttgttgcgcgtggtg aacagggcagagcgggccgtgtcgtttggc atcgctcgcatcgtgtccggccacggcgca atatcgaacaaggaaagctgcatttccttg atctgctgcttcgtgtgtttcagcaacgcg gcctgcttggcctcgctgacctgttttgcc aggtcctcgccggcggtttttcgcttcttg gtcgtcatagttcctcgcgtgtcgatggtc atcgacttcgccaaacctgccgcctcctgt tcgagacgacgcgaacgctccacggcggcc gatggcgcgggcagggcagggggagccagt tgcacgctgtcgcgctcgatcttggccgta gcttgctggaccatcgagccgacggactgg aaggtttcgcggggcgcacgcatgacggtg cggcttgcgatggtttcggcatcctcggcg gaaaaccccgcgtcgatcagttcttgcctg tatgccttccggtcaaacgtccgattcatt caccctccttgcgggattgccccgactcac gccggggcaatgtgcccttattcctgattt gacccgcctggtgccttggtgtccagataa tccaccttatcggcaatgaagtcggtcccg tagaccgtctggccgtccttctcgtacttg gtattccgaatcttgccctgcacgaatacc agcgaccccttgcccaaatacttgccgtgg gcctcggcctgagagccaaaacacttgatg cggaagaagtcggtgcgctcctgcttgtcg ccggcatcgttgcgccacatctaggtacta aaacaattcatccagtaaaatataatattt tattttctcccaatcaggcttgatccccag taagtcaaaaaatagctcgacatactgttc ttccccgatatcctccctgatcgaccggac gcagaaggcaatgtcataccacttgtccgc cctgccgcttctcccaagatcaataaagcc acttactttgccatctttcacaaagatgtt gctgtctcccaggtcgccgtgggaaaagac aagttcctcttcgggcttttccgtctttaa aaaatcatacagctcgcgcggatctttaaa tggagtgtcttcttcccagttttcgcaatc cacatcggccagatcgttattcagtaagta atccaattcggctaagcggctgtctaagct attcgtatagggacaatccgatatgtcgat ggagtgaaagagcctgatgcactccgcata |

TABLE 5-continued

Psilocybin Expression Vector Sequences.

| SEQ ID NO | Name | Sequence |
| --- | --- | --- |
| | | cagctcgataatcttttcagggctttgttc<br>atcttcatactcttccgagcaaaggacgcc<br>atcggcctcactcatgagcagattgctcca<br>gccatcatgccgttcaaagtgcaggacctt<br>tggaacaggcagctttccttccagccatag<br>catcatgtccttttcccgttccacatcata<br>ggtggtccctttataccggctgtccgtcat<br>ttttaaatataggttttcattttctcccac<br>cagcttatataccttagcaggagacattcc<br>ttccgtatcttttacgcagcggtatttttc<br>gatcagtttttcaattccggtgatattct<br>cattttagccatttattatttccttcctct<br>tttctacagtatttaaagataccccaagaa<br>gctaattataacaagacgaactccaattca<br>ctgttccttgcattctaaaaccttaaatac<br>cagaaaacagcttttcaaagttgttttca<br>aagttggcgtataacatagtatcgacggag<br>ccgattttgaaaccacaattatgggtgatg<br>ctgccaacttactgatttagtgtatgatgg<br>tgtttttgaggtgctccagtggcttctgtg<br>tctatcagctgtccctcctgttcagctact<br>gacggggtggtgcgtaacggcaaaagcacc<br>gccggacatcagcgctatctctgctctcac<br>tgccgtaaaacatggcaactgcagttcact<br>tacaccgcttctcaacccggtacgcaccag<br>aaaatcattgatatggccatgaatggcgtt<br>ggatgccgggcaacagcccgcattatgggc<br>gttggcctcaacacgattttacgtcactta<br>aaaaactcaggccgcagtcggtaacctcgc<br>gcatacagccgggcagtgacgtcatcgtct<br>gcgcggaaatggacgaacagtggggctatg<br>tcggggctaaatcgcgccagcgctggctgt<br>tttacgcgtatgacagtctccggaagacgg<br>ttgttgcgcacgtattcggtgaacgcacta<br>tggcgacgctggggcgtcttatgagcctgc<br>tgtcaccctttgacgtggtgatatggatga<br>cggatggctggccgctgtatgaatcccgcc<br>tgaagggaaagctgcacgtaatcagcaagc<br>gatatacgcagcgaattgagcggcataacc<br>tgaatctgaggcagcacctggcacggctgg<br>gacggaagtcgctgtcgttctcaaaatcgg<br>tggagctgcatgacaaagtcatcgggcatt<br>atctgaacataaaacactatcaataagttg<br>gagtcattacccaattatgatagaatttac<br>aagctataaggttattgtcctgggtttcaa<br>gcattagtccatgcaagtttttatgctttg<br>cccattctatagatatattgataagcgcgc<br>tgcctatgccttgccccctgaaatccttac<br>atacggcgatatcttctatataaaagatat<br>attatcttatcagtattgtcaatatattca<br>aggcaatctgcctcctcatcctcttcatcc<br>tcttcgtcttggtagctttttaaatatggc<br>gcttcatagagtaattctgtaaaggtccaa<br>ttctcgttttcatacctcggtataatctta<br>cctatcacctcaaatggttcgctgggttta<br>tcgcacccccgaacacgagcacggcacccg<br>cgaccactatgccaagaatgcccaaggtaa<br>aaattgccggccccgccatgaagtccgtga<br>atgccccgacggccgaagtgaagggcaggc<br>cgccacccaggccgccgccctcactgcccg<br>gcacctggtcgctgaatgtcgatgccagca<br>cctgcggcacgtcaatgcttccgggcgtcg<br>cgctcgggctgatcgcccatcccgttactg<br>ccccgatcccggcaatggcaaggactgcca<br>gcgctgccatttttggggtgaggccgttcg<br>cggccgaggggcgcagcccctgggggggatg<br>ggaggcccgcgttagcgggccgggagggtt<br>cgagaagggggggcacccccttcggcgtg<br>cgcggtcacgcgcacagggcgcagccctgg<br>ttaaaaacaaggtttataaatattggttta<br>aaagcaggttaaaagacaggttagcggtgg<br>ccgaaaaacgggcggaaacccttgcaaatg<br>ctggattttctgcctgtggacagcccctca<br>aatgtcaataggtgcgcccctcatctgtca |

TABLE 5-continued

Psilocybin Expression Vector Sequences.

| SEQ ID NO | Name | Sequence |
| --- | --- | --- |
| | | gcactctgcccctcaagtgtcaaggatcgc<br>gcccctcatctgtcagtagtcgcgcccctc<br>aagtgtcaataccgcagggcacttatcccc<br>aggcttgtccacatcatctgtgggaaactc<br>gcgtaaaatcaggcgttttcgccgatttgc<br>gaggctggccagctccacgtcgccggccga<br>aatcgagcctgcccctcatctgtcaacgcc<br>gcgccgggtgagtcggcccctcaagtgtca<br>acgtccgcccctcatctgtcagtgagggcc<br>aagttttccgcgaggtatccacaacgccgg<br>cggccgcggtgtctcgcacacggcttcgac<br>ggcgtttctggcgcgtttgcagggccatag<br>acggccgccagcccagcggcgagggcaacc<br>agcccgg |
| 19 | pGHGWY: Cc DED1 promoter_ intron: GW Cassette_ YFP | AGATCTCTAATTCCGGGGATCGGAAATCCA<br>GAAGCCCGAGAGGTTGCCGCCTTTCGGGCT<br>TTTTCTTTTTCAAAAAAAAAAATTTATAAA<br>ACGATCTGTTGCGGCCGGCCGCCGGGTTGT<br>GGGCAAAGGCGCTGGCGCTCGACGGTGGGC<br>AACCGCTTGCGGTTGTCCACGGGCGGAGCC<br>GGTGCGCGTAGCGCATTGTCCACAAGCCAA<br>GGGCGACCAATAATTGATATATATATTCAT<br>AATTGAAAAGCTAATTGAACATACTACTTG<br>CTGTAACTACTTGCCGGAGCGAGGGGTGTT<br>TGCAAGCTGTTGATCTGAAAGGGCTATTAG<br>CGTTCTCACGTGCCTTTTTGATTAGCGATT<br>TCACGTGACCTTATTAGCGATTTCACGTAC<br>TCCGATTAGCGATTTCACGTACCCTGATTA<br>GCGATTTCACGTGGATAGTTTTTGGAGCGG<br>GCCGGAAAGCCCCGTGAATCAAGGCTTTGC<br>GGGGCATTAGCGGTTTCACGTGGATAACTA<br>CCCTCTATCCACAGGCTTCCGGGGATAAAA<br>AAGCCCGCTCGACGGCGGGCTGTTGGATGG<br>GGATCGCCTGAATCGCCCCATCATCCAGCC<br>AGAAAGTGAGGGAGCCACGGTTGATGAGAG<br>CTTTGTTGTAGGTGGACCAGTTGGTGATTT<br>TGAACTTTTGCTTTGCCACGGAACGGTCTG<br>CGTTGTCGGGAAGATGCGTGATCTGATCCT<br>TCAACTCAGCAAAAGTTCGATTTATTCAAC<br>AAAGCCACGTTGTGTCTCAAAATCTCTGAT<br>GTTACATTGCACAAGATAAAAATATATCAT<br>CATGAACAATAAAACTGTCTGCTTACATAA<br>ACAGTAATACAAGGGGTGTTATGAGCCATA<br>TTCAACGGGAAACGTCTTGCTCAAGGCCGC<br>GATTAAATTCCAACATGGATGCTGATTTAT<br>ATGGGTATAAATGGGCTCGCGATAATGTCG<br>GGCAATCAGGTGCGACAATCTACCGATTGT<br>ATGGGAAGCCCGATGCGCCAGAGTTGTTTC<br>TGAAACATGGCAAAGGTAGCGTTGCCAATG<br>TTGTTACAGATGAGATGGTCAGACTAAACT<br>GGCTGACGGAATTTATGCCTCTTCCGACCA<br>TCAAGCATTTTATCCGTACTCCTGATGATG<br>CATGGTTACTCACCACTGCGATCCCAGGGA<br>AAACAGCATTCCAGGTATTAGAAGAATATC<br>CTGATTCAGGTGAAAATATTGTTGATGCGC<br>TGGCAGTGTTCCTGCGCCGGTTGCATTCGA<br>TTCCTGTTTGTAATTGTCCTTTTAACAGCG<br>ATCGCGTATTTCGTCTCGCTCAGGCGCAAT<br>CACGAATGAATAACGGTTTGGTTGATGCGA<br>GTGATTTTGATGACGAGCGTAATGGCTGGC<br>CTGTTGAACAAGTCTGGAAAGAAATGCATA<br>AACTTTTGCCATTCTCACCGGATTCAGTCG<br>TCACTCATGGTGATTTCTCACTTGATAACC<br>TTATTTTTGACGAGGGGAAATTAATAGGTT<br>GTATTGATGTTGGACGAGTCGGAATCGCAG<br>ACCGATACCAGGATCTTGCCATCCTATGGA<br>ACTGCCTCGGTGAGTTTTCTCCTTCATTAC<br>AGAAACGGCTTTTTCAAAAATATGGTATTG<br>ATAATCCTGATATGAATAAATTGCAGTTTC<br>ATTTGATGCTCGATGAGTTTTTCTAATCAC<br>TAGACCAATGTTACACATATATACTTTAGA<br>TTGATTTAAAACTTCATTTTTAATTTAAAA<br>GGATCTAGGTGAAGATCCTTTTTGATAATC |

TABLE 5-continued

Psilocybin Expression Vector Sequences.

| SEQ ID NO | Name | Sequence |
|---|---|---|
| | | TCATGACCAAAATCCCTTAACGTGAGTTTT |
| | | CGTTCCACTGAGCGTCAGACCCCGTAGAAA |
| | | AGATCAAAGGATCTTCTTGAGATCCTTTTT |
| | | TTCTGCGCGTAATCTGCTGCTTGCAAACAA |
| | | AAAAACCACCGCTACCAGCGGTGGTTTGTT |
| | | TGCCGGATCAAGAGCTACCAACTCTTCTTC |
| | | CGAAGGTAACTGGCTTCAGCAGAGCGCAGA |
| | | TACCAAATACTGTTCTTCTAGTGTAGCCGT |
| | | AGTTAGGCCACCACTTCAAGAACTCTGTAG |
| | | CACCGCCTACATACCTCGCTCTGCTAATCC |
| | | TGTTACCAGTGGCTGCTGCCAGTGGCGATA |
| | | AGTCGTGTCTTACCGGGTTGGACTCAAGAC |
| | | GATAGTTACCGGATAAGGCGCAGCGGTCGG |
| | | GCTGAACGGGGGGTTCGTGCACACAGCCCA |
| | | GCTTGGAGCGAACGACCTACACCGAACTGA |
| | | GATACCTACAGCGTGAGCTATGAGAAAGCG |
| | | CCACGCTTCCCGAAGGGAGAAAGGCGGACA |
| | | GGTATCCGGTAAGCGGCAGGGTCGGAACAG |
| | | GAGAGCGCACGAGGGAGCTTCCAGGGGGAA |
| | | ACGCCTGGTATCTTTATAGTCCTGTCGGGT |
| | | TTCGCCACCTCTGACTTGAGCGTCGATTTT |
| | | TGTGATGCTCGTCAGGGGGGCGGAGCCTAT |
| | | GGAAAAACGCCAGCAACGCGGCCTTTTTAC |
| | | GGTTCCTGGCCTTTTGCTGGCCTTTTGCTC |
| | | ACATGAGATCTCAAACAAACACATACAGCG |
| | | ACTTAGTTTACCCGCCAATATATCCTGTCA |
| | | AGGATCGTACCCCTACTCCAAAAATGTCAA |
| | | AGATACAGTCTCAGAAGACCAAAGGGCTAT |
| | | TGAGACTTTTCAACAAAGGGTAATTTCGGG |
| | | AAACCTCCTCGGATTCCATTGCCCAGCTAT |
| | | CTGTCACTTCATCGAAAGGACAGTAGAAAA |
| | | GGAAGGTGGCTCCTACAAATGCCATCATTG |
| | | CGATAAAGGAAAGGCTATCATTCAAGATGC |
| | | CTCTGCCGACAGTGGTCCCAAAGATGGACC |
| | | CCCACCCACGAGGAGCATCGTGGAAAAAGA |
| | | AGACGTTCCAACCACGTCTTCAAAGCAAGT |
| | | GGATTGATGTGACATCTCCACTGACGTAAG |
| | | GGATGACGCACAATCCCACTATCCTTCGCA |
| | | AGACCCTTCCTCTATATAAGGAAGTTCATT |
| | | TCATTTGGAGAGGACAGCCCAAGCTGATCC |
| | | CTATGAAAAAGCCTGAACTCACCGCGACGT |
| | | CTGTCGAGAAGTTTCTGATCGAAAAGTTCG |
| | | ACAGCGTCTCCGACCTGATGCAGCTCTCGG |
| | | AGGGCGAAGAATCTCGTGCTTTCAGCTTCG |
| | | ATGTAGGAGGGCGTGGATATGTCCTGCGGG |
| | | TAAATAGCTGCGCCGATGGTTTCTACAAAG |
| | | ATCGTTATGTTTATCGGCACTTTGCATCGG |
| | | CCGCGCTCCCGATTCCGGAAGTGCTTGACA |
| | | TTGGGGAGTTCAGCGAGAGCCTGACCTATT |
| | | GCATCTCCCGCCGTGCACAGGGTGTCACGT |
| | | TGCAAGACCTGCCTGAAACCGAACTGCCCG |
| | | CTGTTCTTCAGCCGGTCGCGGAGGCTATGG |
| | | ATGCGATCGCTGCGGCCGATCTTAGCCAGA |
| | | CGAGCGGGTTCGGCCCATTCGGACCGCAAG |
| | | GAATCGGTCAATACACTACATGGCGTGATT |
| | | TCATATGCGCGATTGCTGATCCCCATGTGT |
| | | ATCACTGGCAAACTGTGATGGACGACACCG |
| | | TCAGTGCGTCCGTCGCGCAGGCTCTCGATG |
| | | AGCTGATGCTTTGGGCCGAGGACTGCCCCG |
| | | AAGTCCGGCACCTCGTGCACGCGGATTTCG |
| | | GCTCCAACAATGTCCTGACGGACAATGGCC |
| | | GCATAACAGCGGTCATTGACTGGAGCGAGG |
| | | CGATGTTCGGGGATTCCCAATACGAGGTCG |
| | | CCAACATCTTCTTCTGGAGGCCGTGGTTGG |
| | | CTTGTATGGAGCAGCAGACGCGCTACTTCG |
| | | AGCGGAGGCATCCGGAGCTTGCAGGATCGC |
| | | CACGCCTCCGGGCGTATATGCTCCGCATTG |
| | | GTCTTGACCAACTCTATCAGAGCTTGGTTG |
| | | ACGGCAATTTCGATGATGCAGCTTGGGCGC |
| | | AGGGTCGATGCGACGCAATCGTCCGATCCG |
| | | GAGCCGGGACTGTCGGGCGTACACAAATCG |
| | | CCCGCAGAAGCGCGGCCGTCTGGACCGATG |
| | | GCTGTGTAGAAGTACTCGCCGATAGTGGAA |
| | | ACCGACGCCCCAGCACTCGTCCGAGGGCAA |
| | | AGGAATAGAGTAGATGCCGACCGAACAAGA |
| | | GCTGATTTCGAGAACGCCTCAGCCAGCAAC |
| | | TCGCGCGAGCCTAGCAAGGCAAATGCGAGA |
| | | GAACGGCCTTACGCTTGGTGGCACAGTTCT |
| | | CGTCCACAGTTCGCTAAGCTCGCTCGGCTG |
| | | GTCGCGGGAGAATTAATTCGGTACGCTGAA |
| | | ATCACCAGTCTCTCTCTACAAATCTATCTC |
| | | TCTCTATTTTCTCCATAAATAATGTGTGAG |
| | | TAGTTTCCCGATAAGGGAAATTAGGGTTCT |
| | | TATAGGGTTTCGCTCATGTGTTGAGCATAT |
| | | AAGAAACCCTTAGTATGTATTTGTATTTGT |
| | | AAAATACTTCTATCAATAAAATTTCTAATT |
| | | CCTAAAACCAAAATCCAGTACTAAAATCCA |
| | | GATCGATCCTTCATGTTCTTTCCTGCGTTA |
| | | TCCCCTGATTCTGTGGATAACCGTATTACC |
| | | GCCTTTGAGTGAGCTGATACCGCTCGCCGC |
| | | AGCCGAACGACCGAGCGCAGCGAGTCAGTG |
| | | AGCGAGGAAGCGGAAGAGCGCCCAATACGC |
| | | AAACCGCCTCTCCCCGCGCGTTGGCCGATT |
| | | CATTAATGCAGCTGGCACGACAGGTTTCCC |
| | | GACTGGAAAGCGGGCAGTGAGCGCAACGCA |
| | | ATTAATGTGAGTTAGCTCACTCATTAGGCA |
| | | CCCCAGGCTTTACACTTTATGACTTCCGGC |
| | | TCGTATGTTGTGTGGAATTGTGAGCGGATA |
| | | ACAATTTCACACAGGAAACAGCTATGACCA |
| | | TGATTACGCCAAGCTCGGAATTAACCCTCA |
| | | CTAAAGGGAACAAAAGCTGGAGCTCTGGTC |
| | | CCGCAGGGGCGGCGGCTGAAACATCTGCAC |
| | | AAGCTACTGCCACGGCGCAGAGTAGTGGAC |
| | | GGGCGACGCCGCAGGCGACTGCGAACCCCT |
| | | CTAGTGCAGCTTCGCAACAATCTGTCGCTG |
| | | CTGCGGCAGCGACGCCATCTTCTGCGAGGG |
| | | CGAGTCCGATGCCTGCTATGCACGCCCAAC |
| | | AGAATCCCACTCAGTCGCAACAAGCCCAGC |
| | | AAGCGAATGCGGCCATACTTCAAGCTGCGA |
| | | TTCAACAACAACAACTACAGCGACAACAGC |
| | | AACAATACCAGCGCACGTTGACCCCCATTC |
| | | AGCCACAGAAGACGAACTCTCAAGGAGGGC |
| | | AGGTGCAGATGCAGGTTCAGCCGCAATTGG |
| | | CCGCAAATGGACAATATACGTTCACGACGC |
| | | CGTTCAATGCTGCCGCATTGCGAGCCGCAA |
| | | CGCCCTTGACCGCTAGTCAGCAAGCTGCTG |
| | | CTCAACGGATGGCTGCTGCCCAAGCAAATG |
| | | CAGCTAAAATGAGCGCGGGGACCCCTGCAC |
| | | AGAATGCAGGCAGTAACATTCACGTACAGC |
| | | CGTCACCGCAACAAGCCCAGGCTCAAATCC |
| | | AGGTACAGCAGCAGCAGACGCTTCAGGTCC |
| | | CGCAACAGCAACAGGCGAGGACACCACAAA |
| | | TGCAAACGCAGCAGCTACGGACGCCTCAAA |
| | | TTCAGGCTCAGCAATTACGGACGCCACAGA |
| | | TGCAAACGCAACAGCTTCAGCGAACGCCTC |
| | | AGATGCAGACGCAACAACTTCAACCGACGC |
| | | CGCAGATGCAGCCTCAGCAGCTCCAGTCTC |
| | | AAATGGGGCAGATGCAACGCCAGCCGACTC |
| | | CTCAGCAACATACGCCTCAGCAACAACATG |
| | | CTCAACTTCAGCCTGTGCAGGCTCAGCAGT |
| | | TAGCGATGGCCCAGCAGCAACAGCAACAGC |
| | | AGCAAATGCAGGCTCAAATTCAGCAGCAAC |
| | | AACCACAACAAGCGCATCTGACTCCGCAAC |
| | | AGTATCAGCAGTATCAGATGTATAGCAATT |
| | | ATTATCAAGCTGCGGCGGCAATGCAACAAC |
| | | ACGGGGGACAGAGACTGACTCCGCAACAAC |
| | | AACAGGCAATTTGGAACGCGCAGTTCCAGC |
| | | GTGCTGCTGCTGCTGCTGGTATGCAGGGGC |
| | | AGCATGGCGGGGTACCTATGAACCAGGTAC |
| | | AACAGGCTGCGCTGGCCGCACACATAGCGA |
| | | AACAGCAGCAACAACAGCAACAGCATCAAG |
| | | GTCAAGGTCCACGGTGAATGGGTTTAGCTT |
| | | CGTAGATAGTGTATTAGTATTTTGTAATGG |
| | | ACATTGGGATTGGGTGAAGACAAACCCGAG |
| | | AACGTCATCTTTGTGGAGTGTTTGTTCGGA |
| | | TTTGGTGTGAGGCCGTGCAAGCTTAGTCAG |
| | | CAGTTAGTGGAAAAGGTGGAGGTAGAAAGA |
| | | GGGCAAGGGAAGTTTTCGTCTCCTTTCTGA |

TABLE 5-continued

Psilocybin Expression Vector Sequences.

| SEQ ID NO | Name | Sequence |
| --- | --- | --- |
| | | TCTGGTACCACCATCATCACCCCAGCAAAA |
| | | CTCTCTACTCTCTTAGACCTTCACTTTATC |
| | | CTTCACTTTTATTCTTTTTCAACTCTTTTC |
| | | GTTTCTCAAGTTCTACTCCCAAAGTCGCTC |
| | | GTTTCTTTCGAATTTCACGAAAGACTGCAC |
| | | AAAAAGACGTATCTTTGCTAGCCCTGCAAG |
| | | CATCGACCACCGATATCCACAGCGATTCAA |
| | | GAACGATTCGAGTTCAACAAATCTTCAACT |
| | | AATgtaattctctttcttttgggataagtt |
| | | gaaacccgaacgaggaactaatctttcact |
| | | cggtgtagAAGCTTATCGATACCGTCGACC |
| | | TCGAGGGGGGGCCCGGTACCCACCGGATCC |
| | | ACAAGTTTGTACAAAAAAGCTGAACGAGAA |
| | | ACGTAAAATGATATAAATATCAATATATTA |
| | | AATTAGATTTTGCATAAAAAACAGACTACA |
| | | TAATACTGTAAAACACAACATATCCAGTCA |
| | | CTATGGCGGCCGCATTAGGCACCCCAGGCT |
| | | TTACACTTTATGCTTCCGGCTCGTATAATG |
| | | TGTGGATTTTGAGTTAGGATCCGGCGAGAT |
| | | TTTCAGGAGCTAAGGAAGCTAAAATGGAGA |
| | | AAAAAATCACTGGATATACCACCGTTGATA |
| | | TATCCCAATGGCATCGTAAAGAACATTTTG |
| | | AGGCATTTCAGTCAGTTGCTCAATGTACCT |
| | | ATAACCAGACCGTTCAGCTGGATATTACGG |
| | | CCTTTTTAAAGACCGTAAAGAAAAATAAGC |
| | | ACAAGTTTTATCCGGCCTTTATTCACATTC |
| | | TTGCCCGCCTGATGAATGCTCATCCGGAAT |
| | | TCCGTATGGCAATGAAAGACGGTGAGCTGG |
| | | TGATATGGGATAGTGTTCACCCTTGTTACA |
| | | CCGTTTTCCATGAGCAAACTGAAACGTTTT |
| | | CATCGCTCTGGAGTGAATACCACGACGATT |
| | | TCCGGCAGTTTCTACACATATATTCGCAAG |
| | | ATGTGGCGTGTTACGGTGAAAACCTGGCCT |
| | | ATTTCCCTAAAGGGTTTATTGAGAATATGT |
| | | TTTTCGTCTCAGCCAATCCCTGGGTGAGTT |
| | | TCACCAGTTTTGATTTAAACGTGGCCAATA |
| | | TGGACAACTTCTTCGCCCCCGTTTTCACCA |
| | | TGGGCAAATATTATACGCAAGGCGACAAGG |
| | | TGCTGATGCCGCTGGCGATTCAGGTTCATC |
| | | ATGCCGTCTGTGATGGCTTCCATGTCGGCA |
| | | GAATGCTTAATGAATTACAACAGTACTGCG |
| | | ATGAGTGGCAGGGCGGGGCGTAAACGCGTG |
| | | GATCCGGCTTACTAAAAGCCAGATAACAGT |
| | | ATGCGTATTTGCGCGCTGATTTTTGCGGTA |
| | | TAAGAATATATACTGATATGTATACCCGAA |
| | | GTATGTCAAAAAGAGGTGTGCTATGAAGCA |
| | | GCGTATTACAGTGACAGTTGACAGCGACAG |
| | | CTATCAGTTGCTCAAGGCATATATGATGTC |
| | | AATATCTCCGGTCTGGTAAGCACAACCATG |
| | | CAGAATGAAGCCCGTCGTCTGCGTGCCGAA |
| | | CGCTGGAAAGCGGAAAATCAGGAAGGGATG |
| | | GCTGAGGTCGCCCGGTTTATTGAAATGAAC |
| | | GGCTCTTTTGCTGACGAGAACAGGGACTGG |
| | | TGAAATGCAGTTTAAGGTTTACACCTATAA |
| | | AAGAGAGAGCCGTTATCGTCTGTTTGTGGA |
| | | TGTACAGAGTGATATTATTGACACGCCCGG |
| | | GCGACGGATGGTGATCCCCCTGGCCAGTGC |
| | | ACGTCTGCTGTCAGATAAAGTCTCCCGTGA |
| | | ACTTTACCCGGTGGTGCATATCGGGGATGA |
| | | AAGCTGGCGCATGATGACCACCGATATGGC |
| | | CAGTGTGCCGGTCTCCGTTATCGGGGAAGA |
| | | AGTGGCTGATCTCAGCCACCGCGAAAATGA |
| | | CATCAAAAACGCCATTAACCTGATGTTCTG |
| | | GGGAATATAAATGTCAGGCTCCCTTATACA |
| | | CAGCCAGTCTGCAGGTCGACCATAGTGACT |
| | | GGATATGTTGTGTTTTACAGTATTATGTAG |
| | | TCTGTTTTTTATGCAAAATCTAATTTAATA |
| | | TATTGATATTTATATCATTTTACGTTTCTC |
| | | GTTCAGCTTTCTTGTACAAAGTGGTGCTCG |
| | | AGATGGTGAGCAAGGGCGAGGAGCTGTTCA |
| | | CCGGGGTGGTGCCCATCCTGGTCGAGCTGG |
| | | ACGGCGACGTAAACGGCCACAAGTTCAGCG |
| | | TGTCCGGCGAGGGCGAGGGCGATGCCACCT |
| | | ACGGCAAGCTGACCCTGAAGCTGATCTGCA |

TABLE 5-continued

Psilocybin Expression Vector Sequences.

| SEQ ID NO | Name | Sequence |
| --- | --- | --- |
| | | CCACCGGCAAGCTGCCCGTGCCCTGGCCCA |
| | | CCCTCGTGACCACCCTGGGCTACGGCCTGC |
| | | AGTGCTTCGCCCGCTACCCCGACCACATGA |
| | | AGCAGCACGACTTCTTCAAGTCCGCCATGC |
| | | CCGAAGGCTACGTCCAGGAGCGCACCATCT |
| | | TCTTCAAGGACGACGGCAACTACAAGACCC |
| | | GCGCCGAGGTGAAGTTCGAGGGCGACACCC |
| | | TGGTGAACCGCATCGAGCTGAAGGGCATCG |
| | | ACTTCAAGGAGGACGGCAACATCCTGGGGC |
| | | ACAAGCTGGAGTACAACTACAACAGCCACA |
| | | ACGTCTATATCACCGCCGACAAGCAGAAGA |
| | | ACGGCATCAAGGCCAACTTCAAGATCCGCC |
| | | ACAACATCGAGGACGGCGGCGTGCAGCTCG |
| | | CCGACCACTACCAGCAGAACACCCCCATCG |
| | | GCGACGGCCCCGTGCTGCTGCCCGACAACC |
| | | ACTACCTGAGCTACCAGTCCGCCCTGAGCA |
| | | AAGACCCCAACGAGAAGCGCGATCACATGG |
| | | TCCTGCTGGAGTTCGTGACCGCCGCCGGGA |
| | | TCACTCTCGGCATGGACGAGCTGTACAAGT |
| | | AAGTCGACCTGCAGGCATGCGCTGAAATCA |
| | | CCAGTCTCTCTCTACAAATCTATCTCTCTC |
| | | TATAATAATGTGTGAGTAGTTCCCAGATAA |
| | | GGGAATTAGGGTTCTTATAGGGTTTCGCTC |
| | | ATGTGTTGAGCATATAAGAAACCCTTAGTA |
| | | TGTATTTGTATTTGTAAAATACTTCTATCA |
| | | ATAAAATTTCTAATTCCTAAAACCAAAATC |
| | | CAGTGGGTACCCAATTCGCCCTATAGTGAG |
| | | TCGTATTACAATTCACTGGCCGTCGTTTTA |
| | | CAACGTCGTGACTGGGAAAACCCTGGCGTT |
| | | ACCCAACTTAATCGCCTTGCAGCACATCCC |
| | | CCTTTCGCCAGCTGGCGTAATAGCGAAGAG |
| | | GCCCGCACCGATCGCCCTTCCCAACAGTTG |
| | | CGCAGCCTGAATGGCGAATGGCGCGAAATT |
| | | GTAAACGTTAATGTTAACGTTACACCACAA |
| | | TATATCCTGCCA |
| 20 | pGHGWY: | AGATCTCTAATTCCGGGGATCGGAAATCCA |
| | GPD | GAAGCCCGAGAGGTTGCCGCCTTTCGGGCT |
| | promoter_ | TTTTCTTTTTCAAAAAAAAAAATTTATAAA |
| | intron: | ACGATCTGTTGCGGCCGGCCGCCGGGTTGT |
| | GW | GGGCAAAGGCGCTGGCGCTCGACGGTGGGC |
| | cassette: | AACCGCTTGCGGTTGTCCACGGGCGGAGCC |
| | YFP | GGTGCGCGTAGCGCATTGTCCACAAGCCAA |
| | | GGGCGACCAATAATTGATATATATATTCAT |
| | | AATTGAAAAGCTAATTGAACATACTACTTG |
| | | CTGTAACTACTTGCCGGAGCGAGGGGTGTT |
| | | TGCAAGCTGTTGATCTGAAAGGGCTATTAG |
| | | CGTTCTCACGTGCCTTTTTGATTAGCGATT |
| | | TCACGTGACCTTATTAGCGATTTCACGTAC |
| | | TCCGATTAGCGATTTCACGTACCCTGATTA |
| | | GCGATTTCACGTGGATAGTTTTTGGAGCGG |
| | | GCCGGAAAGCCCCGTGAATCAAGGCTTTGC |
| | | GGGGCATTAGCGGTTTCACGTGGATAACTA |
| | | CCCTCTATCCACAGGCTTCCGGGGATAAAA |
| | | AAGCCCGCTCGACGGCGGGCTGTTGGATGG |
| | | GGATCGCCTGAATCGCCCCATCATCCAGCC |
| | | AGAAAGTGAGGGAGCCACGGTTGATGAGAG |
| | | CTTTGTTGTAGGTGGACCAGTTGGTGATTT |
| | | TGAACTTTTGCTTTGCCACGGAACGGTCTG |
| | | CGTTGTCGGGAAGATGCGTGATCTGATCCT |
| | | TCAACTCAGCAAAAGTTCGATTTATTCAAC |
| | | AAAGCCACGTTGTGTCTCAAAATCTCTGAT |
| | | GTTACATTGCACAAGATAAAAATATATCAT |
| | | CATGAACAATAAAACTGTCTGCTTACATAA |
| | | ACAGTAATACAAGGGGTGTTATGAGCCATA |
| | | TTCAACGGGAAACGTCTTGCTCAAGGCCGC |
| | | GATTAAATTCCAACATGGATGCTGATTTAT |
| | | ATGGGTATAAATGGGCTCGCGATAATGTCG |
| | | GGCAATCAGGTGCGACAATCTACCGATTGT |
| | | ATGGGAAGCCCGATGCGCCAGAGTTGTTTC |
| | | TGAAACATGGCAAAGGTAGCGTTGCCAATG |
| | | TTGTTACAGATGAGATGGTCAGACTAAACT |
| | | GGCTGACGGAATTTATGCCTCTTCCGACCA |
| | | TCAAGCATTTTATCCGTACTCCTGATGATG |

TABLE 5-continued

Psilocybin Expression Vector Sequences.

| SEQ ID NO | Name | Sequence |
|---|---|---|
| | | CATGGTTACTCACCACTGCGATCCCAGGGA |
| | | AAACAGCATTCCAGGTATTAGAAGAATATC |
| | | CTGATTCAGGTGAAAATATTGTTGATGCGC |
| | | TGGCAGTGTTCCTGCGCCGGTTGCATTCGA |
| | | TTCCTGTTTGTAATTGTCCTTTTAACAGCG |
| | | ATCGCGTATTTCGTCTCGCTCAGGCGCAAT |
| | | CACGAATGAATAACGGTTTGGTTGATGCGA |
| | | GTGATTTTGATGACGAGCGTAATGGCTGGC |
| | | CTGTTGAACAAGTCTGGAAAGAAATGCATA |
| | | AACTTTTGCCATTCTCACCGGATTCAGTCG |
| | | TCACTCATGGTGATTTCTCACTTGATAACC |
| | | TTATTTTTGACGAGGGGAAATTAATAGGTT |
| | | GTATTGATGTTGGACGAGTCGGAATCGCAG |
| | | ACCGATACCAGGATCTTGCCATCCTATGGA |
| | | ACTGCCTCGGTGAGTTTTCTCCTTCATTAC |
| | | AGAAACGGCTTTTTCAAAAATATGGTATTG |
| | | ATAATCCTGATATGAATAAATTGCAGTTTC |
| | | ATTTGATGCTCGATGAGTTTTTCTAATCAC |
| | | TAGACCAATGTTACACATATATACTTTAGA |
| | | TTGATTTAAAACTTCATTTTTAATTTAAAA |
| | | GGATCTAGGTGAAGATCCTTTTTGATAATC |
| | | TCATGACCAAAATCCCTTAACGTGAGTTTT |
| | | CGTTCCACTGAGCGTCAGACCCCGTAGAAA |
| | | AGATCAAAGGATCTTCTTGAGATCCTTTTT |
| | | TTCTGCGCGTAATCTGCTGCTTGCAAACAA |
| | | AAAAACCACCGCTACCAGCGGTGGTTTGTT |
| | | TGCCGGATCAAGAGCTACCAACTCTTCTTC |
| | | CGAAGGTAACTGGCTTCAGCAGAGCGCAGA |
| | | TACCAAATACTGTTCTTCTAGTGTAGCCGT |
| | | AGTTAGGCCACCACTTCAAGAACTCTGTAG |
| | | CACCGCCTACATACCTCGCTCTGCTAATCC |
| | | TGTTACCAGTGGCTGCTGCCAGTGGCGATA |
| | | AGTCGTGTCTTACCGGGTTGGACTCAAGAC |
| | | GATAGTTACCGGATAAGGCGCAGCGGTCGG |
| | | GCTGAACGGGGGGTTCGTGCACACAGCCCA |
| | | GCTTGGAGCGAACGACCTACACCGAACTGA |
| | | GATACCTACAGCGTGAGCTATGAGAAAGCG |
| | | CCACGCTTCCCGAAGGGAGAAAGGCGGACA |
| | | GGTATCCGGTAAGCGGCAGGGTCGGAACAG |
| | | GAGAGCGCACGAGGGAGCTTCCAGGGGGAA |
| | | ACGCCTGGTATCTTTATAGTCCTGTCGGGT |
| | | TTCGCCACCTCTGACTTGAGCGTCGATTTT |
| | | TGTGATGCTCGTCAGGGGGGCGGAGCCTAT |
| | | GGAAAAACGCCAGCAACGCGGCCTTTTTAC |
| | | GGTTCCTGGCCTTTTGCTGGCCTTTTGCTC |
| | | ACATGAGATCTCAAACAAACACATACAGCG |
| | | ACTTAGTTTACCCGCCAATATATCCTGTCA |
| | | AGGATCGTACCCCTACTCCAAAAATGTCAA |
| | | AGATACAGTCTCAGAAGACCAAAGGGCTAT |
| | | TGAGACTTTTCAACAAAGGGTAATTTCGGG |
| | | AAACCTCCTCGGATTCCATTGCCCAGCTAT |
| | | CTGTCACTTCATCGAAAGGACAGTAGAAAA |
| | | GGAAGGTGGCTCCTACAAATGCCATCATTG |
| | | CGATAAAGGAAAGGCTATCATTCAAGATGC |
| | | CTCTGCCGACAGTGGTCCCAAAGATGGACC |
| | | CCCACCCACGAGGAGCATCGTGGAAAAAGA |
| | | AGACGTTCCAACCACGTCTTCAAAGCAAGT |
| | | GGATTGATGTGACATCTCCACTGACGTAAG |
| | | GGATGACGCACAATCCCACTATCCTTCGCA |
| | | AGACCCTTCCTCTATATAAGGAAGTTCATT |
| | | TCATTTGGAGAGGACAGCCCAAGCTGATCC |
| | | CTATGAAAAAGCCTGAACTCACCGCGACGT |
| | | CTGTCGAGAAGTTTCTGATCGAAAAGTTCG |
| | | ACAGCGTCTCCGACCTGATGCAGCTCTCGG |
| | | AGGGCGAAGAATCTCGTGCTTTCAGCTTCG |
| | | ATGTAGGAGGGCGTGGATATGTCCTGCGGG |
| | | TAAATAGCTGCGCCGATGGTTTCTACAAAG |
| | | ATCGTTATGTTTATCGGCACTTTGCATCGG |
| | | CCGCGCTCCCGATTCCGGAAGTGCTTGACA |
| | | TTGGGGAGTTCAGCGAGAGCCTGACCTATT |
| | | GCATCTCCCGCCGTGCACAGGGTGTCACGT |
| | | TGCAAGACCTGCCTGAAACCGAACTGCCCG |
| | | CTGTTCTTCAGCCGGTCGCGGAGGCTATGG |
| | | ATGCGATCGCTGCGGCCGATCTTAGCCAGA |

TABLE 5-continued

Psilocybin Expression Vector Sequences.

| SEQ ID NO | Name | Sequence |
|---|---|---|
| | | CGAGCGGGTTCGGCCCATTCGGACCGCAAG |
| | | GAATCGGTCAATACACTACATGGCGTGATT |
| | | TCATATGCGCGATTGCTGATCCCCATGTGT |
| | | ATCACTGGCAAACTGTGATGGACGACACCG |
| | | TCAGTGCGTCCGTCGCGCAGGCTCTCGATG |
| | | AGCTGATGCTTTGGGCCGAGGACTGCCCCG |
| | | AAGTCCGGCACCTCGTGCACGCGGATTTCG |
| | | GCTCCAACAATGTCCTGACGGACAATGGCC |
| | | GCATAACAGCGGTCATTGACTGGAGCGAGG |
| | | CGATGTTCGGGGATTCCCAATACGAGGTCG |
| | | CCAACATCTTCTTCTGGAGGCCGTGGTTGG |
| | | CTTGTATGGAGCAGCAGACGCGCTACTTCG |
| | | AGCGGAGGCATCCGGAGCTTGCAGGATCGC |
| | | CACGCCTCCGGGCGTATATGCTCCGCATTG |
| | | GTCTTGACCAACTCTATCAGAGCTTGGTTG |
| | | ACGGCAATTTCGATGATGCAGCTTGGGCGC |
| | | AGGGTCGATGCGACGCAATCGTCCGATCCG |
| | | GAGCCGGGACTGTCGGGCGTACACAAATCG |
| | | CCCGCAGAAGCGCGGCCGTCTGGACCGATG |
| | | GCTGTGTAGAAGTACTCGCCGATAGTGGAA |
| | | ACCGACGCCCCAGCACTCGTCCGAGGGCAA |
| | | AGGAATAGAGTAGATGCCGACCGAACAAGA |
| | | GCTGATTTCGAGAACGCCTCAGCCAGCAAC |
| | | TCGCGCGAGCCTAGCAAGGCAAATGCGAGA |
| | | GAACGGCCTTACGCTTGGTGGCACAGTTCT |
| | | CGTCCACAGTTCGCTAAGCTCGCTCGGCTG |
| | | GTCGCGGGAGAATTAATTCGGTACGCTGAA |
| | | ATCACCAGTCTCTCTCTACAAATCTATCTC |
| | | TCTCTATTTTCTCCATAAATAATGTGTGAG |
| | | TAGTTTCCCGATAAGGGAAATTAGGGTTCT |
| | | TATAGGGTTTCGCTCATGTGTTGAGCATAT |
| | | AAGAAACCCTTAGTATGTATTTGTATTTGT |
| | | AAAATACTTCTATCAATAAAATTTCTAATT |
| | | CCTAAAACCAAAATCCAGTACTAAAATCCA |
| | | GATCGATCCTTCATGTTCTTTCCTGCGTTA |
| | | TCCCCTGATTCTGTGGATAACCGTATTACC |
| | | GCCTTTGAGTGAGCTGATACCGCTCGCCGC |
| | | AGCCGAACGACCGAGCGCAGCGAGTCAGTG |
| | | AGCGAGGAAGCGGAAGAGCGCCCAATACGC |
| | | AAACCGCCTCTCCCCGCGCGTTGGCCGATT |
| | | CATTAATGCAGCTGGCACGACAGGTTTCCC |
| | | GACTGGAAAGCGGGCAGTGAGCGCAACGCA |
| | | ATTAATGTGAGTTAGCTCACTCATTAGGCA |
| | | CCCCAGGCTTTACACTTTATGACTTCCGGC |
| | | TCGTATGTTGTGTGGAATTGTGAGCGGATA |
| | | ACAATTTCACACAGGAAACAGCTATGACCA |
| | | TGATTACGCCAAGCTCGGAATTAACCCTCA |
| | | CTAAAGGGAACAAAAGCTGGAGCTCgaggt |
| | | ccgcaagtagattgaaagttcagtacgttt |
| | | ttaacaatagagcattctcgaggcttgcgt |
| | | cattctgtgtcaggctagcagtttataagc |
| | | gttgaggatctagagctgctgtttccgcgt |
| | | ctcgaatgttctcggtgtttaggggttagc |
| | | aatctgatatgataataatttgtgatgaca |
| | | tcgatagtacaaaaaccccaattccggtca |
| | | catccacctctccgttttctcccatctaca |
| | | cacaacaagcttatcgccgtaattctcttt |
| | | cttttgggataagttgaaacccgaacgagg |
| | | aactaatctttcactcggtgtagAAGCTTA |
| | | TCGATACCGTCGACCTCGAGGGGGGGCCCG |
| | | GTACCCACCGGATCCACAAGTTTGTACAAA |
| | | AAAGCTGAACGAGAAACGTAAAATGATATA |
| | | AATATCAATATATTAAATTAGATTTTGCAT |
| | | AAAAAACAGACTACATAATACTGTAAAACA |
| | | CAACATATCCAGTCACTATGGCGGCCGCAT |
| | | TAGGCACCCCAGGCTTTACACTTTATGCTT |
| | | CCGGCTCGTATAATGTGTGGATTTTGAGTT |
| | | AGGATCCGGCGAGATTTTCAGGAGCTAAGG |
| | | AAGCTAAAATGGAGAAAAAAATCACTGGAT |
| | | ATACCACCGTTGATATATCCCAATGGCATC |
| | | GTAAAGAACATTTTGAGGCATTTCAGTCAG |
| | | TTGCTCAATGTACCTATAACCAGACCGTTC |
| | | AGCTGGATATTACGGCCTTTTTAAAGACCG |
| | | TAAAGAAAAATAAGCACAAGTTTTATCCGG |

TABLE 5-continued

Psilocybin Expression Vector Sequences.

| SEQ ID NO | Name | Sequence |
|---|---|---|
| | | CCTTTATTCACATTCTTGCCCGCCTGATGA ATGCTCATCCGGAATTCCGTATGGCAATGA AAGACGGTGAGCTGGTGATATGGGATAGTG TTCACCCTTGTTACACCGTTTTCCATGAGC AAACTGAAACGTTTTCATCGCTCTGGAGTG AATACCACGACGATTTCCGGCAGTTTCTAC ACATATATTCGCAAGATGTGGCGTGTTACG GTGAAAACCTGGCCTATTTCCCTAAAGGGT TTATTGAGAATATGTTTTTCGTCTCAGCCA ATCCCTGGGTGAGTTTCACCAGTTTTGATT TAAACGTGGCCAATATGGACAACTTCTTCG CCCCCGTTTTCACCATGGGCAAATATTATA CGCAAGGCGACAAGGTGCTGATGCCGCTGG CGATTCAGGTTCATCATGCCGTCTGTGATG GCTTCCATGTCGGCAGAATGCTTAATGAAT TACAACAGTACTGCGATGAGTGGCAGGGCG GGGCGTAAACGCGTGGATCCGGCTTACTAA AAGCCAGATAACAGTATGCGTATTTGCGCG CTGATTTTTGCGGTATAAGAATATATACTG ATATGTATACCCGAAGTATGTCAAAAAGAG GTGTGCTATGAAGCAGCGTATTACAGTGAC AGTTGACAGCGACAGCTATCAGTTGCTCAA GGCATATATGATGTCAATATCTCCGGTCTG GTAAGCACAACCATGCAGAATGAAGCCCGT CGTCTGCGTGCCGAACGCTGGAAAGCGGAA AATCAGGAAGGGATGGCTGAGGTCGCCCGG TTTATTGAAATGAACGGCTCTTTTGCTGAC GAGAACAGGGACTGGTGAAATGCAGTTTAA GGTTTACACCTATAAAAGAGAGAGCCGTTA TCGTCTGTTTGTGGATGTACAGAGTGATAT TATTGACACGCCCGGGCGACGGATGGTGAT CCCCCTGGCCAGTGCACGTCTGCTGTCAGA TAAAGTCTCCCGTGAACTTTACCCGGTGGT GCATATCGGGGATGAAAGCTGGCGCATGAT GACCACCGATATGGCCAGTGTGCCGGTCTC CGTTATCGGGGAAGAAGTGGCTGATCTCAG CCACCGCGAAAATGACATCAAAAACGCCAT TAACCTGATGTTCTGGGGAATATAAATGTC AGGCTCCCTTATACACAGCCAGTCTGCAGG TCGACCATAGTGACTGGATATGTTGTGTTT TACAGTATTATGTAGTCTGTTTTTTATGCA AAATCTAATTTAATATATTGATATTTATAT CATTTTACGTTTCTCGTTCAGCTTTCTTGT ACAAAGTGGTGCTCGAGATGGTGAGCAAGG GCGAGGAGCTGTTCACCGGGGTGGTGCCCA TCCTGGTCGAGCTGGACGGCGACGTAAACG GCCACAAGTTCAGCGTGTCCGGCGAGGGCG AGGGCGATGCCACCTACGGCAAGCTGACCC TGAAGCTGATCTGCACCACCGGCAAGCTGC CCGTGCCCTGGCCCACCCTCGTGACCACCC TGGGCTACGGCCTGCAGTGCTTCGCCCGCT ACCCCGACCACATGAAGCAGCACGACTTCT TCAAGTCCGCCATGCCCGAAGGCTACGTCC AGGAGCGCACCATCTTCTTCAAGGACGACG GCAACTACAAGACCCGCGCCGAGGTGAAGT TCGAGGGCGACACCCTGGTGAACCGCATCG AGCTGAAGGGCATCGACTTCAAGGAGGACG GCAACATCCTGGGGCACAAGCTGGAGTACA ACTACAACAGCCACAACGTCTATATCACCG CCGACAAGCAGAAGAACGGCATCAAGGCCA ACTTCAAGATCCGCCACAACATCGAGGACG GCGGCGTGCAGCTCGCCGACCACTACCAGC AGAACACCCCCATCGGCGACGGCCCCGTGC TGCTGCCCGACAACCACTACCTGAGCTACC AGTCCGCCCTGAGCAAAGACCCCAACGAGA AGCGCGATCACATGGTCCTGCTGGAGTTCG TGACCGCCGCCGGGATCACTCTCGGCATGG ACGAGCTGTACAAGTAAGTCGACCTGCAGG CATGCGCTGAAATCACCAGTCTCTCTCTAC AAATCTATCTCTCTCTATAATAATGTGTGA GTAGTTCCCAGATAAGGGAATTAGGGTTCT TATAGGGTTTCGCTCATGTGTTGAGCATAT AAGAAACCCTTAGTATGTATTTGTATTTGT AAAATACTTCTATCAATAAAATTTCTAATT CCTAAAACCAAAATCCAGTGGGTACCCAAT TCGCCCTATAGTGAGTCGTATTACAATTCA CTGGCCGTCGTTTTACAACGTCGTGACTGG GAAAACCCTGGCGTTACCCAACTTAATCGC CTTGCAGCACATCCCCCTTTCGCCAGCTGG CGTAATAGCGAAGAGGCCCGCACCGATCGC CCTTCCCAACAGTTGCGCAGCCTGAATGGC GAATGGCGCGAAATTGTAAACGTTAATGTT AACGTTACACCACAATATATCCTGCCA |

What is claimed is:

1. A method of treating a depression or an anxiety in a subject, the method comprising:

administering to the subject an effective amount of a pharmaceutical composition comprising:

a genetically modified psilocybe fungus, comprising a genetic modification in at least one psilocybin biosynthesis gene selected from: a PsiD gene, a PsiH, gene, a PsiM, gene, a PsiK gene, or a combination thereof, wherein the genetic modification results in an increased amount of a compound selected from:

(Formula I, Dimethyltryptamine (DMT))

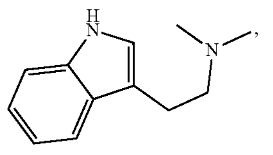

(Formula II, Psilocybin)

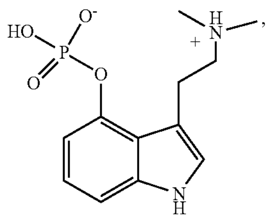

-continued (Formula III, Psilocin)

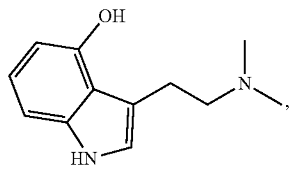

(Formula IV, Tryptamine)

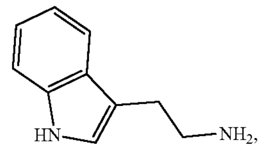

or derivatives or analogs thereof, compared to production of the same compound in a comparable control psilocybe fungus without the genetic modification, wherein:

the genetic modification comprises an insertion of a polynucleotide encoding the at least one psilocybin biosynthesis gene into a genome of the genetically modified psilocybe fungus, a substitution of at least one nucleobase in a psilocybin biosynthesis gene sequence in the genome of the genetically modified psilocybe fungus, or a combination thereof, the genetic modification results in an increased expression of the at least one psilocybin biosynthesis gene compared to the expression of the at least one psilocybin biosynthesis gene in a comparable control psilocybe fungus without the genetic modification; and the genetically modified psilocybe fungus comprises at least 200% more of the compound measured by dry weight of the fungus compared to the amount of the compound in a comparable control psilocybe fungus without the genetic modification, thereby treating the depression or the anxiety in the subject.

2. The method of claim 1, wherein the genetic modification is a substitution of at least one nucleobase in the psilocybin biosynthesis gene sequence in the genome of the genetically modified psilocybe fungus, wherein the substitution is conducted by contacting a cell of the psilocybe fungus with an endonuclease system and a guide RNA that targets the at least one psilocybin biosynthesis gene.

3. The method of claim 2, wherein the endonuclease system comprises a CRISPR enzyme, TALE-Nuclease, transposon-based nuclease, Zinc finger nuclease, meganuclease, Mega-TAL or DNA guided nuclease.

4. The method of claim 1, wherein the at least one psilocybin biosynthesis gene encodes for: a PLP-independent phosphatidylserine decarboxylase, a tryptophan decarboxylase (TDC), a putative monooxygenase, a 5-methylthionribose family small molecule kinase, or a 4-hydroxytryptamine kinase.

5. The method of claim 1, wherein the at least one psilocybin biosynthesis gene results in (i) upregulated expression of: a tryptophan decarboxylase gene, a psilocybin-related hydroxylase gene, a psilocybin-related N-methyltransferase gene, or a psilocybin-related phosphotransferase gene; (ii) reduced synthesis of non-psilocybin tryptamines; or (iii) increased production of tryptophan in the genetically modified psilocybe fungus comprising the genetic modification compared to a comparable control psilocybe fungus without the psilocybin biosynthesis gene.

6. The method of claim 1, wherein the genetic modification results in at least one of:

(a) increased tryptophan decarboxylation, (b) increased tryptamine 4-hydroxylation, (c) increased 4-hydroxytryptamine-O-phosphorylation, and (d) increased psilocybin production via sequential N-methylations, thereby resulting in the increased production of psilocybin measured by dry weight of the psilocybe fungus compared to the amount of psilocybin measured by dry weight in a comparable control psilocybe fungus without the genetic modification.

7. The method of claim 1, wherein the genetically modified psilocybe fungus is a *Psilocybe cubensis* fungus.

8. The method of claim 1, wherein the pharmaceutical composition is in the form of a tablet, a gel, a syrup, a food substrate, an elixir, or a powder.

9. The method of claim 1, wherein the pharmaceutical composition is in a transdermal form, an oil formulation, an aqueous dispersion, an emulsion, a solution, or a suspension.

10. The method of claim 1, wherein the pharmaceutical composition is in the form of an aerosol or a mist.

11. The method of claim 1, wherein the pharmaceutical composition is in the form of a paste, a balm, a cream, or an ointment.

12. The method of claim 1, wherein the subject is administered a monoamine oxidase inhibitor.

* * * * *